(12) United States Patent
Yukimasa et al.

(10) Patent No.: US 10,781,210 B2
(45) Date of Patent: *Sep. 22, 2020

(54) NITROGEN-CONTAINING HETEROCYCLE AND CARBOCYCLE DERIVATIVES HAVING TRKA INHIBITORY ACTIVITY

(71) Applicant: Shionogi & Co., Ltd., Osaka (JP)

(72) Inventors: Akira Yukimasa, Osaka (JP); Kazuya Kano, Osaka (JP); Kenichiroh Nakamura, Osaka (JP); Takatsugu Inoue, Osaka (JP); Motohiro Fujiu, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/684,807

(22) Filed: Nov. 15, 2019

(65) Prior Publication Data

US 2020/0087302 A1 Mar. 19, 2020

Related U.S. Application Data

(63) Continuation of application No. 16/075,409, filed as application No. PCT/JP2017/003919 on Feb. 3, 2017.

(30) Foreign Application Priority Data

Feb. 4, 2016 (JP) .................. 2016-019396

(51) Int. Cl.

| | |
|---|---|
| *C07D 401/14* | (2006.01) |
| *C07D 471/04* | (2006.01) |
| *C07D 401/04* | (2006.01) |
| *C07D 403/14* | (2006.01) |
| *C07D 409/14* | (2006.01) |
| *C07D 487/04* | (2006.01) |
| *C07D 498/04* | (2006.01) |
| *C07D 417/14* | (2006.01) |
| *A61K 31/519* | (2006.01) |
| *A61K 31/427* | (2006.01) |
| *C07D 405/14* | (2006.01) |
| *A61K 31/4439* | (2006.01) |
| *A61K 31/454* | (2006.01) |
| *A61K 31/4375* | (2006.01) |
| *A61K 31/4545* | (2006.01) |
| *A61K 31/4985* | (2006.01) |

(Continued)

(52) U.S. Cl.

CPC .......... *C07D 471/04* (2013.01); *A61K 31/416* (2013.01); *A61K 31/427* (2013.01); *A61K 31/437* (2013.01); *A61K 31/4375* (2013.01); *A61K 31/4439* (2013.01); *A61K 31/454* (2013.01); *A61K 31/4545* (2013.01); *A61K 31/4985* (2013.01); *A61K 31/506* (2013.01); *A61K 31/519* (2013.01); *C07D 401/04* (2013.01); *C07D 401/12* (2013.01); *C07D 401/14* (2013.01); *C07D 403/04* (2013.01); *C07D 403/14* (2013.01); *C07D 405/14* (2013.01); *C07D 407/14* (2013.01); *C07D 409/14* (2013.01); *C07D 417/14* (2013.01); *C07D 487/04* (2013.01); *C07D 498/04* (2013.01)

(58) Field of Classification Search
CPC .. C07D 401/04; C07D 401/14; A61K 31/416; A61K 31/427; A61K 31/437; A61K 31/4375

See application file for complete search history.

(56) References Cited

U.S. PATENT DOCUMENTS

| | | |
|---|---|---|
| 4,855,316 A | 8/1989 | Horwell et al. |
| 4,906,655 A | 3/1990 | Horwell et al. |

(Continued)

FOREIGN PATENT DOCUMENTS

| | | |
|---|---|---|
| EP | 0372466 A2 | 6/1990 |
| EP | 2842955 A1 | 3/2015 |

(Continued)

OTHER PUBLICATIONS

Schulz, Molecular Biology of Human Cancers: Chapter 1, Springer, pp. 1-23 (2007).*

(Continued)

*Primary Examiner* — Deepak R Rao
(74) *Attorney, Agent, or Firm* — Sterne, Kessler, Goldstein & Fox P.L.L.C.

(57) ABSTRACT

The present invention provides a compound having TrkA inhibitory activity, or a pharmaceutically acceptable salt thereof. The present invention relates to a compound represented by Formula (I):

wherein =X is =O or the like, $R^5$ and $R^{5A}$ are hydrogen atoms or the like, —A— is —$NR^1$— or the like, B is substituted or unsubstituted aromatic carbocyclyl or the like, $R^1$ is substituted or unsubstituted alkyl or the like, $R^2$ is a hydrogen atom or the like, —W— is —$CH_2$— or the like, —$W^A$— is —$CH_2$— or the like, $R^{13}$ is substituted or unsubstituted aromatic carbocyclyl or the like, $R^{14}$ is substituted or unsubstituted aromatic heterocyclyl or the like, $R^{15}$ is substituted or unsubstituted alkyl or the like, or a pharmaceutically acceptable salt thereof, and a pharmaceutical composition containing the same.

17 Claims, No Drawings

(51) Int. Cl.
| | |
|---|---|
| A61K 31/416 | (2006.01) |
| A61K 31/506 | (2006.01) |
| A61K 31/437 | (2006.01) |
| C07D 401/12 | (2006.01) |
| C07D 403/04 | (2006.01) |
| C07D 407/14 | (2006.01) |

(56) References Cited

U.S. PATENT DOCUMENTS

| | | | |
|---|---|---|---|
| 9,242,977 | B2 | 1/2016 | Takeuchi et al. |
| 10,160,727 | B2* | 12/2018 | Nakamura ............ C07D 403/12 |
| 10,533,006 | B2 | 1/2020 | Yukimasa et al. |
| 2007/0043013 | A1* | 2/2007 | Le Grand ............ C07D 403/12 514/210.01 |
| 2016/0000783 | A1 | 1/2016 | Takeuchi et al. |
| 2016/0280684 | A1 | 9/2016 | Takeuchi et al. |
| 2017/0240512 | A1* | 8/2017 | Yukimasa ............ C07D 403/12 |
| 2019/0047998 | A1 | 2/2019 | Yukimasa et al. |

FOREIGN PATENT DOCUMENTS

| | | |
|---|---|---|
| EP | 2960234 A1 | 12/2015 |
| EP | 3330256 A1 | 6/2018 |
| JP | 2007505080 A | 3/2007 |
| WO | WO-9916431 A1 | 4/1999 |
| WO | WO-0035452 A1 | 6/2000 |
| WO | WO-2004110993 A2 | 12/2004 |
| WO | WO-2005026113 A1 | 3/2005 |
| WO | WO-2005110994 A2 | 11/2005 |
| WO | WO-2009074260 A1 | 6/2009 |
| WO | WO-2009131196 A1 | 10/2009 |
| WO | WO-2012158413 A2 | 11/2012 |
| WO | WO-2012174199 A1 | 12/2012 |
| WO | WO-2013161919 A1 | 10/2013 |
| WO | WO-2014052563 A2 | 4/2014 |
| WO | WO-2014053965 A1 | 4/2014 |
| WO | WO-2014053967 A1 | 4/2014 |
| WO | WO-2014053968 A1 | 4/2014 |
| WO | WO-2014078322 A1 | 5/2014 |
| WO | WO-2014078323 A1 | 5/2014 |
| WO | WO-2014078325 A1 | 5/2014 |
| WO | WO-2014078328 A1 | 5/2014 |
| WO | WO-2014078331 A1 | 5/2014 |
| WO | WO-2014078372 A1 | 5/2014 |
| WO | WO-2014078378 A1 | 5/2014 |
| WO | WO-2014078408 A1 | 5/2014 |
| WO | WO-2014078417 A1 | 5/2014 |
| WO | WO-2014078454 A1 | 5/2014 |
| WO | WO-2014129431 A1 | 8/2014 |
| WO | WO-2015039333 A1 | 3/2015 |
| WO | WO-2015039334 A1 | 3/2015 |
| WO | WO-2015042085 A2 | 3/2015 |
| WO | WO-2015042088 A1 | 3/2015 |
| WO | WO-2015159175 A1 | 10/2015 |
| WO | WO-2015170218 A1 | 11/2015 |
| WO | WO-2015175788 A1 | 11/2015 |
| WO | WO-2016021629 A1 | 2/2016 |
| WO | WO-2016116900 A1 | 7/2016 |
| WO | WO-2017006953 A1 | 1/2017 |
| WO | WO-2017135399 A1 | 8/2017 |

OTHER PUBLICATIONS

Herbrich et al., Characterization of TRKA signaling in acute myeloid leukemia, Oncotarget, 2018, vol. 9, (No. 53), pp. 30092-30105.*
Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Ashraf et al., Selective inhibition of tropomysin-receptor-kinase A (TrkA) reduces pain and joint damage in two rat models of inflammatory arthritis, Arthritis Research & Therapy, 2016, 18:97, 11 pages.*
Merck Manual Professional Online Edition, Acute Leukemia, 6 pages, 2013.*
Ghilardi et al., Sustained blockade of neurotrophin receptors TrkA, TrkB and TrkC reduces non-malignant skeletal pain but not the maintenance of sensory and sympathetic nerve fibers, Bone, 48, pp. 389-398 (2011).*
STN Registry (Supplier: Ukrorgsyntez Ltd.) 2 pages, Jul. 19, 2016.*
STN Registry (Supplier: Aurora Fine Chemicals) 1 page, Jan. 25, 2017.*
STN Registry #2 (Supplier: Ukrorgsyntez Ltd.) 38 pages, Jul. 2016.*
STN Registry #2 (Supplier: Aurora Fine Chemicals) 1 page, May 10, 2016.*
STN Registry (Supplier: Enamine LLC) 1 page, Sep. 29, 2015.*
STN Registry #3 (Supplier: Aurora Fine Chemicals) 1 page, Jul. 9, 2015.*
STN Registry (Supplier: ChemBridge Corporation) 1 page, Mar. 11, 2014.*
STN Registry #3 (Supplier: Ukrorgsyntez Ltd.) 1 page, Jun. 2013.*
STN Registry #2 (Supplier: Enamine LLC) 1 page, Sep. 18, 2012.*
STN Registry #4 (Supplier: Ukrorgsyntez Ltd.) 1 page, Aug. 2012.*
STN Registry (Database: GVK BIO) 2 pages, Dec. 2011.*
STN Registry #3 (Supplier: Enamine LLC) 1 page, Jul. 7, 2011.*
STN Registry #4 (Supplier: Enamine LLC) 1 page, Sep. 16, 2010.*
STN Registry (Database: Ambinter SARL) 1 page, Nov. 2007.*
Allen, S.J., et al., "Clinical Relevance of the Neurotrophins and their Receptors," Clinical Science (London) 110(2):175-191, Portland Press on behalf of the Medical Research Society and the Biochemical Society, England (Feb. 2006).
Avontis, F., "2-2-Dimethyl-3-[N'-alkyl(aryl) ureido]-1[[N'-alkyl(aryl)ureido]methyl] cyclobutanes". Latvijas Kimijas Zurnals;715-720, Riga, Latvia (1991).
Chao, M.V, "Neurotrophins and Their Receptors: a Convergence Point for Many Signalling Pathways," Nature Reviews Neuroscience 4(4):299-309, Nature Publishing Group, England (Apr. 2003).
File Registry on STN, RN 410069-68-0, Entered STN: May 2, 2002.
Ghilardi, J.R., et al., "Administration of a Tropomyosin Receptor Kinase Inhibitor Attenuates Sarcoma-induced Nerve Sprouting, Neuroma Formation and Bone Cancer Pain," Molecular Pain 6:87, Sage Publications Inc, United States (Dec. 2010).
Ghilardi, J.R., et al., "Sustained Blockade of Neurotrophin Receptors TrKa, TrKB and TrKC Reduces Non-malignant Skeletal Pain but Not the Maintenance of Sensory and Sympathetic Nerve Fibers," Bone 48(2):389-398, Elsevier Science, United States (Feb. 2011).
Halfpenny, P.R., et al., "Highly Selective Kappa-opioid Analgesics. 2. Synthesis and Structure-activity Relationships of Novel N-[(2-aminocyclohexyl)aryl]acetamide Derivatives," Journal of Medicinal Chemistry 32(7):1620-1626, American Chemical Society, United States (Jul. 1989).
Halfpenny, P.R., et al., "Highly Selective Kappa-opioid Analgesics. 3. Synthesis and Structure-activity Relationships of Novel N-[2-(1-pyrrolidinyl)-4- or -5-substituted-cyclohexyl]arylacetamide Derivatives," Journal of Medicinal Chemistry 33(1):286-291, American Chemical Society, United States (Jan. 1990).
Indo, Y, "Nerve Growth Factor and the Physiology of Pain: Lessons From Congenital Insensitivity to Pain With Anhidrosis," Clinical Genetics 82(4):341-350, Munksgaard, Denmark (Oct. 2012).
International Search Report for International Application No. PCT/JP2017/003919, Japanese Patent Office, Japan, dated Apr. 11, 2017, 10 pages.
Mantyh, P.W., et al., "Antagonism of Nerve Growth Factor-TrKA Signaling and the Relief of Pain," Anesthesiology 115(1):189-204, Lippincott Williams & Wilkins, United States (Jul. 2011).
McCarthy, C., et al., "Tropomyosin Receptor Kinase Inhibitors: a Patent Update 2009-2013," Expert Opinion on Therapeutic Patents 24(7):731-744, Informa Healthcare, England (Jul. 2014).

(56) References Cited

OTHER PUBLICATIONS

McKelvey, L., et al., "Nerve Growth Factor-mediated Regulation of Pain Signalling and Proposed New Intervention Strategies in Clinical Pain Management," Journal of Neurochemistry 124(3):276-289, Wiley on behalf of the International Society for Neurochemistry, England (Feb. 2013).

Meyer, J., et al., "Remarkable Leukemogenic Potency and Quality of a Constitutively Active Neurotrophin Receptor, Delta TrkA," Leukemia 21(10):2171-2180, Nature Publishing Group, Specialist Journals, England (Oct. 2007).

Pinski, J., et al., "TrK Receptor Inhibition Induces Apoptosis of Proliferating but not Quiescent Human Osteoblasts," Cancer Research 62(4):986-989, American Association for Cancer Research, United States (Feb. 2002).

Zhao, G.L., et al., "One-pot Catalytic Enantioselective Domino Nitro-Michael/Michael Synthesis of Cyclopentanes with Four Stereocenters," Chemistry, 14(32):10007-10011, Wiley-VCH, Germany (2008).

Registry [STN online, retrieved on Mar. 27, 2017], Aug. 7, 2012, RN:1387450-63-6.

Registry [STN online, retrieved on Mar. 27, 2017], Mar. 11, 2014, RN:1566600-95-0.

Registry [STN online, retrieved on Mar. 27, 2017] Nov. 29, 2007, RN:956229-07-5.

Registry [STN online, retrieved on Mar. 27, 2017] Sep. 16, 2010, RN:1241652-79-8.

Registry [STN online, retrieved on Mar. 27, 2017] Dec. 6, 2011, RN:1349586-29-3.

Registry [STN online, retrieved on Mar. 27, 2017] Dec. 7, 2011, RN:1350227-10-9.

Registry [STN online, retrieved on Mar. 27, 2017] Jul. 7, 2011, RN:1311879-33-0.

Registry [STN online, retrieved on Mar. 27, 2017] Sep. 18, 2012, RN:1394695-21-6.

Registry [STN online, retrieved on Mar. 27, 2017] Sep. 18, 2012, RN:1394757-50-6.

Stachel, S.J., et al., "Maximizing Diversity From a Kinase Screen: Identification of Novel and Selective Pan-TrK Inhibitors for Chronic Pain," Journal of Medicinal Chemistry 57(13):5800-5816, American Chemical Society, United States (Jul. 2014).

Truzzi, F., et al., "Neurotrophins in Healthy and Diseased Skin," Dermato-Endocrinology 3(1):32-36, Taylor & Francis, United States (Jan. 2011).

Vaishnavi, A., et al., "Oncogenic and Drug-sensitive NTRK1 Rearrangements in Lung Cancer," Nature Medicine 19(11):1469-1472, Nature Publishing Company, United States (Nov. 2013).

Wang, T., et al., "Trk Kinase Inhibitors as New Treatments for Cancer and Pain," Expert Opinion on Therapeutic Patents 19(3):305-319, Informa Healthcare, England (Mar. 2009).

Notification of Transmittal of the Translation of the International Preliminary Report on Patentability for International Application No. PCT/JP2017/003919, International Bureau of WIPO, Switzerland, dated Aug. 16, 2018, 1 page.

International Preliminary Report on Patentability for International Application No. PCT/JP2017/003919, International Bureau of WIPO, Switzerland, dated Aug. 7, 2018, 1 page.

English Translation of Written Opinion for International Application No. PCT/JP2017/003919, International Bureau of WIPO, Switzerland, dated Apr. 11, 2017, 7 pages.

* cited by examiner

NITROGEN-CONTAINING HETEROCYCLE AND CARBOCYCLE DERIVATIVES HAVING TRKA INHIBITORY ACTIVITY

TECHNICAL FIELD

The present invention relates to a compound that has a TrkA inhibitory activity and is useful in the treatment and/or prevention of TrkA mediated disorders, or a pharmaceutically acceptable salt thereof, and a pharmaceutical composition comprising the same.

BACKGROUND ART

The tropomyosin receptor kinase (Trk) is a family of receptor tyrosine kinases and has a function as a receptor of neurotrophin (NT). Three major subtypes of Trk receptors are TrkA high-affinity receptor for nerve growth factor (NGF), TrkB high-affinity receptor for brain-derived neurotrophic factor (BDNF) and NT-4/5, and TrkC high-affinity receptor for NT-3. All receptors involve in various physiological function in vivo. TrkA is mainly expressed in peripheral and central nerves, and involves in neuronal development and differentiation, and maintenance of neuronal functions. The gene mutation in TrkA is associated with painless anhidrosis in human (Patent Documents 1, 2 and Non-patent Documents 1 to 3). The activation of NGF-TrkA signal produces hypralgesia (Non-patent Documents 4 to 6). Clinical and non-clinical researches regarding anti-NGF antibodies and non-clinical researches regarding Trk inhibitors reveal the involvement of NGF-TrkA signal or NT-Trk signal in the pain of osteoarthritis, rheumatoid arthritis, bone fracture, interstitial cystitis, chronic pancreatitis, prostatitis and the like in addition to nociceptive pain such as chronic low back pain, neuropathic pain such as diabetic peripheral neuropathic pain, acute pain such as postoperative pain and chronic pain such as pelvic pain and cancer pain (Patent Documents 1, 2 and Non-patent documents 7, 8).

Trk receptors are also expressed in several types of cancer cells such as neuroblastoma, prostate cancer, lung cancer, breast cancer, gastric cancer and pancreatic cancer, and involve in the proliferation and migration of cancer cells. The fusion protein combined with TrkA kinase domain causes the proliferation of lung cancer cells. Trk inhibitor is shown to suppress the proliferation and metastasis of cancer cells in animal model. (Patent Document 1 and Non-patent Documents 9 to 12). Furthermore, Trk receptors are expressed in mast cells, eosinophils, immunocompetent cells such as T and B cells and keratinocytes, and NGF-trkA signal or NT-Trk signal involves in inflammatory bowel diseases such as ulcerative colitis and Crohn's disease, allergic diseases such as asthma and rhinitis, and skin diseases such as psoriasis, atopic dermatitis and pruritus (Patent Documents 1, 2). In addition, the inhibition of NGF-TrkA signal improves the overactive bladder (Patent Document 1). NT-Trk signal also involves in Sjogren's syndrome (Patent Document 1) and endometriosis (Patent Document 1). TrkA receptor plays a critical role in the infection process of the parasitic infection of Trypanosoma cruzi (Chagas disease) (Patent Document 1). Therefore, the compounds having an inhibitory activity for TrkA will be effective for various diseases including nociceptive pain, neuropathic pain, cancer, inflammatory diseases, allergic diseases and dermatological diseases.

The compounds that have an inhibitory activity for TrkA are disclosed in Patent Documents 1 to 18 and Non-patent Documents 6, 13 to 14. However, the compounds related to the present invention aren't indicated and suggested in any documents.

PRIOR ART REFERENCES

Patent Document

[Patent Document 1] International Publication No. 2014/078325 pamphlet
[Patent Document 2] International Publication No. 2013/161919 pamphlet
[Patent Document 3] International Publication No. 2012/158413 pamphlet
[Patent Document 4] International Publication No. 2014/078454 pamphlet
[Patent Document 5] International Publication No. 2014/078417 pamphlet
[Patent Document 6] International Publication No. 2014/078408 pamphlet
[Patent Document 7] International Publication No. 2014/078378 pamphlet
[Patent Document 8] International Publication No. 2014/078372 pamphlet
[Patent Document 9] International Publication No. 2014/078331 pamphlet
[Patent Document 10] International Publication No. 2014/078328 pamphlet
[Patent Document 11] International Publication No. 2014/078323 pamphlet
[Patent Document 12] International Publication No. 2014/078322 pamphlet
[Patent Document 13] International Publication No. 2014/053967 pamphlet
[Patent Document 14] International Publication No. 2014/053965 pamphlet
[Patent Document 15] International Publication No. 2014/053968 pamphlet
[Patent Document 16] International Publication No. 2015/175788 pamphlet
[Patent Document 17] International Publication No. 2016/116900 pamphlet
[Patent Document 18] International Publication No. 2016/021629 pamphlet
[Non-patent Document 1] Clinical Science, Vol. 110, 175-191(2006)
[Non-patent Document 2] Nature Reviews Neuroscience, Vol. 4, 299-309(2003)
[Non-patent Document 3] Clinical Genetics, Vol. 82, 341-350(2012)
[Non-patent Document 4] Anesthesiology, Vol. 115, 189-204(2011)
[Non-patent Document 5] Journal of Neurochemistry, Vol. 124, 276-289(2013)
[Non-patent Document 6] Expert Opinion on Therapeutic Patents, Vol. 24, 731-744(2014)
[Non-patent Document 7] Bone, Vol. 48, 389-398(2011)
[Non-patent Document 8] Molecular Pain, Vol. 6, 87(2010)
[Non-patent Document 9] Dermato-Endocrinology, Vol. 3, 32-36(2011)
[Non-patent Document 10] Leukemia, Vol. 21, 2171-2180 (2007)
[Non-patent Document 11] Cancer Research, Vol. 62, 986-989(2002)
[Non-patent Document 12] Nature Medicine, Vol. 19, 1469-1472(2013)

[Non-patent Document 13] Journal of Medicinal Chemistry, Vol. 57, 5800-5816(2014)

[Non-patent Document 14] Expert Opinion on Therapeutic Patents, Vol. 19, 305-319(2009)

SUMMARY OF THE INVENTION

Problems to be Solved by the Invention

The present invention is to provide a compound that has a TrkA inhibitory activity or a pharmaceutically acceptable salt thereof, or a pharmaceutical composition comprising the same.

Means for Solving the Problem

The present invention relates to a compound that has a TrkA inhibitory activity and is useful in the treatment and/or prevention of TrkA mediated disorders, or a pharmaceutically acceptable salt thereof.

The present invention relates to the following items 1') to 24'), 16'A) to 19'A), 19'B) and 101') to 107'):

1') A compound represented by Formula (I):

[Chemical Formula 1]

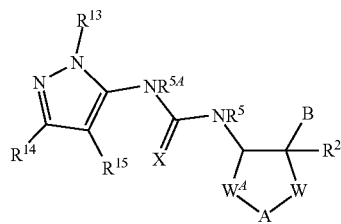

(I)

wherein =X is =O, =S, =NR$^{10}$ or =CR$^{11}$R$^{12}$;
—W— is —C(R$^8$R$^9$)n-;
—W$^A$— is —C(R$^3$R$^4$)m-;
n is 0, 1 or 2;
m is 1 or 2;
n is 0, 1 or 2 when m is 1, and n is 0 when m is 2;
—A— is —NR$^1$— or —CR$^{1D}$R$^{1E}$—;
B is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkyl, or substituted or unsubstituted alkyloxy;
R$^1$ is a hydrogen atom, cyano, substituted or unsubstituted alkyl, substituted or unsubstituted alkenyl, substituted or unsubstituted acyl, substituted or unsubstituted alkyl sulfonyl, substituted or unsubstituted alkenyl sulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
R$^{1D}$ and R$^{1E}$ are each independently a hydrogen atom, hydroxy, halogen, carboxy, substituted or unsubstituted alkyl, substituted or unsubstituted alkenyl, substituted or unsubstituted acyl, substituted or unsubstituted alkyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted amino, substituted or unsubstituted alkyl sulfonyl, substituted or unsubstituted alkenyl sulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsufonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
or R$^{1D}$ and R$^{1E}$ may be taken together to form =CR$^{1F}$R$^{1G}$, oxo, =N—O—R$^{1H}$, a substituted or unsubstituted non-aromatic carbocycle, or a substituted or unsubstituted non-aromatic heterocycle;
R$^{1F}$ and R$^{1G}$ are each independently a hydrogen atom, substituted or unsubstituted alkyl, substituted or unsubstituted alkyloxy, or substituted or unsubstituted alkyloxycarbonyl;
R$^{1H}$ is a hydrogen atom, substituted or unsubstituted alkyl, substituted or unsubstituted alkenyl, or substituted or unsubstituted alkynyl;
R$^2$ is a hydrogen atom, substituted or unsubstituted alkyl, substituted or unsubstituted alkyloxy, cyano, carboxy, substituted or unsubstituted alkyloxycarbonyl, substituted or unsubstituted carbamoyl, halogen, or hydroxy;
R$^3$ is each independently a hydrogen atom, substituted or unsubstituted alkyl, substituted or unsubstituted alkenyl, substituted or unsubstituted alkynyl, substituted or unsubstituted alkyloxycarbonyl, or substituted or unsubstituted carbamoyl;
R$^4$ is each independently a hydrogen atom, substituted or unsubstituted alkyl, substituted or unsubstituted alkenyl, or substituted or unsubstituted alkynyl, or R$^3$ and R$^4$ may be taken together to form oxo;
R$^5$ and R$^{5A}$ are each independently a hydrogen atom, or substituted or unsubstituted alkyl;
R$^8$ is each independently a hydrogen atom, halogen, hydroxy, substituted or unsubstituted alkyl, substituted or unsubstituted alkenyl, substituted or unsubstituted alkynyl, or substituted or unsubstituted alkyloxy;
R$^9$ is each independently a hydrogen atom, halogen, hydroxy, substituted or unsubstituted alkyl, substituted or unsubstituted alkenyl, substituted or unsubstituted alkynyl, or substituted or unsubstituted alkyloxy, or R$^8$ and R$^9$ may be taken together to form oxo;
R$^{10}$ is substituted or unsubstituted alkyl, substituted or unsubstituted acyl, substituted or unsubstituted alkyloxycarbonyl, substituted or unsubstituted alkyl sulfonyl, nitro, substituted or unsubstituted alkyloxy, or hydroxy;
R$^{11}$ is a hydrogen atom, cyano, substituted or unsubstituted acyl, substituted or unsubstituted alkyloxycarbonyl, substituted or unsubstituted carbamoyl, substituted or unsubstituted alkylsulfonyl, or nitro;
R$^{12}$ is a hydrogen atom or cyano;
R$^{13}$ is a hydrogen atom, substituted or unsubstituted alkyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

R$^{14}$ is a hydrogen atom, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted carbamoyl, substituted or unsubstituted alkyl sulfonyl, substituted or unsubstituted alkenyl sulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

R$^{15}$ is a hydrogen atom, halogen, cyano, substituted or unsubstituted alkyl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted alkyl sulfanyl, substituted or unsubstituted alkenylsulfanyl, substituted or unsubstituted alkynylsulfanyl, substituted or unsubstituted amino, substituted or unsubstituted carbamoyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl, or R$^{14}$ and R$^{15}$ may be taken together to form a substituted or unsubstituted non-aromatic carbocycle or a substituted or unsubstituted non-aromatic heterocycle;

provided that (α) when —W— is —CH$_2$—, —W$^A$— is —CH$_2$—, =X is =O, R$^5$ is a hydrogen atom, R$^{5A}$ is a hydrogen atom, and —A— is —NR$^1$—, at least one of the following (1) and (2) is satisfied:

(1) B is a group represented by the following formula:

[Chemical Formula 2]

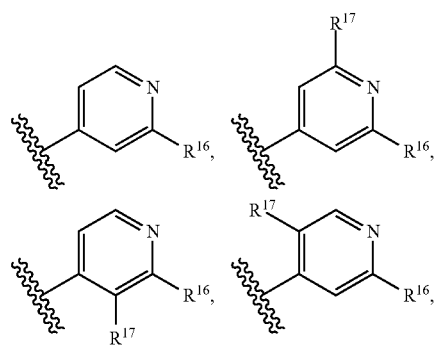

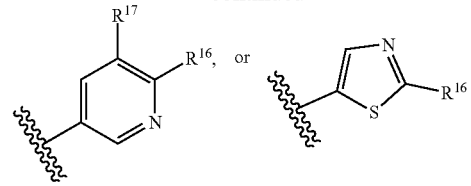

wherein R$^{16}$ and R$^{17}$ are each independently halogen; or (2) R$^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 3]

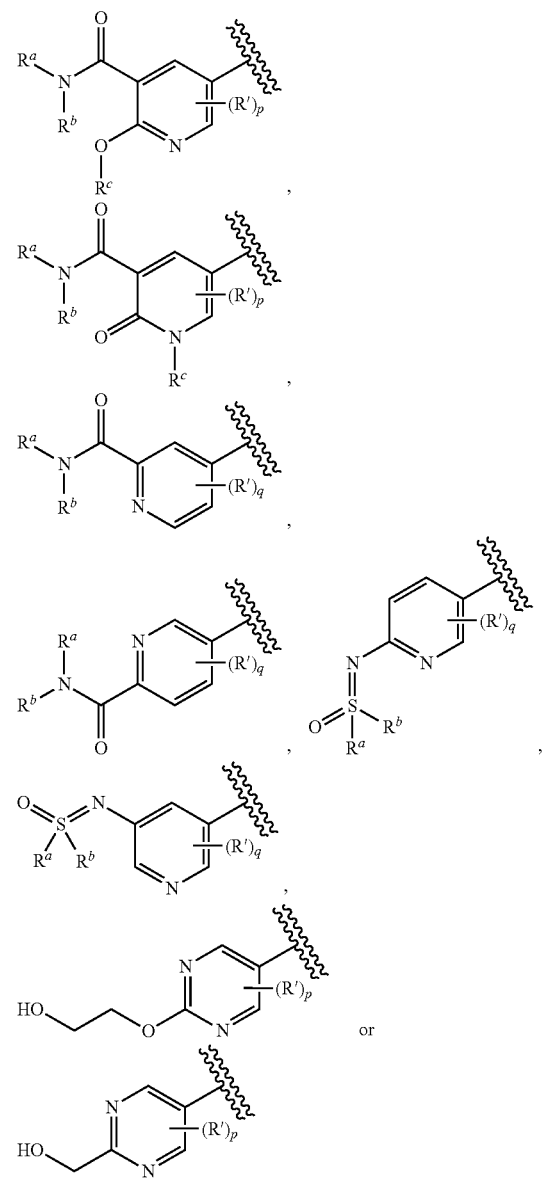

wherein R$^a$ and R$^b$ are each independently a hydrogen atom, cyano, hydroxy, substituted or unsubstituted alkyl, substituted or unsubstituted alkyloxy, substituted or unsubstituted alkyloxycarbonyl, substituted or unsubstituted alkylsulfonyl, substituted or unsubstituted carbamoyl, substituted or unsubstituted non-aromatic carbocyclyl, or substituted or unsubstituted non-aromatic heterocyclyl; $R^c$ is a hydrogen atom, or substituted or unsubstituted alkyl; R' is each independently halogen, cyano, hydroxy, carboxy, substituted or unsubstituted alkyl, substituted or unsubstituted alkyloxy, substituted or unsubstituted carbamoyl, or substituted or unsubstituted sulfamoyl; p is 0, 1 or 2; and q is 0, 1, 2 or 3; and (β) when —$W^A$— is —$CH_2$—$C(R^3R^4)$—, —A— is —NR'—, and n is 0, and (γ) when —$W^A$— is —$CH_2$—, —W— is —$CH_2$—, and —A— is —$CR^{1D}R^{1E}$—, at least one of the following (1) and (2) is satisfied:

(1) B is a group represented by the following formula:

[Chemical Formula 4]

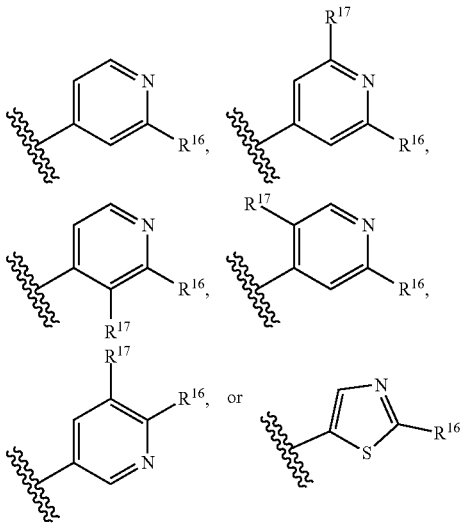

wherein $R^{16}$ and $R^{17}$ are each independently halogen; and (2) $R^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 5]

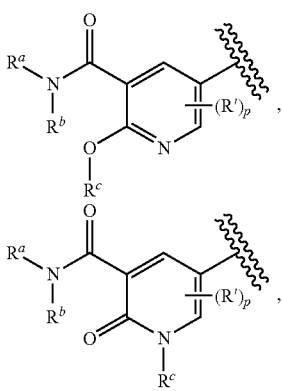

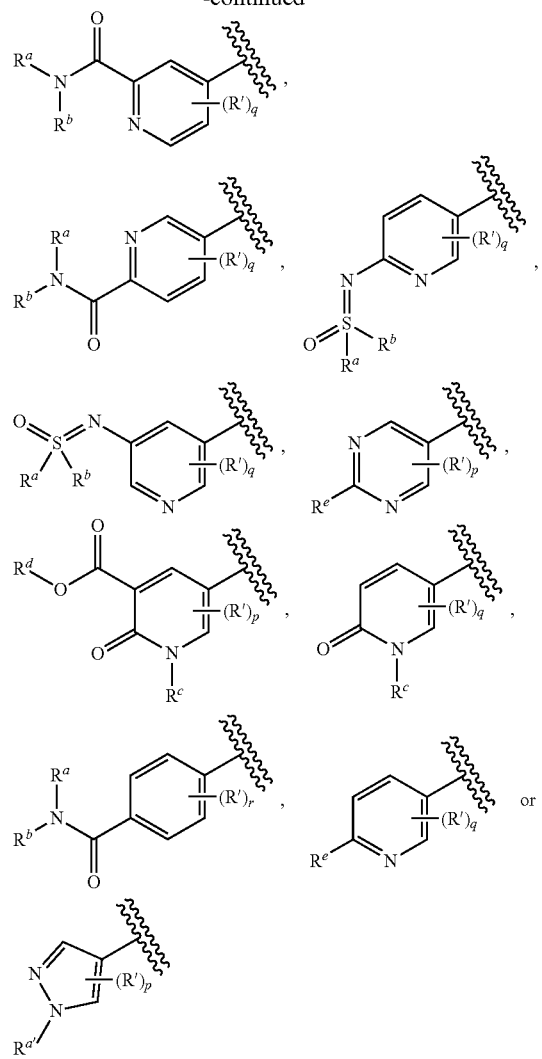

wherein $R^a$ and $R^b$ are each independently a hydrogen atom, cyano, hydroxy, substituted or unsubstituted alkyl, substituted or unsubstituted alkyloxy, substituted or unsubstituted alkyloxycarbonyl, substituted or unsubstituted alkylsulfonyl, substituted or unsubstituted carbamoyl, substituted or unsubstituted non-aromatic carbocyclyl, or substituted or unsubstituted non-aromatic heterocyclyl; $R^{a'}$ is a hydrogen atom, substituted or unsubstituted alkyl (excluding unsubstituted methyl), substituted or unsubstituted non-aromatic carbocyclyl, or substituted or unsubstituted non-aromatic heterocyclyl; $R^c$ is a hydrogen atom, or substituted or unsubstituted alkyl; $R^d$ is a hydrogen atom, or substituted or unsubstituted alkyl; $R^e$ is a hydrogen atom, hydroxy, cyano, halogen, carboxy, substituted or unsubstituted alkyl, substituted or unsubstituted alkyloxy, substituted or unsubstituted amino, substituted or unsubstituted non-aromatic carbocyclyl, or substituted or unsubstituted non-aromatic heterocyclyl; R' is each independently halogen, cyano, hydroxy, carboxy, substituted or unsubstituted alkyl, substituted or unsubstituted alkyloxy, substituted or unsubstituted carbamoyl, or substituted or unsubstituted sulfamoyl; p is 0, 1 or 2; q is 0, 1, 2 or 3; r is 0, 1, 2, 3 or 4, provided that the following compounds are excluded:
[Chemical Formula 6]
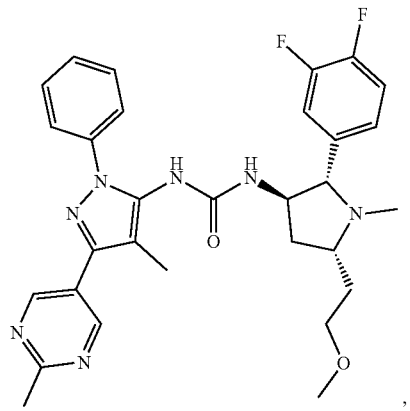
,
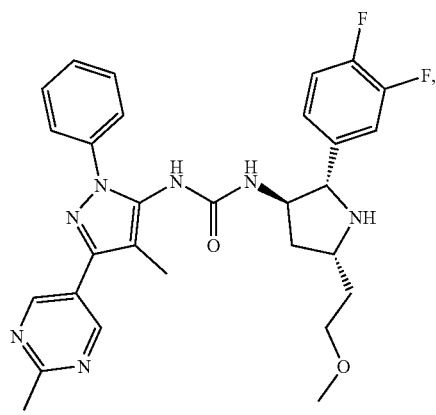
,
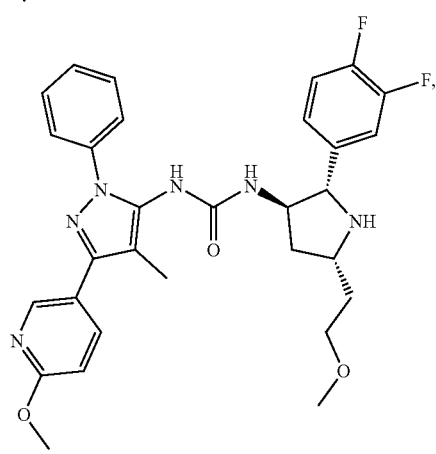
,
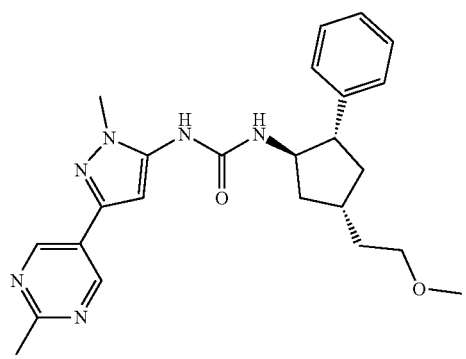
,
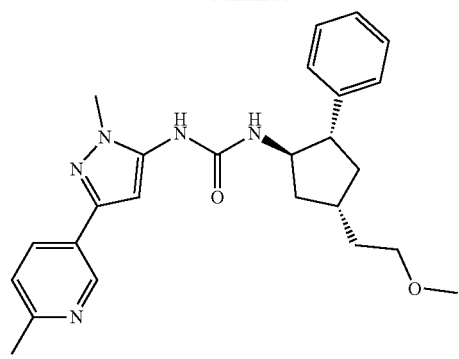
,
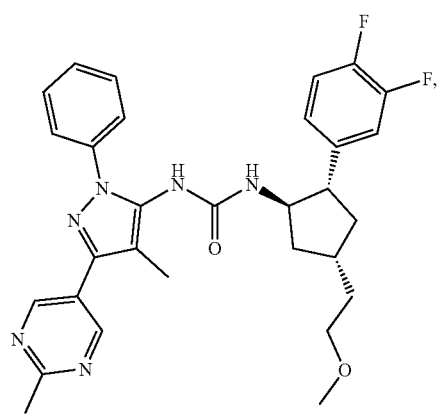
,
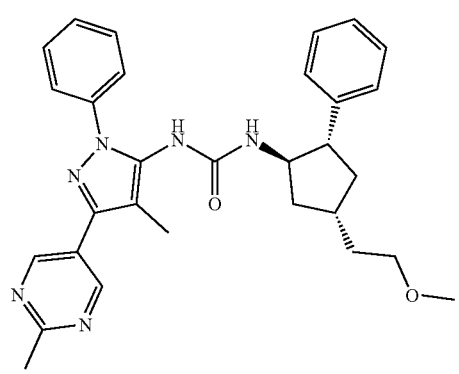
,
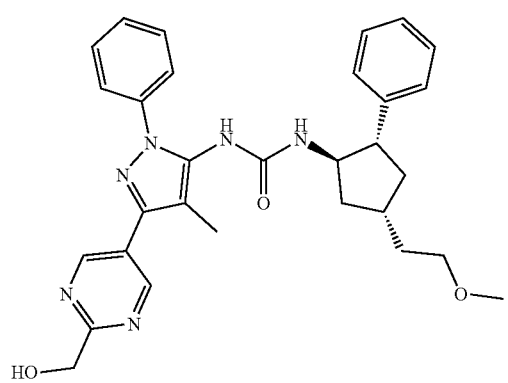
, -continued
[Chemical Formula 7]
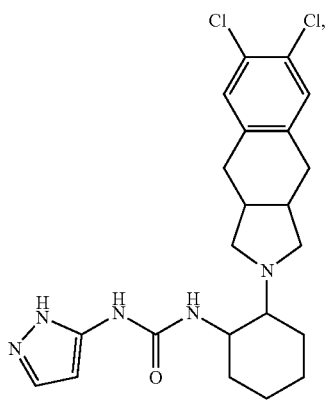
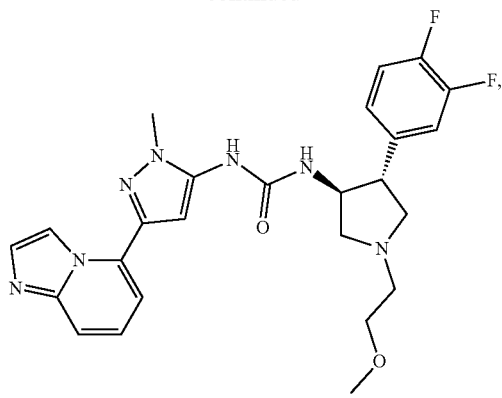
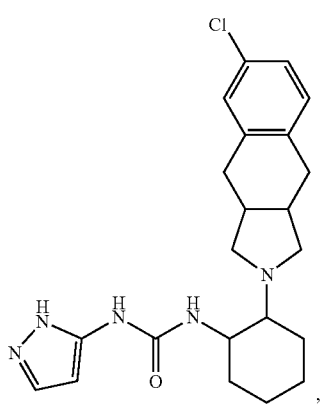
,
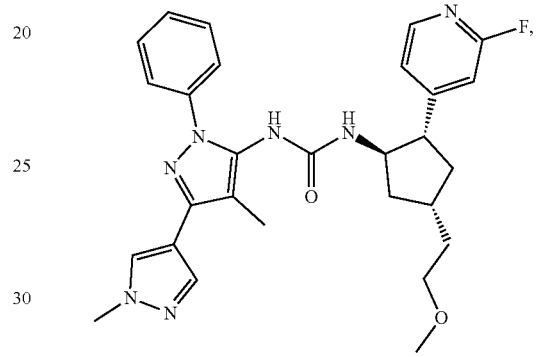
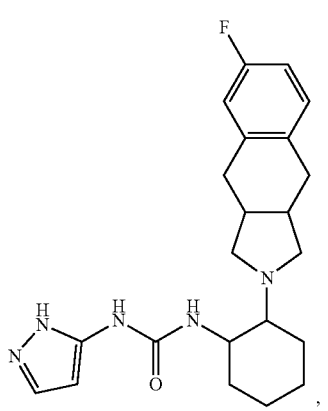
,
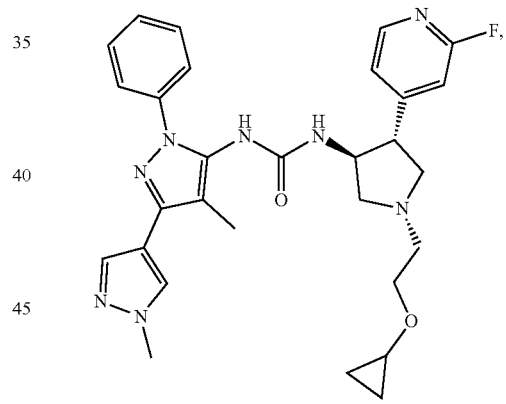
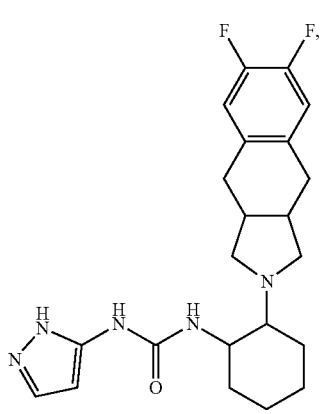
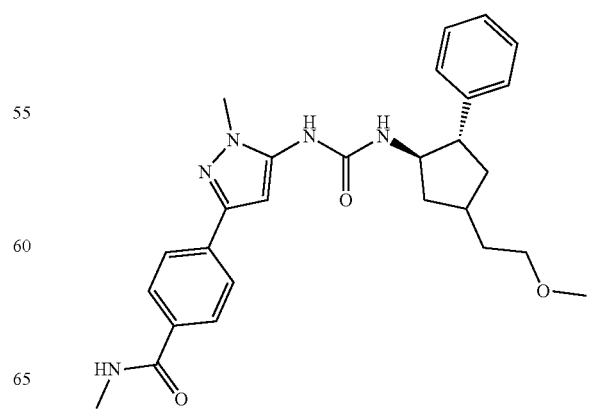
, 13
-continued
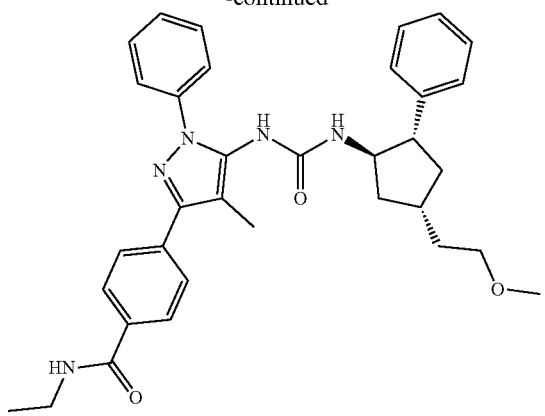
[Chemical Formula 8]
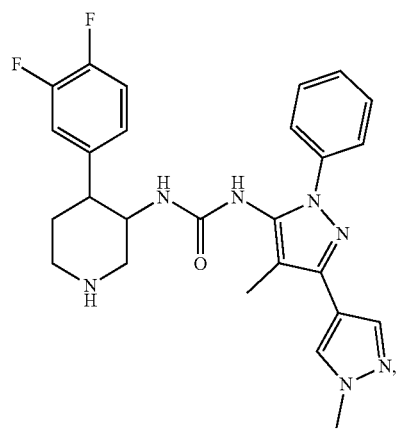
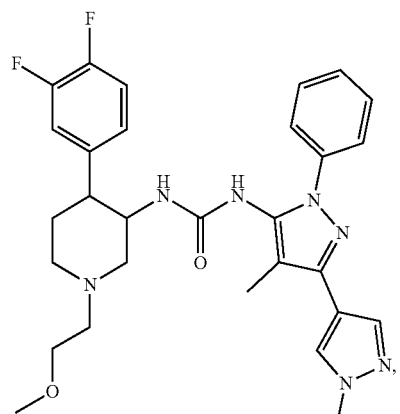
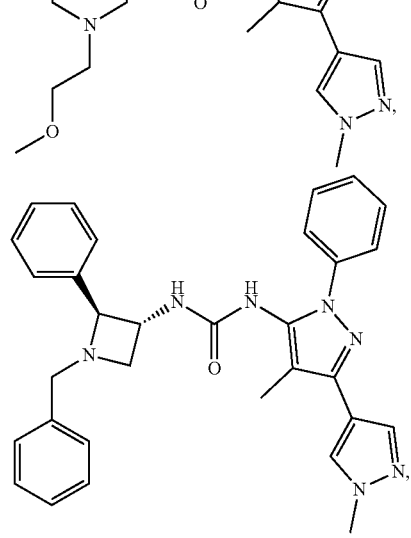
14
-continued
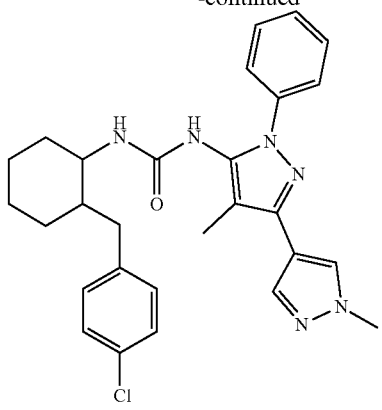
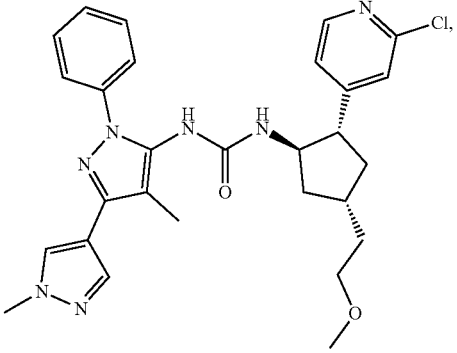
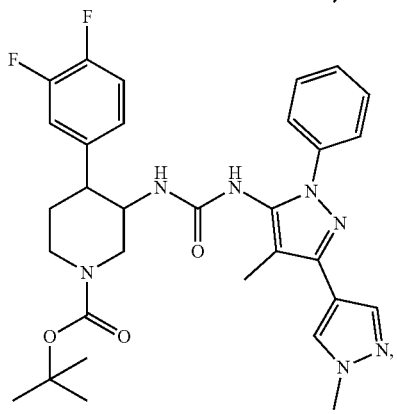
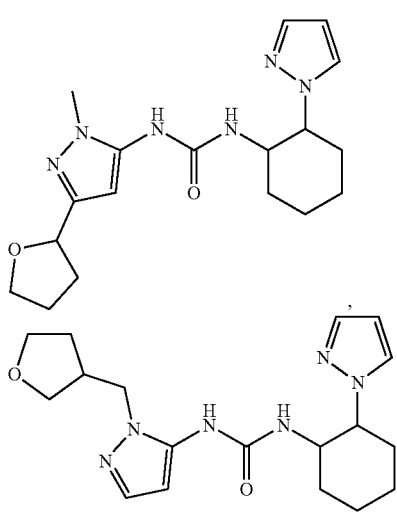
and -continued

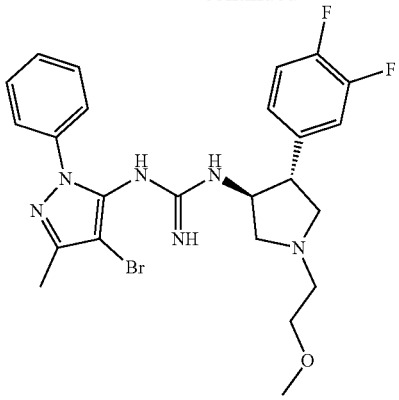 [SMILES: COCCN1C[C@@H](NC(=N)Nc2c(Br)c(C)nn2-c2ccccc2)[C@H](c2ccc(F)c(F)c2)C1]

or a pharmaceutically acceptable salt thereof.

2') The compound according to the above item 1'),
wherein B is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl,
or a pharmaceutically acceptable salt thereof.

3') The compound according to the above item 1') or 2'),
wherein —$W^A$— is —$C(R^3R^4)_2$—, and —A— is —$NR^1$—,
or a pharmaceutically acceptable salt thereof.

4') The compound according to any one of the above items 1') to 3'),
wherein —$W^A$— is —$CH_2$—$C(R^3R^4)$—,
or a pharmaceutically acceptable salt thereof.

5') The compound according to the above item 4'),
wherein $R^3$ is substituted or unsubstituted alkyl, and $R^4$ is a hydrogen atom,
or a pharmaceutically acceptable salt thereof.

6') The compound according to any one of the above items 1') to 5'),
wherein $R^1$ is a hydrogen atom, or substituted or unsubstituted alkyl,
or a pharmaceutically acceptable salt thereof.

7') The compound according to the above item 1') or 2'),
wherein —$W^A$— is —$C(R^3R^4)$—, —W— is —$C(R^8R^9)$—, and —A— is —$CR^{1D}R^{1E}$—,
or a pharmaceutically acceptable salt thereof.

8') The compound according to the above item 7'),
wherein —$W^A$— is —$CH_2$-, —W— is —$CH_2$—, $R^{1D}$ is substituted or unsubstituted alkyl, and $R^{1E}$ is a hydrogen atom,
or a pharmaceutically acceptable salt thereof.

9') The compound according to the above item 1') or 2'),
wherein —$W^A$— is —$C(R^3R^4)$—, —W— is —$C(R^8R^9)$—, and —A— is —$NR^1$—,
or a pharmaceutically acceptable salt thereof.

10') The compound according to the above item 9'),
wherein —$W^A$— is —$CH_2$—, —W— is —$CH_2$—, and $R^1$ is substituted or unsubstituted alkyl,
or a pharmaceutically acceptable salt thereof.

11') The compound according to any one of the above items 1') to 10'),
wherein $R^5$ and $R^{5A}$ are hydrogen atoms, and =X is =O,
or a pharmaceutically acceptable salt thereof.

12') The compound according to any one of the above items 1') to 11'),
wherein $R^2$ is a hydrogen atom,
or a pharmaceutically acceptable salt thereof.

13') The compound according to any one of the above items 1') to 12'),
wherein $R^{13}$ s substituted or unsubstituted aromatic carbocyclyl, substituted or unsubstituted alkyl, or substituted or unsubstituted non-aromatic carbocyclyl,
or a pharmaceutically acceptable salt thereof.

14') The compound according to the above item 2')
wherein R14 is substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 9]

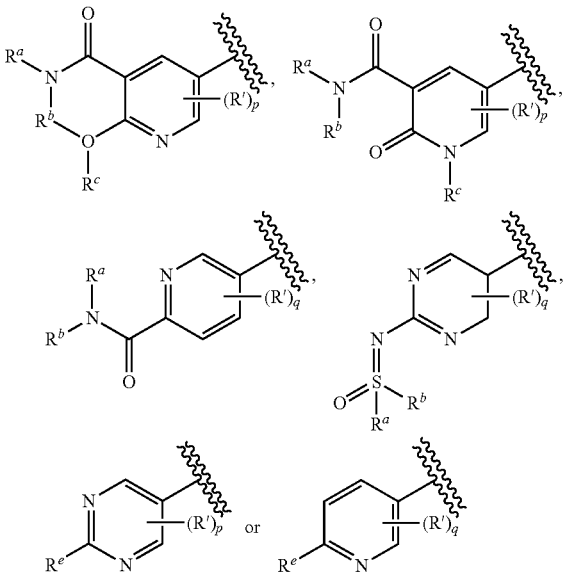

wherein $R^a$, $R^b$, $R^c$, $R^e$, R', p and q are the same as defined in the above item 1'),
or a pharmaceutically acceptable salt thereof.

15') The compound according to any one of the above items 1') to 13'),
wherein $R^{15}$ is a hydrogen atom, or substituted or unsubstituted alkyl,
or a pharmaceutically acceptable salt thereof.

16'A) The compound according to the above item 1') or 2'), represented by Formula (I'):

[Chemical Formula 10]

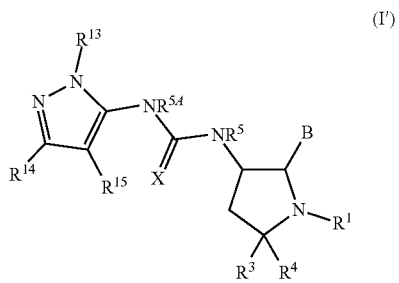

(I')

wherein =X, $R^1$, $R^3$, $R^4$, $R^5$, $R^{5A}$, $R^{13}$ and $R^{15}$ are the same as defined in the above item 1');

B is a group represented by the following formula:

[Chemical Formula 11]

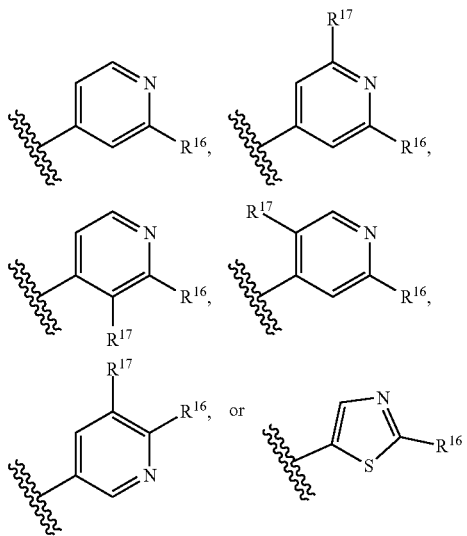

wherein $R^{16}$ and $R^{17}$ are the same as defined in the above item 1');

$R^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 12]

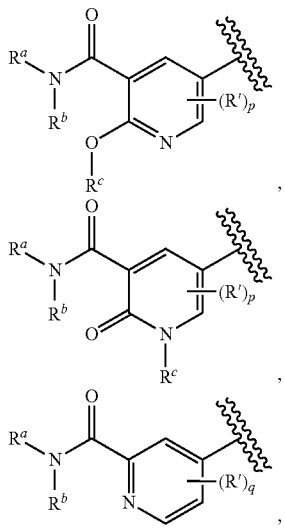

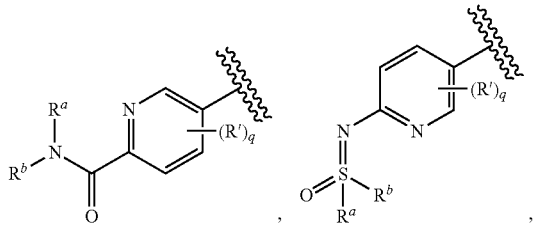

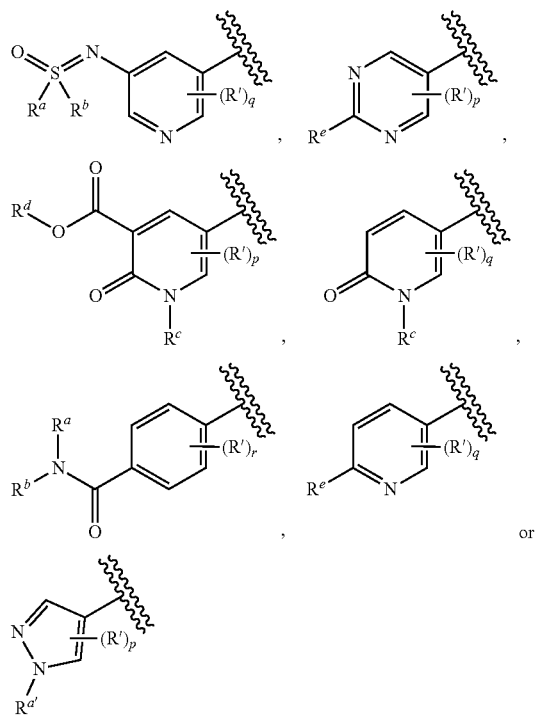

wherein $R^a$, $R^{a\prime}$, $R^b$, $R^c$, $R^d$, $R^e$, R', p, q, and r are the same as defined in the above item 1'), or a pharmaceutically acceptable salt thereof:

16') The compound according to the above item 1') or 2'), represented by Formula (I'):

[Chemical Formula 13]

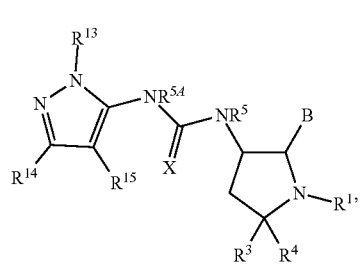

wherein =X, $R^1$, $R^3$, $R^4$, $R^5$, $R^{5A}$, $R^{13}$ and $R^{15}$ are the same as defined in the above item 1');

B is a group represented by the following formula:

[Chemical Formula 14]

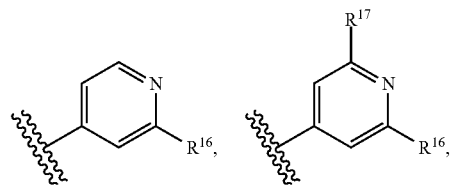

-continued

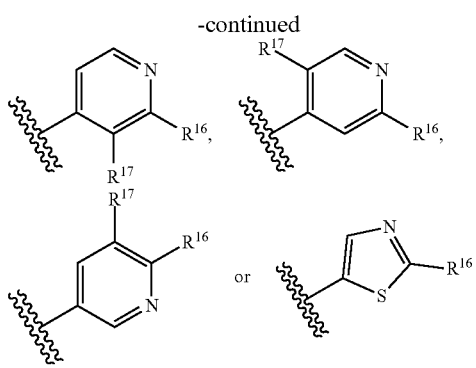

wherein R$^{16}$ and R$^{17}$ are the same as defined in the above item 1');
R$^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 15]

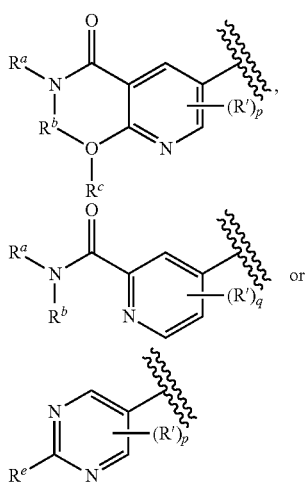

wherein R$^a$, R$^b$, R$^c$, R$^d$, R$^e$, R', p and q are the same as defined in the above item 1'),
or a pharmaceutically acceptable salt thereof.

17') The compound according to the above item 1') or 2'), represented by Formula (I'):

[Chemical Formula 16]

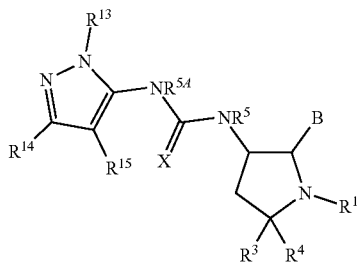

(I')

wherein =X, R$^1$, R$^3$, R$^4$, R$^5$, R$^{5A}$, R$^{13}$ and R$^{15}$ are the same as defined in the above item 1');

B is a group represented by the following formula:

[Chemical Formula 17]

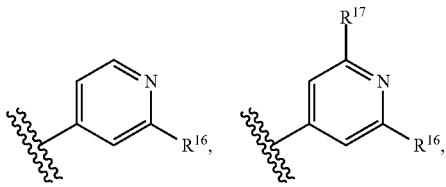

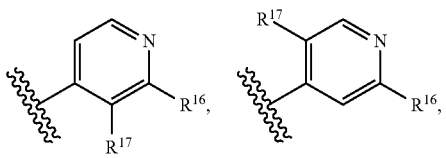

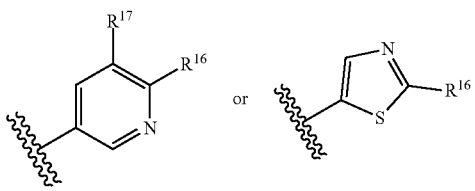

wherein R$^{16}$ and R$^{17}$ are the same as defined in the above item 1');
R$^{14}$ is a hydrogen atom, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted carbamoyl, substituted or unsubstituted alkyl sulfonyl, substituted or unsubstituted alkenyl sulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl,
or a pharmaceutically acceptable salt thereof.

18'A) The compound according to the above item 1') or 2'), represented by Formula (I''):

[Chemical Formula 18]

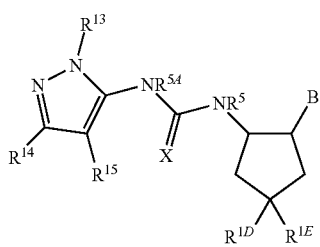

(I″)

wherein =X, $R^{1D}$, $R^{1E}$, $R^5$, $R^{5A}$, $R^{13}$ and $R^{15}$ are the same as defined in the above item 1');
B is a group represented by the following formula:

[Chemical Formula 19]

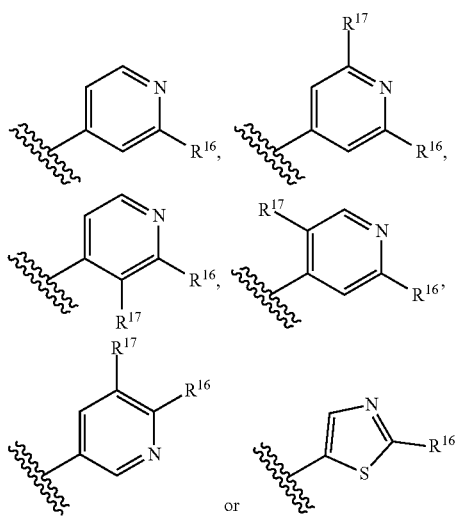

wherein $R^{16}$ and $R^{17}$ are the same as defined in the above item 1');
$R^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 20]

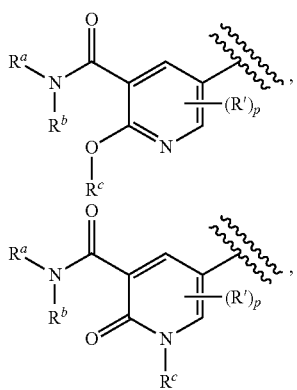

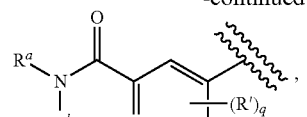

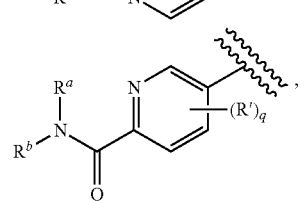

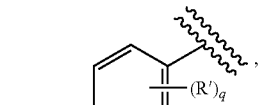

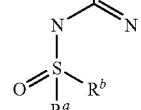

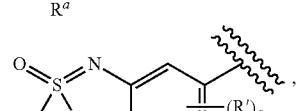

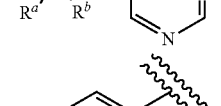

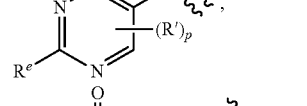

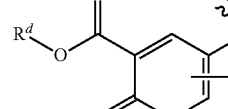

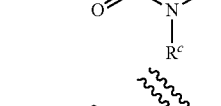

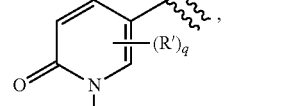

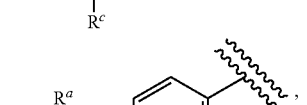

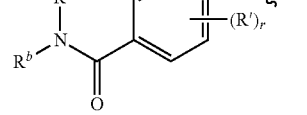

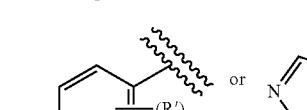

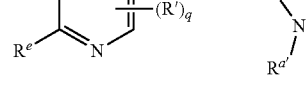

wherein $R^a$, $R^{a\prime}$, $R^b$, $R^c$, $R^d$, $R^e$, R', p, q, and r are the same as defined in the above item 1'), or a pharmaceutically acceptable salt thereof.

18') The compound according to the above item 1') or 2'), represented by Formula (I″):

[Chemical Formula 21]

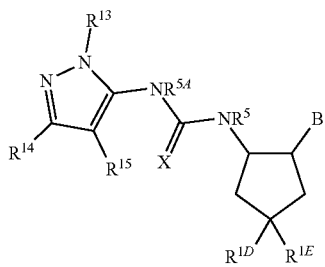
(I″)

wherein =X, $R^{1D}$, $R^{1E}$, $R^5$, $R^{5A}$, $R^{13}$ and $R^{15}$ are the same as defined in the above item 1');

B is a group represented by the following formula:

[Chemical Formula 22]

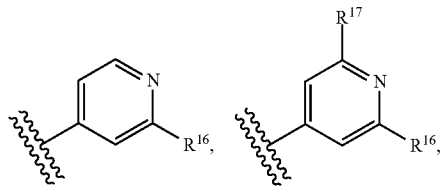

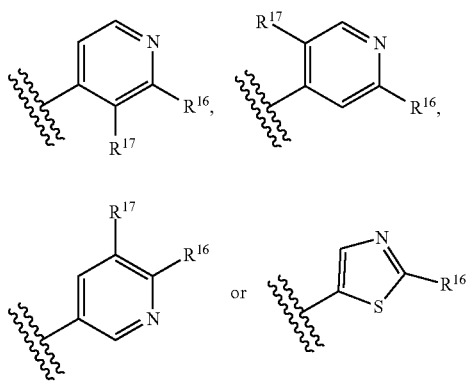

wherein $R^{16}$ and $R^{17}$ are the same as defined in the above item 1');

$R^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 23]

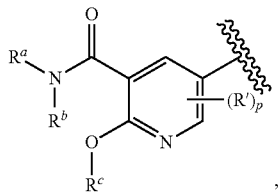

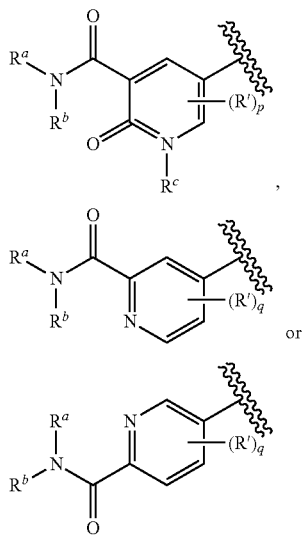

wherein $R^a$, $R^b$, $R^c$, p and q are the same as defined in the above item 1'), or a pharmaceutically acceptable salt thereof.

19') The compound according to the above item 1') or 2'), represented by Formula (I″):

[Chemical Formula 24]

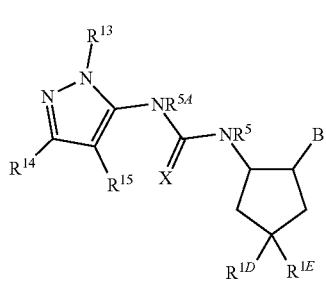
(I″)

wherein =X, $R^{1D}$, $R^{1E}$, $R^5$, $R^{5A}$, $R^{13}$ and $R^{15}$ are the same as defined in the above item 1');

B is a group represented by the following formula:

[Chemical Formula 25]

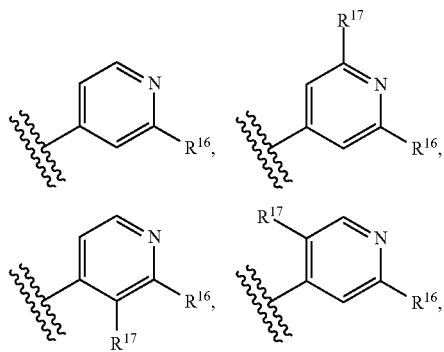

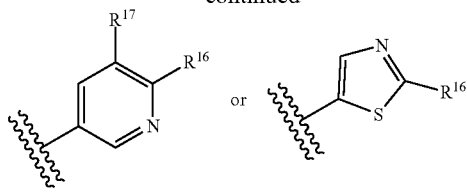

wherein $R^{16}$ and $R^{17}$ are the same as defined in the above item 1');

$R^{14}$ is a hydrogen atom, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted carbamoyl, substituted or unsubstituted alkyl sulfonyl, substituted or unsubstituted alkenyl sulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl, or a pharmaceutically acceptable salt thereof.

20'A) The compound according to the above item 1') or 2'), represented by Formula (I'''):

[Chemical Formula 26]

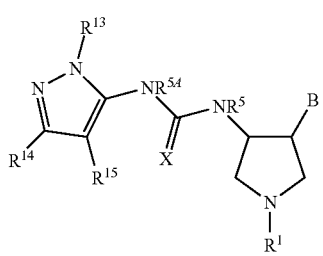

wherein =X, $R^1$, $R^5$, $R^{54}$, $R^{13}$ and $R^{15}$ are the same as defined in the above item 1');

B is a group represented by the following formula:

[Chemical Formula 27]

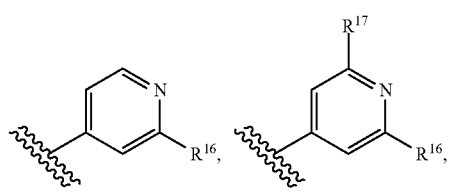

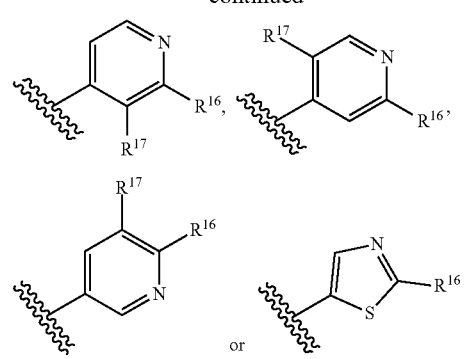

wherein $R^{16}$ and $R^{17}$ are the same as defined in the above item 1');

$R^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 28]

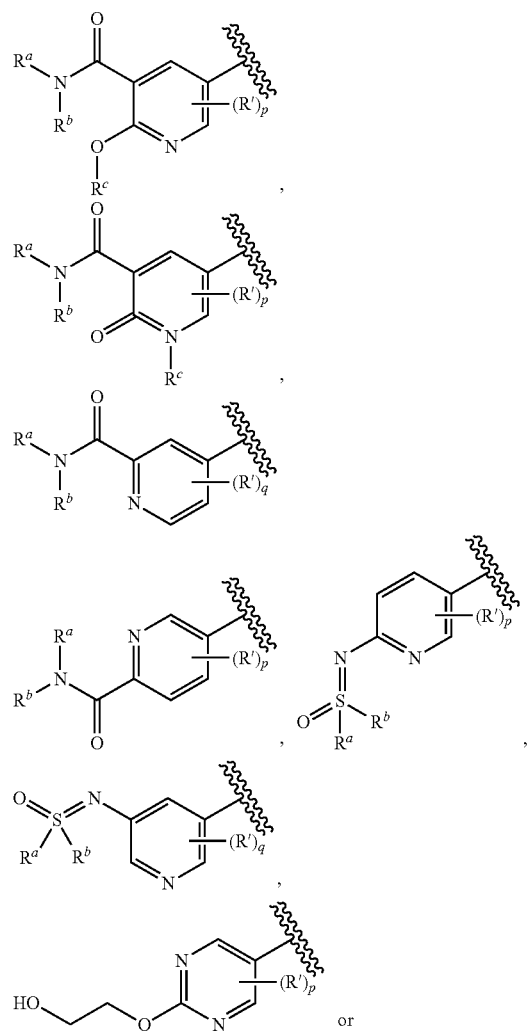

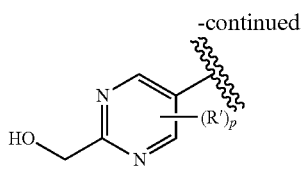

wherein $R^a$, $R^b$, $R^c$, R', p and q are the same as defined in the above item 1'),
or a pharmaceutically acceptable salt thereof.

20') The compound according to the above item 1') or 2'), represented by Formula (I'''):

[Chemical Formula 29]

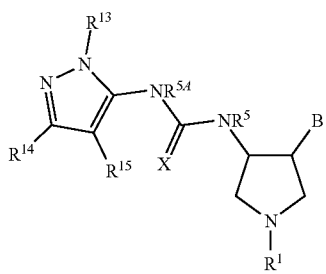

(I''')

wherein =X, $R^1$, $R^5$, $R^{5A}$, $R^{13}$ and $R^{15}$ are the same as defined in the above item 1');
B is a group represented by the following formula:

[Chemical Formula 30]

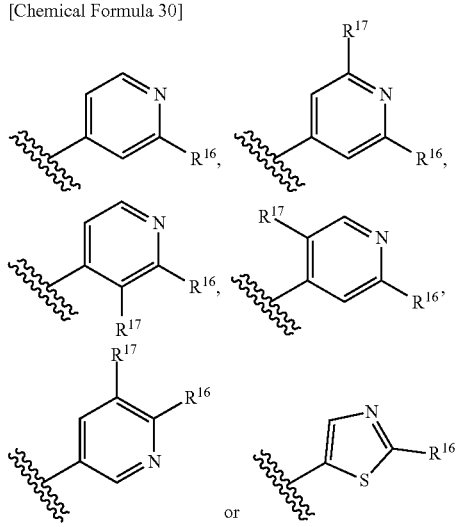

or wherein $R^{16}$ and $R^{17}$ are the same as defined in the above item 1');

$R^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 31]

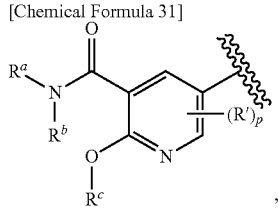

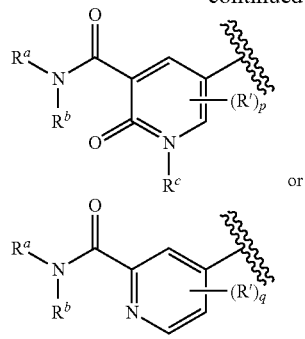

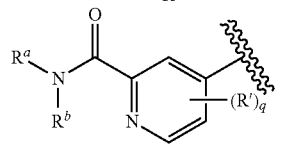

or wherein $R^a$, $R^b$, $R^c$, R', p and q are the same as defined in the above item 1'), or a pharmaceutically acceptable salt thereof.

21') The compound according to the above item 1') or 2'), represented by Formula (I'''):

[Chemical Formula 32]

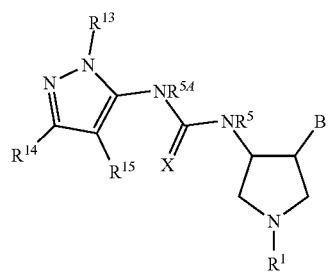

(I''')

wherein =X, $R^1$, $R^5$, $R^{5A}$, $R^{13}$ and $R^{15}$ are the same as defined in the above item 1');
B is a group represented by the following formula:

[Chemical Formula 33]

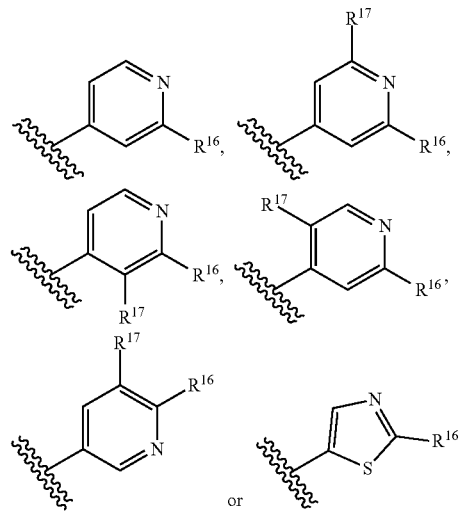

or wherein $R^{16}$ and $R^{17}$ are the same as defined in the above item 1');

$R^{114}$ is a hydrogen atom, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted carbamoyl, substituted or unsubstituted alkyl sulfonyl, substituted or unsubstituted alkenyl sulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl,
or a pharmaceutically acceptable salt thereof.

22') The compound according to the above item 1'), selected from the group consisting of Compounds I-5, I-10, I-20, I-52, I-66, I-67, I-68, I-92, I-93, I-117, I-145, I-159, I-164, I-166 and I-173,
or a pharmaceutically acceptable salt thereof.

22'A) The compound according to the above item 1'), selected from the group consisting of compounds I-5, I-10, I-20, I-52, I-66, I-67, I-68, I-92, I-93, I-117, I-145 and I-159,
or a pharmaceutically acceptable salt thereof.

22'B) The compound according to the above item 1'), selected from the group consisting of Compounds I-164, I-166 and I-173,
or a pharmaceutically acceptable salt thereof.

23') A pharmaceutical composition, comprising the compound according to any one of the above items 1') to 22'), 16'A), 18'A), 20'A), 22'A) and 22'B), or a pharmaceutically acceptable salt thereof.

24') The pharmaceutical composition according to the above item 23'), having TrkA inhibitory activity.

25') A method for treating or preventing a disease related to TrkA, comprising administering the compound according to any one of the above items 1') to 22'), 16'A), 18'A), 20'A), 22'A) and 22'B), or a pharmaceutically acceptable salt thereof.

26') The compound according to any one of the above items 1') to 22'), 16'A), 18'A), 20'A), 22'A) and 22'B), or a pharmaceutically acceptable salt thereof, for use in treating or preventing a disease related to TrkA.

27') Use of the compound according to any one of the above items 1') to 22'), 16'A), 18'A), 20'A), 22'A) and 22'B), or a pharmaceutically acceptable salt thereof, for the manufacture of a medicament for treating or preventing a disease related to TrkA.

101') A pharmaceutical composition for oral administration, comprising the compound according to any one of the above items 1') to 22'), 16'A), 18'A), 20'A), 22'A) and 22'B), or a pharmaceutically acceptable salt thereof.

102') The pharmaceutical composition according to the above item 101'), which is in the form of a tablet, a powder, a granule, a capsule, a pill, a film, a suspension, an emulsion, an elixir, a syrup, a lemonade, a spirit, an aromatic water, an extract, a decoction or a tincture.

103') The pharmaceutical composition according to the above item 102'), which is in the form of a sugar-coated tablet, a film-coated tablet, an enteric-coated tablet, a sustained-release tablet, a troche tablet, a sublingual tablet, a buccal tablet, a chewable tablet, an orally disintegrating tablet, a dry syrup, a soft capsule, a micro capsule or a sustained-release capsule.

104') A pharmaceutical composition for parenteral administration, comprising the compound according to any one of the above items 1') to 22'), 16'A), 18'A), 20'A), 22'A) and 22'B), or a pharmaceutically acceptable salt thereof.

105') The pharmaceutical composition according to the above item 104'), for dermal, subcutaneous, intravenous, intraarterial, intramuscular, intraperitoneal, transmucosal, inhalation, transnasal, ophthalmic, inner ear or vaginal administration.

106') The pharmaceutical composition according to the above item 104') or 105'), which is in the form of an injection, an infusion, an eye drop, a nose drop, an ear drop, an aerosol, an inhalant, a lotion, an impregnation, a liniment, a mouthwash, an enema, an ointment, a plaster, a jelly, a cream, a patch, a cataplasm, an external powder or a suppository.

107') A pharmaceutical composition for a pediatric or geriatric patient, comprising the compound according to any one of the above items 1') to 22'), 16'A), 18'A), 20'A), 22'A) and 22'B), or a pharmaceutically acceptable salt thereof.

Besides, the present invention relates to the following items 1) to 23), 16A) to 18A) and 101) to 107):

1) A compound represented by Formula (I):

[Chemical Formula 34]

(I)

wherein =X is =O, =S, =NR$^{10}$ or =CR$^{11}$R$^{12}$;
—W— is —C(R$^8$R$^9$)n—;
—W$^A$— is —C(R$^3$R$^4$)m—;
n is 0, 1 or 2;
m is 1 or 2;
n is 0, 1 or 2 when m is 1, and n is 0 when m is 2;
—A— is —NR$^1$— or —CR$^{1D}$R$^{1E}$—;
B is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkyl, or substituted or unsubstituted alkyloxy;
R$^1$ is a hydrogen atom, cyano, substituted or unsubstituted alkyl, substituted or unsubstituted alkenyl, substituted or unsubstituted acyl, substituted or unsubstituted alkyl sulfonyl, substituted or unsubstituted alkenyl sulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{1D}$ and $R^{1E}$ are each independently a hydrogen atom, hydroxy, halogen, carboxy, substituted or unsubstituted alkyl, substituted or unsubstituted alkenyl, substituted or unsubstituted acyl, substituted or unsubstituted alkyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted amino, substituted or unsubstituted alkyl sulfonyl, substituted or unsubstituted alkenyl sulfonyl, substituted or unsubstituted alkylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsufonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

or $R^{1D}$ and $R^{1E}$ may be taken together to form =$CR^{1F}R^{1G}$, oxo, =N—O—$R^{1H}$, a substituted or unsubstituted non-aromatic carbocycle, or a substituted or unsubstituted non-aromatic heterocycle;

$R^{1F}$ and $R^{1G}$ are each independently a hydrogen atom, substituted or unsubstituted alkyl, substituted or unsubstituted alkyloxy, or substituted or unsubstituted alkyloxycarbonyl;

$R^{1H}$ is a hydrogen atom, substituted or unsubstituted alkyl, substituted or unsubstituted alkenyl, or substituted or unsubstituted alkynyl;

$R^2$ is a hydrogen atom, substituted or unsubstituted alkyl, substituted or unsubstituted alkyloxy, cyano, carboxy, substituted or unsubstituted alkyloxycarbonyl, substituted or unsubstituted carbamoyl, halogen, or hydroxy;

$R^3$ is each independently a hydrogen atom, substituted or unsubstituted alkyl, substituted or unsubstituted alkenyl, substituted or unsubstituted alkynyl, substituted or unsubstituted alkyloxycarbonyl, or substituted or unsubstituted carbamoyl;

$R^4$ is each independently a hydrogen atom, substituted or unsubstituted alkyl, substituted or unsubstituted alkenyl, or substituted or unsubstituted alkynyl, or $R^3$ and $R^4$ may be taken together to form oxo;

$R^5$ and $R^{5A}$ are each independently a hydrogen atom, or substituted or unsubstituted alkyl;

$R^8$ is each independently a hydrogen atom, halogen, hydroxy, substituted or unsubstituted alkyl, substituted or unsubstituted alkenyl, substituted or unsubstituted alkynyl, or substituted or unsubstituted alkyloxy;

$R^9$ is each independently a hydrogen atom, halogen, hydroxy, substituted or unsubstituted alkyl, substituted or unsubstituted alkenyl, substituted or unsubstituted alkynyl, or substituted or unsubstituted alkyloxy, or R8 and R9 may be taken together to form oxo;

$R^{10}$ is substituted or unsubstituted alkyl, substituted or unsubstituted acyl, substituted or unsubstituted alkyloxycarbonyl, substituted or unsubstituted alkylsulfonyl, nitro, substituted or unsubstituted alkyloxy, or hydroxy;

$R^{11}$ is a hydrogen atom, cyano, substituted or unsubstituted acyl, substituted or unsubstituted alkyloxycarbonyl, substituted or unsubstituted carbamoyl, substituted or unsubstituted alkylsulfonyl, or nitro;

$R^{12}$ is a hydrogen atom, or cyano;

$R^{13}$ is a hydrogen atom, substituted or unsubstituted alkyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

$R^{14}$ is a hydrogen atom, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted carbamoyl, substituted or unsubstituted alkyl sulfonyl, substituted or unsubstituted alkenyl sulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

$R^{15}$ is a hydrogen atom, halogen, cyano, substituted or unsubstituted alkyl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

provided that (α) when —W— is —$CH_2$—, —$W^4$— is —$CH_2$—, =X is =O, $R_5$ is a hydrogen atom, R5A is a hydrogen atom, and —A— is —$NR^1$—, (1) B is a group represented by the following formula:

[Chemical Formula 35]

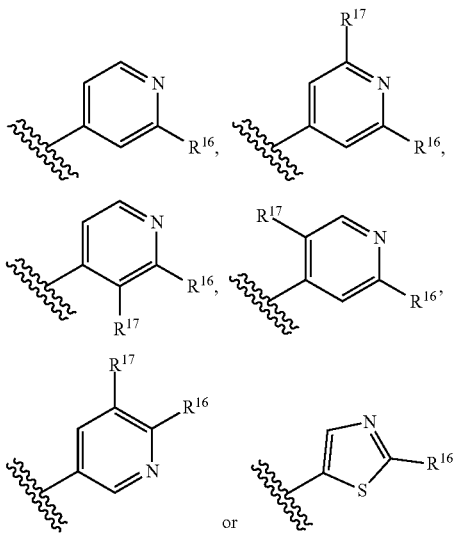

or wherein $R^{16}$ and $R^{17}$ are each independently halogen; or (2) $R^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 36]

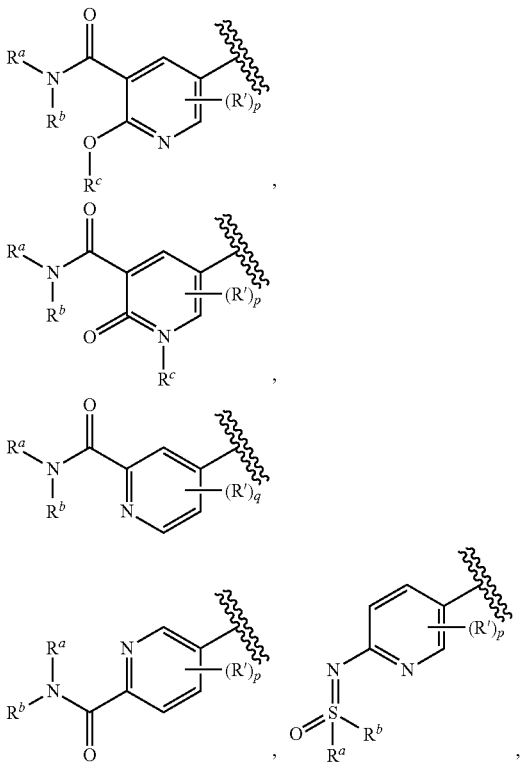

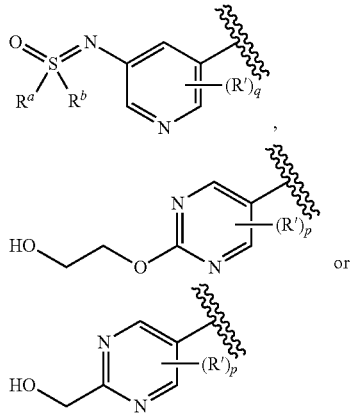

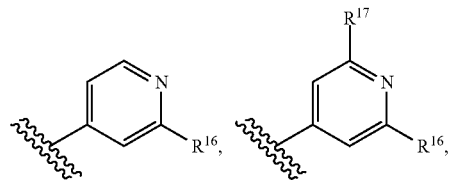

or

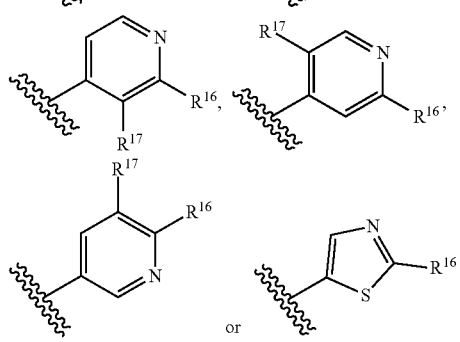

wherein $R^a$ and $R^b$ are each independently a hydrogen atom, cyano, hydroxy, substituted or unsubstituted alkyl, substituted or unsubstituted alkyloxy, substituted or unsubstituted alkyloxycarbonyl, substituted or unsubstituted alkylsulfonyl, substituted or unsubstituted carbamoyl, substituted or unsubstituted non-aromatic carbocyclyl, or substituted or unsubstituted non-aromatic heterocyclyl; $R^c$ is a hydrogen atom, or substituted or unsubstituted alkyl; R' is each independently halogen, cyano, hydroxy, carboxy, substituted or unsubstituted alkyl, substituted or unsubstituted alkyloxy, substituted or unsubstituted carbamoyl, or substituted or unsubstituted sulfamoyl; p is 0, 1 or 2; and q is 0, 1, 2 or 3; and (β) when —$W^A$— is —$CH_2$—$C(R^3R^4)$—, and —A— is —$NR^1$—, and (γ) when —$W^A$— is —$CH_2$—, —W— is —$CH_2$—, and —A— is —$CR^{1D}R^{1E}$, (1) B is a group represented by the following formula:

[Chemical Formula 37]

wherein $R^{16}$ and $R^{17}$ are each independently halogen; or (2) $R^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 38]

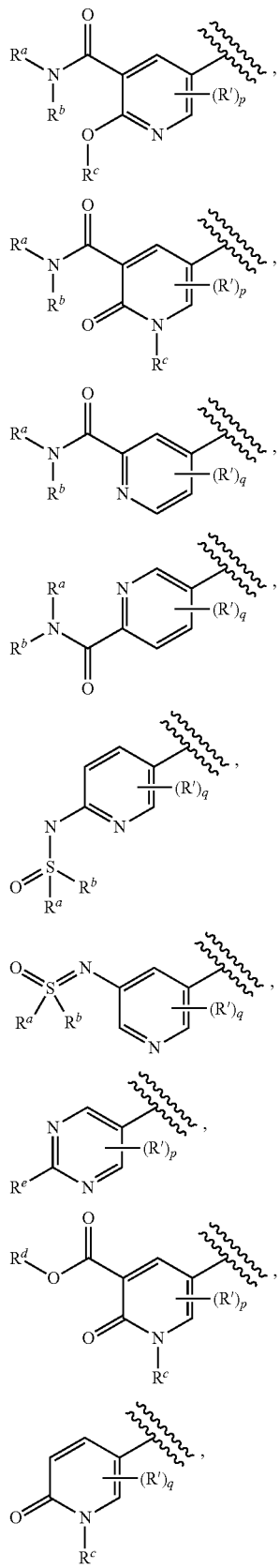

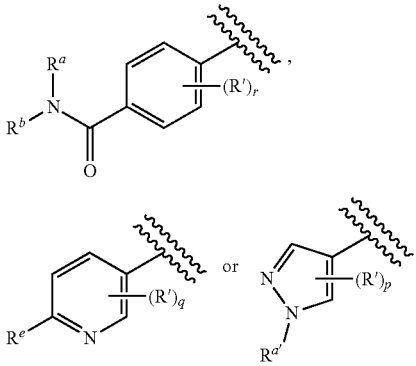

wherein $R^a$ and $R^b$ are each independently a hydrogen atom, cyano, hydroxy, substituted or unsubstituted alkyl, substituted or unsubstituted alkyloxy, substituted or unsubstituted alkyloxycarbonyl, substituted or unsubstituted alkylsulfonyl, substituted or unsubstituted carbamoyl, substituted or unsubstituted non-aromatic carbocyclyl, or substituted or unsubstituted non-aromatic heterocyclyl; $R^{a'}$ is a hydrogen atom, substituted or unsubstituted alkyl (excluding unsubstituted methyl), substituted or unsubstituted non-aromatic carbocyclyl, or substituted or unsubstituted non-aromatic heterocyclyl; $R^c$ is a hydrogen atom, or substituted or unsubstituted alkyl; $R^d$ is a hydrogen atom, or substituted or unsubstituted alkyl; $R^e$ is a hydrogen atom, hydroxy, cyano, halogen, carboxy, substituted or unsubstituted alkyl, substituted or unsubstituted alkyloxy, substituted or unsubstituted amino, substituted or unsubstituted non-aromatic carbocyclyl, or substituted or unsubstituted non-aromatic heterocyclyl; R' is each independently halogen, cyano, hydroxy, carboxy, substituted or unsubstituted alkyl, substituted or unsubstituted alkyloxy, substituted or unsubstituted carbamoyl, or substituted or unsubstituted sulfamoyl; p is 0, 1 or 2; q is 0, 1, 2 or 3; r is 0, 1, 2, 3 or 4, provided that the following compounds are excluded:

[Chemical Formula 39]

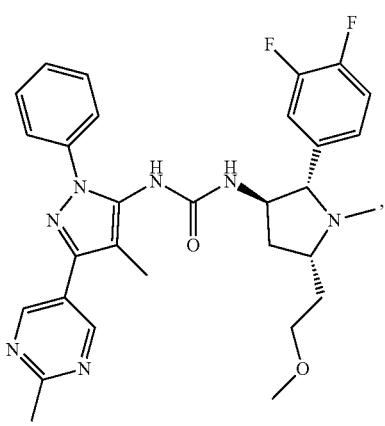

37
-continued
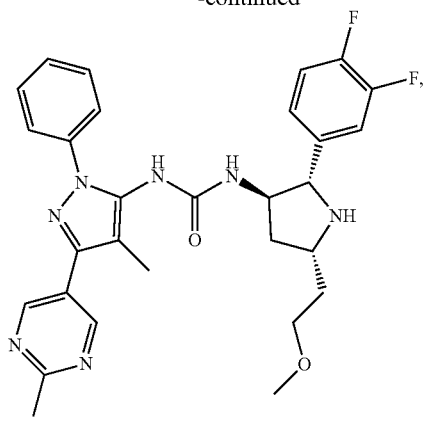
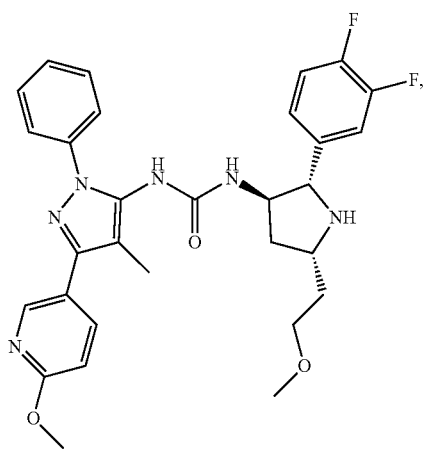
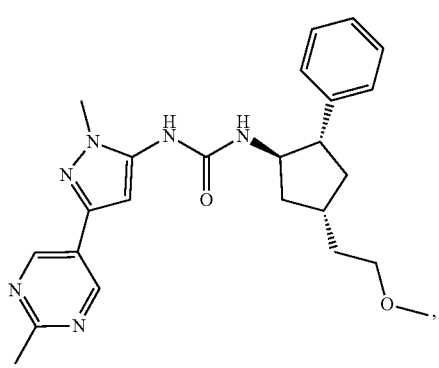
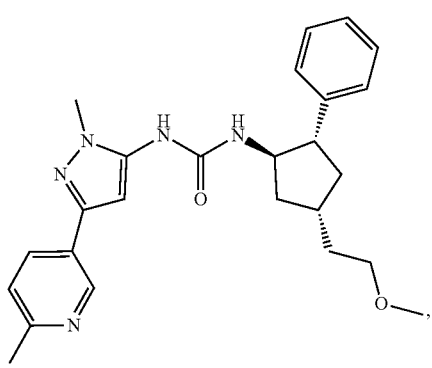
38
-continued
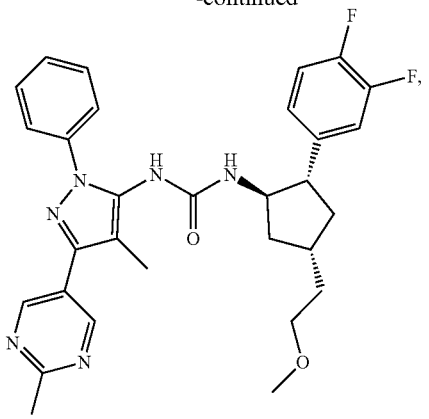
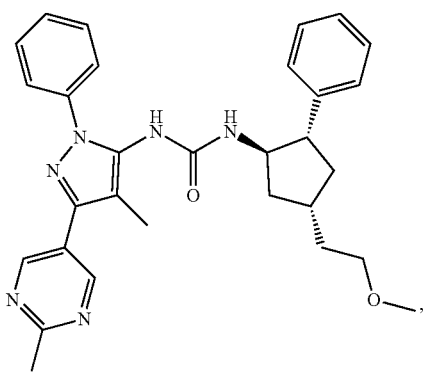
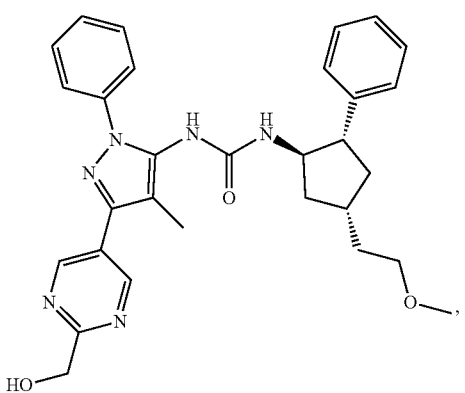
[Chemical Formula 40]
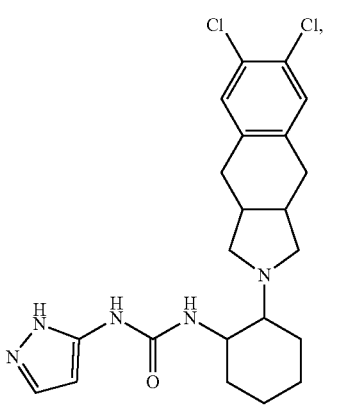

-continued
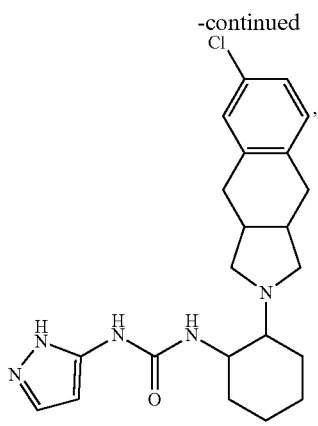
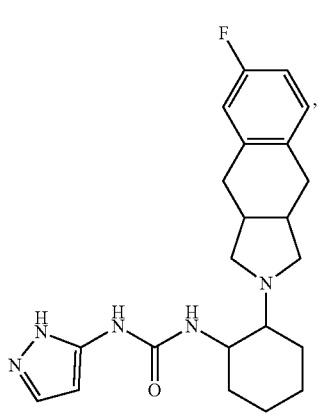
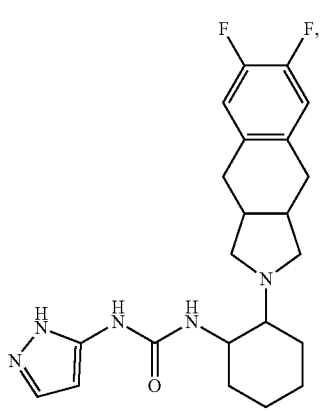
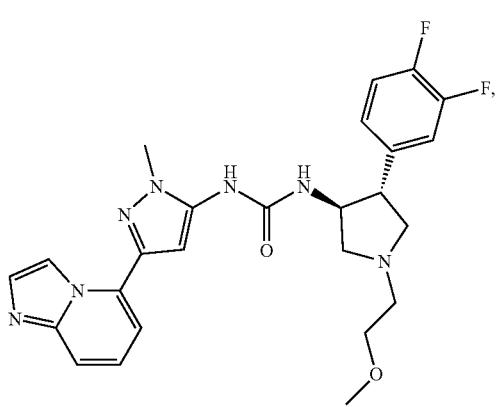
-continued
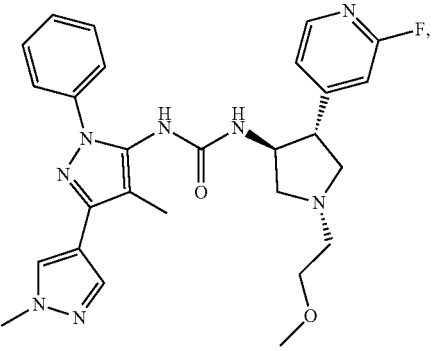
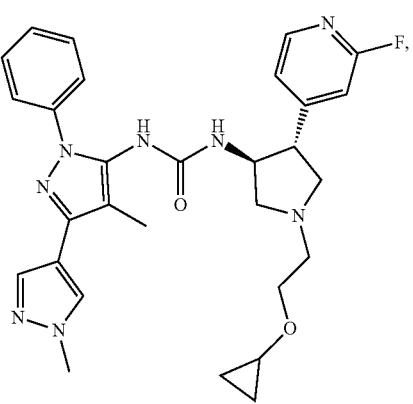
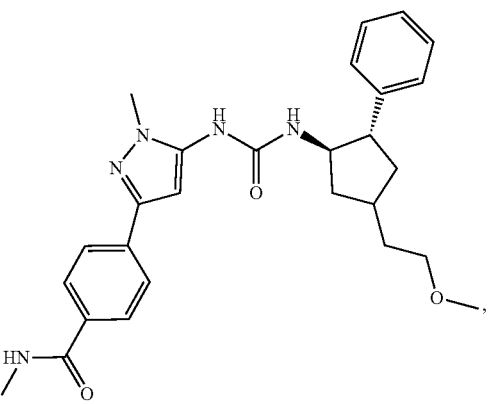
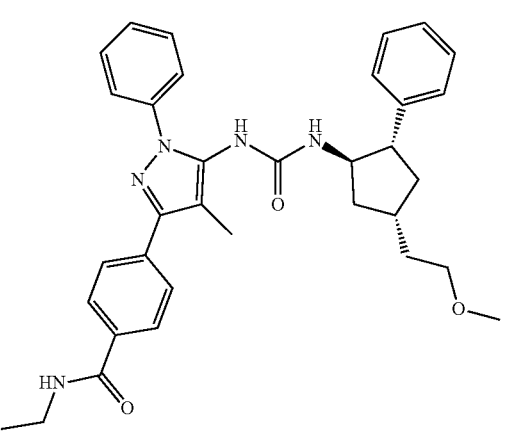

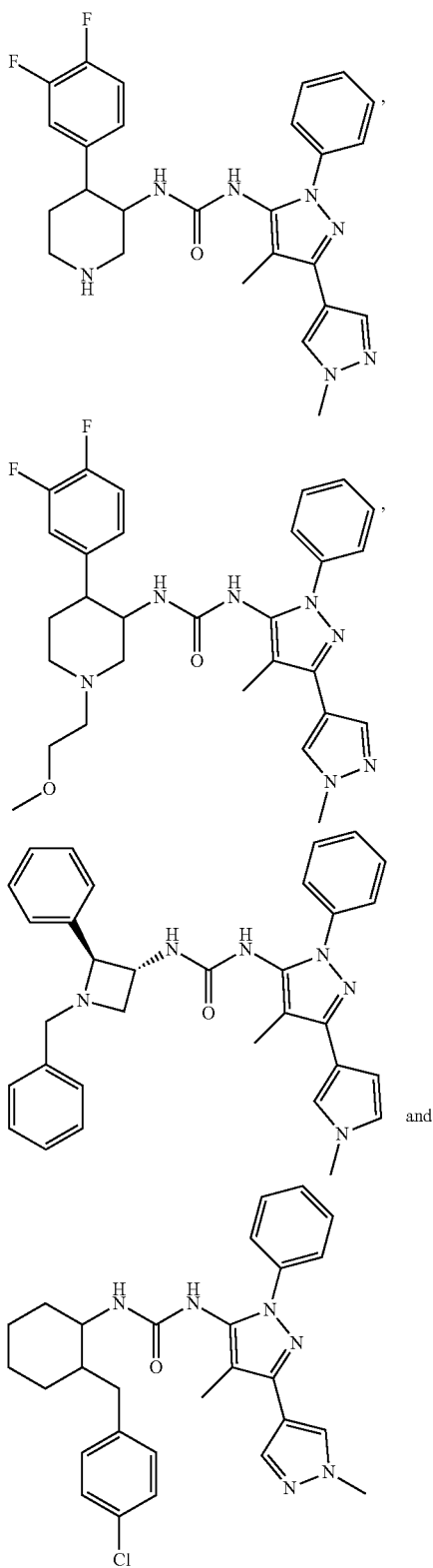

or a pharmaceutically acceptable salt thereof.

2) The compound according to the above item 1), wherein B is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or a pharmaceutically acceptable salt thereof.

3) The compound according to the above item 1) or 2), wherein —$W^A$— is —$C(R^3R^4)_2$—, and —A— is —$NR^1$—, or a pharmaceutically acceptable salt thereof.

4) The compound according any one of to the above items 1) to 3), wherein —$W^A$— is —$CH_2$—$C(R^3R^4)$—, or a pharmaceutically acceptable salt thereof.

5) The compound according to the above item 4), wherein $R^3$ is substituted or unsubstituted alkyl, and $R^4$ is a hydrogen atom, or a pharmaceutically acceptable salt thereof.

6) The compound according to any one of the above items 1) to 5), wherein $R^1$ is a hydrogen atom, or substituted or unsubstituted alkyl, or a pharmaceutically acceptable salt thereof.

7) The compound according to the above item 1) or 2), wherein —$W^A$— is —$C(R^3R^4)$—, —W— is —$C(R^8R^9)$—, and —A— is —$CR^{1D}R^{1E}$—, or a pharmaceutically acceptable salt thereof.

8) The compound according to the above item 7), wherein —$W^A$— is —$CH_2$—, —W— is —$CH_2$—, $R^{1D}$ is substituted or unsubstituted alkyl, and $R^{1E}$ is a hydrogen atom, or a pharmaceutically acceptable salt thereof.

9) The compound according to the above item 1) or 2), wherein —$W^A$— is —$C(R^3R^4)$—, —W— is —$C(R^8R^9)$—, and —A— is —$NR^1$—, or a pharmaceutically acceptable salt thereof.

10) The compound according to the above item 9), wherein —$W^A$— is —$CH_2$—, —W— is —$CH_2$—, and $R^1$ is substituted or unsubstituted alkyl, or a pharmaceutically acceptable salt thereof.

11) The compound according to any one of the above items 1) to 10), wherein $R^5$ and $R^{5A}$ are hydrogen atoms, and =X is =O, or a pharmaceutically acceptable salt thereof.

12) The compound according to any one of the above items 1) to 11), wherein $R^2$ is a hydrogen atom, or a pharmaceutically acceptable salt thereof.

13) The compound according to any one of the above items 1) to 12), wherein $R^{13}$ is substituted or unsubstituted aromatic carbocyclyl, substituted or unsubstituted alkyl, or substituted or unsubstituted non-aromatic carbocyclyl, or a pharmaceutically acceptable salt thereof.

14) The compound according to any one of the above items 1) to 13)

wherein $R^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 42]

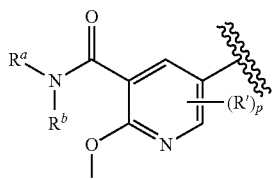

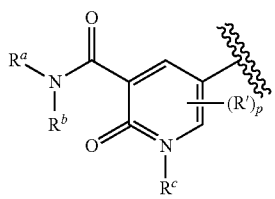

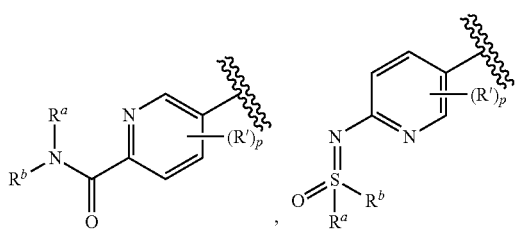

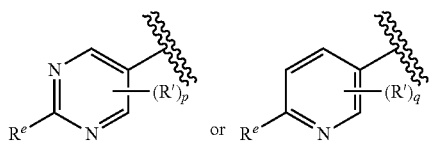

wherein $R^a$, $R^b$, Rc, $R^e$, R', p and q are the same as defined in the above item 1),
or a pharmaceutically acceptable salt thereof.

15) The compound according to any one of the above items 1) to 4),
wherein $R^{15}$ is a hydrogen atom, or substituted or unsubstituted alkyl,
or a pharmaceutically acceptable salt thereof.

16A) The compound according to any one of the above items 1) to 15), represented by Formula (I'):

[Chemical Formula 43]

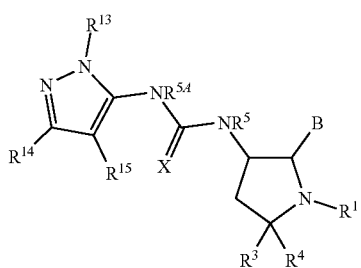

(I')

wherein =X, $R^1$, $R^3$, $R^4$, $R^5$, $R^{5A}$, $R^{13}$ and $R^{15}$ are the same as defined in the above item 1);

B is a group represented by the following formula:

[Chemical Formula 44]

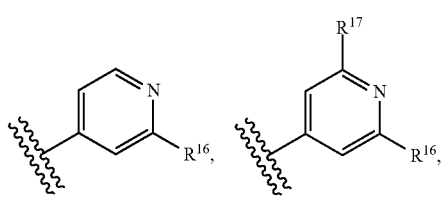

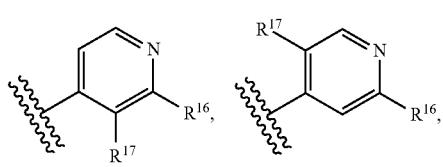

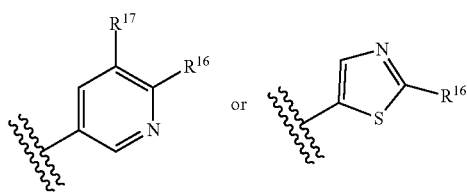

wherein $R^{16}$ and $R^{17}$ are the same as defined in the above item 1);

$R^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 45]

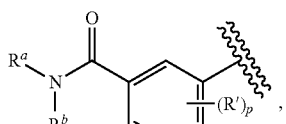

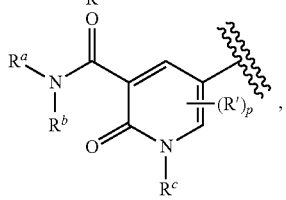

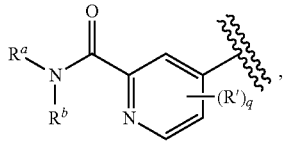

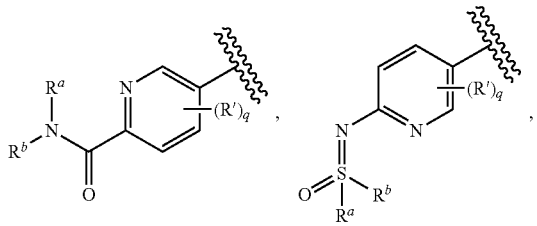

-continued

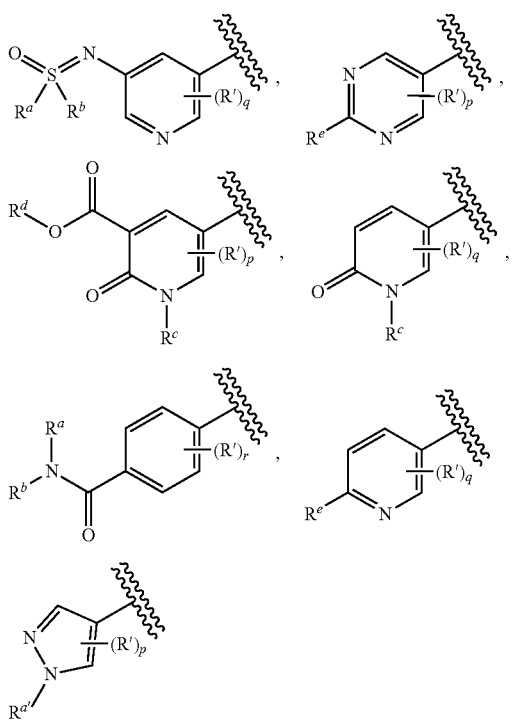

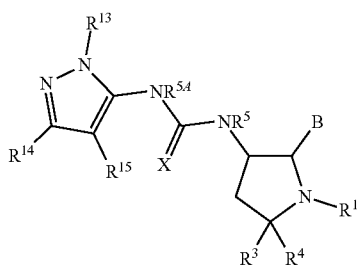

wherein $R^a$, $R^{a'}$, $R^b$, $R^c$, $R^d$, $R^e$, $R'$, p, q, and r are the same as defined in the above item 1), or a pharmaceutically acceptable salt thereof.

16) The compound according to any one of the above items 1) to 15), represented by Formula (I'):

[Chemical Formula 46]

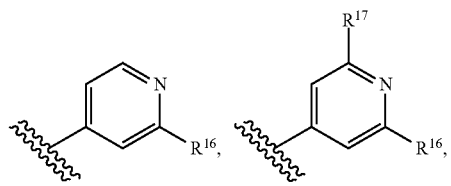

(I')

wherein =X, $R^1$, $R^3$, $R^4$, $R^5$, $R^{5A}$, $R^{13}$ and $R^{15}$ are the same as defined in the above item 1);

B is a group represented by the following formula:

[Chemical Formula 47]

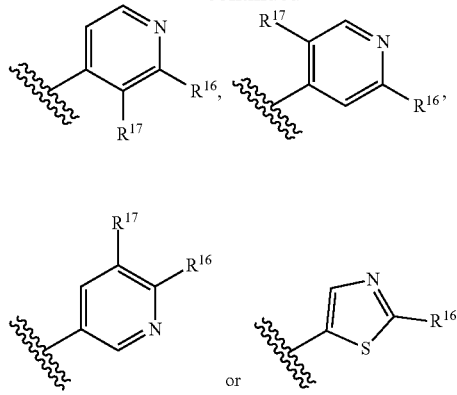

wherein $R^{16}$ and $R^{17}$ are the same as defined in the above item 1);

$R^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 48]

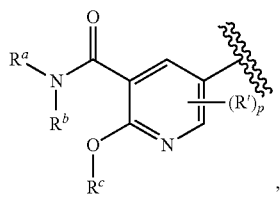

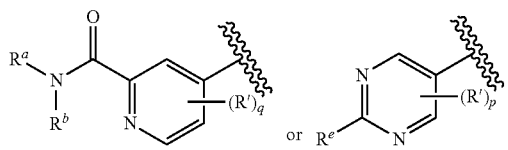

wherein $R^a$, $R^b$, $R^c$, $R^e$, $R'$, p and q are the same as defined in the above item 1), or a pharmaceutically acceptable salt thereof.

17A) The compound according to any one of the above items 1) to 15), represented by Formula (I"):

[Chemical Formula 49]

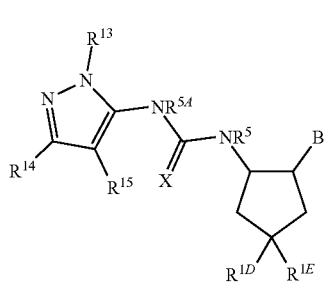

(I")

wherein =X, $R^{1D}$, $R^{1E}$, $R^5$, $R^{5A}$, $R^{13}$ and $R^{15}$ are the same as defined in the above item 1);

B is a group represented by the following formula:

[Chemical Formula 50]

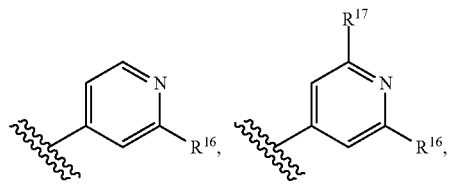
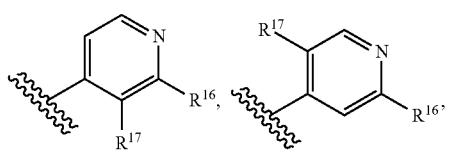
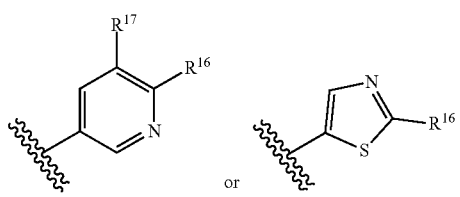

wherein $R^{16}$ and $R^{17}$ are the same as defined in the above item 1);

$R^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 51]

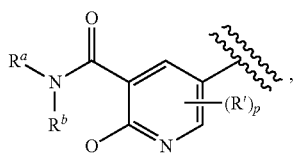
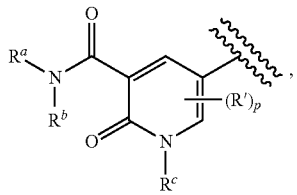
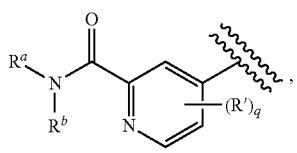
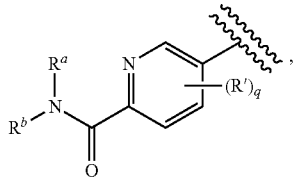

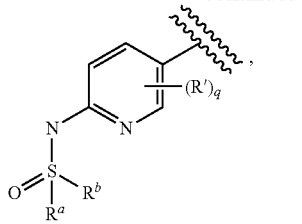
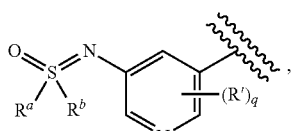
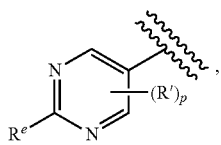
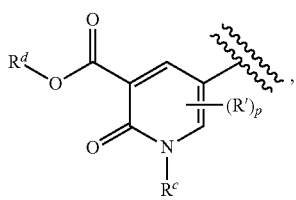
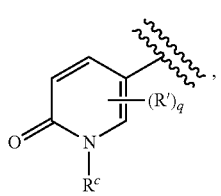
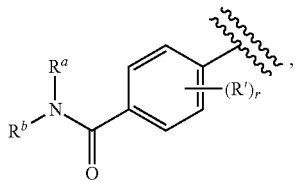
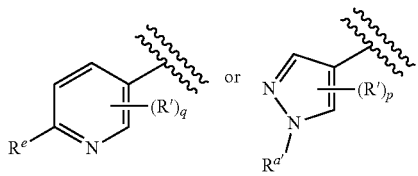

wherein $R^a$, $R^{a'}$, $R^b$, $R^c$, $R^d$, $R^e$, R', p, q, and r are the same as defined in the above item 1), or a pharmaceutically acceptable salt thereof 17) The compound according to any one of the above items 1) to 15), represented by Formula (I″):

[Chemical Formula 52]

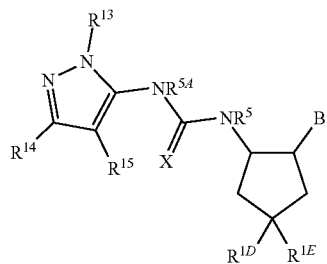

(I″)

wherein =X, $R^{1D}$, $R^{1E}$, $R^5$, $R^{5A}$, $R^{13}$ and $R^{15}$ are the same as defined in the above item 1);

B is a group represented by the following formula:

[Chemical Formula 53]

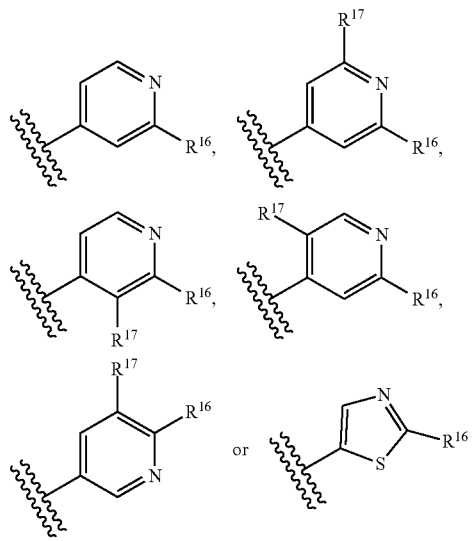

wherein $R^{16}$ and $R^{17}$ are the same as defined in the above item 1);

$R^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 54]

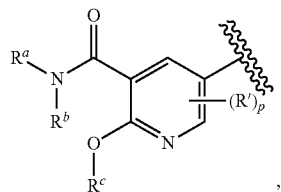

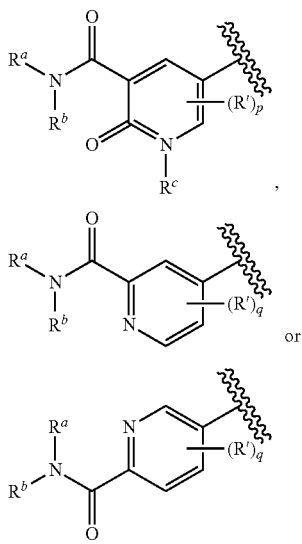

wherein $R^a$, $R^b$, $R^c$, $R'$, p and q are the same as defined in the above item 1), or a pharmaceutically acceptable salt thereof.

18A) The compound according to any one of the above items 1) to 15), represented by Formula (I‴):

[Chemical Formula 55]

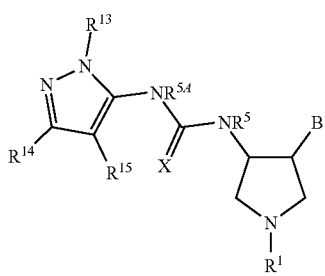

(I‴)

wherein =X, $R^1$, $R^5$, $R^{5A}$, $R^{13}$ and $R^{15}$ are the same as defined in the above item 1);

B is a group represented by the following formula:

[Chemical Formula 56]

-continued

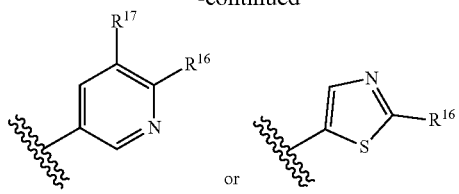

wherein $R^{16}$ and $R^{17}$ are the same as defined in the above item 1);
$R^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 57]

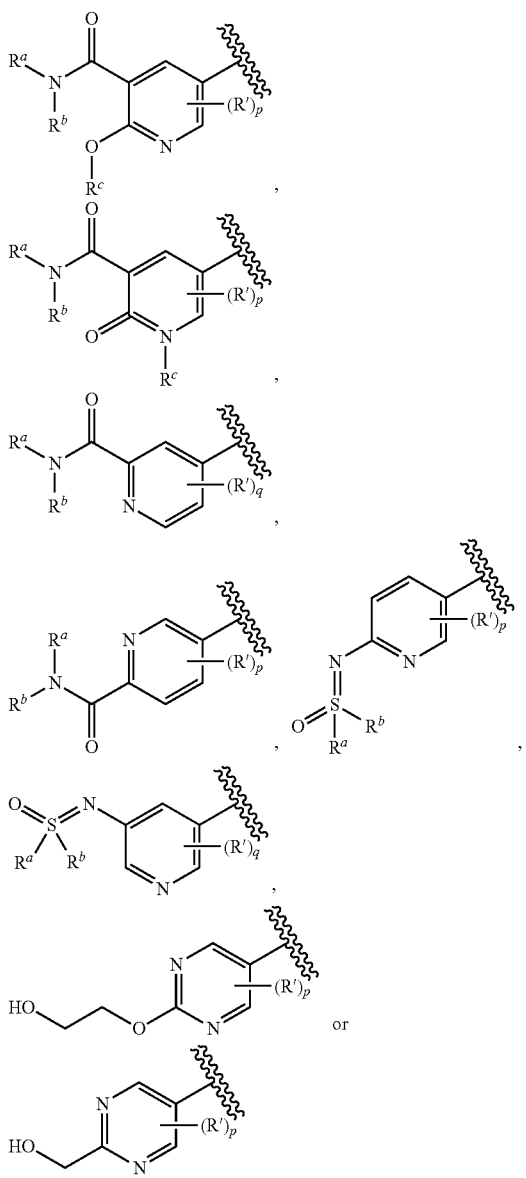

wherein $R^a$, $R^b$, $R^c$, R', p and q are the same as defined in the above item 1),
or a pharmaceutically acceptable salt thereof.

18) The compound according to any one of the above items 1) to 15), represented by Formula (I'''):

[Chemical Formula 58]

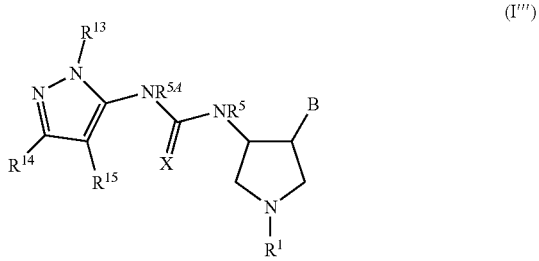

(I''')

wherein =X, $R^1$, $R^5$, $R^{5A}$, $R^{13}$ and $R^{15}$ are the same as defined in the above item 1);
B is a group represented by the following formula:

[Chemical Formula 59]

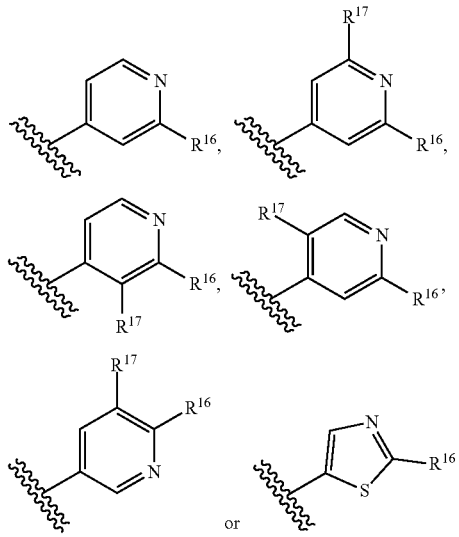

wherein $R^{16}$ and $R^{17}$ are the same as defined in the above item 1);
$R^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 60]

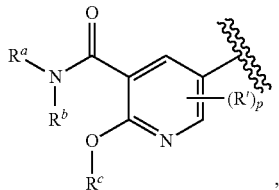

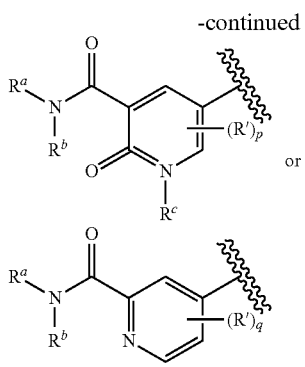

wherein $R^a$, $R^b$, $R^c$, R', p and q are the same as defined in the above item 1),
or a pharmaceutically acceptable salt thereof.

19) A pharmaceutical composition, comprising the compound according to any one of the above items 1) to 18) and 16A) to 18A), or a pharmaceutically acceptable salt thereof.

20) The pharmaceutical composition according to the above item 19), wherein the composition has a TrkA inhibitory activity.

21) A method for treating or preventing a disease related to TrkA comprising administering the compound according to any one of the above items 1) to 18) and 16A) to 18A), or a pharmaceutically acceptable salt thereof.

22) The compound according to any one of the above items 1) to 18) and 16A) to 18A), or a pharmaceutically acceptable salt thereof, for use in a method for treating or preventing a disease related to TrkA.

23) Use of the compound according to any one of the above items 1) to 18) and 16A) to 18A), or a pharmaceutically acceptable salt thereof, for the manufacture of a medicament for treating or preventing a disease related to TrkA.

101) A pharmaceutical composition comprising the compound according to any one of the above items 1) to 18) and 16A) to 18A), or a pharmaceutically acceptable salt thereof, for oral administration.

102) The pharmaceutical composition according to the above item 101), which is a tablet, powder, granule, capsule, pill, film, suspension, emulsion, elixir, syrup, lemonade, spirit, aromatic water, extract, decoction or tincture.

103) The pharmaceutical composition according to the above item 102), which is a sugar-coated tablet, film-coated tablet, enteric-coated tablet, sustained-release tablet, troche tablet, sublingual tablet, buccal tablet, chewable tablet, orally disintegrating tablet, dry syrup, soft capsule, micro capsule or sustained-release capsule.

104) A pharmaceutical composition comprising the compound according to any one of the above items 1) to 18) and 16A) to 18A), or a pharmaceutically acceptable salt thereof, for parenteral administration.

105) The pharmaceutical composition according to the above item 104), for dermal, subcutaneous, intravenous, intraarterial, intramuscular, intraperitoneal, transmucosal, inhalation, transnasal, ophthalmic, inner ear or vaginal administration.

106) The pharmaceutical composition according to the above item 104) or 105), which is injection, infusion, eye drop, nose drop, ear drop, aerosol, inhalation, lotion, impregnation, liniment, mouthwash, enema, ointment, plaster, jelly, cream, patch, cataplasm, external powder or suppository.

107) A pharmaceutical composition comprising the compound according to any one of the above items 1) to 18) and 16A) to 18A), or a pharmaceutically acceptable salt thereof, for a pediatric or geriatric patient.

Effect of the Invention

The present invention provides a compound useful in the treatment and/or prevention of TrkA mediated disorder, or a pharmaceutically acceptable salt thereof. The compound of the present invention shows an excellent TrkA kinase inhibitory activity as described in the following test examples. Thereby, a pharmaceutical composition of the present invention is available for therapeutic agent and/or prophylactic agent for pain associated with osteoarthritis, rheumatoid arthritis, fracture, interstitial cystitis, chronic pancreatitis and prostate inflammation; and nociceptive pain as typified by chronic low back pain, diabetic peripheral neuropathy pain, postoperative pain, pelvic pain and cancer pain; neuropathic pain, acute pain, chronic pain, cancer, inflammatory disease, allergic disease, dermatological disease and the like.

A compound of the present invention is the one having utility as a medicament. Herein, utility as a medicament includes the following points: the compound has good solubility; good metabolic stability; the induction of a drug-metabolizing enzyme is low; the inhibition of a drug-metabolizing enzyme which metabolizes another drug is low; the compound has high oral absorbency; the inhibition of hERG is low; the clearance is low; and/or the half-life is sufficiently long to express the efficacy; or the like.

MODE FOR CARRYING OUT THE INVENTION

Hereinafter, the present invention is described with reference to embodiments. It should be understood that, throughout the present specification, the expression of a singular form includes the concept of its plural form unless specified otherwise. Accordingly, it should be understood that an article in singular form (for example, in the English language, "a," "an," and "the") includes the concept of its plural form unless specified otherwise. Furthermore, it should be understood that the terms used herein are used in a meaning normally used in the art unless specified otherwise. Thus, unless defined otherwise, all technical and scientific terms used herein have the same meaning as those generally understood by those skilled in the art in the field to which the present invention pertains. If there is a contradiction, the present specification (including definitions) precedes.

Terms used in this description are explained below. Each term, unless otherwise indicated, has the same meaning when it is used alone or together with other terms.

The term of "consisting of" means having only components.

The term of "comprising" means not restricting with components and not excluding undescribed factors.

The term "halogen" includes a fluorine atom, a chlorine atom, a bromine atom and an iodine atom. A fluorine atom and a chlorine atom are especially preferable.

The term "alkyl" includes a C1 to C15, preferably C1 to C10, more preferably C1 to C6 and further preferably C1 to C4 linear or branched hydrocarbon group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, and n-decyl.

A preferred embodiment of "alkyl" is methyl, ethyl, n-propyl, isopropyl, n-butyl, isobutyl, sec-butyl, tert-butyl or n-pentyl. A more preferred embodiment is methyl, ethyl, n-propyl, isopropyl or tert-butyl.

The term "alkenyl" includes a C2 to C15, preferably a C2 to C10, more preferably a C2 to C6 and further preferably a C2 to C4 linear or branched hydrocarbon group having one or more double bond(s) at any position(s). Examples include vinyl, allyl, n-propenyl, isopropenyl, n-butenyl, isobutenyl, prenyl, n-butadienyl, n-pentenyl, isopentenyl, n-pentadienyl, n-hexenyl, isohexenyl, n-hexadienyl, n-heptenyl, n-octenyl, n-nonenyl, n-decenyl, n-undecenyl, n-dodecenyl, n-tridecenyl, n-tetradecenyl, and n-pentadecenyl.

A preferred embodiment of "alkenyl" is vinyl, allyl, n-propenyl, isopropenyl or butenyl.

The term "alkynyl" includes a C2 to C10, preferably a C2 to C8, more preferably a C2 to C6 and further preferably a C2 to C4 linear or branched hydrocarbon group having one or more triple bond(s) at any position(s). Furthermore, it may have double bond(s) at any position(s). Examples include ethynyl, n-propynyl, n-butynyl, n-pentynyl, n-hexynyl, n-heptynyl, n-octynyl, n-nonynyl, and n-decynyl.

A preferred embodiment of "alkynyl" is ethynyl, n-propynyl, n-butynyl or n-pentynyl.

The term "alkylene" includes a C1 to C15, preferably a C1 to C10, more preferably a C1 to C6 and further preferably a C1 to C4 liner or branched divalent hydrocarbon group. Examples include methylene, ethylene, trimethylene, tetramethylene, pentamethylene, and hexamethylene.

The term "aromatic carbocyclyl" means a cyclic aromatic hydrocarbon group which is monocyclic or polycyclic having two or more rings. Examples include phenyl, naphthyl, anthryl, and phenanthryl.

A preferred embodiment of "aromatic carbocyclyl" is phenyl.

The term "aromatic carbocycle" means a cyclic aromatic hydrocarbon ring which is monocyclic or polycyclic having two or more rings. Examples include a benzene ring, a naphthalene ring, an anthracene ring, and a phenanthrene ring.

A preferred embodiment of "aromatic carbocycle" is a benzene ring and a naphthalene ring.

The term "non-aromatic carbocyclyl" means a cyclic saturated hydrocarbon group or a cyclic unsaturated non-aromatic hydrocarbon group, which is monocyclic or polycyclic having two or more rings. The "non-aromatic carbocyclyl" which is polycyclic having two or more rings includes a fused ring group wherein a non-aromatic carbocyclyl, which is monocyclic or polycyclic having two or more rings, is fused with a ring of the above "aromatic carbocyclyl".

In addition, examples of the "non-aromatic carbocyclyl" also include a group having a bridge or a group to form a spiro ring as follows:

[Chemical Formula 61]

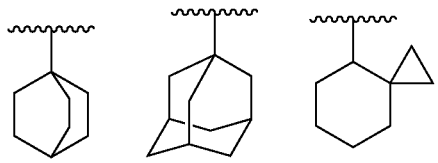

The non-aromatic carbocyclyl which is monocyclic is preferably C3 to C16, more preferably C3 to C12 and further preferably C4 to C8 carbocyclyl. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, and cyclohexadienyl.

Examples of non-aromatic carbocyclyl, which is polycyclic having two or more rings, include indanyl, indenyl, acenaphthyl, tetrahydronaphthyl, and fluorenyl.

The term "non-aromatic carbocycle" means a cyclic saturated hydrocarbon ring or a cyclic unsaturated non-aromatic hydrocarbon ring, which is monocyclic or polycyclic having two or more rings. The "non-aromatic carbocycle", which is polycyclic having two or more rings, includes a fused ring wherein the non-aromatic carbocycle, which is monocyclic or polycyclic having two or more rings, is fused with a ring of the above "aromatic carbocycle".

In addition, examples of the "non-aromatic carbocycle" also include a ring having a bridge or a ring to form a spiro ring as follows:

[Chemical Formula 62]

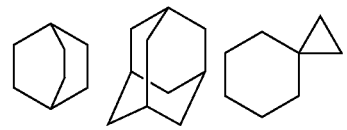

The non-aromatic carbocycle which is monocyclic is preferably C3 to C16, more preferably C3 to C12 and further preferably C4 to C8 carbocyclyl. Examples include cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, and cyclohexadiene.

Examples of a non-aromatic carbocycle, which is polycyclic having two or more rings, include indane, indene, acenaphthene, tetrahydronaphthalene, and fluorene.

Examples of a non-aromatic carbocycle which may be formed by I1D and R1E together include a ring as follows:

[Chemical Formula 63]

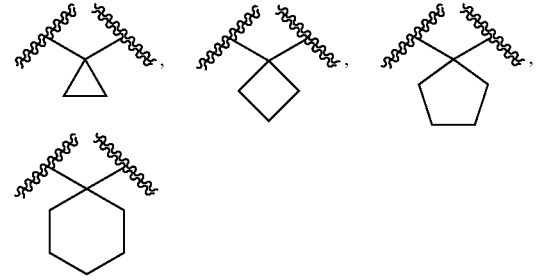

The term "aromatic heterocyclyl" means an aromatic cyclyl, which is monocyclic or polycyclic having two or more rings, containing one or more, same or different heteroatom(s) selected independently from O, S and N. The "aromatic heterocyclyl", which is polycyclic having two or more rings, includes a fused ring group wherein an aromatic heterocyclyl, which is monocyclic or polycyclic having two or more rings, is fused with a ring of the above "aromatic carbocyclyl".

The aromatic heterocyclyl, which is monocyclic, is preferably a 5- to 8-membered ring and more preferably a 5- to 6- membered ring. Examples include pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, and thiadiazolyl.

Examples of aromatic heterocyclyl, which is bicyclic, include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, and thiazolopyridyl.

Examples of aromatic heterocyclyl, which is bicyclic, include a group as follows:

[Chemical Formula 64]

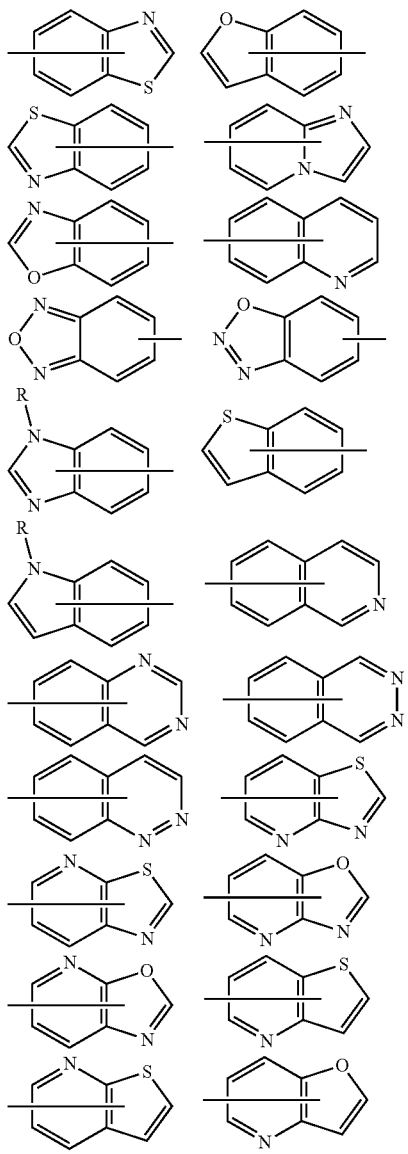
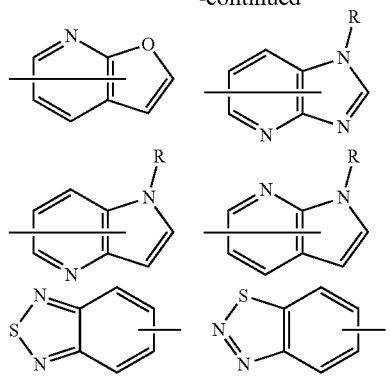

wherein R is a hydrogen atom, CH3, CH2CF3, in the case that one of the binding group attaches to one ring, it may be attached to a connectable annular atom on the ring, in the case that one of the binding group attached to two rings, it may be attached to a connectable annular atom on the two rings.

Examples of aromatic heterocyclyl, which is polycyclic having three or more rings, include carbazolyl, acridinyl, xanthenyl, phenothiazinyl, phenoxathiinyl, phenoxazinyl, and dibenzofuryl.

The term "aromatic heterocycle" means an aromatic ring, which is monocyclic or polycyclic having two or more rings, containing one or more, same or different heteroatom(s) selected independently from O, S and N.

The "aromatic heterocycle", which is polycyclic having two or more rings, includes a fused ring wherein an aromatic heterocycle, which is monocyclic or polycyclic having two or more rings, is fused with a ring of the above "aromatic carbocycle".

The aromatic heterocycle, which is monocyclic, is preferably a 5- to 8-membered ring and more preferably a 5- or 6- membered ring. Examples include pyrrole, imidazole, pyrazole, pyridine, pyridazine, pyrimidine, pyrazine, triazole, triazine, tetrazole, furan, thiophen, isoxazole, oxazole, oxadiazole, isothiazole, thiazole, and thiadiazole.

Examples of an aromatic heterocycle, which is bicyclic, include indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, oxazolopyridine, and thiazolopyridine.

Examples of an aromatic heterocycle, which is polycyclic having three or more rings, include carbazole, acridine, xanthene, phenothiazine, phenoxathiine, phenoxazine, and dibenzofuran.

The term "non-aromatic heterocyclyl" means a non-aromatic cyclyl, which is monocyclic or polycyclic having two or more rings, containing one or more, same or different heteroatom(s) selected independently from O, S and N. The "non-aromatic heterocyclyl", which is polycyclic having two or more rings, includes an above-mentioned non-aromatic heterocyclyl fused with a ring of the above "aromatic carbocyclyl", "non-aromatic carbocyclyl" and/or "aromatic heterocyclyl". The "non-aromatic heterocyclyl", which is polycyclic having two or more rings, includes an aromatic heterocyclyl, which is monocyclic or polycyclic having two or more rings, fused with a ring of the above "non-aromatic carbocyclyl" and/or "aromatic heterocyclyl".

In addition, examples of the "non-aromatic heterocyclyl" also include a group having a bridge or a group to form a spiro ring as follows:

[Chemical Formula 65]

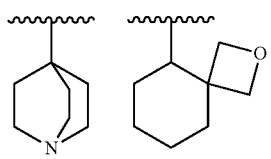

The non-aromatic heterocyclyl, which is monocyclic, is preferably a 3- to 8-membered and more preferably a 5- to 6-membered ring. Examples include dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolynyl, oxepanyl, thiolanyl, thiinyl, and thiazinyl.

Examples of non-aromatic heterocyclyl, which is polycyclic having two or more rings, include indolinyl, isoindolinyl, chromanyl, and isochromanyl.

The term "non-aromatic heterocycle" means a cyclic non-aromatic ring, which is monocyclic or polycyclic having two or more rings, containing one or more, same or different heteroatom(s) selected from O, S and N.

The "non-aromatic heterocycle", which is polycyclic having two or more rings, includes an above-mentioned non-aromatic heterocycle fused with a ring of the above "aromatic carbocycle", "non-aromatic carbocycle" and/or "aromatic heterocycle".

In addition, the "non-aromatic heterocycle" also includes a ring having a bridge or a ring to form a spiro ring as follows:

[Chemical Formula 66]

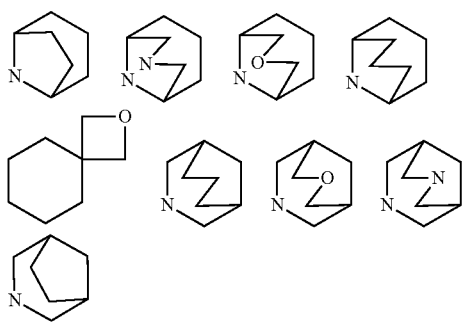

The non-aromatic heterocycle which is non-bridged is preferably a 3 to 8-membered ring, more preferably a 4 to 8-membered ring, and further preferably a 5 or 6-membered ring.

The non-aromatic heterocycle which is bridged is preferably a 6 to 10-membered ring and more preferably a 8 or 9-membered ring. Herein, a number of members mean a number of all annular atoms of a bridged non-aromatic heterocycle.

The non-aromatic heterocycle which is monocyclic is preferably a 3 to 8-membered ring, and more preferably a 5 or 6-membered ring. Examples include dioxane, thiirane, oxirane, oxetane, oxathiolane, azetidine, thiane, thiazolidine, pyrrolidine, pyrroline, imidazolidine, imidazoline, pyrazolidine, pyrazoline, piperidine, piperazine, pyridone, morpholine, thiomorpholine, dihydropyridine, tetrahydropyridine, tetrahydrofuran, tetrahydropyran, dihydrothiazole, tetrahydrothiazole, tetrahydroisothiazole, dihydrooxazine, hexahydroazepine, tetrahydrodiazepine, tetrahydropyridazine, hexahydropyrimidine, dioxolane, dioxazine, aziridine, dioxoline, oxepane, thiolane, thiine, and thiazine.

Examples of a non-aromatic heterocycle, which is polycyclic having two or more rings, include indoline, isoindoline, chromane, and isochromane.

Examples of a non-aromatic heterocycle which may be formed by R1D and R1E together include a ring as follows:

[Chemical Formula 67]

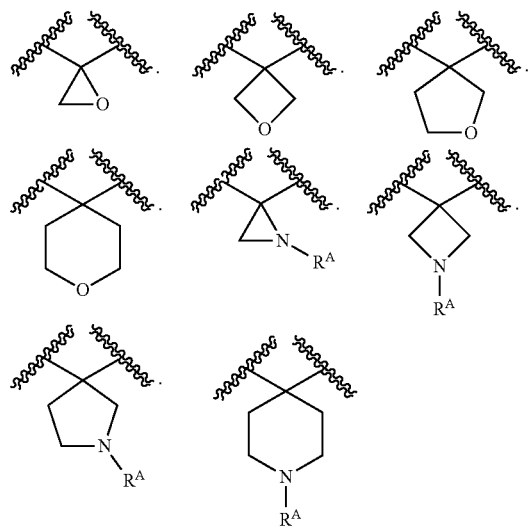

wherein RA is substituted or unsubstituted alkyl, substituted or unsubstituted alkenyl, substituted or unsubstituted alkyloxycarbonyl, or substituted or unsubstituted alkylcarbonyl.

The term "hydroxyalkyl" means a group wherein one or more hydrogen atom(s) attached to a carbon atom of the above "alkyl" is replaced with a hydroxyl group. Examples include hydroxymethyl, 1-hydroxyethyl, 2-hydroxyethyl, 1-hydroxy-n-propyl, 2-hydroxy-n-propyl, and 1,2-dihydroxyethyl.

A preferred embodiment of "hydroxyalkyl" is hydroxymethyl.

The term "alkyloxy" means a group wherein the above "alkyl" is bonded to an oxygen atom. Examples include methoxy, ethoxy, n-propyloxy, isopropyloxy, n-butyloxy, tert-butyloxy, isobutyloxy, sec-butyloxy, n-pentyloxy, isopentyloxy, and n-hexyloxy.

A preferred embodiment of "alkyloxy" is methoxy, ethoxy, n-propyloxy, isopropyloxy, and tert-butyloxy.

The term "alkenyloxy" means a group wherein the above "alkenyl" is bonded to an oxygen atom. Examples include vinyloxy, allyloxy, 1-n-propenyloxy, 2-n-butenyloxy, 2-n-pentenyloxy, 2-n-hexenyloxy, 2-n-heptenyloxy, and 2-n-octenyloxy.

The term "alkynyloxy" means a group wherein the above "alkynyl" is bonded to an oxygen atom. Examples include ethynyloxy, 1-n-propynyloxy, 2-n-propynyloxy, 2-n-butynyloxy, 2-n-pentynyloxy, 2-n-hexynyloxy, 2-n-heptynyloxy, and 2-n-octynyloxy.

The term "haloalkyl" includes a group wherein one or more hydrogen atom(s) attached to a carbon atom of the above "alkyl" is replaced with the above "halogen". Examples include monofluoromethyl, monofluoroethyl, monofluoro-n-propyl, 2,2,3,3,3-n-pentafluoropropyl, monochloromethyl, trifluoromethyl, trichloromethyl, 2,2,2-trifluoroethyl, 2,2,2-trichloroethyl, 1,2-dibromoethyl, and 1,1,1-trifluoro-n-propan-2-yl.

A preferred embodiment of "haloalkyl" is trifluoromethyl and trichloromethyl.

The term "haloalkyloxy" means a group wherein the above "haloalkyl" is bonded to an oxygen atom. Examples include monofluoromethoxy, monofluoroethoxy, trifluoromethoxy, trichloromethoxy, trifluoroethoxy, and trichloroethoxy.

A preferred embodiment of "haloalkyloxy" is trifluoromethoxy and trichloromethoxy.

The term "alkyloxyalkyl" means a group wherein the above "alkyloxy" is bonded to the above "alkyl". Examples include methoxymethyl, methoxyethyl, and ethoxymethyl.

The term "alkyloxyalkyloxy" means a group wherein the above "alkyloxy" is bonded to the above "alkyloxy". Examples include methoxymethoxy, methoxyethoxy, ethoxymethoxy, and ethoxyethoxy.

The term "alkylcarbonyl" means a group wherein the above "alkyl" is bonded to a carbonyl group. Examples include methylcarbonyl, ethylcarbonyl, n-propylcarbonyl, isopropylcarbonyl, n-butylcarbonyl, tert-butylcarbonyl, isobutylcarbonyl, sec-butylcarbonyl, n-pentylcarbonyl, isopentylcarbonyl, and n-hexylcarbonyl.

A preferred embodiment of "alkylcarbonyl" is methylcarbonyl, ethylcarbonyl and n-propylcarbonyl.

The term "alkenylcarbonyl" means a group wherein the above "alkenyl" is bonded to a carbonyl group. Examples include vinylcarbonyl, allylcarbonyl and n-propenylcarbonyl.

The term "alkynylcarbonyl" means a group wherein the above "alkynyl" is bonded to a carbonyl group. Examples include ethynylcarbonyl and n-propynylcarbonyl.

The term "alkylamino" means a group wherein one or two hydrogen atom(s) attached to a nitrogen atom of an amino group is(are) replaced with the above "alkyl". Examples include methylamino, dimethylamino, ethylamino, diethylamino, isopropylamino, N,N-diisopropylamino, and N-methyl-N-ethylamino.

A preferred embodiment of "alkylamino" is methylamino and ethylamino.

The term "alkylsulfonyl" means a group wherein the above "alkyl" is bonded to a sulfonyl group. Examples include methylsulfonyl, ethylsulfonyl, n-propylsulfonyl, isopropylsulfonyl, n-butyl sulfonyl, tert-butyl sulfonyl, isobutylsulfonyl, and sec-butylsulfonyl.

A preferred embodiment of "alkylulfonyl" is methylsulfonyl and ethylsulfonyl.

The term "alkenylsulfonyl" means a group wherein the above "alkenyl" is bonded to a sulfonyl group. Examples include vinylsulfonyl, allylsulfonyl, and n-propenylsulfonyl.

The term "alkynylsulfonyl" means a group wherein the above "alkynyl" is bonded to a sulfonyl group. Examples include ethynylsulfonyl, and n-propynylsulfonyl.

The term "alkylcarbonylamino" means a group wherein one or two hydrogen atom(s) attached to a nitrogen atom of an amino group is(are) replaced with the above "alkylcarbonyl". Examples include methylcarbonylamino, dimethylcarbonylamino, ethylcarbonylamino, diethylcarbonylamino, n-propylcarbonylamino, isopropylcarbonylamino, N,N-diisopropylcarbonylamino, n-butylcarbonylamino, tert-butylcarbonylamino, isobutylcarbonylamino, and sec-butylcarbonylamino.

The term "alkylsulfonylamino" means a group wherein one or two hydrogen atom(s) attached to a nitrogen atom of an amino group is(are) replaced with the above "alkylsulfonyl". Examples include methylsulfonylamino, dimethylsulfonylamino, ethylsulfonylamino, diethylsulfonylamino, n-propylsulfonylamino, isopropylsulfonylamino, N,N-diisopropylsulfonylamino, n-butylsulfonylamino, tert-butylsulfonylamino, isobutylsulfonylamino, and sec-butylsulfonylamino.

A preferred embodiment of "alkylsulfonylamino" is methylsulfonylamino and ethylsulfonylamino.

The term "alkylimino" means a group wherein a hydrogen atom attached to a nitrogen atom of an imino group is replaced with the above "alkyl". Examples include methylimino, ethylimino, n-propylimino, and isopropylimino.

The term "alkenylimino" means a group wherein a hydrogen atom attached to a nitrogen atom of an imino group is replaced with the above "alkenyl". Examples include ethylenylimino, and n-propenylimino.

The term "alkynylimino" means a group wherein a hydrogen atom attached to a nitrogen atom of an imino group is replaced with the above "alkynyl". Examples include ethynylimino, and n-propynylimino.

The term "alkylcarbonylimino" means a group wherein a hydrogen atom attached to a nitrogen atom of an imino group is replaced with the above "alkylcarbonyl". Examples include methylcarbonylimino, ethylcarbonylimino, n-propylcarbonylimino, and isopropylcarbonylimino.

The term "alkenylcarbonylimino" means a group wherein a hydrogen atom attached to a nitrogen atom of an imino group is replaced with the above "alkenylcarbonyl". Examples include ethylenylcarbonylimino, and n-propenylcarbonylimino.

The term "alkynylcarbonylimino" means a group wherein a hydrogen atom attached to a nitrogen atom of an imino group is replaced with the above "alkynylcarbonyl". Examples include ethynylcarbonylimino and n-propynylcarbonylimino.

The term "alkyloxyimino" means a group wherein a hydrogen atom attached to a nitrogen atom of an imino group is replaced with the above "alkyloxy". Examples include methyloxyimino, ethyloxyimino, n-propyloxyimino, and isopropyloxyimino.

The term "alkenyloxyimino" means a group wherein a hydrogen atom attached to a nitrogen atom of an imino group is replaced with the above "alkenyloxy". Examples include ethylenyloxyimino, and n-propenyloxyimino.

The term "alkynyloxyimino" means a group wherein a hydrogen atom attached to a nitrogen atom of an imino group is replaced with the above "alkynyloxy". Examples include ethynyloxyimino, and n-propynyloxyimino.

The term "alkylcarbonyloxy" means a group wherein the above "alkylcarbonyl" is bonded to an oxygen atom. Examples include methylcarbonyloxy, ethylcarbonyloxy, n-propylcarbonyloxy, isopropylcarbonyloxy, tert-butylcarbonyloxy, isobutylcarbonyloxy, and sec-butylcarbonyloxy.

A preferred embodiment of "alkylcarbonyloxy" is methylcarbonyloxy and ethylcarbonyloxy.

The term "alkenylcarbonyloxy" means a group wherein the above "alkenylcarbonyl" is bonded to an oxygen atom. Examples include ethylenylcarbonyloxy and n-propenylcarbonyloxy.

The term "alkynylcarbonyloxy" means a group wherein the above "alkynylcarbonyl" is bonded to an oxygen atom. Examples include ethynylcarbonyloxy and n-propynylcarbonyloxy.

The term "alkyloxycarbonyl" means a group wherein the above "alkyloxy" is bonded to a carbonyl group. Examples include methyloxycarbonyl, ethyloxycarbonyl, n-propyloxycarbonyl, isopropyloxycarbonyl, n-butyloxycarbonyl, tert-butyloxycarbonyl, isobutyloxycarbonyl, sec-butyloxycarbonyl, n-pentyloxycarbonyl, isopentyloxycarbonyl, and n-hexyloxycarbonyl.

A preferred embodiment of "alkyloxycarbonyl" is methyloxycarbonyl, ethyloxycarbonyl and n-propyloxycarbonyl.

The term "alkenyloxycarbonyl" means a group wherein the above "alkenyloxy" is bonded to a carbonyl group. Examples include ethylenyloxycarbonyl and n-propenyloxycarbonyl.

The term "alkynyloxycarbonyl" means a group wherein the above "alkynyloxy" is bonded to a carbonyl group. Examples include ethynyloxycarbonyl and n-propynyloxycarbonyl.

The term "alkylsulfanyl" means a group wherein a hydrogen atom attached to a sulfur atom of a sulfanyl group is replaced with the above "alkyl". Examples include methylsulfanyl, ethylsulfanyl, n-propylsulfanyl, and isopropylsulfanyl.

The term "alkenylsulfanyl" means a group wherein a hydrogen atom attached to a sulfur atom of a sulfanyl group is replaced with the above "alkenyl". Examples include ethylenylsulfanyl, and n-propenylsulfanyl.

The term "alkynylsulfanyl" means a group wherein a hydrogen atom attached to a sulfur atom of a sulfanyl group is replaced with the above "alkynyl". Examples include ethynylsulfanyl, and n-propynylsulfanyl.

The term "alkylsulfinyl" means a group wherein the above "alkyl" is bonded to a sulfinyl group. Examples include methylsulfinyl, ethylsulfinyl, n-propylsulfinyl, and isopropylsulfinyl.

The term "alkenylsulfinyl" means a group wherein the above "alkenyl" is bonded to a sulfinyl group. Examples include ethylenylsulfinyl, and n-propenylsulfinyl.

The term "alkynylsulfinyl" means a group wherein the above "alkynyl" is bonded to a sulfinyl group. Examples include ethynylsulfinyl and n-propynylsulfinyl.

The term "alkylcarbamoyl" means a group wherein one or two hydrogen atom(s) attached to a nitrogen atom of a carbamoyl group is(are) replaced with the above "alkyl". Examples include methylcarbamoyl, dimethylcarbamoyl, ethylcarbamoyl, and diethylcarbamoyl.

The term "alkylsulfamoyl" means a group wherein one or two hydrogen atom(s) attached to a nitrogen atom of a sulfamoyl group is(are) replaced with the above "alkyl". Examples include methylsulfamoyl, dimethylsulfamoyl, ethylsulfamoyl, and diethylsulfamoyl.

The term "trialkylsilyl" means a group wherein three of the above "alkyl" are bonded to a silyl atom. Three alkyl groups may be the same or different. Examples include trimethylsilyl, triethylsilyl, and tert-butyldimethylsilyl.

The alkyl part of "aromatic carbocyclylalkyl", "non-aromatic carbocyclylalkyl", "aromatic heterocyclylalkyl", and "non-aromatic heterocyclylalkyl", "aromatic carbocyclylalkyloxy", "non-aromatic carbocyclylalkyloxy", "aromatic heterocyclylalkyloxy", and "non-aromatic heterocyclylalkyloxy", "aromatic carbocyclylalkyloxycarbonyl", "non-aromatic carbocyclylalkyloxycarbonyl", "aromatic heterocyclylalkyloxycarbonyl", and "non-aromatic heterocyclylalkyloxycarbonyl", "aromatic carbocyclylalkyloxyalkyl", "non-aromatic carbocyclylalkyloxyalkyl", "aromatic heterocyclylalkyloxyalkyl", and "non-aromatic heterocyclylalkyloxyalkyl", and "aromatic carbocyclylalkylamino", "non-aromatic carbocyclylalkylamino", "aromatic heterocyclylalkylamino", and "non-aromatic heterocyclylalkylamino" is also the same as above "alkyl".

The term "aromatic carbocyclylalkyl" means an alkyl substituted with one or more "aromatic carbocyclyl" described above. Examples include benzyl, phenethyl, phenyl-n-propyl, benzhydryl, trityl, naphthylmethyl, and a group of the following formula:

[Chemical Formula 68]

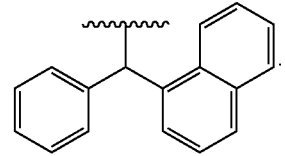

A preferred embodiment of "aromatic carbocyclylalkyl" is benzyl, phenethyl or benzhydryl.

The term "non-aromatic carbocyclylalkyl" means an alkyl substituted with one or more "non-aromatic carbocyclyl" described above. The "non-aromatic carbocyclylalkyl" also includes "non-aromatic carbocyclylalkyl" wherein the alkyl part is substituted with the above "aromatic carbocyclyl". Examples include cyclopropylmethyl, cyclobutylmethyl, cyclopenthylmethyl, cyclohexylmethyl, and a group of the following formula:

[Chemical Formula 69]

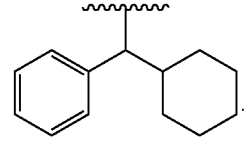

The term "aromatic heterocyclylalkyl" means an alkyl substituted with one or more "aromatic heterocyclyl" described above. The "aromatic heterocyclylalkyl" also includes "aromatic heterocyclylalkyl" wherein the alkyl part is substituted with the above "aromatic carbocyclyl" and/or "non-aromatic carbocyclyl". Examples include pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrrolidinylmethyl, benzoxazolylmethyl, and groups of the following formulae:

[Chemical Formula 70]

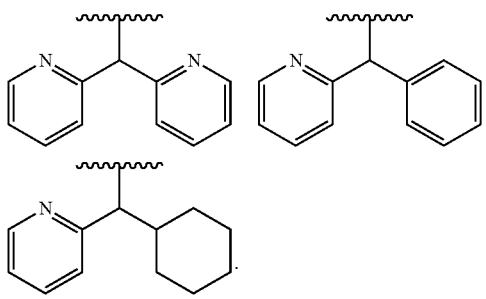

The term "non-aromatic heterocyclylalkyl" means an alkyl substituted with one or more "non-aromatic heterocyclyl" described above. The "non-aromatic heterocyclylalkyl" also includes "non-aromatic heterocyclylalkyl" wherein the alkyl part is substituted with the above "aromatic carbocyclyl", "non-aromatic carbocyclyl" and/or "aromatic heterocyclyl". Examples include tetrahydropyranylmethyl, morpholinylethyl, piperidinylmethyl, piperazinylmethyl, and groups of the following formulae:

[Chemical Formula 71]

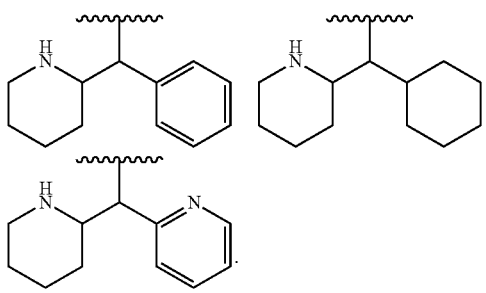

The term "aromatic carbocyclylalkyloxy" means an alkyloxy substituted with one or more "aromatic carbocyclyl" described above. Examples include benzyloxy, phenethyloxy, phenyl-n-propyloxy, benzhydryloxy, trityloxy, naphthylmethyloxy, and a group of the following formula:

[Chemical Formula 72]

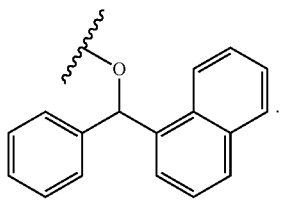

The term "non-aromatic carbocyclylalkyloxy" means an alkyloxy substituted with one or more "non-aromatic carbocyclyl" described above. The "non-aromatic carbocyclylalkyloxy" also includes "non-aromatic carbocyclylalkyloxy" wherein the alkyl part is substituted with the above "aromatic carbocyclyl". Examples include cyclopropylmethyloxy, cyclobutylmethyloxy, cyclopentylmethyloxy, cyclohexylmethyloxy, and a group of the following formula:

[Chemical Formula 73]

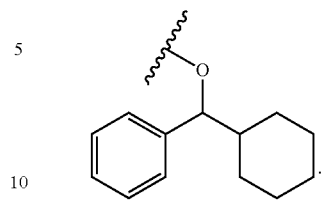

The term "aromatic heterocyclylalkyloxy" means an alkyloxy substituted with one or more "aromatic heterocyclyl" described above. The "aromatic heterocyclylalkyloxy" also includes "aromatic heterocyclylalkyloxy" wherein the alkyl part is substituted with the above "aromatic carbocyclyl" and/or "non-aromatic carbocyclyl". Examples include pyridylmethyloxy, furanylmethyloxy, imidazolylmethyloxy, indolylmethyloxy, benzothiophenylmethyloxy, oxazolylmethyloxy, isoxazolylmethyloxy, thiazolylmethyloxy, isothiazolylmethyloxy, pyrazolylmethyloxy, isopyrazolylmethyloxy, pyrrolidinylmethyloxy, benzoxazolylmethyloxy, and groups of the following formulae:

[Chemical Formula 74]

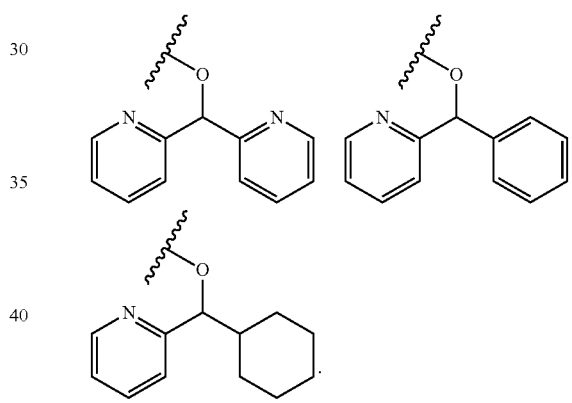

The term "non-aromatic heterocyclylalkyloxy" means an alkyloxy substituted with one or more "non-aromatic heterocyclyl" described above. The "non-aromatic heterocyclylalkyloxy" also includes "non-aromatic heterocyclylalkyloxy" wherein the alkyl part is substituted with the above "aromatic carbocyclyl", "non-aromatic carbocyclyl" and/or "aromatic heterocyclyl". Examples include tetrahydropyranylmethyloxy, morpholinylmethyloxy, morpholinylethyloxy, piperidinylmethyloxy, piperazinylmethyloxy, and groups of the following formulae:

[Chemical Formula 75]

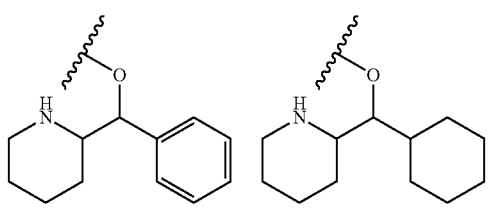

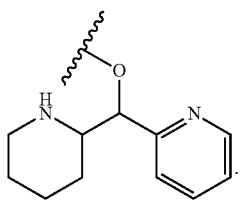

The term "aromatic carbocyclylalkyloxycarbonyl" means an alkyloxycarbonyl substituted with one or more "aromatic carbocyclyl" described above. Examples include benzyloxycarbonyl, phenethyloxycarbonyl, phenyl-n-propyloxycarbonyl, benzhydryloxycarbonyl, trityloxycarbonyl, naphthylmethyloxycarbonyl, and a group of the following formula:

[Chemical Formula 76]

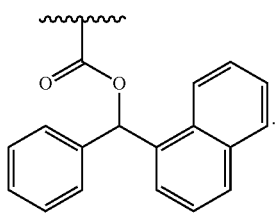

The term "non-aromatic carbocyclylalkyloxycarbonyl" means an alkyloxycarbonyl substituted with one or more "non-aromatic carbocyclyl" described above. The "non-aromatic carbocyclylalkyloxycarbonyl" also includes "non-aromatic carbocyclylalkyloxycarbonyl" wherein the alkyl part is substituted with the above "aromatic carbocyclyl". Examples include cyclopropylmethyloxycarbonyl, cyclobutylmethyloxycarbonyl, cyclopenthylmethyloxycarbonyl, cyclohexylmethyloxycarbonyl, and a group of the following formula:

[Chemical Formula 77]

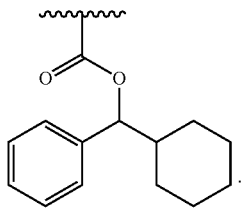

The term "aromatic heterocyclylalkyloxycarbonyl" means an alkyloxycarbonyl substituted with one or more "aromatic heterocyclyl" described above. The "aromatic heterocyclylalkyloxycarbonyl" also include "aromatic heterocyclylalkyloxycarbonyl" wherein the alkyl part is substituted with the above "aromatic carbocyclyl" and/or "non-aromatic carbocyclyl". Examples include pyridylmethyloxycarbonyl, furanylmethyloxycarbonyl, imidazolylmethyloxycarbonyl, indolylmethyloxycarbonyl, benzothiophenylmethyloxycarbonyl, oxazolylmethyloxycarbonyl, isoxazolylmethyloxycarbonyl, thiazolylmethyloxycarbonyl, isothiazolylmethyloxycarbonyl, pyrazolylmethyloxycarbonyl, isopyrazolylmethyloxycarbonyl, pyrrolidinylmethyloxycarbonyl, benzoxazolylmethyloxycarbonyl, and groups of the following formulae:

[Chemical Formula 78]

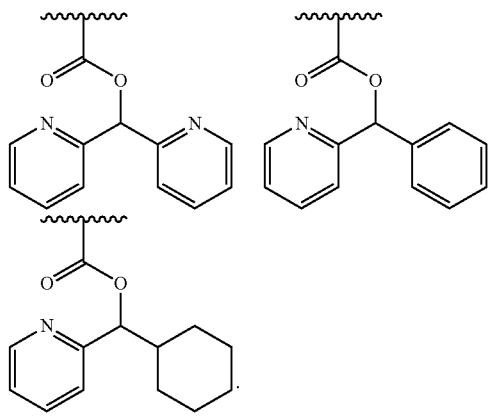

The term "non-aromatic heterocyclylalkyloxycarbonyl" means an alkyloxycarbonyl substituted with one or more "non-aromatic heterocyclyl" described above. The "non-aromatic heterocyclylalkyloxycarbonyl" also includes "non-aromatic heterocyclylalkyloxycarbonyl" wherein the alkyl part is substituted with the above "aromatic carbocyclyl", "non-aromatic carbocyclyl" and/or "aromatic heterocyclyl". Examples include tetrahydropyranylmethyloxycarbonyl, morpholinylethyloxycarbonyl, piperidinylmethyloxycarbonyl, piperazinylmethyloxycarbonyl, and groups of the following formulae:

[Chemical Formula 79]

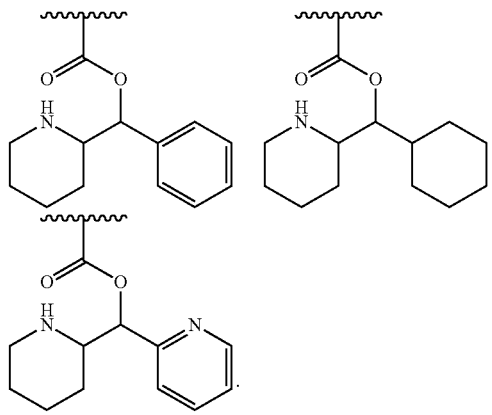

The term "aromatic carbocyclylalkyloxyalkyl" means an alkyloxyalkyl substituted with one or more "aromatic carbocyclyl" described above. Examples include benzyloxymethyl, phenethyloxymethyl, phenylpropyloxymethyl, benzhydryloxymethyl, trityloxymethyl, naphthylmethyloxymethyl, and a group of the following formula:

[Chemical Formula 80]

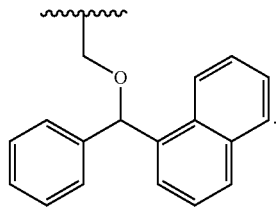

The term "non-aromatic carbocyclylalkyloxyalkyl" means an alkyloxyalkyl substituted with one or more "non-aromatic carbocyclyl" described above. The "non-aromatic carbocyclylalkyloxyalkyl" also includes "non-aromatic carbocyclylalkyloxyalkyl" wherein the alkyl part bonded to the non-aromatic carbocycle is substituted with the above "aromatic carbocyclyl". Examples include cyclopropylmethyloxymethyl, cyclobutylmethyloxymethyl, cyclopenthylmethyloxymethyl, cyclohexylmethyloxymethyl, and a group of the following formula:

[Chemical Formula 81]

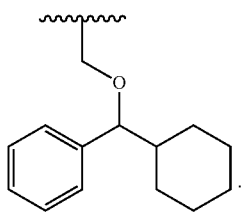

The term "aromatic heterocyclylalkyloxyalkyl" means an alkyloxyalkyl substituted with one or more "aromatic heterocyclyl" described above. The "aromatic heterocyclylalkyloxyalkyl" also includes "aromatic heterocyclylalkyloxyalkyl" wherein the alkyl part bonded to the aromatic heterocycle is substituted with the above "aromatic carbocyclyl" and/or "non-aromatic carbocyclyl". Examples include pyridylmethyloxymethyl, furanylmethyloxymethyl, imidazolylmethyloxymethyl, indolylmethyloxymethyl, benzothiophenylmethyloxymethyl, oxazolylmethyloxymethyl, isoxazolylmethyloxymethyl, thiazolylmethyloxymethyl, isothiazolylmethyloxymethyl, pyrazolylmethyloxymethyl, isopyrazolylmethyloxymethyl, pyrrolidinylmethyloxymethyl, benzoxazolylmethyloxymethyl, and groups of the following formulae:

[Chemical Formula 82]

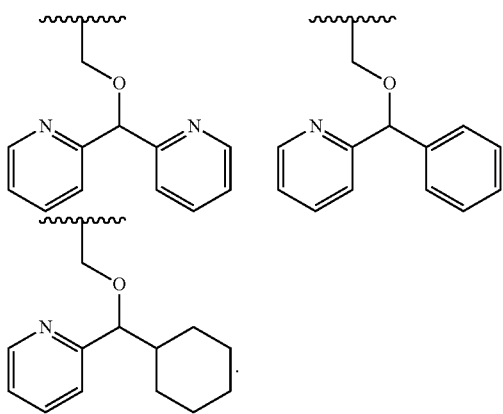

The term "non-aromatic heterocyclylalkyloxyalkyl" means an alkyloxyalkyl substituted with one or more "non-aromatic heterocyclyl" described above. The "non-aromatic heterocyclylalkyloxyalkyl" also includes "non-aromatic heterocyclylalkyloxyalkyl" wherein the alkyl part bonded to the non-aromatic heterocycle is substituted with the above "aromatic carbocyclyl", "non-aromatic carbocyclyl" and/or "aromatic heterocyclyl". Examples include tetrahydropyranylmethyloxymethyl, morpholinylmethyloxymethyl, morpholinylethyloxymethyl, piperidinylmethyloxymethyl, piperazinylmethyloxymethyl, and groups of the following formulae:

[Chemical Formula 83]

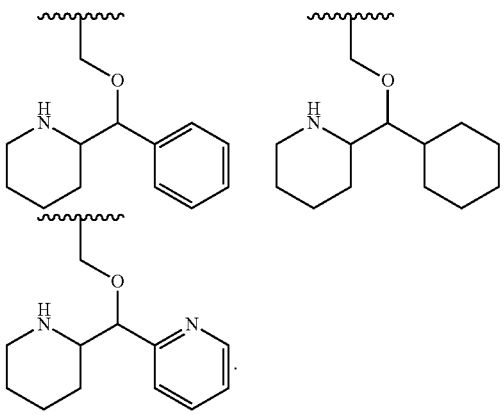

The term "aromatic carbocyclylalkylamino" means a group wherein one or two hydrogen atom(s) attached to a nitrogen atom of an amino group is(are) replaced with the above "aromatic carbocyclylalkyl". Examples include benzylamino, phenethylamino, phenylpropylamino, benzhydrylamino, tritylamino, naphthylmethylamino, and dibenzylamino.

The term "non-aromatic carbocyclylalkylamino" means a group wherein one or two hydrogen atom(s) attached to a nitrogen atom of an amino group is(are) replaced with the above "non-aromatic carbocyclylalkyl". Examples include cyclopropylmethylamino, cyclobutylmethylamino, cyclopentylmethylamino, and cyclohexylmethylamino.

The term "aromatic heterocyclylalkylamino" means a group wherein one or two hydrogen atom(s) attached to a nitrogen atom of an amino group is(are) replaced with the above "aromatic heterocyclylalkyl". Examples include pyridylmethylamino, furanylmethylamino, imidazolylmethylamino, indolylmethylamino, benzothiophenylmethylamino, oxazolylmethylamino, isoxazolylmethylamino, thiazolylmethylamino, isothiazolylmethylamino, pyrazolylmethylamino, isopyrazolylmethylamino, pyrrolylmethylamino, and benzoxazolylmethylamino.

The term "non-aromatic heterocyclylalkylamino" means a group wherein one or two hydrogen atom(s) attached to a nitrogen atom of an amino group is(are) replaced with the above "non-aromatic heterocyclylalkyl". Examples include tetrahydropyranylmethylamino, morpholinylethylamino, piperidinylmethylamino, and piperazinylmethylamino.

The aromatic carbocycle part of "aromatic carbocyclyloxy", "aromatic carbocyclylcarbonyl", "aromatic carbocyclyloxycarbonyl", "aromatic carbocyclylcarbonyloxy", "aromatic carbocyclylsulfanyl", and "aromatic carbocyclylsulfonyl" is also the same as above "aromatic carbocyclyl".

The term "aromatic carbocyclyloxy" means a group wherein the "aromatic carbocycle" is bonded to an oxygen atom. Examples include phenyloxy and naphthyloxy.

The term "aromatic carbocyclylcarbonyl" means a group wherein the "aromatic carbocycle" is bonded to a carbonyl group. Examples include phenylcarbonyl and naphthylcarbonyl.

The term "aromatic carbocyclyloxycarbonyl" means a group wherein the "aromatic carbocyclyloxy" is bonded to a carbonyl group. Examples include phenyloxycarbonyl and naphthyloxycarbonyl.

The term "aromatic carbocyclylcarbonyloxy" means a group wherein the "aromatic carbocyclylcarbonyl" is bonded to an oxygen atom. Examples include phenylcarbonyloxy and naphthylcarbonyloxy.

The term "aromatic carbocyclylsulfanyl" means a group wherein a hydrogen atom attached to a sulfur atom of a sulfanyl group is replaced with the "aromatic carbocycle". Examples include phenylsulfanyl and naphthylsulfanyl.

The term "aromatic carbocyclylsulfonyl" means a group wherein the "aromatic carbocycle" is bonded to a sulfonyl group. Examples include phenylsulfonyl and naphthylsulfonyl.

The non-aromatic carbocycle part of "non-aromatic carbocyclyloxy", "non-aromatic carbocyclylcarbonyl", "non-aromatic carbocyclyloxycarbonyl", "non-aromatic carbocyclylcarbonyloxy", "non-aromatic carbocyclylsulfanyl", and "non-aromatic carbocyclylsulfonyl" is also the same as above "non-aromatic carbocyclyl".

The term "non-aromatic carbocyclyloxy" means a group wherein the "non-aromatic carbocycle" is bonded to an oxygen atom. Examples include cyclopropyloxy, cyclohexyloxy, and cyclohexenyloxy.

The term "non-aromatic carbocyclylcarbonyl" means a group wherein the "non-aromatic carbocycle" is bonded to a carbonyl group. Examples include cyclopropylcarbonyl, cyclohexylcarbonyl, and cyclohexenylcarbonyl.

The term "non-aromatic carbocyclyloxycarbonyl" means a group wherein the "non-aromatic carbocyclyloxy" is bonded to a carbonyl group. Examples include cyclopropyloxycarbonyl, cyclohexyloxycarbonyl, and cyclohexenyloxycarbonyl.

The term "non-aromatic carbocyclylcarbonyloxy" means a group wherein the "non-aromatic carbocyclylcarbonyl" is bonded to an oxygen atom. Examples include cyclopropylcarbonyloxy, cyclohexylcarbonyloxy, and cyclohexenylcarbonyloxy.

The term "non-aromatic carbocyclylsulfanyl" means a group wherein a hydrogen atom attached to a sulfur atom of a sulfanyl group is replaced with the "non-aromatic carbocycle". Examples include cyclopropylsulfanyl, cyclohexylsulfanyl, and cyclohexenylsulfanyl.

The term "non-aromatic carbocyclylsulfonyl" means a group wherein the "non-aromatic carbocycle" is bonded to a sulfonyl group. Examples include cyclopropylsulfonyl, cyclohexylsulfonyl, and cyclohexenylsulfonyl.

The aromatic heterocycle part of "aromatic heterocyclyloxy", "aromatic heterocyclylcarbonyl", "aromatic heterocyclyloxycarbonyl", "aromatic heterocyclylcarbonyloxy", "aromatic heterocyclylsulfanyl", and "aromatic heterocyclylsulfonyl" is also the same as above "aromatic heterocyclyl".

The term "aromatic heterocyclyloxy" means a group wherein the "aromatic heterocycle" is bonded to an oxygen atom. Examples include pyridyloxy and oxazolyloxy.

The term "aromatic heterocyclylcarbonyl" means a group wherein the "aromatic heterocycle" is bonded to a carbonyl group. Examples include pyridylcarbonyl and oxazolylcarbonyl.

The term "aromatic heterocyclyloxycarbonyl" means a group wherein the "aromatic heterocyclyloxy" is bonded to a carbonyl group. Examples include pyridyloxycarbonyl and oxazolyloxycarbonyl.

The term "aromatic heterocyclylcarbonyloxy" means a group wherein the "aromatic heterocyclylcarbonyl" is bonded to an oxygen atom. Examples include pyridylcarbonyloxy, and oxazolylcarbonyloxy.

The term "aromatic heterocyclylsulfanyl" means a group wherein a hydrogen atom attached to a sulfur atom of a sulfanyl group is replaced with the "aromatic heterocycle". Examples include pyridylsulfanyl and oxazolylsulfanyl.

The term "aromatic heterocyclylsulfonyl" means a group wherein the "aromatic heterocycle" is bonded to a sulfonyl group. Examples include pyridylsulfonyl and oxazolylsulfonyl.

The non-aromatic heterocycle part of "non-aromatic heterocyclyloxy", "non-aromatic heterocyclylcarbonyl", "non-aromatic heterocyclyloxycarbonyl", "non-aromatic heterocyclylcarbonyloxy", "non-aromatic heterocyclylsulfanyl", and "non-aromatic heterocyclylsulfonyl" is also the same as above "non-aromatic heterocyclyl".

The term "non-aromatic heterocyclyloxy" means a group wherein the "non-aromatic heterocycle" is bonded to an oxygen atom. Examples include piperidinyloxy and tetrahydrofuryloxy.

The term "non-aromatic heterocyclylcarbonyl" means a group wherein the "non-aromatic heterocycle" is bonded to a carbonyl group. Examples include piperidinylcarbonyl, and tetrahydrofurylcarbonyl.

The term "non-aromatic heterocyclyloxycarbonyl" means a group wherein the "non-aromatic heterocyclyloxy" is bonded to a carbonyl group. Examples include piperidinyloxycarbonyl, and tetrahydrofuryloxycarbonyl.

The term "non-aromatic heterocyclylcarbonyloxy" means a group wherein the "non-aromatic heterocyclylcarbonyl" is bonded to an oxygen atom. Examples include piperidinylcarbonyloxy and tetrahydrofurylcarbonyloxy.

The term "non-aromatic heterocyclylsulfanyl" means a group wherein a hydrogen atom attached to a sulfur atom of a sulfanyl group is replaced with the "non-aromatic heterocycle". Examples include piperidinylsulfanyl and tetrahydrofurylsulfanyl.

The term "non-aromatic heterocyclylsulfonyl" means a group wherein the "non-aromatic heterocycle" is bonded to a sulfonyl group. Examples include piperidinylsulfonyl and tetrahydrofuryl sulfonyl.

The term "acyl" includes "formyl", "alkylcarbonyl", "alkenylcarbonyl", "alkynylcarbonyl", "aromatic heterocyclylcarbonyl", "non-aromatic heterocyclylcarbonyl", "aromatic carbocyclylcarbonyl" and "non-aromatic carbocyclylcarbonyl".

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylcarbonyl", "substituted or unsubstituted alkenylcarbonyl", "substituted or unsubstituted alkynylcarbonyl", "substituted or unsubstituted alkylamino", "substituted or unsubstituted alkenylamino", "substituted or unsubstituted alkynylamino", "substituted or unsubstituted alkyl sulfonyl", "substituted or unsubstituted alkenyl sulfonyl", "substituted or unsubstituted alkynylsulfonyl", "substituted or unsubstituted alkylcarbonylamino", "substituted or unsubstituted alkenylcarbonylamino", "substituted or unsubstituted alkynylcarbonylamino", "substituted or unsubstituted alkyl sulfonylamino", "substituted or unsubstituted alkenyl sulfonylamino", "substituted or unsubstituted alkynylsulfonylamino", "substituted or unsubstituted alkylimino", "substituted or unsubstituted alkenylimino", "substituted or unsubstituted alkynylimino", "substituted or unsubstituted alkylcarbonylimino", "substituted or unsubstituted alkenylcarbonylimino", "substituted or unsubstituted alkynylcarbonylimino", "substituted or unsubstituted alkyloxyimino", "substituted or unsubstituted alkenyloxyimino", "substituted or unsubstituted alkynyloxyimino", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfanyl", "substituted or unsubstituted alkenylsulfanyl", "substituted or unsubstituted alkynylsulfanyl", "substituted or unsubstituted alkylsulfinyl", "substituted or unsubstituted alkenylsulfinyl", "substituted or unsubstituted alkynylsulfinyl", "substituted or unsubstituted carbamoyl", "substituted or unsubstituted alkylcarbamoyl", "substituted or unsubstituted alkenylcarbamoyl", "substituted or unsubstituted alkynylcarbamoyl", "substituted or unsubstituted sulfamoyl", "substituted or unsubstituted alkyl sulfamoyl", "substituted or unsubstituted alkenyl sulfamoyl" and "substituted or unsubstituted alkynylsulfamoyl" include the following substituents. A carbon atom at any positions may be bonded to one or more group(s) selected from the following substituents.

A substituent: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azido, hydrazino, ureido, amidino, guanidino, trialkylsilyl, alkyloxy, alkenyloxy, alkynyloxy, haloalkyloxy, alkylcarbonyl, alkenylcarbonyl, alkynylcarbonyl, alkylamino, alkenylamino, alkynylamino, alkyl sulfonyl, alkenyl sulfonyl, alkynylsulfonyl, alkylcarbonylamino, alkenylcarbonylamino, alkynylcarbonylamino, alkylsulfonylamino, alkenylsulfonylamino, alkynylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, alkylcarbamoyl, alkenylcarbamoyl, alkynylcarbamoyl, alkyl sulfamoyl, alkenyl sulfamoyl, alkynylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl, and non-aromatic heterocyclylsulfonyl.

The substituents on the ring of "aromatic carbocycle", "non-aromatic carbocycle", "aromatic heterocycle", and "non-aromatic heterocycle" part of "substituted or unsubstituted aromatic carbocyclyl", "substituted or unsubstituted non-aromatic carbocyclyl", "substituted or unsubstituted aromatic heterocyclyl", "substituted or unsubstituted 9- to 10-membered bicyclic aromatic heterocyclyl", "substituted or unsubstituted non-aromatic heterocyclyl", and "substituted or unsubstituted 9- to 10-membered bicyclic non-aromatic heterocyclyl", "substituted or unsubstituted aromatic carbocyclyloxy", "substituted or unsubstituted non-aromatic carbocyclyloxy", "substituted or unsubstituted aromatic heterocyclyloxy", and "substituted or unsubstituted non-aromatic heterocyclyloxy", "substituted or unsubstituted aromatic carbocyclylcarbonyl", "substituted or unsubstituted non-aromatic carbocyclylcarbonyl", "substituted or unsubstituted aromatic heterocyclylcarbonyl", and "substituted or unsubstituted non-aromatic heterocyclylcarbonyl", "substituted or unsubstituted aromatic carbocyclyloxycarbonyl", "substituted or unsubstituted non-aromatic carbocyclyloxycarbonyl", "substituted or unsubstituted aromatic heterocyclyloxycarbonyl", and "substituted or unsubstituted non-aromatic heterocyclyloxycarbonyl", "substituted or unsubstituted aromatic carbocyclylsulfanyl", "substituted or unsubstituted non-aromatic carbocyclylsulfanyl", "substituted or unsubstituted aromatic heterocyclylsulfanyl", and "substituted or unsubstituted non-aromatic heterocyclylsulfanyl", and "substituted or unsubstituted aromatic carbocyclylsulfonyl", "substituted or unsubstituted non-aromatic carbocyclylsulfonyl", "substituted or unsubstituted aromatic heterocyclylsulfonyl", and "substituted or unsubstituted non-aromatic heterocyclylsulfonyl" include the following substituents. An atom at any position(s) on the ring may be bonded to one or more group(s) selected from the following substituents.

A substituent: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azido, hydrazino, ureido, amidino, guanidino, trialkylsilyl, alkyl, alkenyl, alkynyl, haloalkyl, alkyloxy, alkenyloxy, alkynyloxy, haloalkyloxy, alkyloxyalkyl, alkyloxyalkyloxy, alkylcarbonyl, alkenylcarbonyl, alkynylcarbonyl, alkylamino, alkenylamino, alkynylamino, alkyl sulfonyl, alkenyl sulfonyl, alkynylsulfonyl, alkylcarbonylamino, alkenylcarbonylamino, alkynylcarbonylamino, alkylsulfonylamino, alkenylsulfonylamino, alkynylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, alkylcarbamoyl, alkenylcarbamoyl, alkynylcarbamoyl, alkylsulfamoyl, alkenylsulfamoyl, alkynylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyl, non-aromatic carbocyclylalkyl, aromatic heterocyclylalkyl, non-aromatic heterocyclylalkyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkyloxyalkyl, non-aromatic carbocyclylalkyloxyalkyl, aromatic heterocyclylalkyloxyalkyl, non-aromatic heterocyclylalkyloxyalkyl, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl, and non-aromatic heterocyclylsulfonyl.

Additionally, "substituted or unsubstituted non-aromatic carbocyclyl" and "substituted or unsubstituted non-aromatic heterocyclyl" may be substituted with "oxo". In this case, it means a group wherein two hydrogen atoms on the same carbon atom are substituted as below.

[Chemical Formula 84]

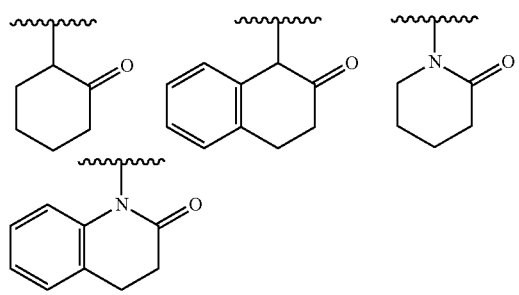

The non-aromatic carbocycle or non-aromatic heterocycle part of the above "substituted or unsubstituted non-aromatic carbocyclyloxy", "substituted or unsubstituted non-aromatic heterocyclyloxy", "substituted or unsubstituted non-aromatic carbocyclylcarbonyl", "substituted or unsubstituted non-aromatic heterocyclylcarbonyl", "substituted or unsubstituted non-aromatic carbocyclyloxycarbonyl", "substituted or unsubstituted non-aromatic heterocyclyloxycarbonyl", "substituted or unsubstituted non-aromatic carbocyclylsulfanyl", "substituted or unsubstituted non-aromatic heterocyclylsulfanyl", "substituted or unsubstituted non-aromatic carbocyclylsulfonyl", and "substituted or unsubstituted non-aromatic heterocyclylsulfonyl" may be substituted with "oxo" as described above.

The substituent of "substituted or unsubstituted alkyl" in R' includes, for example, unsubstituted alkyloxy or substituted alkyloxy (substituent: halogen).

An example includes methoxyethyl.

The substituent of "substituted or unsubstituted aromatic carbocyclyl" in B includes, for example,
halogen.

The substituent of "substituted or unsubstituted aromatic heterocyclyl" in B includes, for example,
halogen.

The substituent of "substituted or unsubstituted aromatic carbocyclyl" in $R^{14}$ includes, for example,
hydroxy;
carboxy;
halogen;
alkyl;
alkyloxy;
cyano; and
unsubstituted carbamoyl or substituted carbamoyl (substituent: non-aromatic heterocyclyl, alkyl, benzyl).

The substituent of "substituted or unsubstituted aromatic heterocyclyl" in $R^{14}$ includes, for example,
carboxy;
halogen;
cyano;
hydroxy;
unsubstituted alkyl or substituted alkyl (substituent: hydroxy, halogen);
unsubstituted carbamoyl or substituted carbamoyl (substituent: haloalkyl, alkyl, non-aromatic heterocyclyl, non-aromatic carbocyclyl, hydroxyalkyl, hydroxy, alkyloxy, cyano, alkyl sulfonyl, alkyloxycarbonyl, alkylcarbamoyl, carbamoyl);
unsubstituted alkyloxy or substituted alkyloxy (substituent: phenyl, hydroxy, alkyloxy, halogen);
unsubstituted alkyloxycarbonyl or substituted alkyloxycarbonyl (substituent: halogen); substituted sulfinylimino (substituent: alkyl); and
unsubstituted non-aromatic heterocyclyl or substituted non-aromatic heterocyclyl (substituent: hydroxy).

The substituent of "substituted or unsubstituted non-aromatic heterocyclyl" in $R^{14}$ includes, for example,
halogen;
hydroxy;
alkyloxy;
oxo;
carboxy;
cyano;
unsubstituted carbamoyl or substituted carbamoyl (substituent: alkyl, hydroxyalkyl, alkyloxy, benzyloxy, hydroxy, non-aromatic heterocyclyl, non-aromatic carbocyclyl);
unsubstituted alkyl or substituted alkyl (substituent: alkyloxy);
unsubstituted alkyloxycarbonyl or substituted alkyloxycarbonyl (substituent: halogen); and
unsubstituted sulfamoyl or substituted sulfamoyl (substituent: alkyl).

The substituent of "substituted or unsubstituted 9- to 10-membered bicyclic aromatic heterocyclyl" in $R^{14}$ includes, for example,
alkyl;
alkyloxycarbonyl;
hydroxyalkyl;
alkyloxy;
alkylsulfinylimino;
hydroxy;
halogen;
cyano; and
carboxy.

The substituent of "substituted or unsubstituted 9- to 10-membered bicyclic aromatic heterocyclyl" in $R^{14}$ includes, for example,
oxo;
alkyl;
hydroxy;
halogen;
cyano;
carboxy; and
alkyloxy.

The substituent of "substituted or unsubstituted alkyloxy" in $R^{14}$ includes, for example, hydroxy.

Exemplified embodiments of the present invention are:
A compound represented by Formula (I'-A):

[Chemical Formula 85]

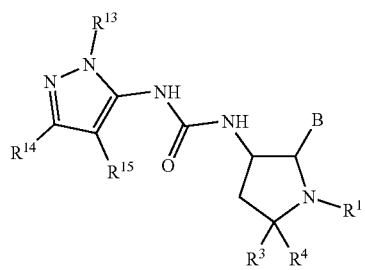

(I'-A)

or a pharmaceutically acceptable salt thereof.

Specific examples of each symbol include the following. Examples of the compound represented by Formula (I'-A) include all possible combinations of these specific examples. It is noted that when B is any one of D-4, D-5, D-6 and D-7, R14 is selected from E-1, E-2, E-3, E-4 and E-11. Besides, the following compounds are excluded:

[Chemical Formula 86]

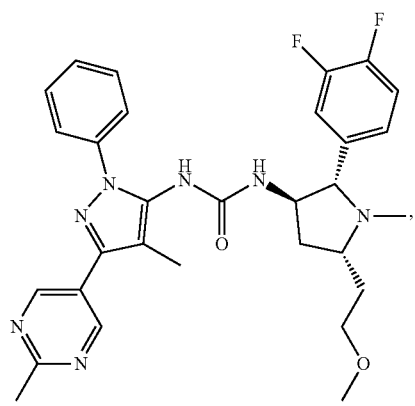

and

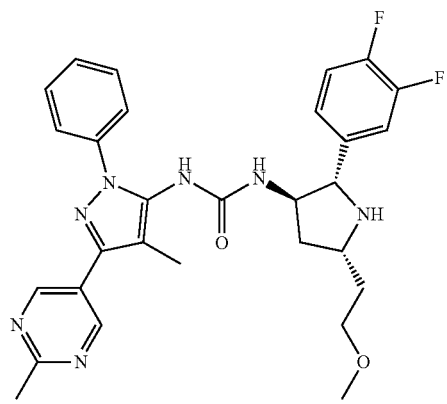

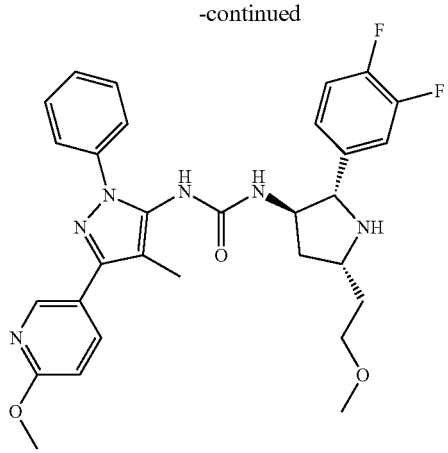

$R^1$ can be a hydrogen atom, or substituted or unsubstituted alkyl. (hereinafter referred to as A-1)

$R^1$ can be substituted or unsubstituted alkyl. (hereinafter referred to as A-2)

$R^1$ can be substituted or unsubstituted C1-C3 alkyl. (hereinafter referred to as A-3)

$R^1$ can be substituted or unsubstituted methyl. (hereinafter referred to as A-4)

$R^1$ can be unsubstituted methyl. (hereinafter referred to as A-5)

$R^3$ can be alkyl substituted with alkyloxy. (hereinafter referred to as B-1)

$R^3$ can be ethyl substituted with methyloxy. (hereinafter referred to as B-2)

$R^4$ can be a hydrogen atom, or substituted or unsubstituted alkyl. (hereinafter referred to as C-1)

$R^4$ can be a hydrogen atom. (hereinafter referred to as C-2)

B can be a group represented by the following formula:

[Chemical Formula 87]

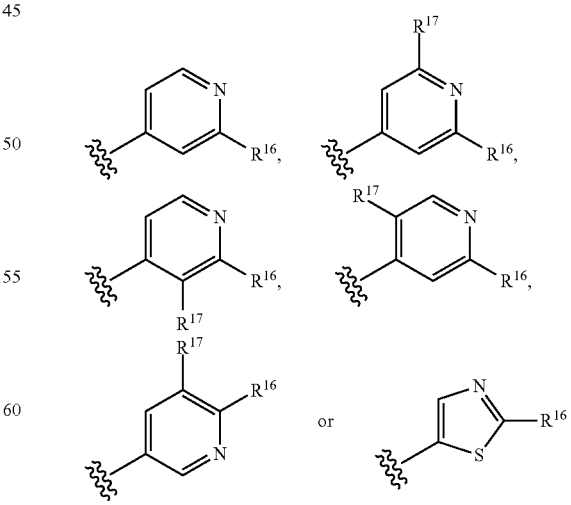

wherein $R^{16}$ and $F^{17}$ are each independently halogen. (hereinafter referred to as D-1)

B can be a group represented by the following formula:

[Chemical Formula 88]

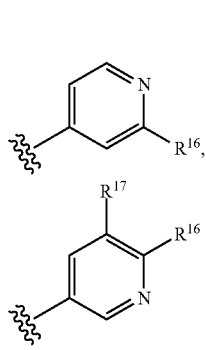

wherein $R^{16}$ and $R^{17}$ are each independently halogen. (hereinafter referred to as D-2)

B can be a group represented by the following formula:

[Chemical Formula 89]

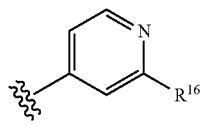

wherein $R^{16}$ is halogen. (hereinafter referred to as D-3)

B can be substituted or unsubstituted aromatic carbocyclyl. (hereinafter referred to as D-4)

B can be aromatic carbocyclyl substituted with halogen, or unsubstituted aromatic carbocyclyl. (hereinafter referred to as D-5)

B can be aromatic carbocyclyl substituted with halogen. (hereinafter referred to as D-6)

B can be unsubstituted aromatic carbocyclyl. (hereinafter referred to as D-7)

$R^{14}$ can be substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 90]

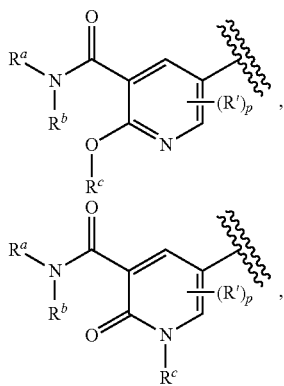

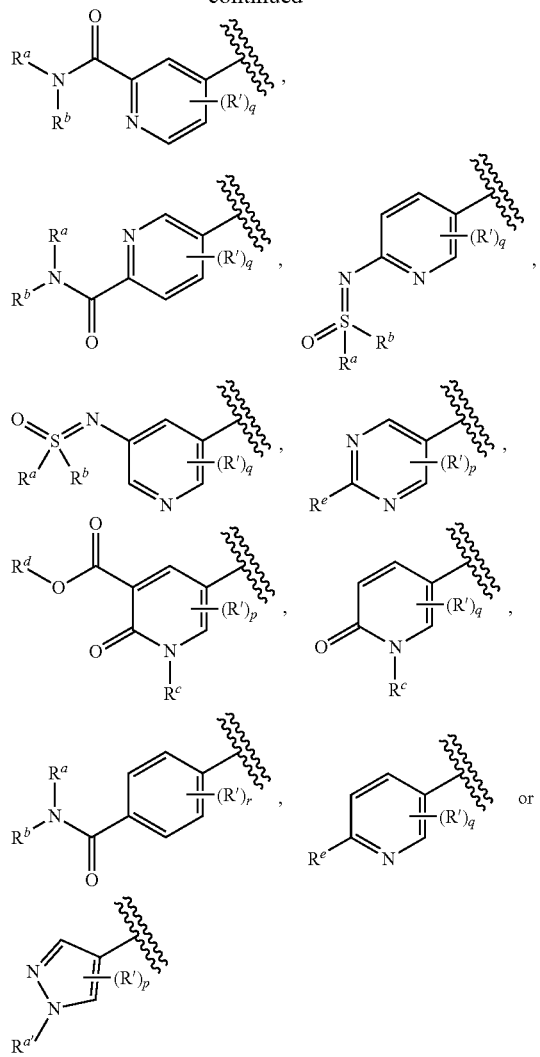

(hereinafter referred to as E-1)

Here, specific examples of $R^a$, $R^{a'}$, $R^b$, $R^e$, $R^d$, $R^e$, R', p, q and r are as follows:

$R^a$ and $R^b$ can be each independently a hydrogen atom, hydroxy, substituted or unsubstituted alkyl, substituted or unsubstituted alkyloxy, substituted or unsubstituted non-aromatic carbocyclyl, or substituted or unsubstituted non-aromatic heterocyclyl. (hereinafter referred to as e-1-1)

$R^a$ and $R^b$ can be each independently a hydrogen atom, substituted or unsubstituted alkyl, substituted or unsubstituted non-aromatic carbocyclyl, or substituted or unsubstituted non-aromatic heterocyclyl. (hereinafter referred to as e-1-2)

$R^a$ and $R^b$ can be each independently a hydrogen atom, or substituted or unsubstituted non-aromatic heterocyclyl. (hereinafter referred to as e-1-3)

$R^a$ and $R^b$ can be each independently a hydrogen atom, or non-aromatic heterocyclyl substituted with alkyl. (hereinafter referred to as e-1-4)

$R^{a'}$ can be substituted or unsubstituted alkyl (excluding unsubstituted methyl), substituted or unsubstituted non-aromatic carbocyclyl, or substituted or unsubstituted non-aromatic heterocyclyl. (hereinafter referred to as e-2)

$R^c$ can be substituted or unsubstituted alkyl. (hereinafter referred to as e-3)

$R^d$ can be a hydrogen atom, or substituted or unsubstituted alkyl. (hereinafter referred to as e-4)

$R^e$ can be substituted or unsubstituted alkyl, substituted or unsubstituted alkyloxy, substituted or unsubstituted amino, substituted or unsubstituted non-aromatic carbocyclyl, or substituted or unsubstituted non-aromatic heterocyclyl. (hereinafter referred to as e-5-1)

$R^e$ can be substituted or unsubstituted alkyl, substituted or unsubstituted non-aromatic alkyloxy, or substituted or unsubstituted non-aromatic heterocyclyl. (hereinafter referred to as e-5-2)

R' can be each independently halogen or substituted or unsubstituted alkyl. (hereinafter referred to as e-6)

p can be 0 or 1. (hereinafter referred to as e-7)

q can be 0 or 1. (hereinafter referred to as e-8)

r can be 0 or 1. (hereinafter referred to as e-9)

$R^{14}$ can be substituted or unsubstituted 9- to 10-membered bicyclic aromatic heterocyclyl. (hereinafter referred to as E-2)

$R^{14}$ can be substituted or unsubstituted 9- to 10-membered bicyclic non-aromatic heterocyclyl. (hereinafter referred to as E-3)

$R^{14}$ can be substituted or unsubstituted tetrahydropyridinyl;
substituted or unsubstituted triazolopyrimidinyl;
substituted or unsubstituted triazolopyridinyl;
substituted or unsubstituted pyrazolopyridinyl;
substituted or unsubstituted oxazolopyridinyl;
substituted or unsubstituted isoxazolopyridinyl;
substituted or unsubstituted imidazopyridinyl;
substituted or unsubstituted dihydropyridinyl;
substituted or unsubstituted dihydropyrazolopyridinyl;
substituted or unsubstituted pyridopyrazinyl;
substituted or unsubstituted naphthyridinyl;
substituted or unsubstituted pyrrolopyrazolyl;
substituted or unsubstituted furopyridinyl;
substituted or unsubstituted dihydrobenzisothiazole dioxide-yl;
substituted or unsubstituted pyridooxazinyl;
substituted or unsubstituted pyrrolopyridinyl;
substituted or unsubstituted dihydropyridazinyl;
substituted or unsubstituted dihydroimidazopyridinyl;
substituted or unsubstituted dihydrooxazolopyridinyl;
substituted or unsubstituted dihydronaphthyridinyl;
substituted or unsubstituted tetrahydropyrrolopyrazolyl;
substituted or unsubstituted dihydrofuropyridinyl;
substituted or unsubstituted dihydroisoxazolopyridinyl;
substituted or unsubstituted dihydropyridooxazinyl; or
substituted or unsubstituted dihydropyrrolopyridinyl. (hereinafter referred to as E-4)

$R^{14}$ can be substituted or unsubstituted aromatic heterocyclyl. (hereinafter referred to as E-5)

$R^{14}$ can be substituted or unsubstituted pyrazolyl. (hereinafter referred to as E-6)

$R^{14}$ can be pyrazolyl substituted with alkyl. (hereinafter referred to as E-7)

$R^{14}$ can be substituted or unsubstituted pyrimidyl. (hereinafter referred to as E-8)

$R^{14}$ can be pyrimidyl substituted with alkyl. (hereinafter referred to as E-9)

$R^{14}$ can be pyrimidyl substituted with alkyloxy. (hereinafter referred to as E-10)

$R^{14}$ can be a group represented by the following formula:

[Chemical Formula 91]

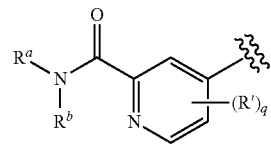

(hereinafter referred to as E-11)

Here, specific examples of $R^a$, $R^b$, R' and q are as follows:

$R^a$ and $R^b$ can be each independently a hydrogen atom, or substituted or unsubstituted non-aromatic heterocyclyl. (hereinafter referred to as e-10-1)

$R^a$ and $R^b$ can be each independently a hydrogen atom, or non-aromatic heterocyclyl substituted with alkyl. (hereinafter referred to as e-10-2)

R' can be each independently halogen, or substituted or unsubstituted alkyl. (hereinafter referred to as e-11)

q can be 0 or 1. (hereinafter referred to as e-12)

$R^{13}$ can be substituted or unsubstituted aromatic carbocyclyl, or substituted or unsubstituted non-aromatic carbocyclyl. (hereinafter referred to as F-1)

$R^{13}$ can be substituted or unsubstituted aromatic carbocyclyl. (hereinafter referred to as F-2)

$R^{13}$ can be substituted or unsubstituted phenyl. (hereinafter referred to as F-3)

$R^{15}$ can be a hydrogen atom, or substituted or unsubstituted alkyl. (hereinafter referred to as G-1)

$R^{15}$ can be substituted or unsubstituted alkyl. (hereinafter referred to as G-2)

$R^{15}$ can be substituted or unsubstituted methyl. (hereinafter referred to as G-3)

A compound represented by Formula (I"-A):

[Chemical Formula 92]

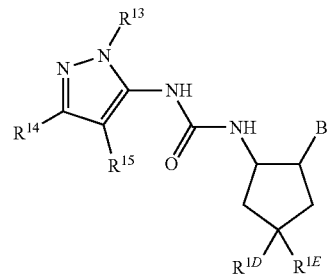

or a pharmaceutically acceptable salt thereof.

Specific examples of each symbol include the following. Examples of the compound represented by Formula (I"-A) include all possible combinations of these specific examples.

It is noted that when B is any one of DD-4, DD-5, DD-6 and DD-7, $R^{14}$ is selected from EE-1, EE-2, EE-3, EE-4 and EE-12. Besides, the following compounds are excluded:

83
[Chemical Formula 93]
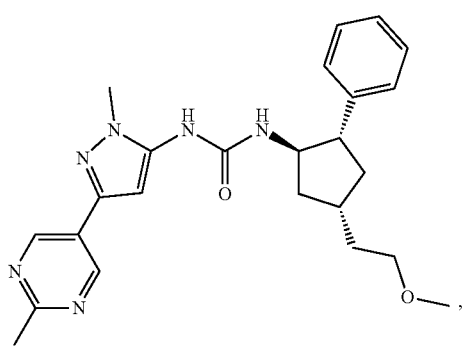
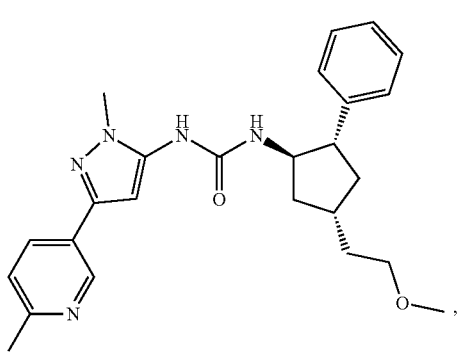
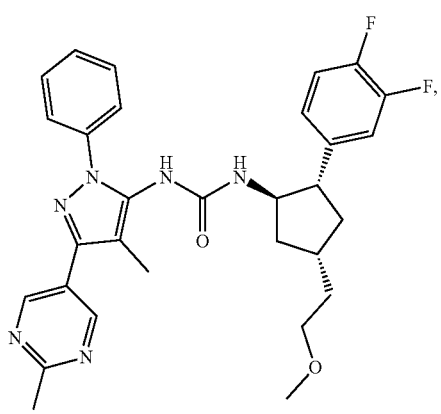
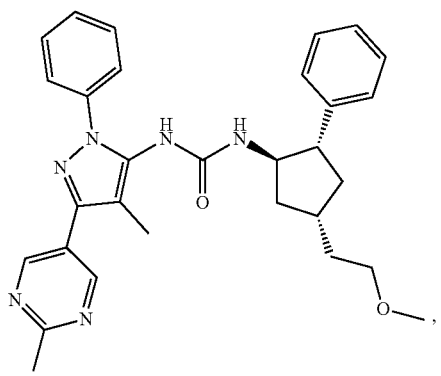
84
-continued
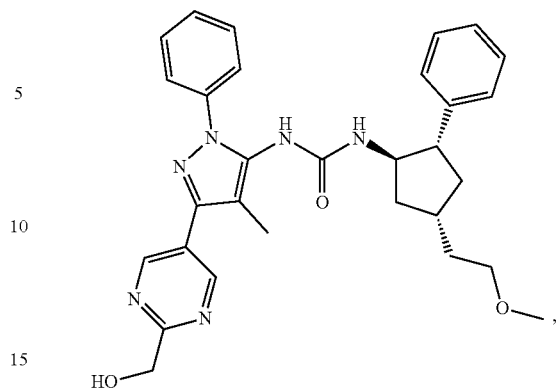
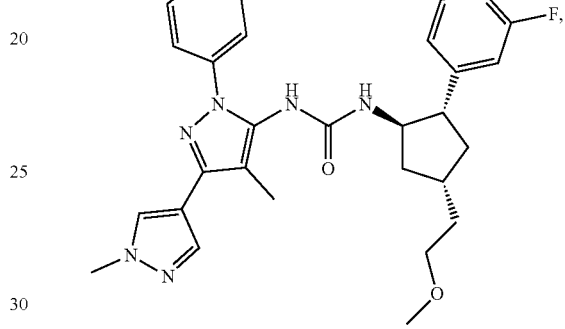
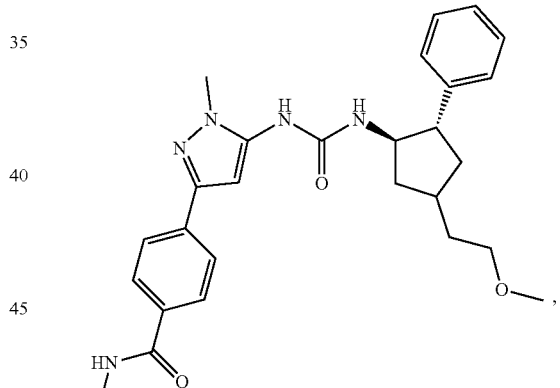
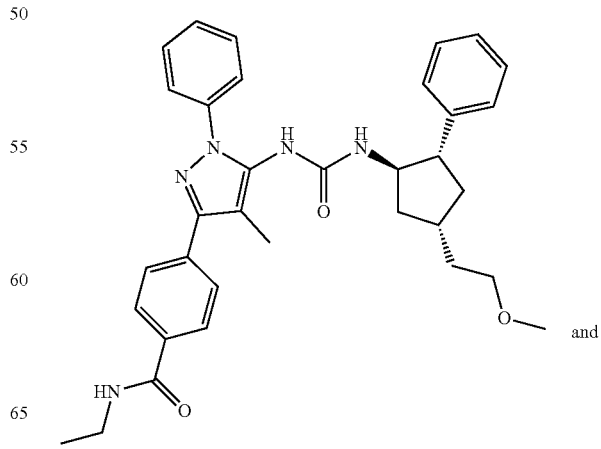
and

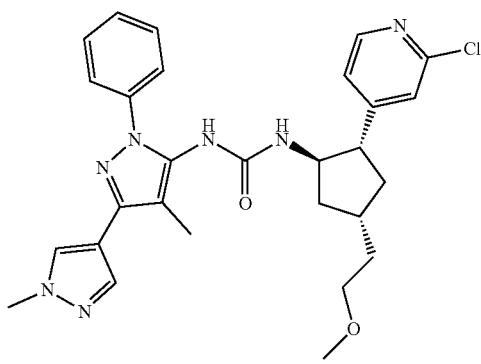 [SMILES: COCC[C@@H]1C[C@@H](NC(=O)Nc2c(C)c(-c3cnn(C)c3)nn2-c2ccccc2)[C@H](c2ccnc(Cl)c2)C1]

$R^{1D}$ can be alkyl substituted with alkyloxy. (hereinafter referred to as AA-1)

$R^{1D}$ can be ethyl substituted with methyloxy. (hereinafter referred to as AA-2)

$R^{1E}$ can be a hydrogen atom, or substituted or unsubstituted alkyl. (hereinafter referred to as BB-1)

$R^{1E}$ can be a hydrogen atom. (hereinafter referred to as BB-2)

B can be a group represented by the following formula:

[Chemical Formula 94]

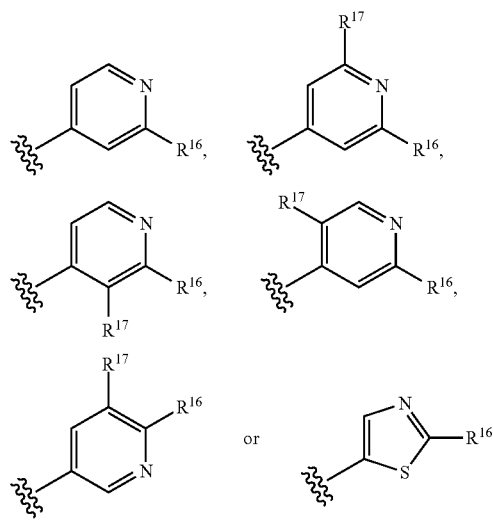

wherein $R^{16}$ and $R^{17}$ are each independently halogen. (hereinafter referred to as DD-1)

B can be a group represented by the following formula:

[Chemical Formula 95]

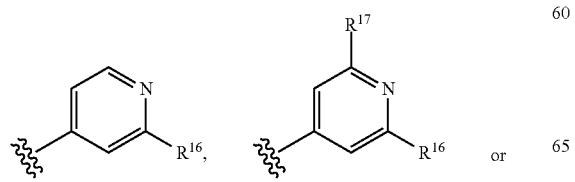

wherein $R^{16}$ and $R^{17}$ are each independently halogen. (hereinafter referred to as DD-2)

B can be a group represented by the following formula:

[Chemical Formula 96]

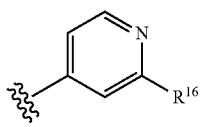

wherein $R^{16}$ is halogen. (hereinafter referred to as DD-3)

B can be substituted or unsubstituted aromatic carbocyclyl. (hereinafter referred to as DD-4)

B can be aromatic carbocyclyl substituted with halogen, or unsubstituted aromatic carbocyclyl. (hereinafter referred to as DD-5)

B can be aromatic carbocyclyl substituted with halogen. (hereinafter referred to as DD-6)

B can be unsubstituted aromatic carbocyclyl. (hereinafter referred to as DD-7)

$R^{14}$ can be substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 97]

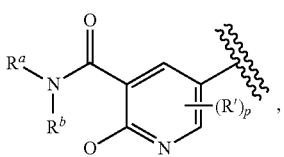

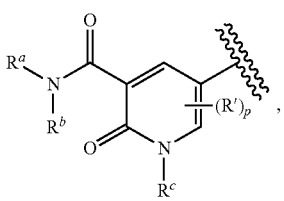

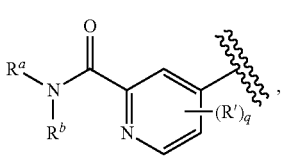

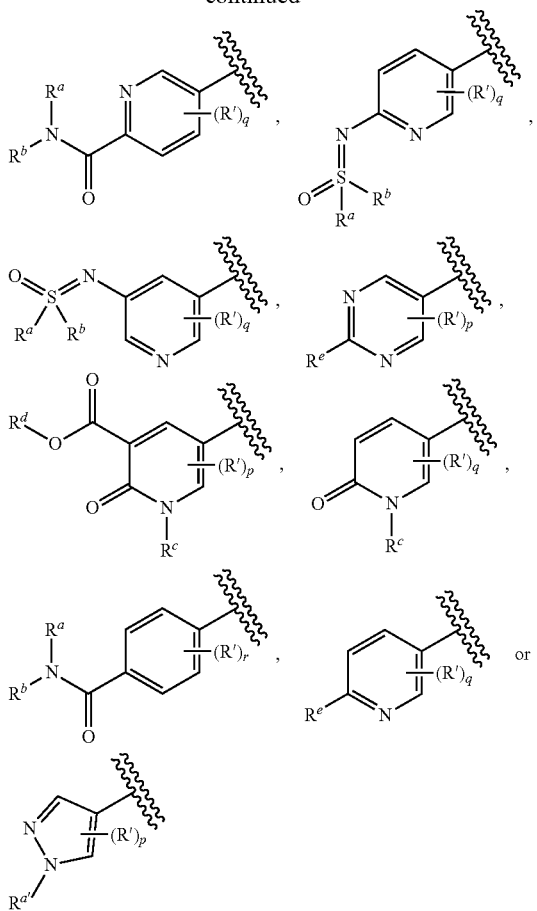

(hereinafter referred to as EE-1)

Here, specific examples of $R^a$, $R^{a'}$, $R^b$, $R^c$, $R^d$, $R^e$, R', p, q and r are as follows:

$R^a$ and $R^b$ can be each independently a hydrogen atom, hydroxy, substituted or unsubstituted alkyl, substituted or unsubstituted alkyloxy, substituted or unsubstituted non-aromatic carbocyclyl, or substituted or unsubstituted non-aromatic heterocyclyl. (hereinafter referred to as ee-1-1)

$R^a$ and $R^b$ can be each independently a hydrogen atom, substituted or unsubstituted alkyl, substituted or unsubstituted non-aromatic carbocyclyl, or substituted or unsubstituted non-aromatic heterocyclyl. (hereinafter referred to as ee-1-2)

$R^a$ and $R^b$ can be each independently a hydrogen atom, or substituted or unsubstituted alkyl. (hereinafter referred to as ee-1-3)

$R^a$ and $R^b$ can be each independently a hydrogen atom, or substituted or unsubstituted non-aromatic heterocyclyl. (hereinafter referred to as ee-1-4)

$R^a$ and $R^b$ can be each independently a hydrogen atom, or non-aromatic heterocyclyl substituted with alkyl (hereinafter referred to as ee-1-5)

$R^{a'}$ can be substituted or unsubstituted alkyl (excluding unsubstituted methyl), substituted or unsubstituted non-aromatic carbocyclyl, or substituted or unsubstituted non-aromatic heterocyclyl. (hereinafter referred to as ee-2)

$R^c$ can be substituted or unsubstituted alkyl. (hereinafter referred to as ee-3)

$R^d$ can be a hydrogen atom, or substituted or unsubstituted alkyl. (hereinafter referred to as ee-4)

$R^e$ can be substituted or unsubstituted alkyl, substituted or unsubstituted alkyloxy, substituted or unsubstituted amino, substituted or unsubstituted non-aromatic carbocyclyl, or substituted or unsubstituted non-aromatic heterocyclyl. (hereinafter referred to as ee-5-1)

$R^e$ can be substituted or unsubstituted alkyl, substituted or unsubstituted alkyloxy, or substituted or unsubstituted non-aromatic heterocyclyl. (hereinafter referred to as ee-5-2)

R' can be each independently halogen, or substituted or unsubstituted alkyl. (hereinafter referred to as ee-6)

p can be 0 or 1. (hereinafter referred to as ee-7)

q can be 0 or 1. (hereinafter referred to as ee-8)

r can be 0 or 1. (hereinafter referred to as ee-9)

$R^{14}$ can be substituted or unsubstituted 9- to 10-membered bicyclic aromatic heterocyclyl. (hereinafter referred to as EE-2)

$R^{14}$ can be substituted or unsubstituted 9- to 10-membered bicyclic non-aromatic heterocyclyl. (hereinafter referred to as EE-3)

$R^{14}$ can be substituted or unsubstituted terahydropyridinyl;
substituted or unsubstituted triazolopyrimidinyl;
substituted or unsubstituted triazolopyridinyl;
substituted or unsubstituted pyrazolopyridinyl;
substituted or unsubstituted oxazolopyridinyl;
substituted or unsubstituted isoxazolopyridinyl;
substituted or unsubstituted imidazopyridinyl;
substituted or unsubstituted dihydropyridinyl;
substituted or unsubstituted dihydropyrazolopyridinyl;
substituted or unsubstituted pyridopyrazinyl;
substituted or unsubstituted naphthyridinyl;
substituted or unsubstituted pyrrolopyrazolyl;
substituted or unsubstituted furopyridinyl;
substituted or unsubstituted dihydrobenzisothiazole dioxide-yl;
substituted or unsubstituted pyridooxazinyl;
substituted or unsubstituted pyrrolopyridinyl;
substituted or unsubstituted dihydropyridazinyl;
substituted or unsubstituted dihydroimidazopyridinyl;
substituted or unsubstituted dihydrooxazolopyridinyl;
substituted or unsubstituted dihydronaphthyridinyl;
substituted or unsubstituted tetrahydropyrrolopyrazolyl;
substituted or unsubstituted dihydrofuropyridinyl;
substituted or unsubstituted dihydroisoxazolopyridinyl;
substituted or unsubstituted dihydropyridooxazinyl; or
substituted or unsubstituted dihydropyrrolopyridinyl. (hereinafter referred to as EE-4)

$R^{14}$ can be substituted or unsubstituted aromatic heterocyclyl. (hereinafter referred to as EE-5)

$R^{14}$ can be substituted or unsubstituted pyrazolyl. (hereinafter referred to as EE-6)

$R^{14}$ can be pyrazolyl substituted with alkyl. (hereinafter referred to as EE-7)

$R^{14}$ can be substituted or unsubstituted pyridyl. (hereinafter referred to as EE-8)

$R^{14}$ can be substituted or unsubstituted pyrimidyl. (hereinafter referred to as EE-9)

$R^{14}$ can be pyrimidyl substituted with alkyl. (hereinafter referred to as EE-10)

$R^{14}$ can be pyrimidyl substituted with substituted non-aromatic heterocyclyl (substituent: hydroxy). (hereinafter referred to as EE-11)

$R^{14}$ can be a group represented by the following formula:

[Chemical Formula 98]

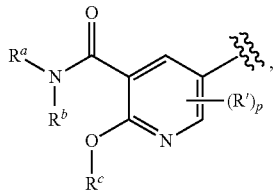

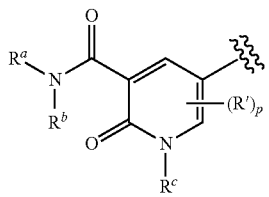 or

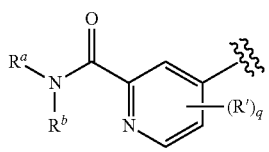

(hereinafter referred to as EE-12)

Here, specific examples of $R^a$, $R^b$, $R^c$, R', p and q are as follows:

$R^a$ and $R^b$ can be each independently a hydrogen atom, or substituted or unsubstituted alkyl. (hereinafter referred to as ee-10-1)

$R^a$ and $R^b$ can be each independently a hydrogen atom, or substituted or unsubstituted non-aromatic heterocyclyl. (hereinafter referred to as ee-10-2)

$R^a$ and $R^b$ can be each independently a hydrogen atom, or non-aromatic heterocyclyl substituted with alkyl. (hereinafter referred to as ee-10-3)

$R^c$ can be substituted or unsubstituted alkyl. (hereinafter referred to as ee-11)

R' can be each independently halogen, or substituted or unsubstituted alkyl. (hereinafter referred to as ee-12)

p can be 0 or 1. (hereinafter referred to as ee-13)

q can be 0 or 1. (hereinafter referred to as ee-14)

$R^{13}$ can be substituted or unsubstituted aromatic carbocyclyl, or substituted or unsubstituted non-aromatic carbocyclyl. (hereinafter referred to as FF-1)

$R^{13}$ can be substituted or unsubstituted aromatic carbocyclyl. (hereinafter referred to as FF-2)

$R^{13}$ can be substituted or unsubstituted phenyl. (hereinafter referred to as FF-3)

$R^{15}$ can be a hydrogen atom, or substituted or unsubstituted alkyl. (hereinafter referred to as GG-1)

$R^{15}$ can be substituted or unsubstituted alkyl. (hereinafter referred to as GG-2)

$R^{15}$ can be substituted or unsubstituted methyl. (hereinafter referred to as GG-3)

A compound represented by Formula (I'''-A):

[Chemical Formula 99]

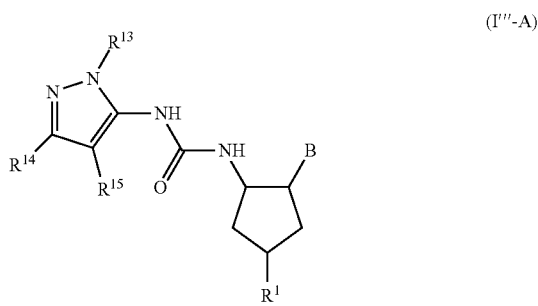

(I'''-A)

or a pharmaceutically acceptable salt thereof.

Specific examples of each symbol include the following. Examples of the compound represented by Formula (I'''-A) include all possible combinations of these specific examples.

It is noted that when B is any one of DDD-4, DDD-5, DDD-6 and DDD-7, $R^{14}$ is selected from EEE-1, EEE-2, EEE-3, EEE-4 and EEE-10. Besides, the following compounds are excluded:

[Chemical Formula 100]

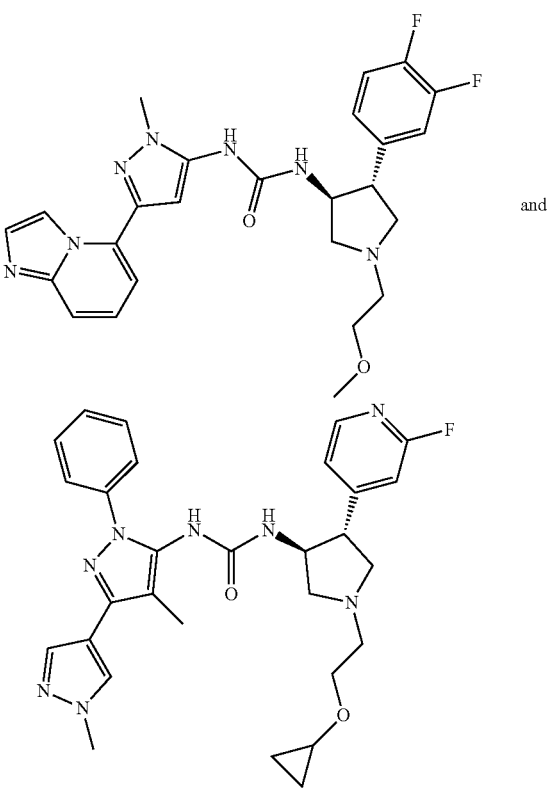

and $R^1$ can be alkyl substituted with alkyloxy. (hereinafter referred to as AAA-1)

$R^1$ can be ethyl substituted with methyloxy. (hereinafter referred to as AAA-2)

$R^1$ can be ethyl substituted with trifluoromethyloxy. (hereinafter referred to as AAA-3)

B can be a group represented by the following formula:

[Chemical Formula 101]

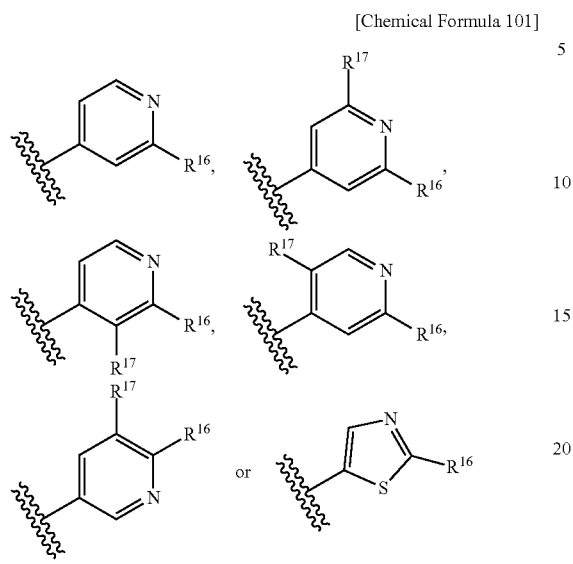

wherein $R^{16}$ and $R^{17}$ are each independently halogen. (hereinafter referred to as DDD-1)

B can be a group represented by the following formula:

[Chemical Formula 102]

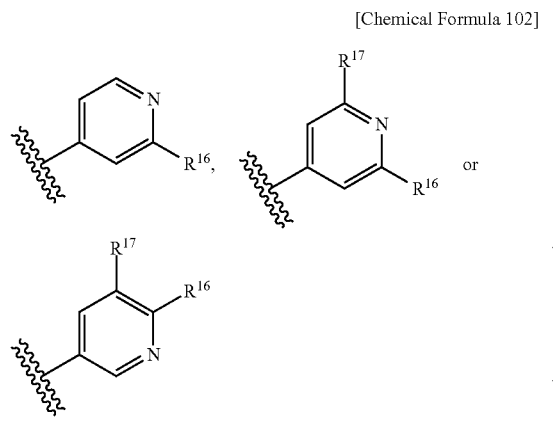

wherein $R^{16}$ and $R^{17}$ are each independently halogen. (hereinafter referred to as DDD-2)

B can be a group represented by the following formula:

[Chemical Formula 103]

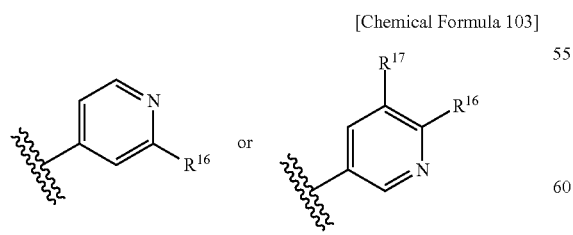

wherein $R^{16}$ and $R^{17}$ are each independently halogen. (hereinafter referred to as DDD-3)

B can be substituted or unsubstituted aromatic carbocyclyl. (hereinafter referred to as DDD-4)

B can be aromatic carbocyclyl substituted with halogen, or unsubstituted aromatic carbocyclyl. (hereinafter referred to as DDD-5)

B can be aromatic carbocyclyl substituted with halogen. (hereinafter referred to as DDD-6)

B can be unsubstituted aromatic carbocyclyl. (hereinafter referred to as DDD-7)

$R^{14}$ can be substituted or unsubstituted 9- to 10-membered bicyclic aromatic heterocyclyl, substituted or unsubstituted 9- to 10-membered bicyclic non-aromatic heterocyclyl, or a group represented by the following formula:

[Chemical Formula 104]

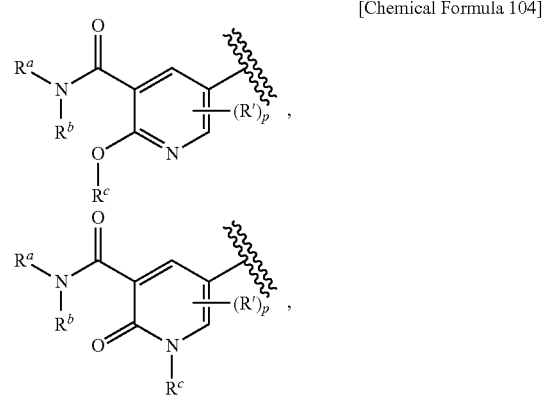

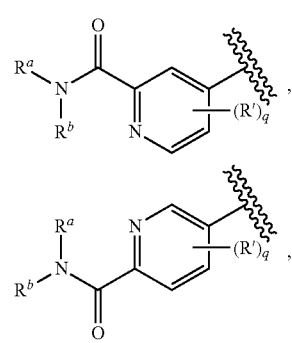

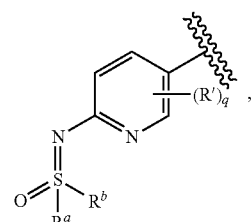

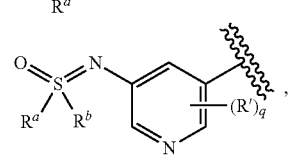

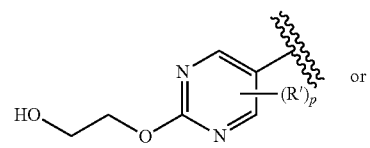 or

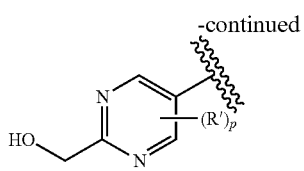

(hereinafter referred to as EEE-1)

Here, specific examples of $R^a$, $R^b$, $R^c$, R', p and q are as follows:

$R^a$ and $R^b$ can be each independently a hydrogen atom, hydroxy, substituted or unsubstituted alkyl, substituted or unsubstituted alkyloxy, substituted or unsubstituted non-aromatic carbocyclyl, or substituted or unsubstituted non-aromatic heterocyclyl. (hereinafter referred to as eee-1-1)

$R^a$ and $R^b$ can be each independently a hydrogen atom, substituted or unsubstituted alkyl, substituted or unsubstituted non-aromatic carbocyclyl, or substituted or unsubstituted non-aromatic heterocyclyl. (hereinafter referred to as eee-1-2)

$R^a$ and $R^b$ can be each independently a hydrogen atom, or substituted or unsubstituted alkyl. (hereinafter referred to as eee-1-3)

$R^c$ can be substituted or unsubstituted alkyl. (hereinafter referred to as eee-3)

R' can be each independently halogen or substituted or unsubstituted alkyl. (hereinafter referred to as eee-6)

p can be 0 or 1. (hereinafter referred to as eee-7)

q can be 0 or 1. (hereinafter referred to as eee-8)

r can be 0 or 1. (hereinafter referred to as eee-9)

$R^{14}$ can be substituted or unsubstituted 9- to 10-membered bicyclic aromatic heterocyclyl. (hereinafter referred to as EEE-2)

$R^{14}$ can be substituted or unsubstituted 9- to 10-membered bicyclic non-aromatic heterocyclyl. (hereinafter referred to as EEE-3)

$R^{14}$ can be substituted or unsubstituted terahydropyridinyl;
substituted or unsubstituted triazolopyrimidinyl;
substituted or unsubstituted triazolopyridinyl;
substituted or unsubstituted pyrazolopyridinyl;
substituted or unsubstituted oxazolopyridinyl;
substituted or unsubstituted isoxazolopyridinyl;
substituted or unsubstituted imidazopyridinyl;
substituted or unsubstituted dihydropyridinyl;
substituted or unsubstituted dihydropyrazolopyridinyl;
substituted or unsubstituted pyridopyrazinyl;
substituted or unsubstituted naphthyridinyl;
substituted or unsubstituted pyrrolopyrazolyl;
substituted or unsubstituted furopyridinyl;
substituted or unsubstituted dihydrobenzisothiazole dioxide-yl;
substituted or unsubstituted pyridooxazinyl;
substituted or unsubstituted pyrrolopyridinyl;
substituted or unsubstituted dihydropyridazinyl;
substituted or unsubstituted dihydroimidazopyridinyl;
substituted or unsubstituted dihydrooxazolopyridinyl;
substituted or unsubstituted dihydronaphthyridinyl;
substituted or unsubstituted tetrahydropyrrolopyrazolyl;
substituted or unsubstituted dihydrofuropyridinyl;
substituted or unsubstituted dihydroisoxazolopyridinyl;
substituted or unsubstituted dihydropyridooxazinyl; or
substituted or unsubstituted dihydropyrrolopyridinyl. (hereinafter referred to as EEE-4)

$R^{14}$ can be substituted or unsubstituted aromatic heterocyclyl. (hereinafter referred to as EEE-5)

$R^{14}$ can be substituted or unsubstituted pyrazolyl. (hereinafter referred to as EEE-6)

$R^{14}$ can be pyrazolyl substituted with alkyl. (hereinafter referred to as EEE-7)

$R^{14}$ can be substituted or unsubstituted pyrimidyl. (hereinafter referred to as EEE-8)

$R^{14}$ can be pyrazolopyridinyl substituted with alkyl. (hereinafter referred to as EEE-9)

$R^{14}$ can be a group represented by the following formula:

[Chemical Formula 105]

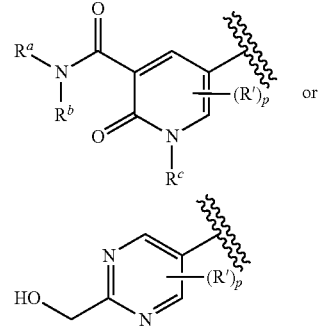

(hereinafter referred to as EEE-10)

Here, specific examples of $R^a$, $R^b$, $R^c$, R' and p are as follows:

$R^a$ and $R^b$ can be each independently a hydrogen atom, or substituted or unsubstituted alkyl. (hereinafter referred to as eee-10)

$R^c$ can be substituted or unsubstituted alkyl. (hereinafter referred to as eee-11)

R' can be each independently halogen, or substituted or unsubstituted alkyl. (hereinafter referred to as eee-12)

p can be 0 or 1. (hereinafter referred to as eee-13)

$R^{13}$ can be substituted or unsubstituted aromatic carbocyclyl, or substituted or unsubstituted non-aromatic carbocyclyl. (hereinafter referred to as FFF-1)

$R^{13}$ can be substituted or unsubstituted aromatic carbocyclyl. (hereinafter referred to as FFF-2)

$R^{13}$ can be substituted or unsubstituted phenyl. (hereinafter referred to as FFF-3)

$R^{15}$ can be a hydrogen atom, or substituted or unsubstituted alkyl. (hereinafter referred to as GGG-1)

$R^{15}$ can be substituted or unsubstituted alkyl. (hereinafter referred to as GGG-2)

$R^{15}$ can be substituted or unsubstituted methyl. (hereinafter referred to as GGG-3)

The compounds of Formula (I), Formula (I'), Formula (I") or Formula (I''') are not limited to specific isomers but include all possible isomers (e.g., keto-enol isomers, imine-enamine isomers, diastereoisomers, enantiomers, or rotamers), racemates or mixtures thereof.

One or more hydrogen, carbon and/or other atom(s) in the compounds of Formula (I), Formula (I'), Formula (I") or Formula (I''') may be replaced with isotopes of hydrogen, carbon and/or other atoms respectively. Examples of isotopes include hydrogen, carbon, nitrogen, oxygen, phosphorus, sulfur, fluorine, iodine and chlorine, such as $^2H$, $^3H$, $^{11}C$, $^{13}C$, $^{14}C$, $^{15}N$, $^{18}O$, $^{17}O$, $^{31}P$, $^{32}$, $^{35}S$, $^{18}F$, $^{123}I$ and $^{36}Cl$ respectively. The compounds of Formula (I), Formula (I'), Formula (I") or Formula (I''') include the compounds replaced with these isotopes. The compounds replaced with the above isotopes are useful as medicines and include all of radiolabeled compounds of the compound of Formula (I), Formula (I'), Formula (I") or Formula (I'''). A "method of radiolabeling" in the manufacture of the "radiolabeled compounds" is encompassed by the present invention, and the "radiolabeled compounds" are useful for studies on metabolized drug pharmacokinetics, studies on binding assay and/or diagnostic tools.

A radiolabeled compound of the compounds of Formula (I), Formula (I'), Formula (I") or Formula (I''') can be prepared using well-known methods in this field of the invention. For example, a tritium-labeled compound of Formula (I), Formula (I'), Formula (I") or Formula (I''') can be prepared by introducing a tritium to a certain compound of Formula (I), Formula (I'), Formula (I") or Formula (I''') through a catalytic dehalogenation reaction using a tritium. This method comprises reacting an appropriately-halogenated precursor of the compound of Formula (I), Formula (I'), Formula (I") or Formula (I''') with tritium gas in the presence of an appropriate catalyst, such as Pd/C, and in the presence or absent of a base. The other appropriate method of preparing a tritium-labeled compound can be referred to "Isotopes in the Physical and Biomedical Sciences, Vol. 1, Labeled Compounds (Part A), Chapter 6 (1987)". A 14C-labeled compound can be prepared by using a raw material having 14C.

The pharmaceutically acceptable salts of the compounds of Formula (I), Formula (I'), Formula (I") or Formula (I''') include, for example, salts with alkaline metal (e.g., lithium, sodium, or potassium), alkaline earth metal (e.g., calcium or barium), magnesium, transition metal (e.g., zinc or iron), ammonia, organic bases (e.g., trimethylamine, triethylamine, dicyclohexylamine, ethanolamine, diethanolamine, triethanolamine, meglumine, diethanolamine, ethylenediamine, pyridine, picoline, or quinoline), amino acids, or salts with inorganic acids (e.g., hydrochloric acid, sulfuric acid, nitric acid, carbonic acid, hydrobromic acid, phosphoric acid, or hydroiodic acid) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, or ethanesulfonic acid). Especially, salts with hydrochloric acid, sulfuric acid, phosphoric acid, tartaric acid, methanesulfonic acid and the like are included. These salts can be formed by the usual methods.

The compounds of Formula (I), Formula (I'), Formula (I") or Formula (I''') or pharmaceutically acceptable salts thereof may form solvates (e.g., hydrates), co-crystal and/or crystal polymorphs. The present invention encompasses those various solvates, co-crystal and crystal polymorphs. "Solvates" may be those wherein any numbers of solvent molecules (e.g., water molecules) are coordinated with the compounds of Formula (I), Formula (I'), Formula (I") or Formula (I'''). When the compounds of Formula (I), Formula (I'), Formula (I") or Formula (I''') or pharmaceutically acceptable salts thereof are allowed to stand in the atmosphere, the compounds may absorb water, resulting in attachment of adsorbed water or formation of hydrates. Recrystallization of the compounds of Formula (I), Formula (I'), Formula (I") or Formula (I''') or pharmaceutically acceptable salts thereof may produce crystal polymorphs. "Co-crystal" means that a compound of Formula (I), Formula (I'), Formula (I") or Formula (I''') or a salt thereof and a counter-molecule exist in the same crystal lattice, and it can be formed with any number of counter-molecules.

The compounds of Formula (I), Formula (I'), Formula (I") or Formula (I''') of the present invention or pharmaceutically acceptable salts thereof may form prodrugs. The present invention also encompasses such various prodrugs. Prodrugs are derivatives of the compounds of the present invention that have chemically or metabolically degradable groups, and compounds that are converted to the pharmaceutically active compounds of the present invention through solvolysis or under physiological conditions in vivo. Prodrugs include compounds that are converted to the compounds of Formula (I), Formula (I'), Formula (I") or Formula (I''') through enzymatic oxidation, reduction, hydrolysis or the like under physiological conditions in vivo, compounds that are converted to the compounds of Formula (I), Formula (I'), Formula (I") or Formula (I''') through hydrolysis by gastric acid etc., and the like. Methods for selecting and preparing suitable prodrug derivatives are described in, for example, "Design of Prodrugs, Elsevier, Amsrdam, 1985". Prodrugs themselves may have some activity.

When the compounds of Formula (I), Formula (I'), Formula (I") or Formula (I''') or pharmaceutically acceptable salts thereof have hydroxyl group(s), prodrugs include acyloxy derivatives and sulfonyloxy derivatives that are prepared by, for example, reacting compounds having hydroxyl group(s) with suitable acyl halide, suitable acid anhydride, suitable sulfonyl chloride, suitable sulfonyl anhydride and mixed anhydride, or with a condensing agent. For example, they include $CH_3COO^-$, $C_2H_5COO^-$, tert-BuCOO—, $C_{15}H_{31}COO^-$, $PhCOO^-$, $(m\text{-}NaOOCPh)COO^-$, $NaOOCCH_2CH_2COO^-$, $CH_3CH(NH_2)COO^-$, $CH_2N(CH_3)_2COO^-$, $CH_3SO_3^-$, $CH_3CH_2SO_3^-$, $CF_3SO_3^-$, $CH_2FSO_3^-$, $CF_3CH_2SO_3^-$, $p\text{-}CH_3O\text{-}PhSO_3^-$, $PhSO_3O_3^-$ and $p\text{-}CH_3PhSO_3^-$.

General procedures for the synthesis of the compounds of the present invention are described below. Starting materials and reaction reagents used in such synthesis are commercially available or can be synthesized according to methods well known in the art using compounds commercially available. Further, extraction, purification and the like may be performed in accordance with the methods carried out in the art.

In the following all steps, when a substituent which impedes a reaction, e.g. hydroxy, mercapto, amino, formyl, carbonyl, carboxy, is possessed, the substituent is protected by the method described in Protective Groups in organic Synthesis, and Theodora W Greene (John Wiley & Sons, hereinafter referred to as literature A) in advance, and the protecting group may be removed at a desirable stage. In addition, in the all steps, an order of steps to be implemented may be appropriately changed, and each intermediate may be isolated, and used in a next step. All of reaction time, reaction temperature, solvents, reagents, protecting groups, etc. are mere exemplification and not limited as long as they do not cause an adverse effect on a reaction.

For example, the compounds represented by Formula (I) of the present invention can be prepared by the general synthetic methods described below.

[Chemical Formula 106]

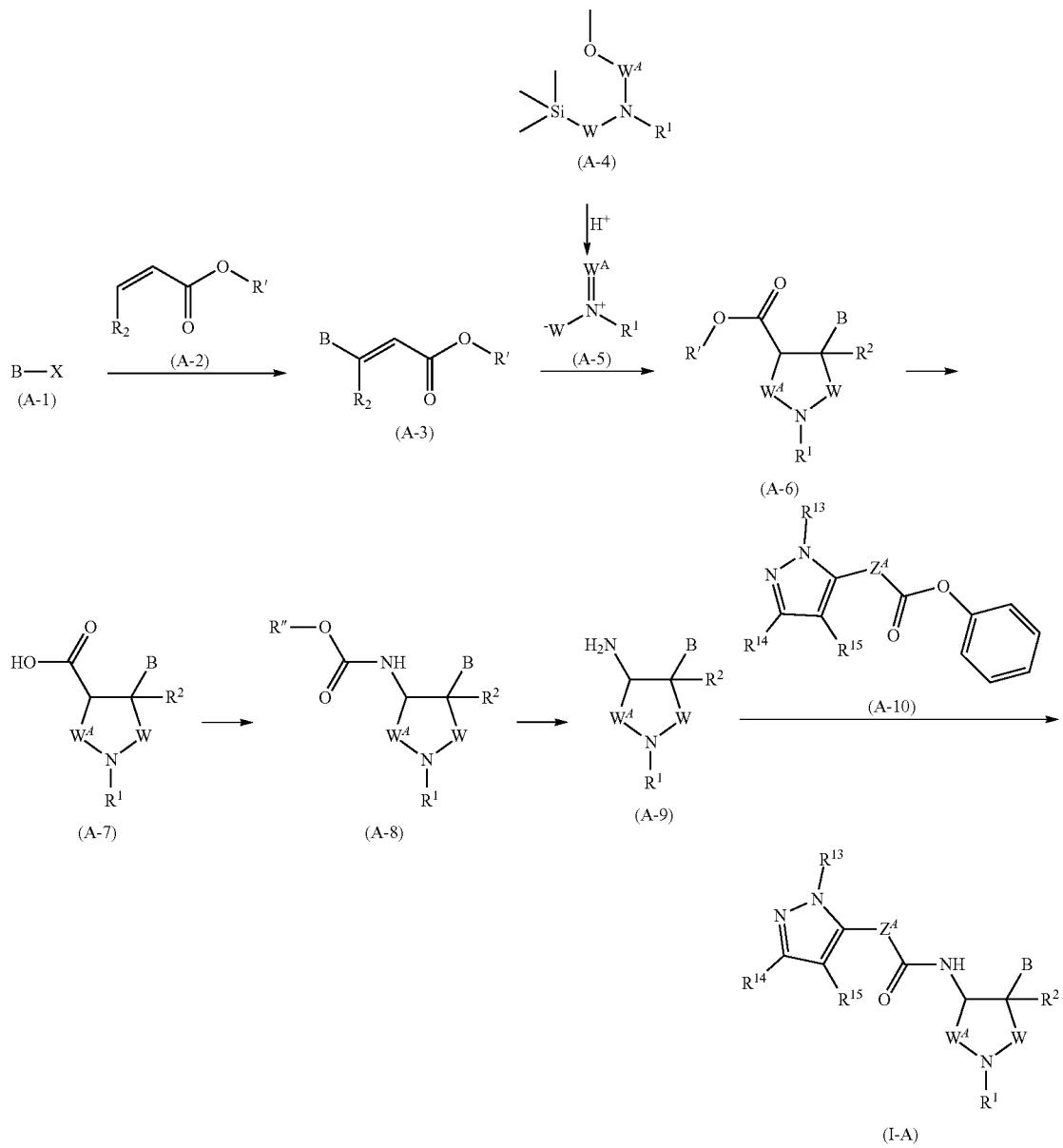

wherein each symbol is the same as defined in the above, R' is C1-C4 alkyl, and R" is substituted or unsubstituted alkyl.

(Method A)

(Step 1)

Compound (A-3) can be obtained by reacting Compound (A-1) with Compound (A-2) in the presence of a base, a palladium catalyst and a phosphine catalyst.

Compound (A-1) is commercially available or can be synthesized according to the known methods.

Compound (A-2) is commercially available or can be synthesized according to the known methods, and can be used at 1 to 2 mol equivalent(s) relative to Compound (A-1).

The base can be triethylamine, diisopropylethylamine, tributylamine or the like, and can be used at 1 to 3 mol equivalent(s) relative to Compound (A-1).

The palladium catalyst can be palladium acetate, tris (dibenzylideneacetone)dipalladium (0), bis(tri-tert-butyl-phosphine)palladium or the like, and can be used at 0.01 to 0.1 mol equivalent relative to Compound (A-1).

The phosphine catalyst can be tris(2-methylphenyl)phosphine, triphenylphosphine or the like, and can be used at 0.01 to 0.1 mol equivalent relative to Compound (A-1).

The reaction temperature is −20° C. to the reflux temperature of the solvent, preferably room temperature to 100° C.

The reaction time is 0.1 to 24 hours, preferably 0.5 to 12 hours.

Examples of the reaction solvent include dimethylacetamide and NMP, and one of or a mixture of these can be used.

(Step 2)

Compound (A-6) can be obtained by a 1,3-dipolar cycloaddition reaction of Compound (A-3) and Compound (A-5).

Compound (A-4) is commercially available or can be synthesized according to the known methods.

Compound (A-5) can be synthesized by treating Compound (A-4) with an acid.

The acid can be hydrochloric acid, sulfuric acid, trifluoroacetic acid or the like, and can be used at 0.1 to 0.5 mol equivalent relative to Compound (A-4).

The reaction temperature is −20° C. to the reflux temperature of the solvent, preferably 0° C. to 60° C.

The reaction time is 0.1 to 24 hours, preferably 0.5 to 12 hours.

Examples of the reaction solvent include dichloromethane, chloroform and toluene, and one of or a mixture of these can be used.

(Step 3)

Compound (A-7) can be obtained by deprotection of protecting group for carboxyl group of Compound (A-6) which is obtained in the above step 2. For example, the method disclosed in the above literature A can be used.

(Step 4)

The carboxyl group of Compound (A-7) which is obtained in the above step 3 can be converted to an amino group by Curtius rearrangement.

As the reagent used for Curtius rearrangement, DPPA and the like are exemplified, and it can be used at 1 to 5 mol equivalent(s) relative to Compound (A-7).

The reaction temperature is room temperature to the reflux temperature of the solvent, preferably 50 to 100° C.

The reaction time is 0.1 to 24 hour(s), preferably 0.5 to 12 hour(s).

As the reaction solvent, 2-(trimethylsilyl)ethanol, t-BuOH, benzyl alcohol and the like can be used.

As the reaction solvent, toluene, benzene and the like can be also used. In this case, carbamate can be obtained by adding the above alcohol after preparation of isocyanate.

The above alcohol can be used at 1 to 5 mol equivalent(s) relative to Compound (A-7).

(Step 5)

Compound (A-9) can be obtained by deprotection of a protecting group for amine group of Compound (A-8) which is obtained in the above step 4. For example, the method described in the above literature A or the like can be used.

(Step 6)

Compound (I-A) can be obtained by reacting Compound (A-9) with Compound (A-10) in the presence of a base.

Compound (A-10) can be synthesized in accordance with the method described in WO2012158413. It can be used at 1 to 1.5 mol equivalent(s) relative to Compound (A-9).

As the base, pyridine, triethylamine, diisopropylethylamine, N-methylmorpholine and the like are exemplified, and it can be used at 1 to 5 mol equivalent(s) relative to Compound (A-9).

The reaction temperature is 0° C. to the reflux temperature of the solvent, preferably room temperature to 50° C.

The reaction time is 0.1 to 24 hour(s), preferably 0.5 to 12 hour(s).

As the reaction solvent, dichloromethane, chloroform, THF, toluene, DMF, DMSO, NMP, dioxane and the like are exemplified, and it can be used alone or in combination.

[Chemical Formula 107]

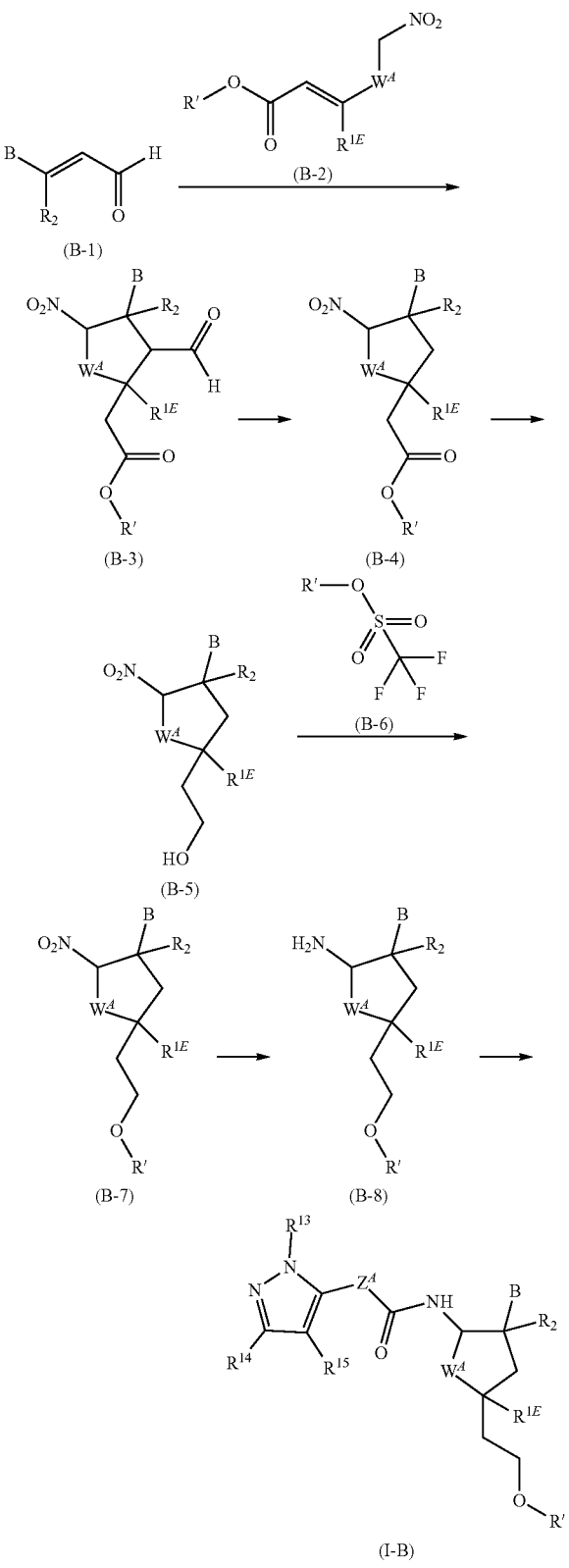

wherein each symbol is the same as defined in the above, and R' is C1-C3 alkyl.

(Method B)

(Step 1)

Compound (B-3) can be obtained by reacting Compound (B-1) with Compound (B-2) in the presence of a catalyst and an additive.

Compound (B-1) is commercially available or can be synthesized according to the known methods.

Compound (B-2) is commercially available or can be synthesized according to the known methods, and can be used at 1 to 2 mol equivalent(s) relative to Compound (B-1).

The catalyst can be proline, (S)-(−)-α, α-diphenyl-2-pyrrolidine methanol trimethylsilyl ether or the like, and can be used at 0.1 to 0.5 mol equivalent relative to Compound (B-1).

The additive can be 1,4-diazabicyclo[2,2,2]octane, triethylamine, sodium acetate or the like, and can be used at 0.1 to 0.5 mol equivalent relative to Compound (B-1).

The reaction temperature is −20° C. to the reflux temperature of the solvent, preferably room temperature to 50° C.

The reaction time is 12 to 96 hours, preferably 24 to 48 hours.

Examples of the reaction solvent include chloroform, dichloromethane and toluene, and one of or a mixture of these can be used.

(Step 2)

Compound (B-4) can be obtained by reacting Compound (B-3) with chlorotris(triphenylphosphine)rhodium (I).

The chlorotris(triphenylphosphine)rhodium (I) can be used at 1 to 2 mol equivalent(s) relative to Compound (B-3).

The reaction temperature is −20° C. to the reflux temperature of the solvent, preferably 60° C. to the reflux temperature of the solvent.

The reaction time is 0.5 to 24 hours, preferably 1 to 6 hours.

Examples of the reaction solvent acetonitrile, tetrahydrofuran and toluene, and one of or a mixture of these can be used.

(Step 3)

Compound (B-5) can be obtained by reacting Compound (B-4) with diisobutylaluminum hydride.

The diisobutylaluminum hydride can be used at 2 to 4 mol equivalents relative to Compound (B-4).

The reaction temperature is −78° C. to 40° C., preferably −78° C. to room temperature.

The reaction time is 0.5 to 24 hours, preferably 1 to 3 hours.

Examples of the reaction solvent include dichloromethane and tetrahydrofuran, and one of or a mixture of these can be used.

(Step 4)

Compound (B-7) can be obtained by reacting Compound (B-5) with Compound (B-6) in the presence of 2,6-di-tert-butyl-4-methylpyridine.

Compound (B-6) is commercially available or can be synthesized according to the known methods, and can be used at 1 to 5 mol equivalent(s) relative to Compound (B-5).

The 2,6-di-tert-butyl-4-methylpyridine can be used at 1 to 5 mol equivalent(s) relative to Compound (B-5).

The reaction temperature is −20° C. to the reflux temperature of the solvent, preferably room temperature to the reflux temperature of the solvent.

The reaction time is 0.5 to 24 hours, preferably 1 to 6 hours.

Examples of the reaction solvent include dichloromethane and chloroform, and one of or a mixture of these can be used.

(Step 5)

Compound (B-8) can be obtained by reacting Compound (B-7) with zinc in the presence of an acid.

The zinc can be used at 5 to 20 mol equivalents relative to Compound (B-7).

The acid can be concentrated hydrochloric acid or concentrated sulfuric acid, and can be used at 10 to 100 mol equivalents relative to Compound (B-7).

The reaction temperature is −20° C. to the reflux temperature of the solvent, preferably room temperature to the reflux temperature of the solvent.

The reaction time is 0.5 to 24 hours, preferably 0.5 to 6 hours.

Examples of the reaction solvent include methanol, ethanol and water, and one of or a mixture of these can be used.

(Step 6)

Compound (I-B) can be obtained from Compound (B-8) obtained in the step 5 in accordance with the step 6 of Method A.

[Chemical Formula 108]

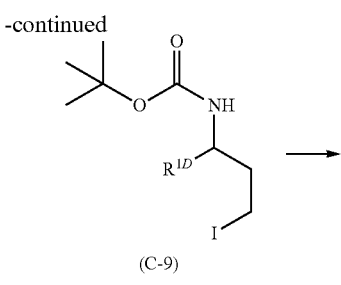

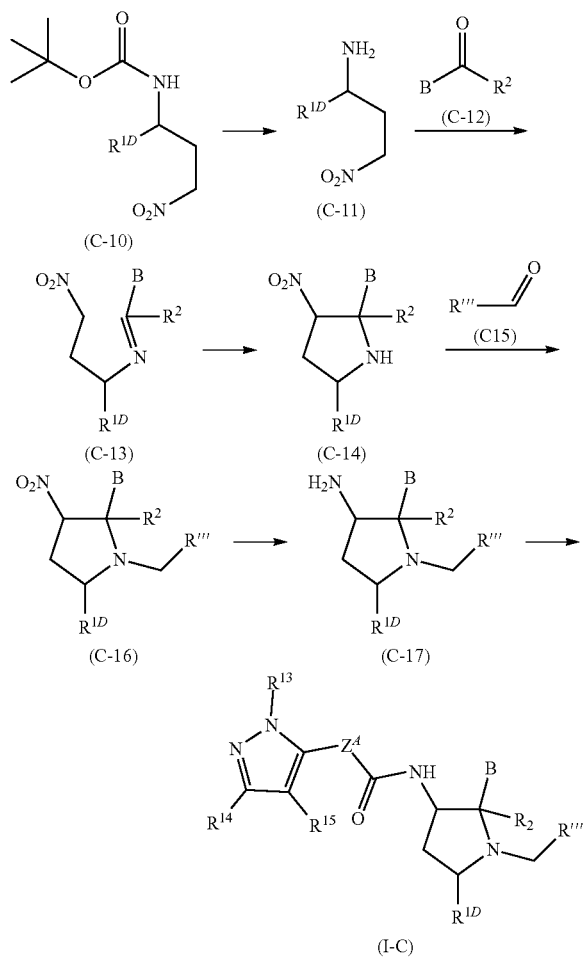

wherein each symbol is the same as defined in the above, and R''' is a hydrogen atom, or substituted or unsubstituted alkyl.

(Method C)

(Step 1)

Compound (C-2) can be obtained by reacting Compound (C-1) with 2-methylpropane-2-sulfinamide in the presence of a desiccant.

The 2-methylpropane-2-sulfinamide can be used at 1 to 1.5 mol equivalent(s) relative to Compound (C-1).

The desiccant can be magnesium sulfate, copper sulfate or the like, and can be used at 1 to 3 mol equivalent(s) relative to Compound (C-1).

The reaction temperature is −20° C. to the reflux temperature of the solvent, preferably room temperature to 50° C.

The reaction time is 12 to 96 hours, preferably 24 to 48 hours.

Examples of the reaction solvent include chloroform, dichloromethane and toluene, and one of or a mixture of these can be used.

(Step 2)

Compound (C-3) can be obtained by reacting Compound (C-2) with ethynyltrimethylsilane in the presence of a base.

The ethynyltrimethylsilane can be used at 1 to 3 mol equivalent(s) relative to Compound (C-2).

The base can be lithium bis(trimethylsilyl)amide, sodium bis(trimethylsilyl)amide, lithium diisopropylamide or the like, and can be used at 1 to 3 mol equivalent(s) relative to Compound (C-2).

The reaction temperature is −78° C. to 40° C., preferably −78° C. to room temperature.

The reaction time is 0.5 to 24 hours, preferably 0.5 to 6 hours.

Examples of the reaction solvent include tetrahydrofuran, hexane and toluene, and one of or a mixture of these can be used.

(Step 3)

Compound (C-4) can be obtained by reacting Compound (C-3) with TBAF.

The TBAF can be used at 1 to 3 mol equivalent(s) relative to Compound (C-3).

The reaction temperature is −20° C. to the reflux temperature of the solvent, preferably room temperature to 50° C.

The reaction time is 0.5 to 24 hours, preferably 0.5 to 6 hours.

An example of the reaction solvent includes tetrahydrofuran.

(Step 4)

Compound (C-5) can be obtained by subjecting Compound (C-4) to a catalytic hydrogenation reaction in the presence of quinoline and a Lindlar catalyst.

The quinoline can be used at 0.01 to 0.1 mol equivalent relative to Compound (C-4).

The Lindlar catalyst can be used at 0.01 to 0.1 mol equivalent relative to Compound (C-4).

The reaction temperature is −20° C. to the reflux temperature of the solvent, preferably room temperature to 50° C.

The reaction time is 0.5 to 72 hours, preferably 0.5 to 24 hours.

Examples of the reaction solvent include tetrahydrofuran, methanol and ethyl acetate, and one of or a mixture of these can be used.

(Step 5)

Compound (C-6) can be obtained by reacting Compound (C-5) with an acid.

The acid can be hydrochloric acid (in dioxane), trifluoroacetic acid or the like, and can be used at 3 to 20 mol equivalents relative to Compound (C-5).

The reaction temperature is −20° C. to the reflux temperature of the solvent, preferably room temperature to 50° C.

The reaction time is 0.5 to 72 hours, preferably 0.5 to 6 hours.

Examples of the reaction solvent include tetrahydrofuran, methanol and ethyl acetate, and one of or a mixture of these can be used.

(Step 6)

Compound (C-7) can be obtained by reacting Compound (C-6) with di-tert-butyl dicarbonate in the presence of a base.

The di-tert-butyl dicarbonate can be used at 1 to 2 mol equivalent(s) relative to Compound (C-6).

The base can be sodium carbonate, potassium carbonate or the like, and can be used at 1 to 10 mol equivalent(s) relative to Compound (C-6).

The reaction temperature is −20° C. to the reflux temperature of the solvent, preferably room temperature to 50° C.

The reaction time is 0.5 to 24 hours, preferably 0.5 to 12 hours.

Examples of the reaction solvent include tetrahydrofuran, methanol and water, and one of or a mixture of these can be used.

(Step 7)

Compound (C-8) can be obtained by reacting Compound (C-7) with 9-borabicyclo[3.3.1]nonane and treating the resultant with sodium hydroxide and a hydrogen peroxide solution.

The 9-borabicyclo[3.3.1]nonane can be used at 1 to 3 mol equivalent(s) relative to Compound (C-7).

The sodium hydroxide can be used at 5 to 10 mol equivalents relative to Compound (C-7).

The hydrogen peroxide solution can be used at 5 to 150 mol equivalents relative to Compound (C-7).

The reaction temperature is −20° C. to the reflux temperature of the solvent, perferably −20° C. to room temperature.

The reaction time is 0.5 to 24 hours, preferably 0.5 to 12 hours.

Examples of the reaction solvent include tetrahydrofuran and water, and one of or a mixture of these can be used.

(Step 8)

Compound (C-9) can be obtained by reacting Compound (C-8) with triphenylphosphine and iodine in the presence of imidazole.

The triphenylphosphine can be used at 1 to 2 mol equivalent(s) relative to Compound (C-8).

The iodine can be used at 1 to 2 mol equivalent(s) relative to Compound (C-8).

The imidazole can be used at 1 to 3 mol equivalent(s) relative to Compound (C-8).

The reaction temperature is −20° C. to the reflux temperature of the solvent, perferably −20° C. to room temperature.

The reaction time is 0.5 to 24 hours, preferably 0.5 to 12 hours.

Examples of the reaction solvent include dichloromethane, tetrahydrofuran and toluene, and one of or a mixture of these can be used.

(Step 9)

Compound (C-10) can be obtained by reacting Compound (C-9) with sodium nitrite.

The sodium nitrite can be used at 1 to 10 mol equivalent(s) relative to Compound (C-9).

The reaction temperature is −20° C. to the reflux temperature of the solvent, preferably −20° C. to room temperature.

The reaction time is 0.5 to 24 hours, preferably 0.5 to 12 hours.

Examples of the reaction solvent include DMF and NMP, and one of or a mixture of these can be used.

(Step 10)

Compound (C-11) can be obtained by deprotection of a protecting group for amine group of Compound (C-10) obtained in the step 9. For example, the method disclosed in the literature A or the like can be used.

(Step 11)

Compound (C-13) can be obtained by reacting Compound (C-11) with Compound (C-12) in the presence of a desiccant.

Compound (C-12) is commercially available or can be synthesized according to the known methods, and can be used at 1 to 2 mol equivalent(s) relative to Compound (C-11).

The desiccant can be magnesium sulfate, sodium sulfate or the like, and can be used at 1 to 3 mol equivalent(s) relative to Compound (C-11).

The reaction temperature is −20° C. to the reflux temperature of the solvent, preferably room temperature to the reflux temperature of the solvent.

The reaction time is 0.5 to 96 hours, preferably 0.5 to 24 hours.

Examples of the reaction solvent include dichloromethane and toluene, and one of or a mixture of these can be used.

(Step 12)

Compound (C-14) can be obtained by reacting Compound (C-13) with a base.

The base can be triethylamine, diisopropylethylamine or the like, and can be used at 0.1 to 1 mol equivalent relative to Compound (C-11).

The reaction temperature is −20° C. to the reflux temperature of the solvent, perferably −20° C. to room temperature.

The reaction time is 0.5 to 96 hours, preferably 0.5 to 24 hours.

Examples of the reaction solvent include acetonitrile, toluene and dichloromethane, and one of or a mixture of these can be used.

(Step 13)

Compound (C-16) can be obtained by reacting Compound (C-14) with Compound (C-15) and a reducing agent in the presence of an acid.

Compound (C-15) is commercially available or can be synthesized according to the known methods, and can be used at 1 to 30 mol equivalent(s) relative to Compound (C-14).

The reducing agent can be sodium triacetoxyborohydride or sodium cyanoborohydride, and can be used at 0.1 to 10 mol equivalent(s) relative to Compound (C-14).

The acid can be acetic acid or the like, and can be used at 0.1 to 1 mol equivalent relative to
Compound (C-14).

The reaction temperature is −20° C. to the reflux temperature of the solvent, perferably −20° C. to room temperature.

The reaction time is 0.5 to 24 hours, preferably 0.5 to 5 hours.

Examples of the reaction solvent include toluene and dichloromethane, and one of or a mixture of these can be used.

(Step 14)

Compound (C-17) can be obtained by reacting Compound (C-16) with zinc in the presence of ammonium chloride.

The zinc can be used at 5 to 20 mol equivalents relative to Compound (C-16). The ammonium chloride can be used at 10 to 100 mol equivalents relative to Compound (C-16).

The reaction temperature is −20° C. to the reflux temperature of the solvent, preferably room temperature to the reflux temperature of the solvent.

The reaction time is 0.5 to 24 hours, preferably 0.5 to 6 hours.

Examples of the reaction solvent include methanol, ethanol and tetrahydrofuran, and one of or a mixture of these can be used.

(Step 15)

Compound (I-C) can be obtained from Compound (C-17) obtained in the step 14 in accordance with the step 6 of Method A.

The Compounds of Formula (I) of the present invention prepared by the above general synthetic method can be purified by referring to the known methods (e.g., chromatography, and recrystallization).

The compound of the present invention has TrkA inhibitory activity and it can be available for therapeutic agent and/or prophylactic agent for pain associated with osteoarthritis, rheumatoid arthritis, fracture, interstitial cystitis, chronic pancreatitis and prostate inflammation; and nociceptive pain as typified by chronic low back pain, diabetic peripheral neuropathy pain, postoperative pain, pelvic pain and cancer pain; neuropathic pain, acute pain, chronic pain, cancer, inflammatory disease, allergic disease, dermatological disease and the like.

The compound of the present invention has not only TrkA inhibitory activity but also are useful as a medicine and has any or all of the following excellent characteristics:

a) The compound is a weak inhibitor of CYP enzymes (e.g., CYP1A2, CYP2C9, CYP2C19, CYP2D6, and CYP3A4).
b) The compound demonstrates good pharmacokinetics, such as a high bioavailability, and moderate clearance.
c) The compound has a high metabolic stability.
d) The compound has no irreversible inhibitory action against CYP enzymes (e.g., CYP3A4) when the concentration is within the range described in the present description as the measurement conditions.
e) The compound has no mutagenicity.
f) The compound is associated with a low cardiovascular risk.
g) The compound has a high solubility.
h) The compound is highly selective for TrkA receptor.

A pharmaceutical composition of the present invention can be administered orally or parenterally. Methods for parenteral administration include dermal, subcutaneous, intravenous, intraarterial, intramuscular, intraperitoneal, transmucosal, inhalation, transnasal, ophthalmic, and inner ear or vaginal administration.

In the case of oral administration, any forms, which are usually used, such as oral solid formulations (e.g., tablets, powders, granules, capsules, pills, or films), and oral liquid formulations (e.g., suspension, emulsion, elixir, syrup, lemonade, spirit, aromatic water, extract, decoction, or tincture) may prepared according to the usual method and administered. The tablets can be sugar-coated tablets, film-coated tablets, enteric-coating tablets, sustained-release tablets, troche tablets, sublingual tablets, buccal tablets, chewable tablets or orally disintegrating tablets. Powders and granules can be dry syrups. Capsules can be soft capsules, micro capsules or sustained-release capsules.

In the case of parenteral administration, any forms, which are usually used, such as injections, drips, and external preparations (e.g., ophthalmic drops, nasal drops, ear drops, aerosols, inhalations, lotion, infusion, liniment, mouthwash, enema, ointment, plaster, jelly, cream, patch, cataplasm, external powder, or suppository) can be preferably administered. Injections can be emulsions whose type is O/W, W/O, O/W/O, W/O/W or the like.

The pharmaceutical composition may be manufactured by mixing an effective amount of the compound of the present invention with various pharmaceutical additives suitable for the formulation, such as excipients, binders, moistening agents, disintegrants, lubricants, and diluents. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old. The geriatric pharmaceutical compositions are preferably administered to patients who are 65 years old or over.

Although the dosage of the pharmaceutical composition of the present invention should be determined in consideration of the patient's age and body weight, the type and degree of diseases, the administration route and the like, a usual oral dosage is 0.05 to 100 and preferably 0.1 to 10 mg/kg/day. For parenteral administration, although the dosage highly varies with administration routes, a usual dosage is 0.005 to 10 and preferably 0.01 to 1 mg/kg/day. The dosage may be administered in one to several divisions per day.

The compound of the present invention can be used in combination of therapeutic agents for pain, anti-inflammatory agents, anticancer agents, or the like (hereinafter referred to as a co-administered drug) to increase the activity of the compound or reduce the dose of the compound, or the like. In this case, the timing of administration for a compound of the present invention and the co-administered drug is not limited. They can be administered to the subjects to be treated, at a time or at different times. Furthermore, a compound of the present invention and the co-administered rug can be administered as two formulations independently comprising each active ingredient or a single formulation comprising the both active ingredients.

The dose for co-administered drugs may be appropriately selected in reference to the clinical dose. The compounding ratio of the compounds of the present invention and co-administered drugs may be appropriately selected depending on the subject to be treated, administration route, disease to be treated, symptoms, combination of the drugs and the like. For administration in humans, for example, 1 part by weight of the compounds of the present invention may be used in combination with 0.01 to 100 parts by weight of co-administered drugs.

For example, the therapeutic agent for pain includes cyclooxygenase inhibitor (e.g., ketoprofen, celecoxib), neuropathic disorder agent (e.g., pregabalin), antidepressant (e.g., duloxetine, amitriptyline), opioid receptor agonist (e.g., morphine, tramadol), regional anesthetic (e.g., lidocaine), ketamine, and acetaminophen.

For example, the anti-inflammatory agent includes steroid agent (e.g., prednisolone), and antihistamine agent (e.g., loratadine).

For example, the anticancer agent includes molecularly-targeted agent (e.g., lapatinib, rituximab), alkylating agent (e.g., cyclophosphamide), antimetabolite (e.g., methotrexate), alkaloid agent (e.g., paclitaxel), platinum agent (e.g., oxaliplatin), and hormonal agent (e.g., tamoxifen, leuprorelin).

EXAMPLES

The present invention will be described in more detail with reference to, but not limited to, the following Examples, Reference Examples and Test Examples.

Besides, abbreviations used herein have the following meanings:

9-BBN: 9-borabicyclo[3.3.1]nonane
Boc: tert-butoxycarbonyl
$CDCl_3$: deuterated chloroform
$CD_3OD$: deuterated methanol
DIBAL: diisobutylaluminum hydride
DMF: N,N-dimethylformamide
DPPA: diphenylphosphoryl azide
LHMDS: lithium bis(trimethylsilyl)amide
Me: methyl
MeOH: methanol
$NH_4Cl$: ammonium chloride
NMP: N-methyl-2-pyrrolidone
$NO_2$: nitro
TBAF: tetra-n-butylammonium fluoride
THF: tetrahydrofuran
TMS: trimethylsilyl
TFA: trifluoroacetic acid NMR analysis of each example was performed by 400 MHz using DMSO-$d_6$ or $CDCl_3$. In the case of indicating NMR data, there are cases in which not all measured peaks are described.

"RT" in the specification means a retention time of LC/MS: liquid chromatography/mass spectrometry, and the measurement conditions are as follows.

(Method 1)
Column: Shim-pack XR-ODS (2.2 μm, i.d.50×3.0 mm) (Shimadzu)
Flow rate: 1.6 mL/min
UV detection wavelength: 254 nm
Mobile phase: [A] is 0.1% formic acid in aqueous solution, and [B] is 0.1% formic acid in acetonitrile solution.
Gradient: Linear gradient of 10% to 100% solvent [B] for 3 minutes was performed, and 100% solvent [B] was maintained for 0.5 minute.

(Method 2)
Column: ACQUITY UPLC(™)BEH C18 (1.7 μm i.d.2.1× 50 mm) (Waters)
Flow rate: 0.8 mL/min
UV detection wavelength: 254 nm
Mobile phase: [A] is 0.1% formic acid in aqueous solution, and [B] is 0.1% formic acid in acetonitrile solution.
Gradient: Linear gradient of 5% to 100% solvent [B] for 3.5 minutes was performed, and 100% solvent [B] was maintained for 0.5 minute.

(Method 3)
Column: ACQUITY UPLC(TM)BEH C18 (1.7 μm i.d.2.1×50 mm) (Waters)
Flow rate: 0.8 mL/min
UV detection wavelength: 254 nm
Mobile phase: [A] is 10 mM ammonium carbonate in aqueous solution, and [B] is acetonitrile.
Gradient: Linear gradient of 5% to 100% solvent [B] for 3.5 minutes was performed, and 100% solvent [B] was maintained for 0.5 minute.

Hereinafter, MS(m/z) indicates the value observed in the mass spectrometry.

Reference Example 1

Synthesis of Compound X

[Chemical Formula 110]

Step 1 Synthesis of Compound 2

Compound 1 (1.72 g, 8.11 mmol) was dissolved in DMF (20 mL) under nitrogen atmosphere, and bis(pinacolato) diboron (4.12 g, 16.2 mmol), potassium acetate (2.39 g, 24.3 mmol), and a dichloromethane adduct of [1,1'-bis(diphenylphosphino)ferrocene]palladium (II) dichloride (0.331 g, 0.406 mmol) were added thereto, followed by stirring at 90° C. for 12 hours.

After the resultant reaction solution was allowed to cool, water was added thereto, followed by extraction with ethyl acetate twice. The organic layer was washed with water twice and dried over anhydrous sodium sulfate, and the solvent was distilled off under reduced pressure.

The thus obtained residue was dissolved in 1,4-dioxane/water (2/1) (30 mL), and Compound V (synthesized in accordance with the method described in WO2012/158413) (2.60 g, 8.10 mmol), tripotassium phosphate (3.44 g, 16.2 mmol), chloro(2,4,6-triisopropyl-2'-dicyclohexylphosphino-biphenyl)[2-(2'-amino-1,1'-biphenyl]palladium (II) (0.128 g, 0.162 mmol) were added thereto, followed by stirring at 90° C. for 4 hours.

After the resultant reaction solution was allowed to cool, a brine was added thereto, followed by the extraction with ethyl acetate twice, and then, the resultant was dried over anhydrous sodium sulfate, and the solvent was distilled off under reduced pressure.

The thus obtained residue was purified by silica gel column chromatography (hexane-ethyl acetate) to give Compound 2 (1.50 g, Yield 61%).

$^1$H-NMR (CDCl$_3$) δ: 2.15 (s, 3H), 3.72 (s, 2H), 4.19 (s, 3H), 7.36-7.39 (m, 1H), 7.51 (t, J=8.0 Hz, 2H), 7.65 (d, J=8.0 Hz, 2H), 8.03 (s, 1H), 8.35 (d, J=1.6 Hz, 1H), 8.93 (d, J=1.6 Hz, 1H).

Step 2 Synthesis of Compound X

Compound 2 (500 mg, 1.643 mmol) was dissolved in dichloromethane (5 mL), and pyridine (0.199 mL, 2.464 mmol) and phenyl chlorocarbonate (0.227 mL, 1.807 mmol) were added thereto under ice-cooling, followed by stirring at room temperature for 1 hour.

Water was added to the resultant, followed by the extraction with ethyl acetate, and then, the organic layer was washed with water and dried over sodium sulfate. The solvent was distilled off under reduced pressure, and the thus obtained residue was purified by the silica gel column chromatography (hexane-ethyl acetate) to give Compound X (550 mg, 78.9%)

LC/MS (Method 1) RT=1.97, MS (m/z)=425

Example 1

Synthesis of Compound (I-90)

[Chemical Formula 111]

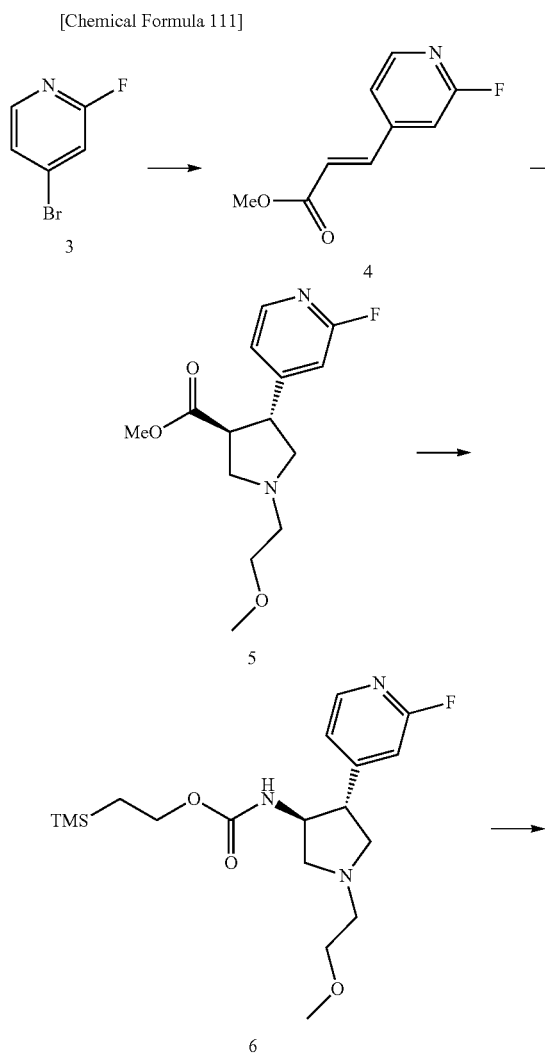

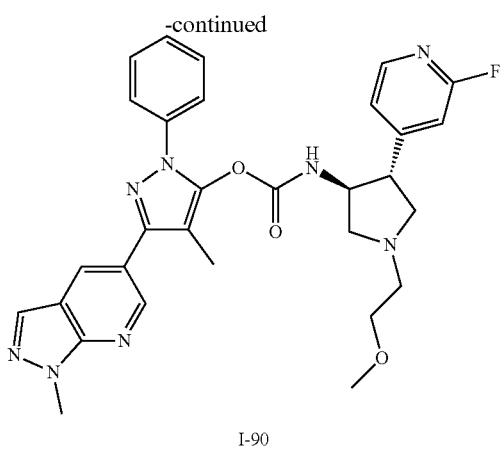

I-90

Step 1 Synthesis of Compound 4

Compound 3 (1.00 g, 5.68 mmol) was dissolved in NMP (5.7 mL), and triethylamine (0.945 mL, 6.82 mmol) and methyl acrylate (0.618 mL, 6.82 mmol) were added thereto. To the resultant, bis(tri-tert-butylphosphine)palladium (5.81 mg, 0.011 mmol) was added under nitrogen atmosphere, followed by stirring at 100° C. overnight.

After the resultant reaction solution was allowed to cool to room temperature, water (15 ml) was added thereto. The thus produced solid was filtered, washed with water and dried to give Compound 4 (854 mg, 83%).

LC/MS (Method 1) RT=1.40, MS (m/z)=182.20

Step 2 Synthesis of Compound 5

Compound 4 (499 mg, 2.75 mmol) was dissolved in toluene (9.2 mL), and TFA (21 μL, 0.275 mmol) and 2-methoxy-N-methoxymethyl-N-((trimethylsilyl)methyl) ethane-1-amine (synthesized in accordance with the method described in WO2012158413) (735 mg, 3.58 mmol) were added thereto, followed by stirring at room temperature overnight.

A saturated sodium hydrogen carbonate aqueous solution was added to the resultant reaction solution, followed by the extraction with ethyl acetate. The organic layer was washed with a brine, and dried over anhydrous sodium sulfate. The solvent was distilled off under reduced pressure, and the thus obtained residue was purified by the silica gel column chromatography (hexane-ethyl acetate) to give Compound 5 (605 mg, Yield 78%).

LC/MS (Method 1) RT=0.54, MS (m/z)=283.20

Sep 3 Synthesis of Compound 6

Compound 5 (605 mg, 2.14 mmol) was dissolved in THF (2.1 mL). A 2 mol/L sodium hydroxide aqueous solution (1.29 mL, 2.57 mmol) was added thereto, followed by stirring at room temperature overnight. To the resultant, 2 mol/L hydrochloric acid (1.29 mL, 2.57 mmol) was added, the solvent was distilled off under reduced pressure, and water was removed by azeotropy with toluene twice.

The thus obtained residue was dissolved in DMF (7.1 mL). Triethylamine (0.594 mL, 4.29 mmol) and DPPA (0.553 mL, 2.57 mmol) were added thereto, followed by stirring at room temperature for 30 minutes. The resultant was heated to 80° C. and stirred for 30 minutes, and then, 2-trimethylsilylethanol (0.916 mL, 6.43 mmol) was added thereto, followed by stirring at 80° C. overnight.

The resultant reaction solution was allowed to cool to room temperature, and a saturated sodium hydrogen carbonate aqueous solution was added thereto, followed by the extraction with ethyl acetate. The organic layer was washed successively with water and a brine, and dried over anhydrous sodium sulfate. The solvent was distilled off under reduced pressure, and the thus obtained residue was purified by the silica gel column chromatography (hexane-ethyl acetate) to give Compound 6 (457 mg, Yield 56%).

LC/MS (Method 1) RT=1.24, MS (m/z)=384.20

Step 4 Synthesis of Compound (I-90)

Compound 6 (39.3 mg, 0.102 mmol) was dissolved in dichloromethane (1.0 mL), and TFA (0.5 mL) was added thereto, followed by stirring overnight. The resultant reaction solution was concentrated, and the thus obtained residue was dissolved in THF (1.0 mL). To the resultant, N-ethyldiisopropylamine (0.178 mL, 1.02 mmol) and Compound X (43.3 mg, 0.102 mmol) were added, followed by stirring overnight.

A saturated sodium hydrogen carbonate aqueous solution was added to the resultant reaction solution, followed by the extraction with ethyl acetate. The organic layer was washed with a brine, and dried over anhydrous sodium sulfate. The solvent was distilled off under reduced pressure, and the thus obtained residue was purified by the silica gel column chromatography (chloroform-methanol) to give Compound (I-90) (racemate, 48.9 mg, Yield 84%).

$^1$H-NMR (CDCl$_3$) δ: 2.23 (s, 3H), 2.32 (t, J=9.2 Hz, 1H), 2.54-2.69 (m, 2H), 2.71-2.83 (m, 2H), 3.04 (br s, 1H), 3.20-3.34 (m, 4H), 3.38-3.47 (m, 2H), 4.20 (s, 3H), 4.35 (br s, 1H), 5.44 (br s, 1H), 6.72 (s, 1H), 6.98 (d, J=5.1 Hz, 1H), 7.32-7.38 (m, 1H), 7.40-7.47 (m, 2H), 7.55-7.61 (m, 2H), 8.06 (s, 1H), 8.09 (d, J=5.1 Hz, 1H), 8.39 (d, J=2.0 Hz, 1H), 8.99 (d, J=2.0 Hz, 1H).

Example 2

Synthesis of Compound (I-102)

[Chemical Formula 112]

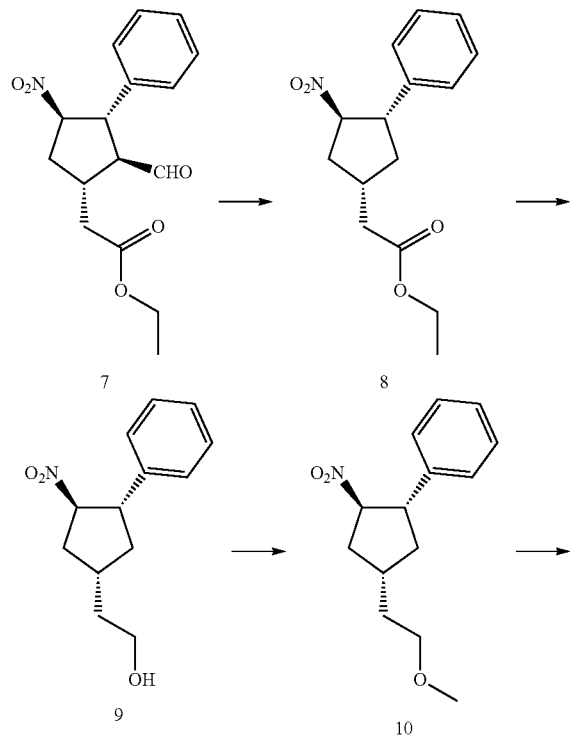

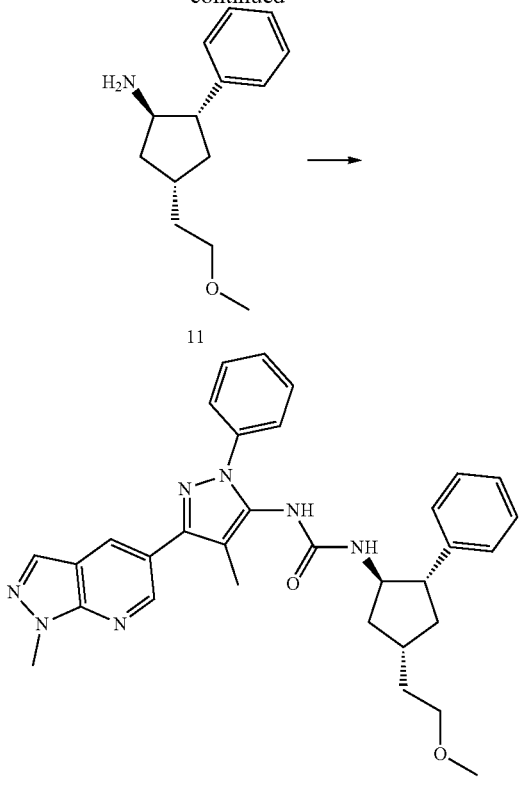

I-102

Step 1 Synthesis of Compound 8

Compound 7 (synthesized by a method described in Chem. Eur. J. 2008, 14, 10007-10011) (23.54 g, 77 mmol) was dissolved in tetrahydrofuran (330 mL) and acetonitrile (33 mL), and chlorotris(triphenylphosphine)rhodium (I) (86 g, 93 mmol) was added thereto, followed by stirring under reflux by heating for 4 hours.

After filtering off insolubles, the resultant residue was washed with ethyl acetate. The filtrate was distilled off under reduced pressure, and the thus obtained residue was purified by the silica gel column chromatography (hexane-ethyl acetate) to give Compound 8 (13.74 g, Yield 64.3%).

$^1$H-NMR (CDCl$_3$) δ: 1.27 (t, J=7.2 Hz, 3H), 1.60 (q, J=12.2 Hz, 1H), 2.04 (dt, J=7.2, 17.6 Hz, 1H), 2.46 (d, J=6.8 Hz, 2H), 2.47 (m, 1H), 2.63 (m, 1H), 2.81 (s, 1H), 3.78 (dt, J=6.2, 13.7 Hz, 1H), 4.16 (t, J=7.2 Hz, 2H), 4.95 (m, 1H), 7.21-7.35 (m, 5H).

Step 2 Synthesis of Compound 9

Compound 8 (13.74 g, 49.5 mmol) was dissolved in tetrahydrofuran (200 mL), the resultant was cooled to −78° C., and a 1.0 mol/L DIBAL-toluene solution (149 mL, 149 mmol) was added dropwise thereto over 40 minutes, followed by stirring at −78° C. for 30 minutes and further at room temperature for 1 hour.

Methanol (50 mL) was added to the resultant reaction solution, the resultant was stirred for 5 minutes, and then, ethyl acetate (100 mL), a saturated potassium sodium tartrate aqueous solution (100 mL) and water (100 mL) were added thereto, followed by stirring at room temperature for 1 hour. The thus obtained mixture was extracted with ethyl acetate, and the organic layer was washed with water and dried over sodium sulfate. The solvent was distilled off under reduced pressure, and the thus obtained residue was purified by the silica gel column chromatography (hexane-ethyl acetate) to give Compound 9 (14.13 g, 99.4%).

$^1$H-NMR (CDCl$_3$) δ: 1.35 (brs, 1H), 1.54 (q, J=12.2 Hz, 1H), 1.73 (q, J=6.6 Hz, 2H), 1.98 (dt, J=6.6, 16.9 Hz, 1H), 2.40-2.61 (m, 3H), 3.71-3.79 (m, 3H), 4.93 (m, 1H), 7.21-7.35 (m, 5H).

Step 3 Synthesis of Compound 10

Compound 9 (14.13 g, 49.2 mmol) was dissolved in dichloromethane (180 mL), and 2,6-di-tert-butyl-4-methyl-pyridine (36.4 g, 177 mmol) and methyl trifluoromethane-sulfonate (24.24 g, 148 mmol) were added thereto, followed by stirring under reflux by heating for 1.5 hours.

Water was added thereto, followed by the extraction with chloroform, and the resultant was dried over sodium sulfate. The solvent was distilled off under reduced pressure, and the thus obtained residue was purified by the silica gel column chromatography (hexane-ethyl acetate) to give Compound 10 (10.50 g, Yield 85.5%).

$^1$H-NMR (CDCl$_3$) δ: 1.53 (q, J=12.2 Hz, 1H), 1.72 (dq, J=1.7, 6.6 Hz, 2H), 1.98 (dt, J=6.6, 16.9 Hz, 1H), 2.39-2.59 (m, 3H), 3.34 (s, 3H), 3.43 (t, J=6.6 Hz, 2H), 3.75 (dt, J=6.1, 13.6 Hz, 1H), 4.93 (m, 1H), 7.21-7.35 (m, 5H).

Step 4 Synthesis of Compound 11

Compound 10 (10.50 g, 42.1 mmol) was dissolved in methanol (200 mL), and concentrated hydrochloric acid (53 mL) and a zinc powder (27.5 g, 421 mmol) were added thereto under ice-cooling, followed by stirring at room temperature for 0.5 hour.

After filtering off insolubles, the thus obtained residue was washed with methanol. A 2 mol/L sodium hydroxide aqueous solution was added to the filtrate for neutralization, followed by the extraction with chloroform. The resultant was dried over sodium sulfate, the solvent was distilled off under reduced pressure, and the thus obtained residue was purified by the silica gel column chromatography (hexane-ethyl acetate) to give Compound 11 (10.84 g, Yield 100%).

LC/MS (Method 2) RT=1.15, MS (m/z)=220

Step 6 Synthesis of Compound (I-102)

Compound 11 (15 mg, 0.068 mmol) was dissolved in tetrahydrofuran (1 mL), and triethylamine (0.019 mL, 0.137 mmol) and Compound X (29 mg, 0.068 mmol) were added thereto, followed by stirring at room temperature for 2 hours.

The solvent was distilled off under reduced pressure, and the thus obtained residue was purified by the silica gel column chromatography (chloroform-methanol) to give Compound (I-102) (35 mg, 93.1%).

LC/MS (Method 1) RT=2.05, MS (m/z)=550

$^1$H-NMR (CDCl$_3$) δ: 1.37 (q, J=12.7 Hz, 1H), 1.68 (m, 3H), 1.98 (m, 1H), 2.00 (s, 3H), 2.21 (m, 2H), 2.74 (m, 1H), 3.31 (s, 3H), 3.37 (t, J=6.4 Hz, 2H), 4.20 (s, 3H), 4.26 (m, 1H), 4.77 (brs, 1H), 6.21 (brs, 1H), 7.16-7.44 (m, 10H), 8.05 (s, 1H), 8.36 (m, 1H), 8.95 (m, 1H).

Example 3

Synthesis of Compound (I-94)

[Chemical Formula 113]

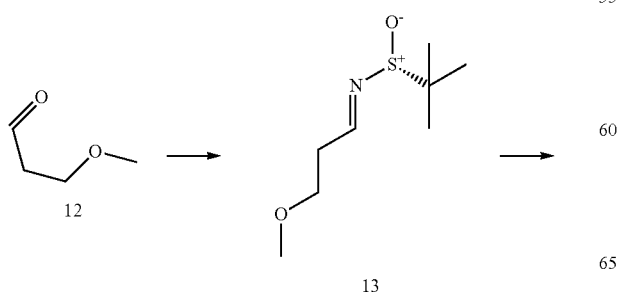

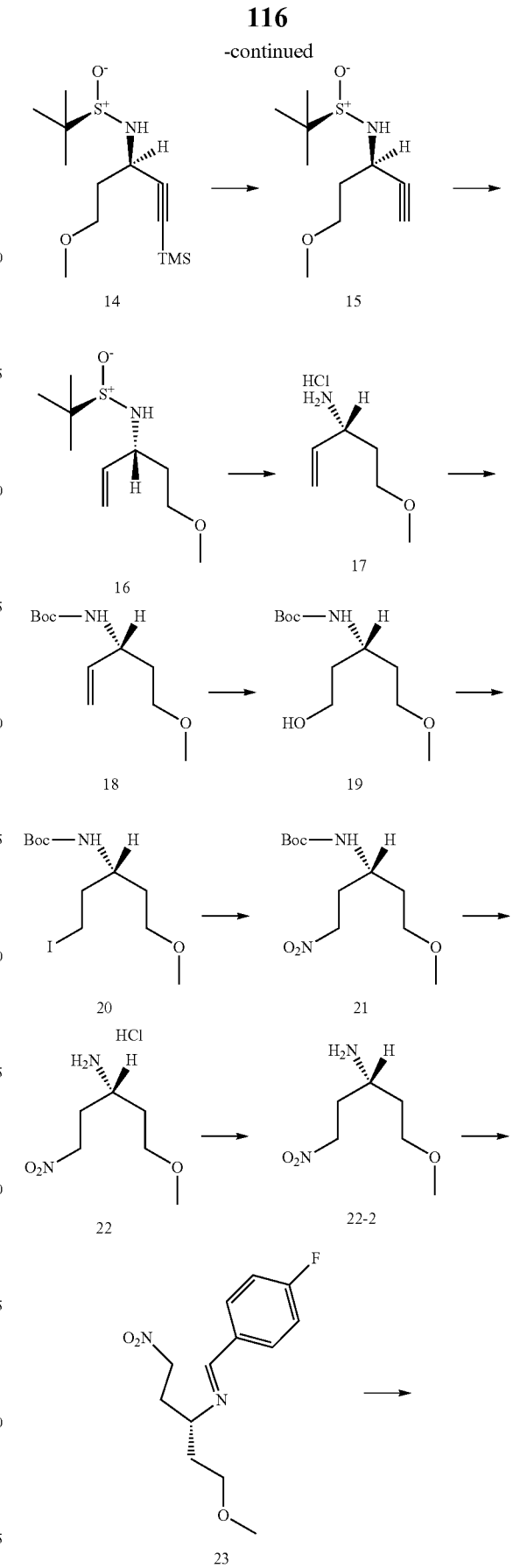

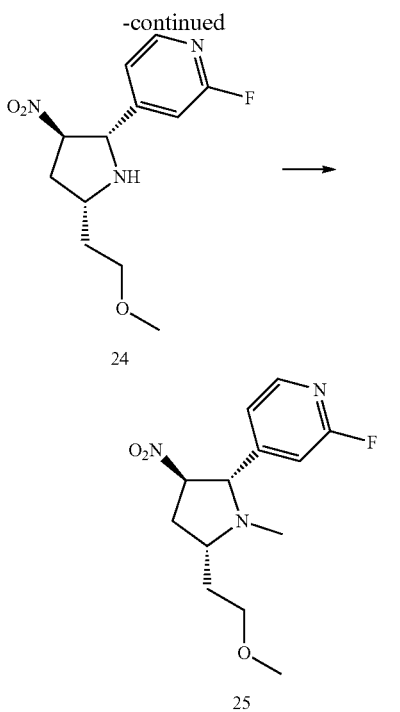

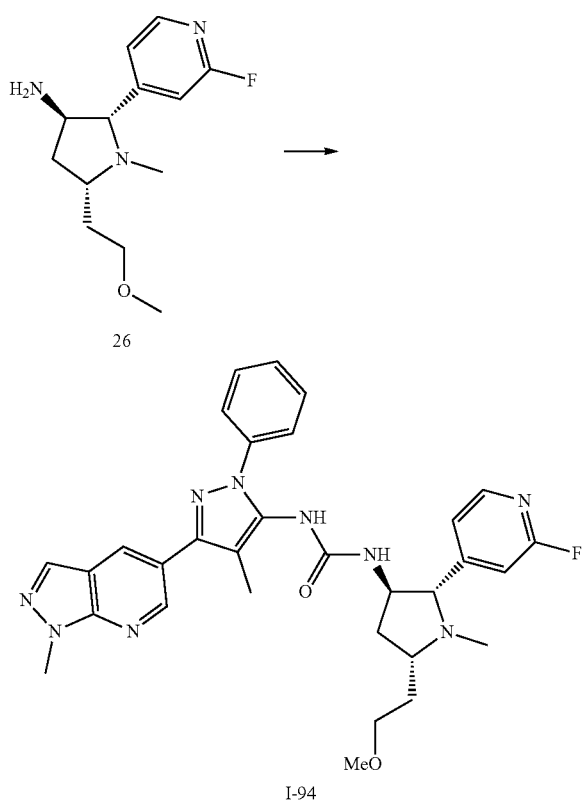

Step 1 Synthesis of Compound 13

Compound 12 (5 g, 56.7 mmol) was dissolved in dichloromethane (125 mL) under nitrogen atmosphere, and (R)-2-methylpropane-2-sulfinamide (6.88 g, 56.7 mmol) and anhydrous copper sulfate (19.9 g, 125 mmol) were added thereto, followed by stirring at room temperature for 2 days.

The thus obtained mixture was filtered through a celite pad, the filtrate was concentrated, and the thus obtained residue was purified by the silica gel column chromatography (hexane-ethyl acetate) to give Compound 13 (10.9 g, Yield 92%).

$^1$H-NMIR (CDCl$_3$) δ: 1.20 (s, 9H), 2.78 (q, J=5.5 Hz, 2H), 3.35 (s, 3H), 3.69 (t, J=6.3 Hz, 2H), 8.07-8.11 (br m, 1H).

LC/MS (Method 1) RT=1.21, MS (m/z)=192.00

Step 2 Synthesis of Compound 14

LHMDS (1 mol/L, in THF, 52.3 mL, 52.3 mmol) was mixed with anhydrous hexane (250 mL), and ethynyltrimethylsilane (5.13 g, 52.3 mmol) was added dropwise to the resultant mixture at −78° C. After the dropwise addition, the resultant reaction solution was heated to room temperature, stirred for 10 minutes, and then cooled to −78° C. again. To the resultant reaction solution, a solution of Compound 13 (5 g, 26.1 mmol) in hexane (50 mL)/THF (10 mL) (temperature of 0° C.) was added dropwise. After the dropwise addition, the reaction solution was heated to room temperature, followed by stirring overnight. The resultant reaction solution was diluted with a saturated ammonium chloride solution, followed by the extraction with ethyl acetate. The organic layer was washed with water, and dried over anhydrous sodium sulfate. The solvent was distilled off under reduced pressure, and the thus obtained residue was purified by the silica gel column chromatography (hexane-ethyl acetate containing 10% triethylamine) to give Compound 14 (5.67 g, Yield 75%).

$^1$H-NMR (CDCl$_3$) δ: 0.00 (s, 9H), 1.04 (s, 9H), 1.77-1.82 (m, 2H), 3.17 (s, 3H), 3.35 (dt, J=10.9, 4.9 Hz, 1H), 3.45 (dt, J=11.4, 4.9 Hz, 1H), 3.50 (d, J=6.5 Hz, 1H), 4.07 (q, J=6.5 Hz, 1H).

LC/MS (Method 1) RT=2.07, MS (m/z)=289.90

Step 3 Synthesis of Compound 15

TBAF (1 mol/L, 19.6 mL) was added to a solution of Compound 14 (5.67 g, 19.6 mmol) in THF (28 mL), followed by stirring at room temperature for 3 hours. The resultant reaction solution was diluted with a saturated ammonium chloride solution, followed by the extraction with ethyl acetate. The organic layer was washed successively with a saturated ammonium chloride solution and brinea saturated saline solution, and dried over anhydrous sodium sulfate to give Compound 15 (4.26 g, Yield 100%).

$^1$H-NMR (CDCl$_3$) δ: 1.21 (s, 9H), 1.90-2.05 (m, 2H), 2.44 (br s, 1H), 3.34 (s, 3H), 3.50-3.58 (m, 1H), 3.61-3.69 (m, 1H), 3.78 (d, J=7.5 Hz, 1H), 4.23 (q, J=6.8 Hz, 1H).

Step 4 Synthesis of Compound 16

Quinoline (0.116 mL, 0.980 mmol) and a Lindlar catalyst (2.09 g, 0.980 mmol) were added to a solution of Compound 15 (4.26 g, 19.60 mmol) in THF (80 mL) to cause a catalytic hydrogenation reaction. After completing the reaction, the reaction solution was filtered through a celite pad, and the filtrate was concentrated to give Compound 16 (4.12 g, Yield 96%).

$^1$H-NMR (CDCl$_3$) δ: 1.14 (s, 9H), 1.68 (br s, 1H), 1.79 (q, J=6.2 Hz, 2H), 3.25 (s, 3H), 3.34-3.46 (m, 2H), 3.82-3.89 (m, 1H), 5.12 (d, J=10.3 Hz,1H), 5.23 (d, J=17.1 Hz, 1H), 5.78-5.87 (m, 1H).

Step 5 Synthesis of Compound 17

To a solution of Compound 16 (801 mg, 3.65 mmol) in dichloromethane (2 mL), 5 mL of hydrochloric acid (4 mol/L, in 1,4-dioxane) was added, followed by stirring at room temperature. The resultant reaction solution was concentrated to give Compound 17 (421 mg, Yield 100%)

Step 6 Synthesis of Compound 18

Compound 17 (5.11 g, 33.7 mmol) and sodium carbonate (17.86 g, 169 mmol) were added to THF (20 mL) and water (20 mL), and di-tert-butyl dicarbonate (8.61 mL, 37.1 mmol) was added to the resultant solution under ice-cooling. The thus obtained mixture was stirred at room temperature overnight. A saturated sodium hydrogen carbonate aqueous solution was added to the resultant, followed by the extraction with dichloromethane. The organic layer was washed with a brine, and dried over anhydrous sodium sulfate. The solvent was distilled off under reduced pressure, and the thus obtained residue was purified by the silica gel column chromatography (hexane-ethyl acetate) to give Compound 18 (6.51 g, Yield 90%).

$^1$H-NMR (CDCl$_3$) δ: 1.46 (br s, 10H), 1.63-1.76 (m, 1H), 1.83-1.95 (m, 1H), 3.32 (s, 3H), 3.41-3.51 (m, 2H), 4.25 (br s, 1H), 4.96 (br s, 1H), 5.12 (d, J=10.3 Hz, 1H), 5.18 (d, J=17.3 Hz, 1H), 5.71-5.84 (m, 1H).

Step 7 Synthesis of Compound 19

9-BBN (169 mL, 85 mmol) was added dropwise to a solution of Compound 18 (6.5 g, 30.2 mmol) in THF (65 mL) under ice-cooling, followed by stirring at room temperature for 4.5 hours. To the resultant reaction solution, 2 mol/L sodium hydroxide (106 mL, 211 mmol) and then a 30% hydrogen peroxide solution (100 mL, 3263 mmol) were successively added, followed by stirring for 1.5 hours. To the resultant reaction solution, a saturated sodium thiosulfate solution was added, followed by the extraction with ethyl acetate. The organic layer was washed successively with a saturated sodium thiosulfate solution and a brine, and dried over anhydrous sodium sulfate, and the solvent was distilled off under reduced pressure. The thus obtained residue was purified by the silica gel column chromatography (hexane-ethyl acetate) to give Compound 19 (5.92 g, Yield 84%).

LC/MS (Method 1) RT=1.18, MS (m/z)=178.25 (M-55)

Step 8 Synthesis of Compound 20

A solution of Compound 19 (440 mg, 1.886 mmol) in dichloromethane (4 mL) was added to a solution of imidazole (244 mg, 3.58 mmol), triphenylphosphine (841 mg, 3.21 mmol) and iodine (862 mg, 3.39 mmol) in dichloromethane under ice-cooling. After stirring the resultant for 5 hours, a sodium thiosulfate solution was added to the resultant reaction solution, followed by the extraction with dichloromethane. The organic layer was washed with a brine, and dried over anhydrous sodium sulfate, and the solvent was distilled off under reduced pressure. The thus obtained residue was purified by the silica gel column chromatography (hexane-ethyl acetate) to give Compound 20 (390 mg, Yield 60%).

$^1$H-NMR (CDCl$_3$) δ: 1.44 (s, 9H), 1.60-1.70 (m, 1H), 1.76-1.87 (m, 1H), 2.00-2.10 (m, 2H), 3.13-3.24 (m, 2H), 3.33 (s, 3H), 3.40-3.52 (m, 2H), 3.70-3.80 (m, 1H), 4.65-4.80 (br m, 1H).

Step 9 Synthesis of Compound 21

Sodium nitrite (619 mg, 8.97 mmol) was added to a solution of Compound 20 (385 mg, 1.12 mmol) in DMF (0.5 mL), followed by stirring at room temperature for 1 hour under shade conditions. Water was added to the resultant reaction solution, followed by the extraction with dichloromethane.

The organic layer was washed with a brine, and dried over anhydrous sodium sulfate, and the solvent was distilled off under reduced pressure. The thus obtained residue was purified by the silica gel column chromatography (hexane-ethyl acetate) to give Compound 21 (197 mg, Yield 67%).

$^1$H-NMR (CDCl$_3$) δ: 1.44 (s, 9H), 1.62-1.76 (m, 1H), 1.81-1.90 (m, 1H), 2.08-2.20 (m, 1H), 2.19-2.30 (m, 1H), 3.33 (s, 3H), 3.40-3.55 (m, 2H), 3.76-3.88 (m, 1H), 4.38-4.57 (m, 2H), 4.75-4.92 (m, 1H).

Step 10 Synthesis of Compound 22

To a solution of Compound 21 (2.15 g, 8.20 mmol) in dichloromethane (10 mL), 20 mL of hydrochloric acid (4 mol/L, in 1,4-dioxane) was added, followed by stirring at room temperature. To the resultant reaction solution, ethyl acetate was added, the thus precipitated white solid was filtered off and dried to give Compound 22 (421 mg, Yield 100%).

LC/MS (Method 1) RT=0.38, MS (m/z)=162.60 (M-55)

Step 11 Synthesis of Compound 22-2

Compound 22 was allowed to pass through an injection column (amino) (eluted with MeOH) for desalination to give Compound 22-2.

$^1$H-NMR (CDCl$_3$) δ: 1.11-1.38 (br m, 2H), 1.50-1.62 (m, 1H), 1.68-1.79 (m, 1H), 1.84-1.97 (m, 1H), 2.13-2.26 (m, 1H), 2.90-3.04 (m, 1H), 3.33 (s, 3H), 3.42-3.56 (m, 2H), 4.48-4.63 (m, 2H).

Step 12 Synthesis of Compound 23

To a solution of Compound 22-2 (300 mg, 1.51 mmol) in dichloromethane (2 mL), 2-fluoroisonicotinaldehyde (198 mg, 1.586 mmol) and magnesium sulfate (191 mg, 1.586 mmol) were added, followed by stirring at room temperature for 1 hour. The resultant reaction solution was filtered through a celite pad and a NH silica gel injection column (MeOH), and the resultant was concentrated to quantitatively give Compound 23.

$^1$H-NMR (CDCl$_3$) δ: 1.84 (ddd, J=18.7, 9.2, 4.7 Hz, 1H), 1.92-2.02 (m, 1H), 2.27-2.38 (m, 1H), 2.39-2.50 (m, 1H), 3.19-3.26 (m, 1H), 3.28 (s, 3H), 3.33-3.42 (m, 1H), 3.54-3.61 (m, 1H), 4.29-4.44 (m, 2H), 7.25-7.27 (m, 1H), 7.50 (dt, J=5.0, 1.4 Hz, 1H), 8.30 (s, 1H).8.31 (d, J=5.1 Hz, 1H).

Step 13 Synthesis of Compound 24

Compound 23 (407 mg, 1.51 mmol) was dissolved in acetonitrile (2 mL), and the resultant was cooled to −20° C. Triethylamine (42 μL, 0.30 mmol) was added thereto, and the resultant was allowed to stand still overnight, and then heated to room temperature. The resultant reaction solution was filtered through a NH silica gel injection column (MeOH), and the resultant was concentrated to give a crude product of Compound 24 (396 mg, Yield 97%).

LC/MS (Method 1) RT=0.75, MS (m/z)=270.00

Step 14 Synthesis of Compound 25

To a solution of Compound 24 (376 mg, 1.40 mmol) in dichloromethane, 2.3 mL of formaldehyde (33% aqueous solution), acetic acid (16 μL, 0.279 mmol) and sodium triacetoxyborohydride (2.96 g, 13.96 mmol) were added, followed by stirring at room temperature for 1 hour. To the resultant reaction solution, water was added, followed by the extraction with dichloromethane. The organic layer was washed with a brine, and dried over anhydrous sodium sulfate, and the solvent was distilled off under reduced pressure. The thus obtained residue was purified by a NH silica gel injection column (MeOH) to give Compound 25 (430 mg, Yield 109%).

$^1$H-NMR (CDCl$_3$) δ: 1.60-1.69 (m, 1H), 2.06-2.22 (m, 3H), 2.24 (s, 3H), 2.67 (ddd, J=14.3, 6.7, 3.1 Hz, 1H), 2.90-2.97 (br m, 1H), 3.36 (s, 3H), 3.46-3.55 (m, 2H), 3.93 (d, J=5.6 Hz, 1H), 4.61-4.66 (m, 1H), 7.03 (s, 1H), 7.22 (dt, J=5.1, 1.4 Hz, 1H), 8.22 (d, J=5.1 Hz, 1H).

LC/MS (Method 1) RT=1.71, MS (m/z)=284.00

Step 15 Synthesis of Compound 26

To a solution of Compound 25 in THF (8 mL) and MeOH (4 mL), zinc (1.77 g, 27.1 mmol) and NH4Cl (14.5 g, 27.1 mmol) were added, followed by stirring at room temperature for 1.5 hours. The resultant reaction solution was filtered through a celite pad, the resultant was concentrated, and the thus obtained residue was purified by NH column chromatography (chloroform-methanol) to give Compound 26 (228 mg, 66%).

$^1$H-NMR (CDCl$_3$) δ: 1.64-1.67 (m, 1H), 1.79 (ddd, J=14.3, 7.3, 5.5 Hz, 1H), 1.95-2.03 (m, 2H), 2.15 (s, 3H), 2.70-2.79 (m, 1H), 2.97 (d, J=7.4 Hz, 1H), 3.10 (dd, J=15.6, 7.2 Hz, 1H), 3.36 (s, 3H), 3.47-3.52 (m, 2H), 6.99 (br s, 1H), 7.21-7.22 (br m, 1H), 8.16 (d, J=5.1 Hz, 1H).

LC/MS (Method 3) RT=1.17, MS (m/z)=254.00

Step 16 Synthesis of Compound (I-94)

Under nitrogen atmosphere, Compound 26 (20 mg, 0.079 mmol) and Compound X (35 mg, 0.083 mmol) were dissolved in THF (1 mL), and triethylamine (0.033 mL, 0.24 mmol) was added thereto under ice-cooling, followed by stirring at room temperature overnight. Water was added to the resultant, followed by the extraction with chloroform. The organic layer was washed with water, and dried over anhydrous magnesium sulfate. The solvent was distilled off under reduced pressure, and the thus obtained residue was purified by amino silica gel column chromatography (chloroform-methanol) to give Compound (1-94) (26 mg, Yield 56%).

$^1$H-NMR (CD$_3$OD) δ: 1.58-1.70 (br m, 1H), 1.83-1.93 (br m, 1H), 1.96-2.05 (br m, 1H), 2.12-2.19 (br m, 3H), 2.13 (s, 3H), 2.16 (br s, 3H), 2.72-2.82 (br m, 1H), 3.23 (d, J=7.8 Hz, 1H), 3.35 (s, 3H), 3.48-3.56 (m, 2H), 3.95-4.03 (m, 1H), 4.15 (s, 3H), 4.58 (s, 1H), 7.01 (s, 1H), 7.21-7.27 (m, 1H), 7.40-7.47 (m, 1H), 7.47-7.57 (m, 4H), 7.90 (s, 1H), 8.09 (d, J=5.0 Hz, 1H), 8.15 (s, 1H), 8.48 (s, 1H), 8.93 (s, 1H).

LC/MS (Method 1) RT=1.21, MS (m/z)=584.50

The following Compounds were obtained in accordance with the general synthetic methods and Examples. The chemical structures and the physical properties(LC/MS data) of Compounds are described below.

In addition, "wedged bond" and "hashed wedged bond" in the chemical structure means configuration. Specifically Compound with "racemate" in item of "configuration" means racemic compound whose relative configuration was determined. A compound with "Diastereo mixture" in the item means a compound whose relative configuration between the group of —NR5-C(=X)—NR5A-pyrazolyl and the group of —B was trans, and other absolute configurations are as described in the chemical structure. A compound with the item blank means a compound in which absolute configurations at the carbon atom binding to the group of —NR5-C(=X)—NR5A-pyrazolyl and the carbon atom binding to the group of —B are as described in the chemical structure.

Moreover, the bond which binds to the asymmetric carbon is indicated as solid line when their configurations were not determined.

TABLE 1

| No. | Structure | LCMS method No | RT | MS | configuration |
|---|---|---|---|---|---|
| I-1 | 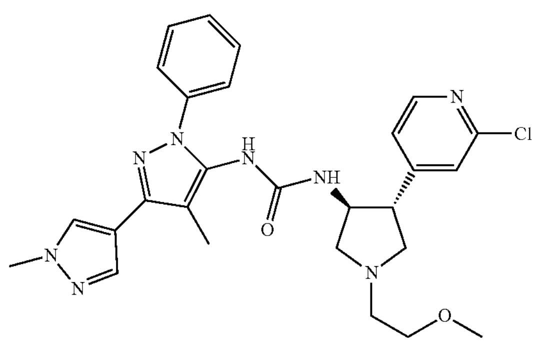 [SMILES: COCCN1C[C@@H](NC(=O)Nc2c(C)c(-c3cnn(C)c3)nn2-c2ccccc2)[C@H](c2ccnc(Cl)c2)C1] | 3 | 1.44 | 535 | racemate |
| I-2 | 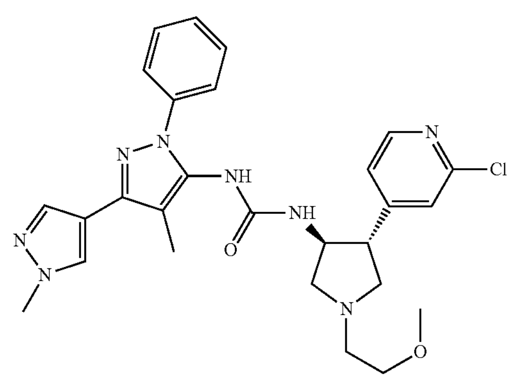 [SMILES: COCCN1C[C@@H](NC(=O)Nc2c(C)c(-c3cnn(C)c3)nn2-c2ccccc2)[C@H](c2ccnc(Cl)c2)C1] | 2 | 1.01 | 519 | racemate |

TABLE 1-continued

| No. | Structure | LCMS method No | RT | MS | configuration |
|---|---|---|---|---|---|
| I-3 | 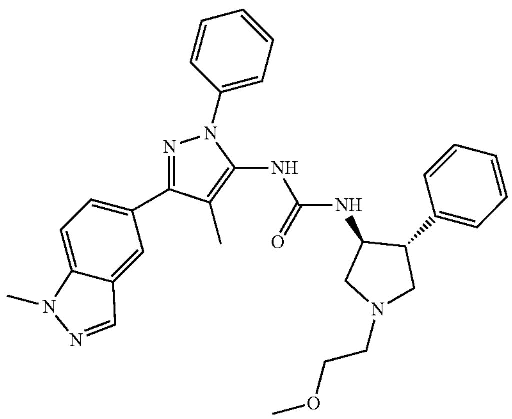 [SMILES: COCCN1C[C@@H](NC(=O)Nc2c(C)c(-c3ccc4c(cnn4C)c3)nn2-c2ccccc2)[C@H](c2ccccc2)C1] | 1 | 1.41 | 550.3 | racemate |
| I-4 | 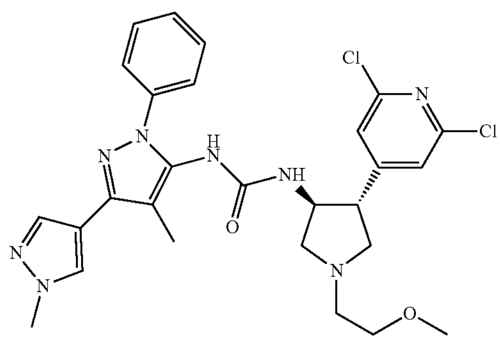 [SMILES: COCCN1C[C@@H](NC(=O)Nc2c(C)c(-c3cnn(C)c3)nn2-c2ccccc2)[C@H](c2cc(Cl)nc(Cl)c2)C1] | 2 | 1.3 | 569 | racemate |

TABLE 2

| No. | Structure | LCMS method No | RT | MS | configuration |
|---|---|---|---|---|---|
| I-5 | 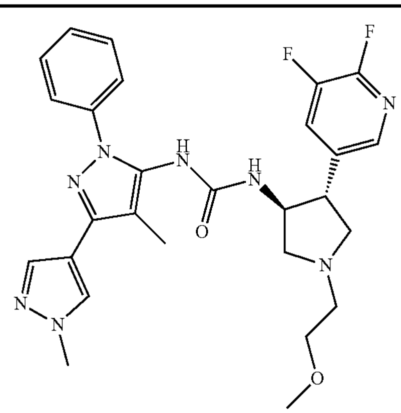 | 1 | 1.15 | 537.3 | racemate |

TABLE 2-continued

| No. | Structure | LCMS method No | RT | MS | configuration |
|---|---|---|---|---|---|
| I-6 | 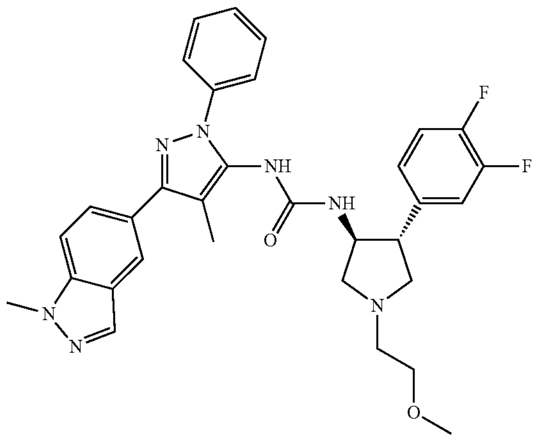 [SMILES: COCCN1C[C@@H](NC(=O)Nc2c(C)c(-c3ccc4c(cnn4C)c3)nn2-c2ccccc2)[C@H](c2ccc(F)c(F)c2)C1] | 1 | 1.49 | 586 | |
| I-7 | 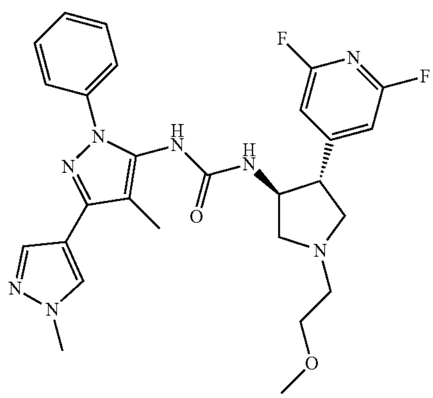 [SMILES: COCCN1C[C@@H](NC(=O)Nc2c(C)c(-c3cnn(C)c3)nn2-c2ccccc2)[C@H](c2cc(F)nc(F)c2)C1] | 1 | 1.14 | 537.3 | racemate |
| I-8 | 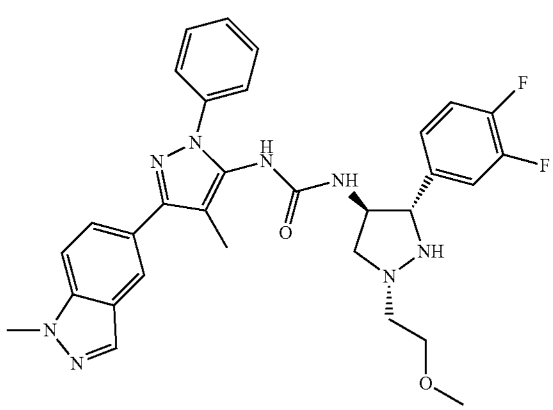 | 2 | 1.61 | 586 | |

TABLE 3

| No. | Structure | LCMS method No | RT | MS | configuration |
|---|---|---|---|---|---|
| I-9 | 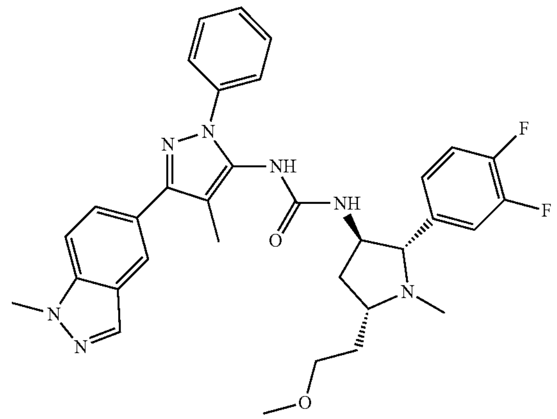 [SMILES: COCC[C@@H]1C[C@@H](NC(=O)Nc2c(C)c(-c3ccc4c(cnn4C)c3)nn2-c2ccccc2)[C@H](c2ccc(F)c(F)c2)N1C] | 2 | 1.49 | 600 | |
| I-10 | 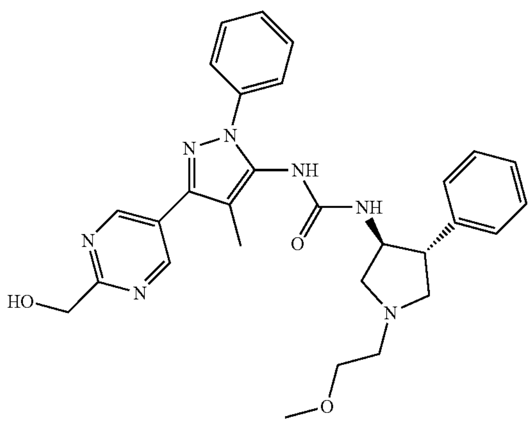 [SMILES: COCCN1C[C@@H](NC(=O)Nc2c(C)c(-c3cnc(CO)nc3)nn2-c2ccccc2)[C@H](c2ccccc2)C1] | 1 | 1.04 | 528.3 | racemate |
| I-11 | 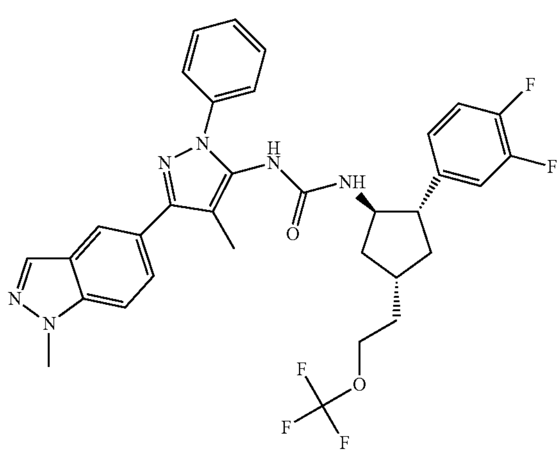 [SMILES: Cc1c(-c2ccc3c(cnn3C)c2)nn(-c2ccccc2)c1NC(=O)N[C@@H]1C[C@@H](CCOC(F)(F)F)C[C@H]1c1ccc(F)c(F)c1] | 2 | 2.63 | 639 | |

TABLE 3-continued
| No. | Structure | LCMS method No | RT | MS | configuration |
|---|---|---|---|---|---|
| I-12 | 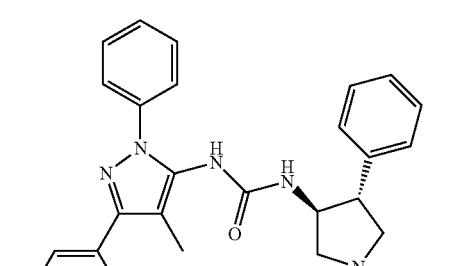 | 2 | 1.6 | 622 | racemate |
TABLE 4
| No. | Structure | LCMS method No | RT | MS | configuration |
|---|---|---|---|---|---|
| I-13 | 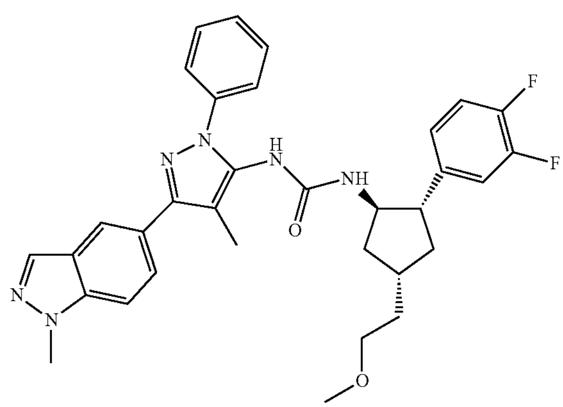 [SMILES: COCC[C@@H]1C[C@@H](NC(=O)Nc2c(C)c(-c3ccc4c(cnn4C)c3)nn2-c2ccccc2)[C@H](c2ccc(F)c(F)c2)C1] | 2 | 2.3 | 585 | |
| I-14 | 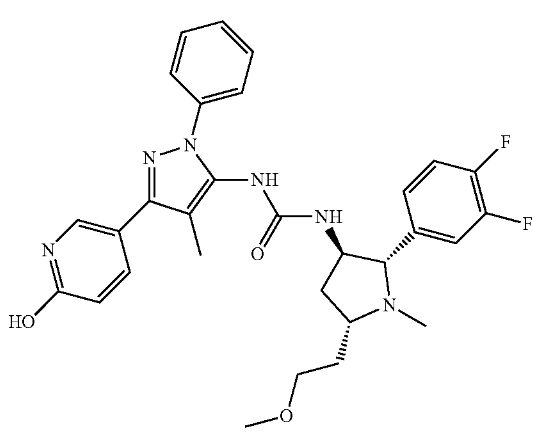 [SMILES: COCC[C@@H]1C[C@@H](NC(=O)Nc2c(C)c(-c3ccc(O)nc3)nn2-c2ccccc2)[C@H](c2ccc(F)c(F)c2)N1C] | 1 | 1.05 | 563.25 | |

TABLE 4-continued

| No. | Structure | LCMS method No | RT | MS | configuration |
|---|---|---|---|---|---|
| I-15 | 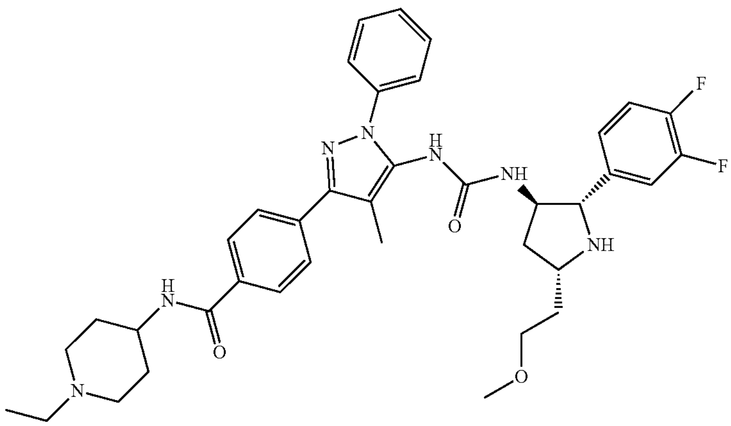 [SMILES: CCN1CCC(NC(=O)c2ccc(-c3nn(-c4ccccc4)c(NC(=O)N[C@@H]4C[C@@H](CCOC)N[C@H]4c4ccc(F)c(F)c4)c3C)cc2)CC1] | 2 | 1.03 | 686 | |
| I-16 | 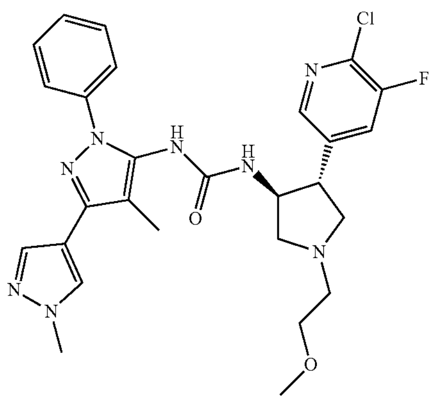 [SMILES: COCCN1C[C@@H](NC(=O)Nc2c(C)c(-c3cnn(C)c3)nn2-c2ccccc2)[C@H](c2cnc(Cl)c(F)c2)C1] | 1 | 1.15 | 553.2 | racemate |

TABLE 5

| No. | Structure | LCMS method No | RT | MS | configuration |
|---|---|---|---|---|---|
| I-17 | 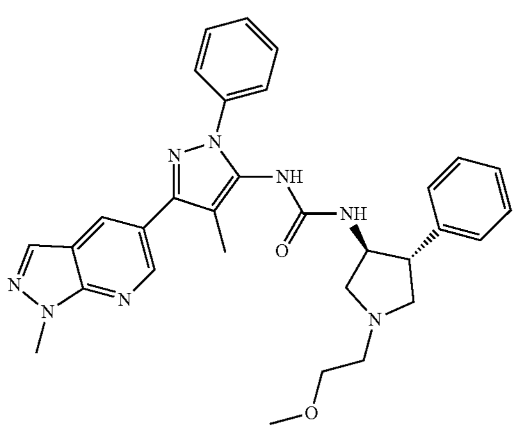 [SMILES: COCCN1C[C@@H](NC(=O)Nc2c(C)c(-c3cnc4c(cnn4C)c3)nn2-c2ccccc2)[C@H](c2ccccc2)C1] | 1 | 1.31 | 551.25 | racemate |

TABLE 5-continued
| No. | Structure | LCMS method No | RT | MS | configuration |
|---|---|---|---|---|---|
| I-18 | 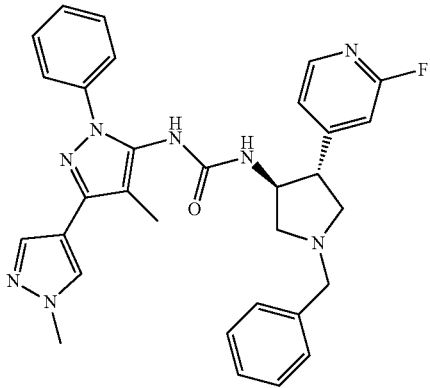 [SMILES: Cc1c(-c2cnn(C)c2)nn(-c2ccccc2)c1NC(=O)N[C@@H]1CN(Cc2ccccc2)C[C@H]1c1ccnc(F)c1] | 1 | 1.19 | 551.25 | racemate |
| I-19 | 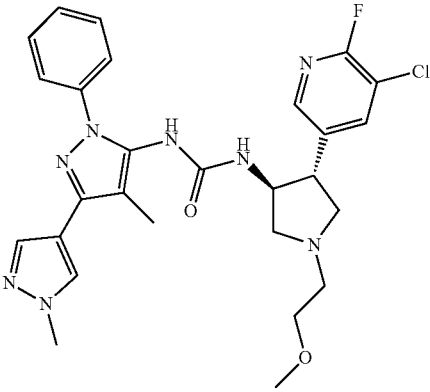 [SMILES: COCCN1C[C@@H](NC(=O)Nc2c(C)c(-c3cnn(C)c3)nn2-c2ccccc2)[C@H](c2cnc(F)c(Cl)c2)C1] | 1 | 1.2 | 553.2 | racemate |
| I-20 | 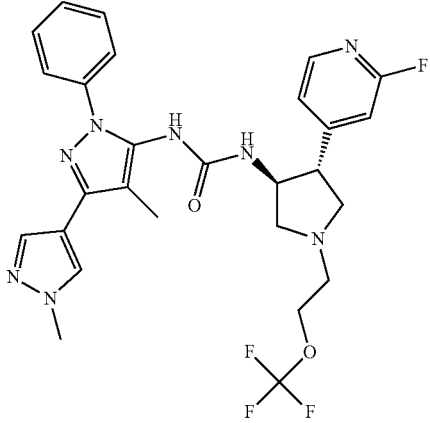 [SMILES: Cc1c(-c2cnn(C)c2)nn(-c2ccccc2)c1NC(=O)N[C@@H]1CN(CCOC(F)(F)F)C[C@H]1c1ccnc(F)c1] | 1 | 1.18 | 573.2 | racemate |

TABLE 6

| No. | Structure | LCMS method No | RT | MS | configuration |
|---|---|---|---|---|---|
| I-21 | 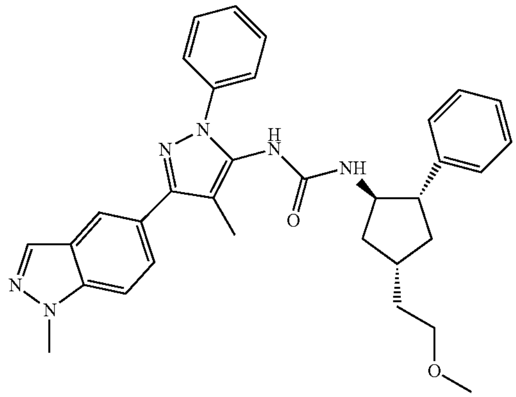 [SMILES: COCC[C@@H]1C[C@@H](NC(=O)Nc2c(C)c(-c3ccc4c(cnn4C)c3)nn2-c2ccccc2)[C@H](c2ccccc2)C1] | 2 | 2.24 | 549 | |
| I-22 | 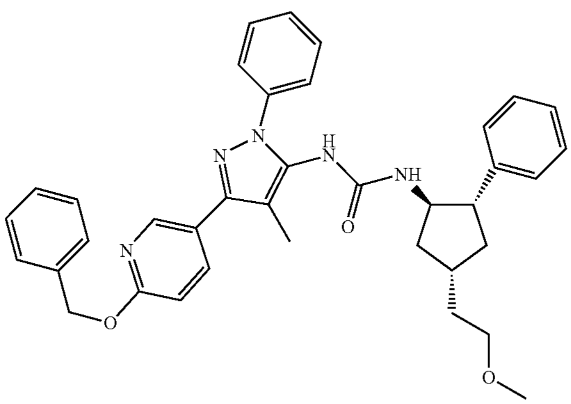 [SMILES: COCC[C@@H]1C[C@@H](NC(=O)Nc2c(C)c(-c3ccc(OCc4ccccc4)nc3)nn2-c2ccccc2)[C@H](c2ccccc2)C1] | 2 | 2.77 | 602 | |
| I-23 | 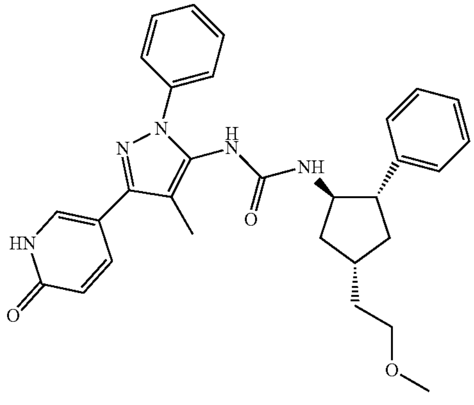 [SMILES: COCC[C@@H]1C[C@@H](NC(=O)Nc2c(C)c(-c3ccc(=O)[nH]c3)nn2-c2ccccc2)[C@H](c2ccccc2)C1] | 2 | 1.78 | 512 | |

TABLE 6-continued

| No. | Structure | LCMS method No | RT | MS | configuration |
|---|---|---|---|---|---|
| I-24 | 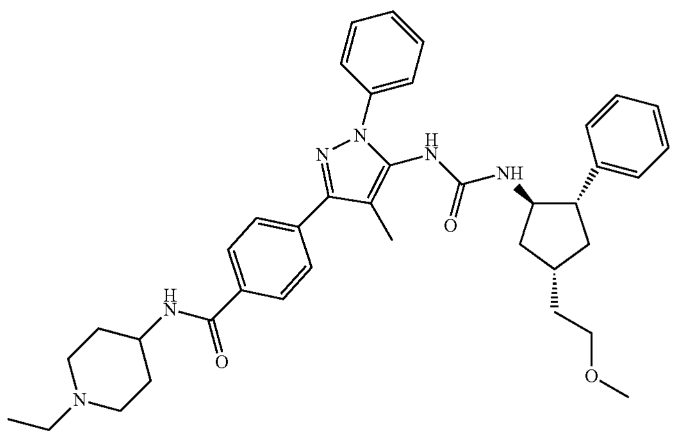 [SMILES: CCN1CCC(NC(=O)c2ccc(-c3nn(-c4ccccc4)c(NC(=O)N[C@@H]4C[C@@H](CCOC)C[C@H]4c4ccccc4)c3C)cc2)CC1] | 2 | 1.82 | 649 | |

TABLE 7

| No. | Structure | LCMS method No | RT | MS | configuration |
|---|---|---|---|---|---|
| I-25 | 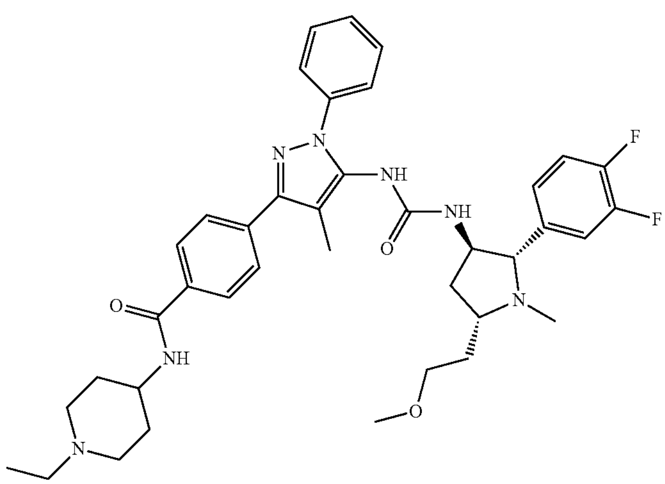 [SMILES: CCN1CCC(NC(=O)c2ccc(-c3nn(-c4ccccc4)c(NC(=O)N[C@@H]4C[C@@H](CCOC)N(C)[C@H]4c4ccc(F)c(F)c4)c3C)cc2)CC1] | 1 | 1.11 | 700.35 | |
| I-26 | 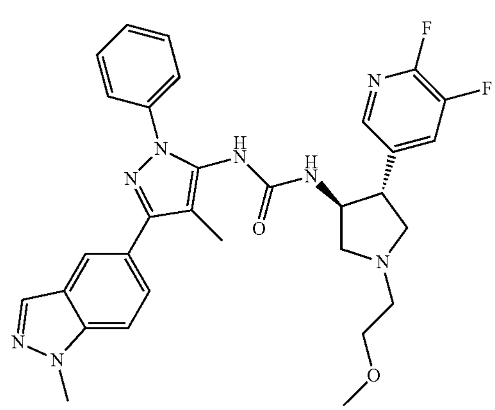 [SMILES: COCCN1C[C@@H](NC(=O)Nc2c(C)c(-c3ccc4c(cnn4C)c3)nn2-c2ccccc2)[C@H](c2cnc(F)c(F)c2)C1] | 1 | 1.4 | 587.2 | racemate |

TABLE 7-continued

| No. | Structure | LCMS method No | RT | MS | configuration |
|---|---|---|---|---|---|
| I-27 | 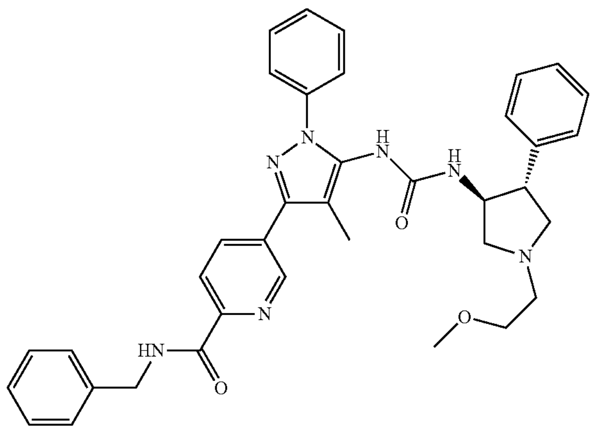 [SMILES: COCCN1C[C@@H](NC(=O)Nc2c(C)c(-c3ccc(C(=O)NCc4ccccc4)nc3)nn2-c2ccccc2)[C@H](c2ccccc2)C1] | 2 | 1.96 | 630 | racemate |
| I-28 | 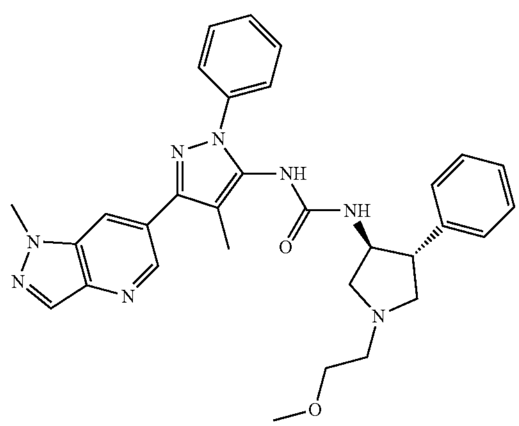 [SMILES: COCCN1C[C@@H](NC(=O)Nc2c(C)c(-c3cnc4cnn(C)c4c3)nn2-c2ccccc2)[C@H](c2ccccc2)C1] | 1 | 1.29 | 551.3 | racemate |

TABLE 8

| No. | Structure | LCMS method No | RT | MS | configuration |
|---|---|---|---|---|---|
| I-29 | 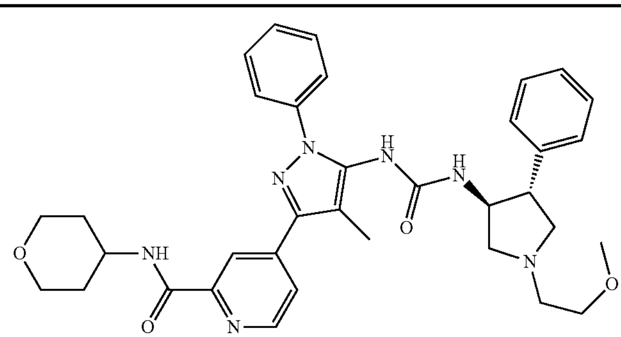 | 2 | 1.87 | 624 | racemate |

TABLE 8-continued

| No. | Structure | LCMS method No | RT | MS | configuration |
|---|---|---|---|---|---|
| I-30 | 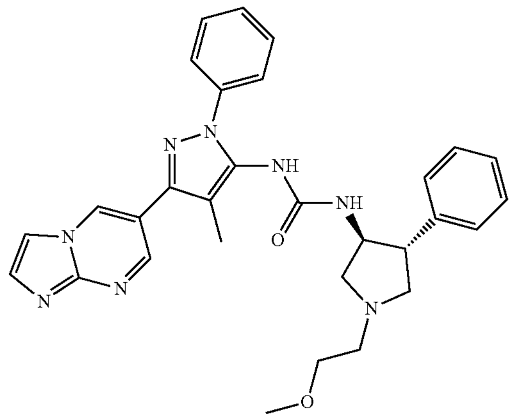 [SMILES: COCCN1C[C@@H](NC(=O)Nc2c(C)c(-c3cnc4nccn4c3)nn2-c2ccccc2)[C@H](c2ccccc2)C1] | 1 | 0.84 | 537.3 | racemate |
| I-31 | 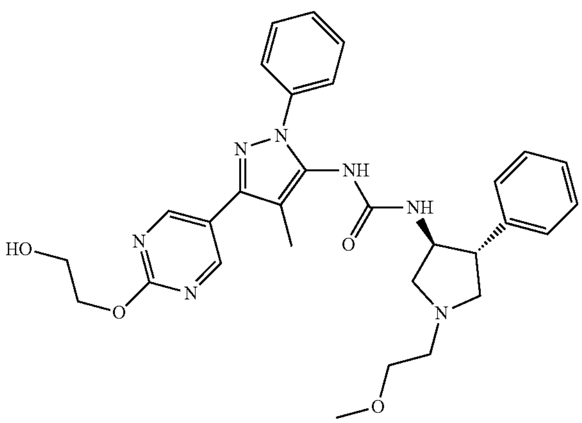 [SMILES: COCCN1C[C@@H](NC(=O)Nc2c(C)c(-c3cnc(OCCO)nc3)nn2-c2ccccc2)[C@H](c2ccccc2)C1] | 1 | 1.02 | 558.25 | racemate |
| I-32 | 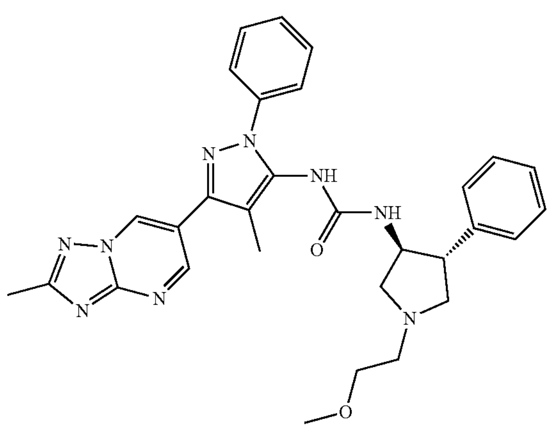 [SMILES: COCCN1C[C@@H](NC(=O)Nc2c(C)c(-c3cnc4nc(C)nn4c3)nn2-c2ccccc2)[C@H](c2ccccc2)C1] | 1 | 1.1 | 552.25 | racemate |

TABLE 9

| No. | Structure | LCMS method No | RT | MS | configuration |
|---|---|---|---|---|---|
| I-33 | 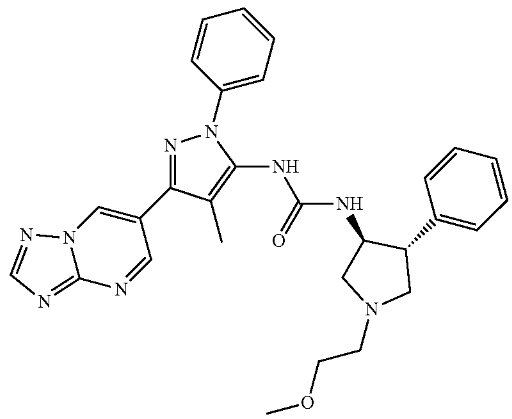 [SMILES: COCCN1C[C@@H](NC(=O)Nc2c(C)c(-c3cnc4ncnn4c3)nn2-c2ccccc2)[C@H](c2ccccc2)C1] | 1 | 1.05 | 538.3 | racemate |
| I-34 | 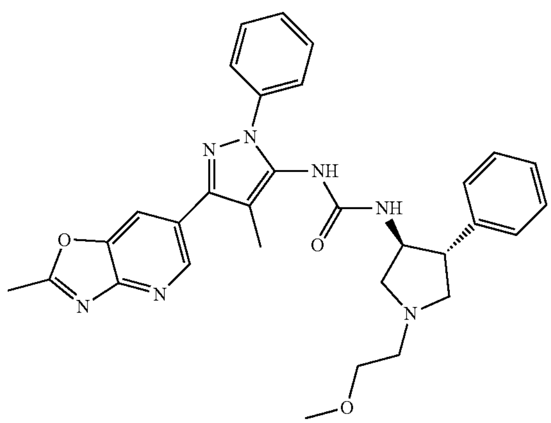 [SMILES: COCCN1C[C@@H](NC(=O)Nc2c(C)c(-c3cnc4nc(C)oc4c3)nn2-c2ccccc2)[C@H](c2ccccc2)C1] | 1 | 1.2 | 552.25 | racemate |
| I-35 | 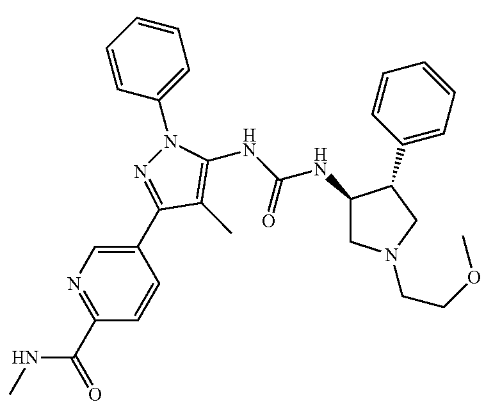 [SMILES: CNC(=O)c1ccc(-c2nn(-c3ccccc3)c(NC(=O)N[C@@H]3CN(CCOC)C[C@H]3c3ccccc3)c2C)cn1] | 2 | 1.31 | 554 | racemate |

TABLE 9-continued

| No. | Structure | LCMS method No | RT | MS | configuration |
|---|---|---|---|---|---|
| I-36 | 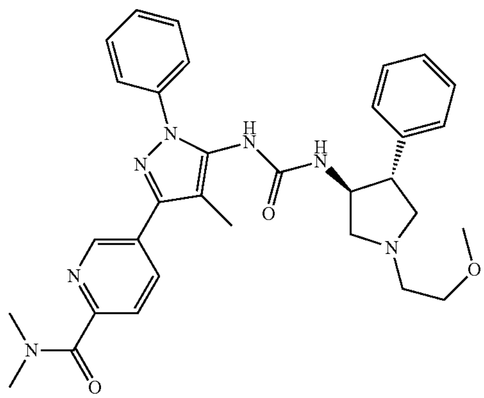 [SMILES: COCCN1C[C@@H](NC(=O)Nc2c(C)c(-c3ccc(C(=O)N(C)C)nc3)nn2-c2ccccc2)[C@H](c2ccccc2)C1] | 2 | 1.21 | 568 | racemate |

TABLE 10

| No. | Structure | LCMS method No | RT | MS | configuration |
|---|---|---|---|---|---|
| I-37 | 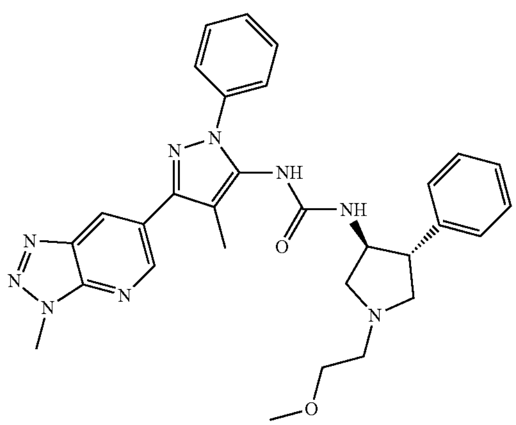 [SMILES: COCCN1C[C@@H](NC(=O)Nc2c(C)c(-c3cnc4c(c3)nnn4C)nn2-c2ccccc2)[C@H](c2ccccc2)C1] | 1 | 1.19 | 552.25 | racemate |
| I-38 | 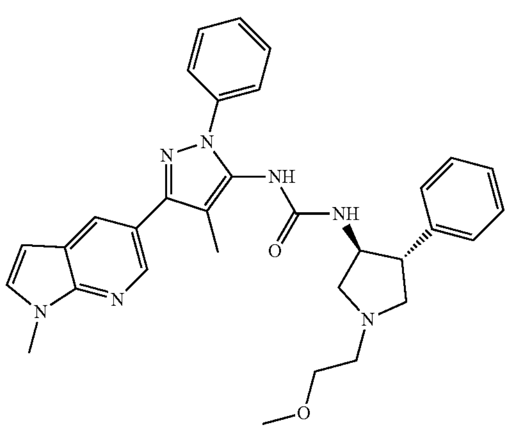 [SMILES: COCCN1C[C@@H](NC(=O)Nc2c(C)c(-c3cnc4c(ccn4C)c3)nn2-c2ccccc2)[C@H](c2ccccc2)C1] | 1 | 1.31 | 550.3 | racemate |

TABLE 10-continued

| No. | Structure | LCMS method No | RT | MS | configuration |
|---|---|---|---|---|---|
| I-39 | 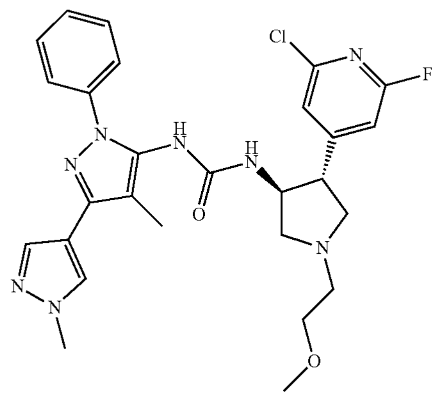 [SMILES: COCCN1C[C@@H](NC(=O)Nc2c(C)c(-c3cnn(C)c3)nn2-c2ccccc2)[C@H](c2cc(F)nc(Cl)c2)C1] | 1 | 1.07 | 553.2 | racemate |
| I-40 | 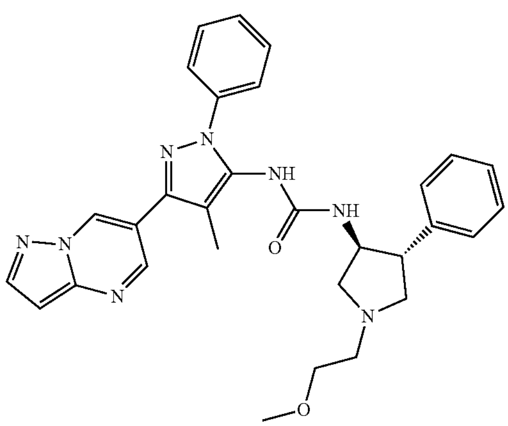 [SMILES: COCCN1C[C@@H](NC(=O)Nc2c(C)c(-c3cnc4ccnn4c3)nn2-c2ccccc2)[C@H](c2ccccc2)C1] | 1 | 1.19 | 537.3 | racemate |

TABLE 11

| No. | Structure | LCMS method No | RT | MS | configuration |
|---|---|---|---|---|---|
| I-41 | 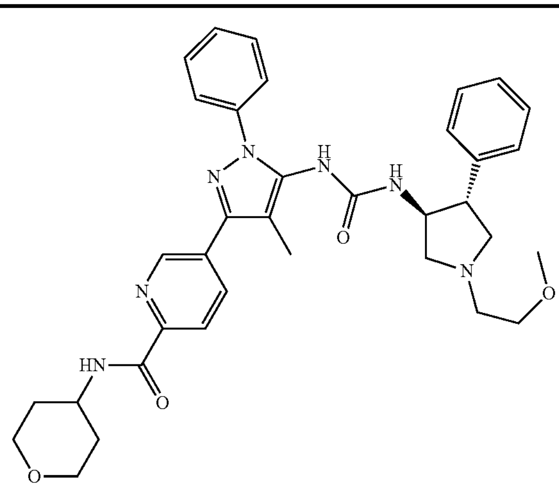 | 2 | 1.4 | 624 | racemate |

TABLE 11-continued

| No. | Structure | LCMS method No | RT | MS | configuration |
|---|---|---|---|---|---|
| I-42 | 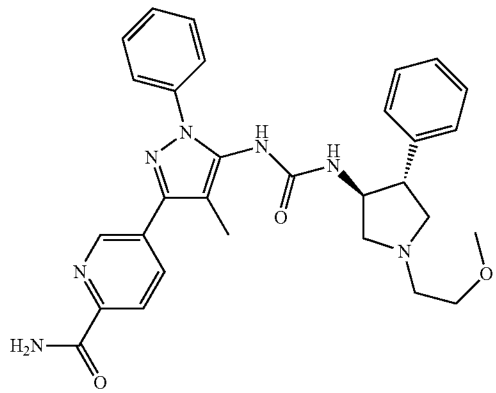 [SMILES: COCCN1C[C@@H](NC(=O)Nc2c(C)c(-c3ccc(C(N)=O)nc3)nn2-c2ccccc2)[C@H](c2ccccc2)C1] | 2 | 1.24 | 540 | racemate |
| I-43 | 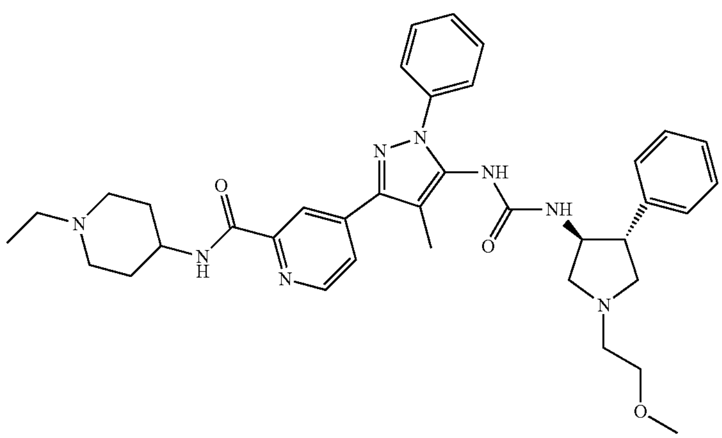 [SMILES: CCN1CCC(NC(=O)c2cc(-c3nn(-c4ccccc4)c(NC(=O)N[C@@H]4CN(CCOC)C[C@H]4c4ccccc4)c3C)ccn2)CC1] | 1 | 0.90 | 651 | racemate |
| I-44 | 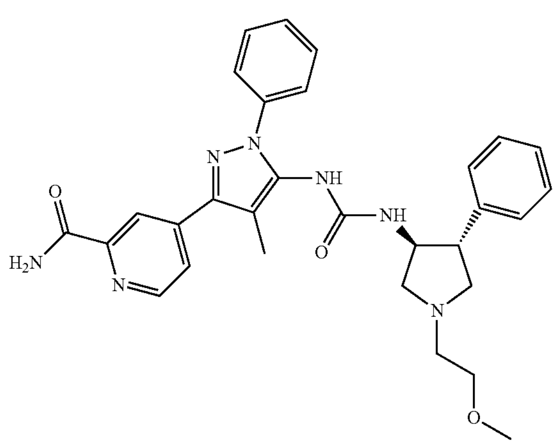 [SMILES: COCCN1C[C@@H](NC(=O)Nc2c(C)c(-c3ccnc(C(N)=O)c3)nn2-c2ccccc2)[C@H](c2ccccc2)C1] | 1 | 1.26 | 540.2 | racemate |

TABLE 12

| No. | Structure | LCMS method No | RT | MS | configuration |
|---|---|---|---|---|---|
| I-45 | 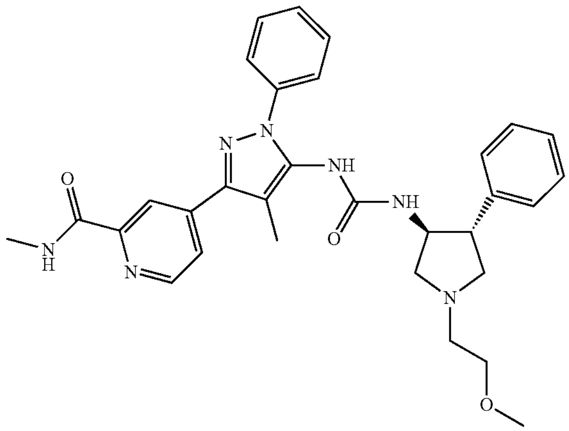 [SMILES: CNC(=O)c1cc(-c2nn(-c3ccccc3)c(NC(=O)N[C@@H]3CN(CCOC)C[C@H]3c3ccccc3)c2C)ccn1] | 1 | 1.35 | 554.2 | racemate |
| I-46 | 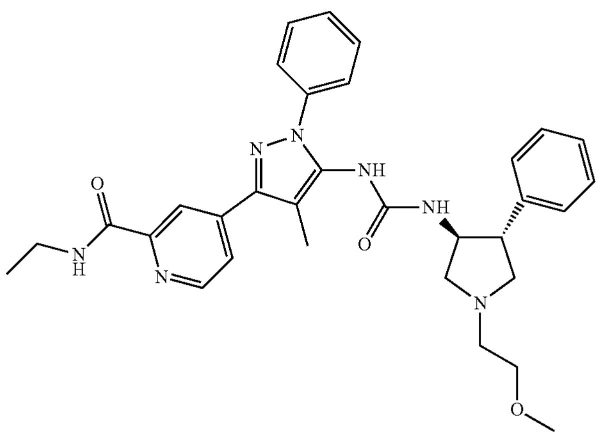 [SMILES: CCNC(=O)c1cc(-c2nn(-c3ccccc3)c(NC(=O)N[C@@H]3CN(CCOC)C[C@H]3c3ccccc3)c2C)ccn1] | 1 | 1.48 | 568.2 | racemate |
| I-47 | 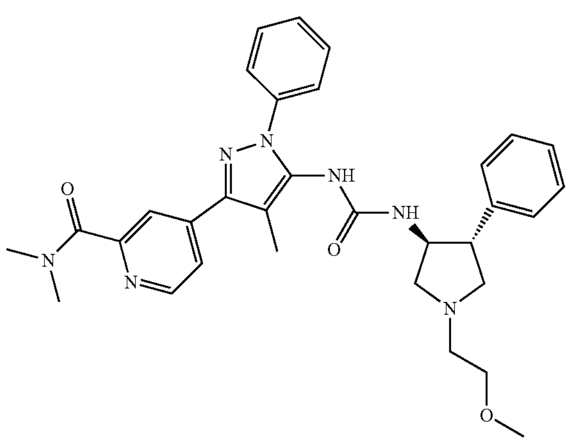 [SMILES: COCCN1C[C@@H](NC(=O)Nc2c(C)c(-c3ccnc(C(=O)N(C)C)c3)nn2-c2ccccc2)[C@H](c2ccccc2)C1] | 1 | 1.22 | 568.2 | racemate |

TABLE 12-continued

| No. | Structure | LCMS method No | RT | MS | configuration |
|---|---|---|---|---|---|
| I-48 | 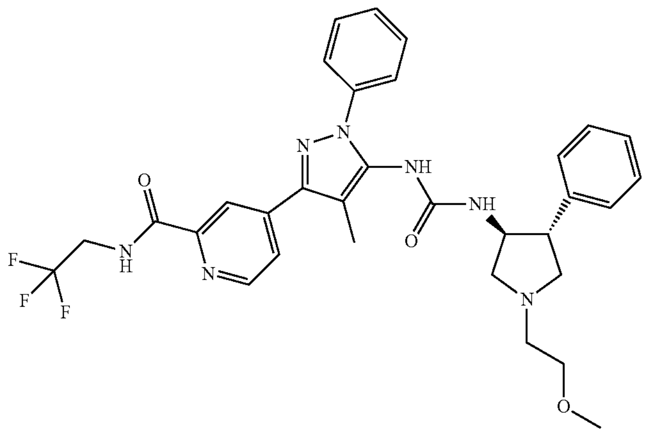 [SMILES: COCCN1C[C@@H](NC(=O)Nc2c(C)c(-c3ccnc(C(=O)NCC(F)(F)F)c3)nn2-c2ccccc2)[C@H](c2ccccc2)C1] | 1 | 1.67 | 622.2 | racemate |

TABLE 13

| No. | Structure | LCMS method No | RT | MS | configuration |
|---|---|---|---|---|---|
| I-49 | 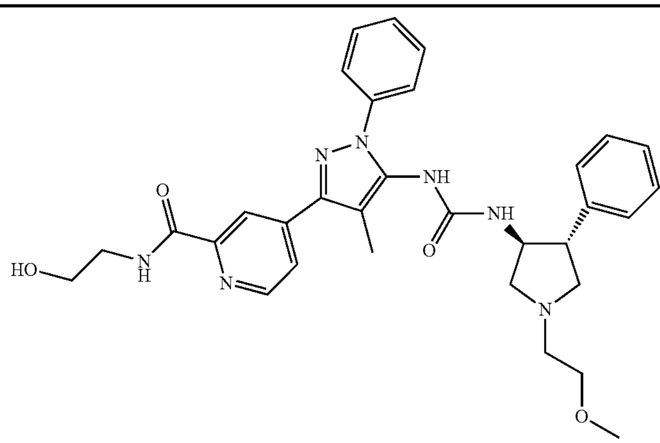 | 1 | 1.23 | 584.2 | racemate |
| I-50 | 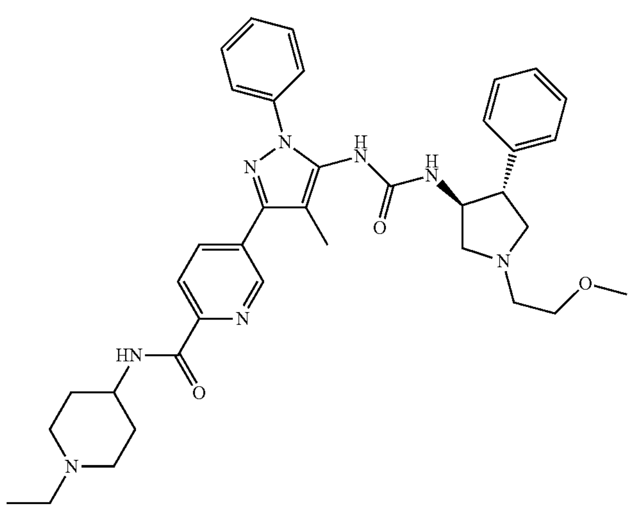 [SMILES: CCN1CCC(NC(=O)c2ccc(-c3nn(-c4ccccc4)c(NC(=O)N[C@@H]4CN(CCOC)C[C@H]4c4ccccc4)c3C)cn2)CC1] | 2 | 1.03 | 651.37 | racemate |

TABLE 13-continued

| No. | Structure | LCMS method No | RT | MS | configuration |
|---|---|---|---|---|---|
| I-51 | 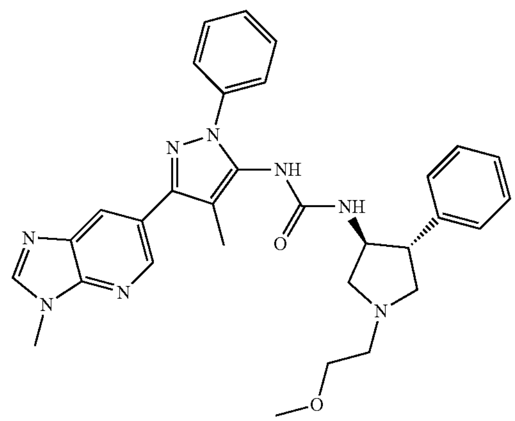 [SMILES: COCCN1C[C@@H](NC(=O)Nc2c(C)c(-c3cnc4c(c3)ncn4C)nn2-c2ccccc2)[C@H](c2ccccc2)C1] | 1 | 1.04 | 551.25 | racemate |
| I-52 | 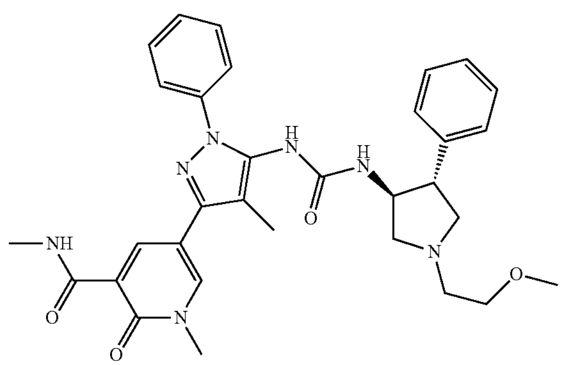 | 2 | 1.21 | 584 | racemate |

TABLE 14

| No. | Structure | LCMS method No | RT | MS | configuration |
|---|---|---|---|---|---|
| I-53 | 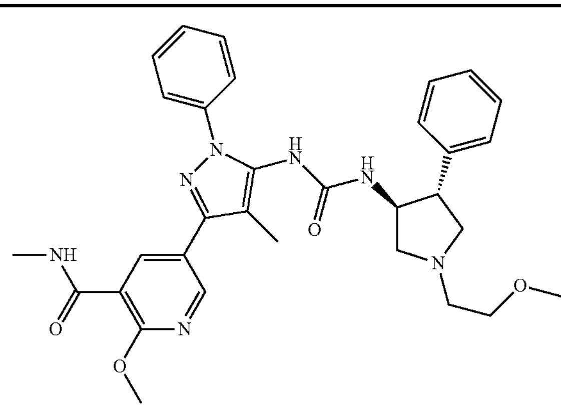 | 2 | 1.36 | 584 | racemate |

TABLE 14-continued
| No. | Structure | LCMS method No | RT | MS | configuration |
|---|---|---|---|---|---|
| I-54 | 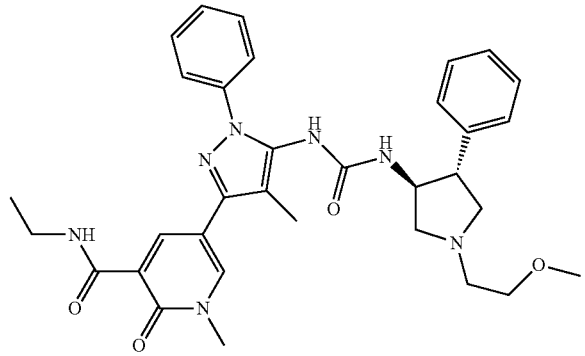 [SMILES: CCNC(=O)c1cc(-c2nn(-c3ccccc3)c(NC(=O)N[C@@H]3CN(CCOC)C[C@H]3c3ccccc3)c2C)cn(C)c1=O] | 2 | 1.3 | 598 | racemate |
| I-55 | 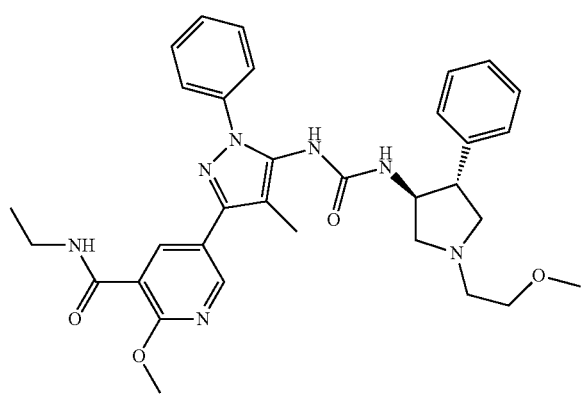 [SMILES: CCNC(=O)c1cc(-c2nn(-c3ccccc3)c(NC(=O)N[C@@H]3CN(CCOC)C[C@H]3c3ccccc3)c2C)cnc1OC] | 2 | 1.47 | 598 | racemate |
| I-56 | 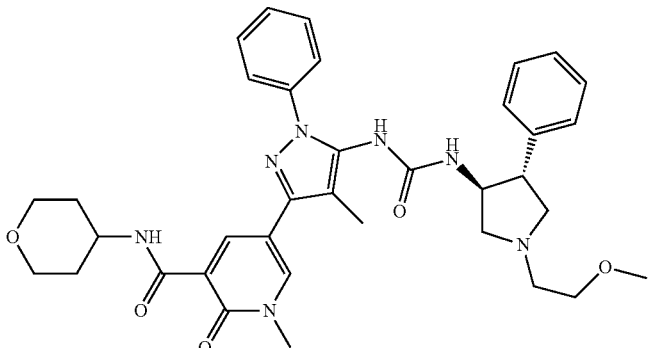 | 2 | 1.28 | 654 | racemate |

TABLE 15
| No. | Structure | LCMS method No | RT | MS | configuration |
|---|---|---|---|---|---|
| I-57 | 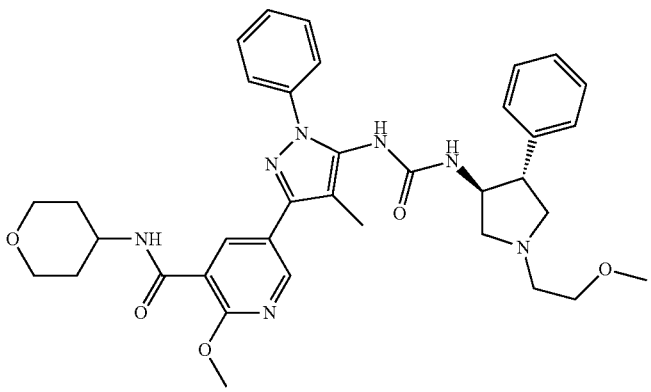 [SMILES: COCCN1C[C@@H](NC(=O)Nc2c(C)c(-c3cnc(OC)c(C(=O)NC4CCOCC4)c3)nn2-c2ccccc2)[C@H](c2ccccc2)C1] | 2 | 1.42 | 654 | racemate |
| I-58 | 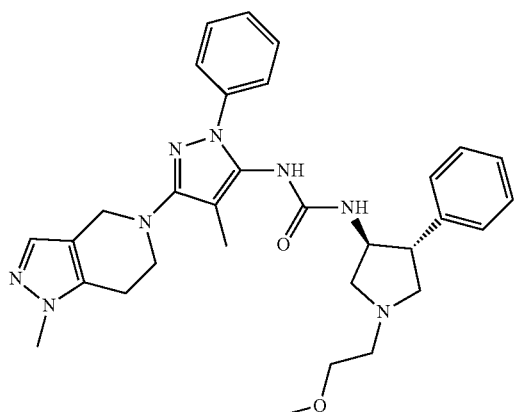 [SMILES: COCCN1C[C@@H](NC(=O)Nc2c(C)c(N3CCc4c(cnn4C)C3)nn2-c2ccccc2)[C@H](c2ccccc2)C1] | 1 | 1.13 | 555.3 | |
| I-59 | 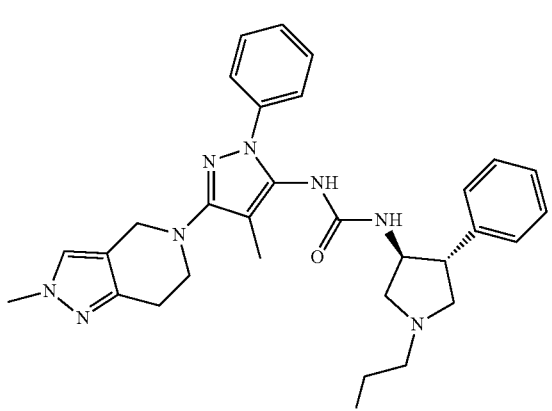 | 1 | 1.11 | 555.3 | |

TABLE 15-continued

| No. | Structure | LCMS method No | RT | MS | configuration |
|---|---|---|---|---|---|
| I-60 | 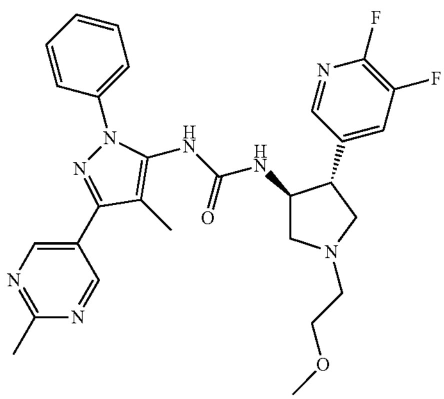 [SMILES: COCCN1C[C@@H](NC(=O)Nc2c(C)c(-c3cnc(C)nc3)nn2-c2ccccc2)[C@H](c2cnc(F)c(F)c2)C1] | 1 | 1.02 | 549.25 | racemate |

TABLE 16

| No. | Structure | LCMS method No | RT | MS | configuration |
|---|---|---|---|---|---|
| I-61 | 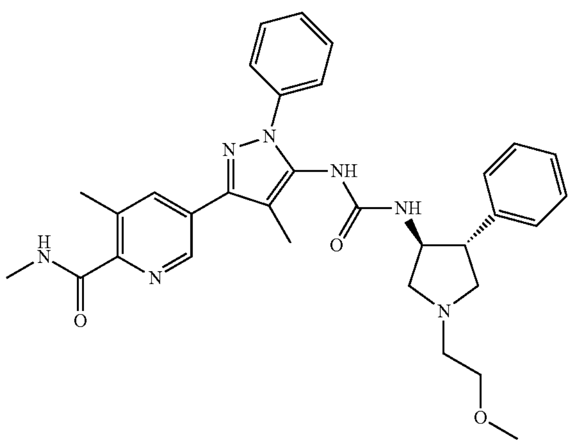 [SMILES: CNC(=O)c1ncc(-c2nn(-c3ccccc3)c(NC(=O)N[C@@H]3CN(CCOC)C[C@H]3c3ccccc3)c2C)cc1C] | 1 | 1.11 | 568 | racemate |
| I-62 | 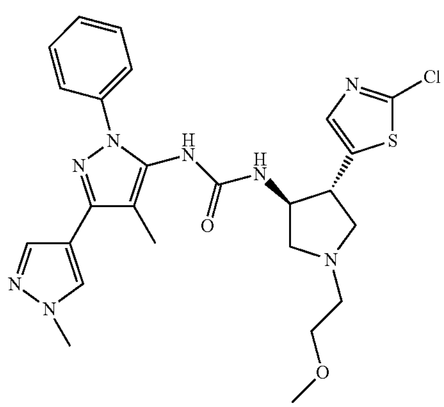 [SMILES: COCCN1C[C@@H](NC(=O)Nc2c(C)c(-c3cnn(C)c3)nn2-c2ccccc2)[C@H](c2cnc(Cl)s2)C1] | 1 | 0.92 | 541.2 | racemate |

TABLE 16-continued

| No. | Structure | LCMS method No | RT | MS | configuration |
|---|---|---|---|---|---|
| I-63 | 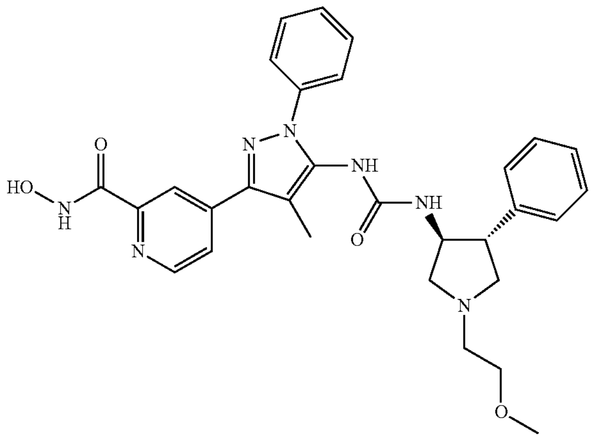 [SMILES: COCCN1C[C@@H](NC(=O)Nc2c(C)c(-c3ccnc(C(=O)NO)c3)nn2-c2ccccc2)[C@H](c2ccccc2)C1] | 1 | 0.95 | 556 | racemate |
| I-64 | 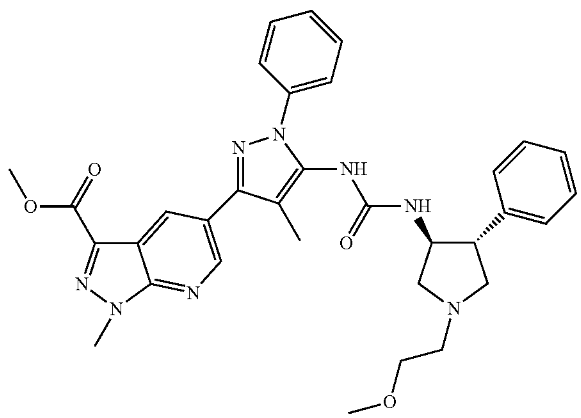 [SMILES: COCCN1C[C@@H](NC(=O)Nc2c(C)c(-c3cnc4c(c3)c(C(=O)OC)nn4C)nn2-c2ccccc2)[C@H](c2ccccc2)C1] | 1 | 1.26 | 609.25 | racemate |

TABLE 17

| No. | Structure | LCMS method No | RT | MS | configuration |
|---|---|---|---|---|---|
| I-65 | 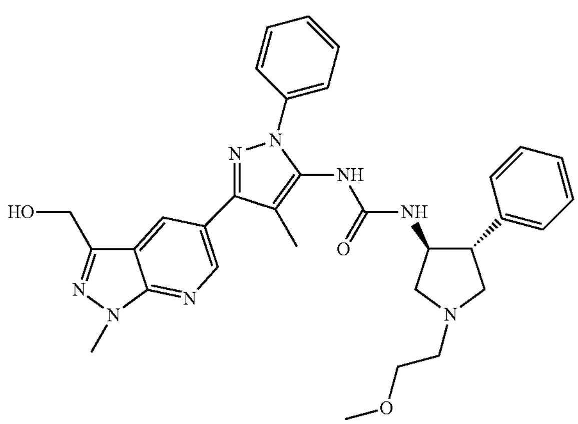 [SMILES: COCCN1C[C@@H](NC(=O)Nc2c(C)c(-c3cnc4c(c3)c(CO)nn4C)nn2-c2ccccc2)[C@H](c2ccccc2)C1] | 1 | 1.06 | 581.25 | racemate |

TABLE 17-continued

| No. | Structure | LCMS method No | RT | MS | configuration |
|---|---|---|---|---|---|
| I-66 | 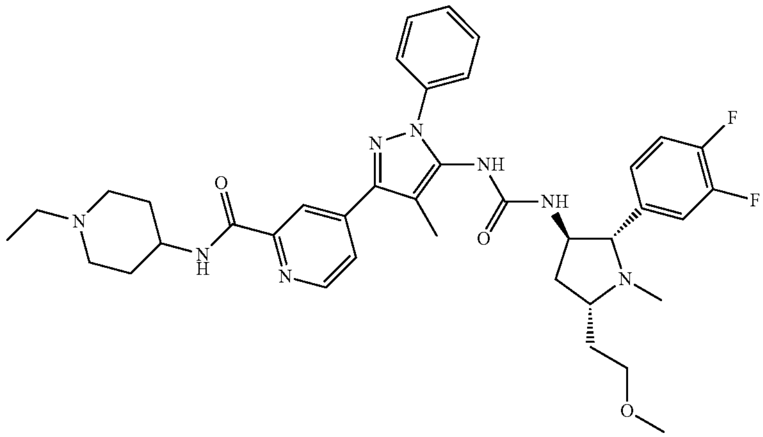 [SMILES: CCN1CCC(NC(=O)c2cc(-c3nn(-c4ccccc4)c(NC(=O)N[C@@H]4C[C@@H](CCOC)N(C)[C@H]4c4ccc(F)c(F)c4)c3C)ccn2)CC1] | 2 | 1.07 | 702 | |
| I-67 | 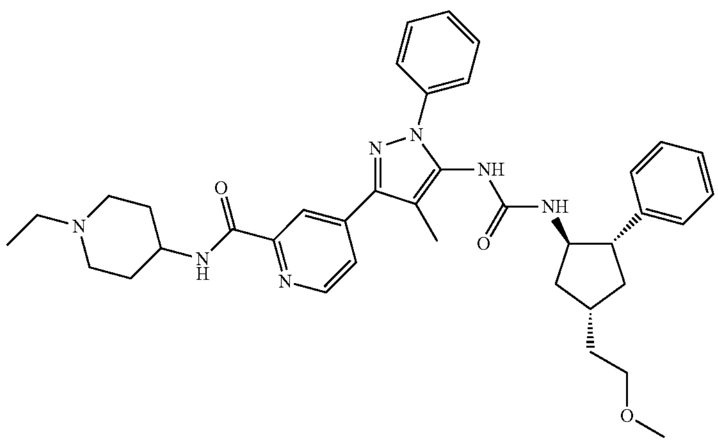 [SMILES: CCN1CCC(NC(=O)c2cc(-c3nn(-c4ccccc4)c(NC(=O)N[C@@H]4C[C@@H](CCOC)C[C@H]4c4ccccc4)c3C)ccn2)CC1] | 2 | 1.81 | 650 | |
| I-68 | 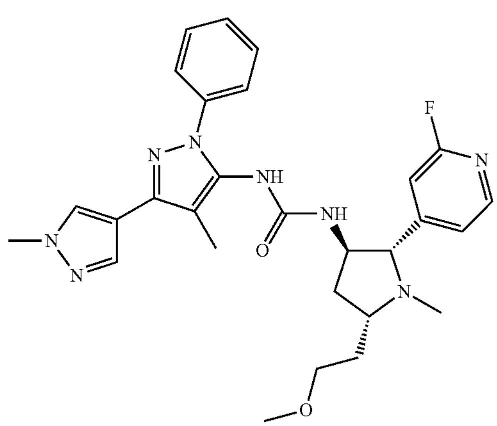 [SMILES: COCC[C@@H]1C[C@@H](NC(=O)Nc2c(C)c(-c3cnn(C)c3)nn2-c2ccccc2)[C@H](c2ccnc(F)c2)N1C] | 3 | 1.58 | 533 | |

TABLE 18

| No. | Structure | LCMS method No | RT | MS | configuration |
|---|---|---|---|---|---|
| I-69 | 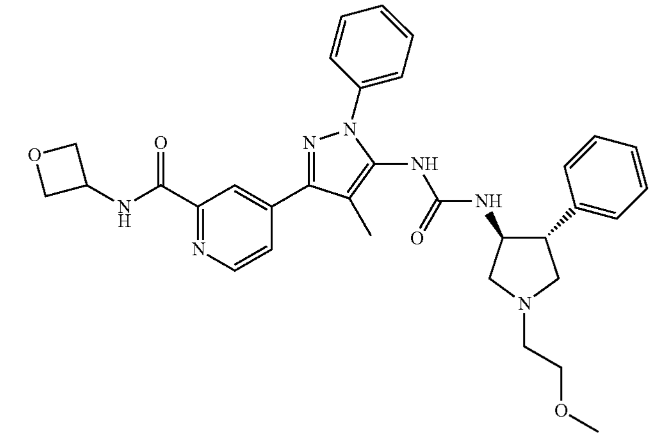 [SMILES: COCCN1C[C@@H](NC(=O)Nc2c(C)c(-c3ccnc(C(=O)NC4COC4)c3)nn2-c2ccccc2)[C@H](c2ccccc2)C1] | 3 | 1.74 | 596.4 | racemate |
| I-70 | 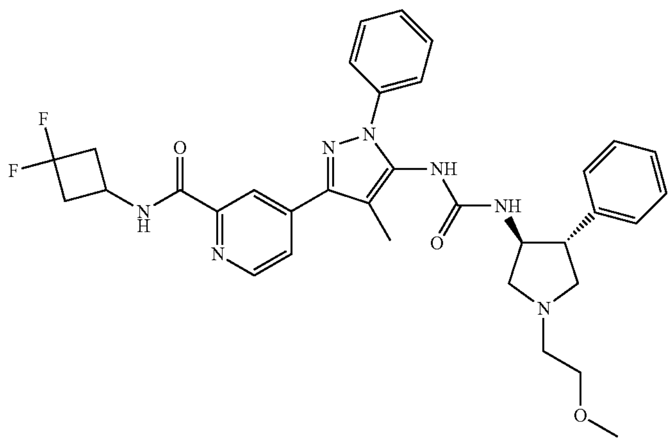 [SMILES: COCCN1C[C@@H](NC(=O)Nc2c(C)c(-c3ccnc(C(=O)NC4CC(F)(F)C4)c3)nn2-c2ccccc2)[C@H](c2ccccc2)C1] | 3 | 2.14 | 630.4 | racemate |
| I-71 | 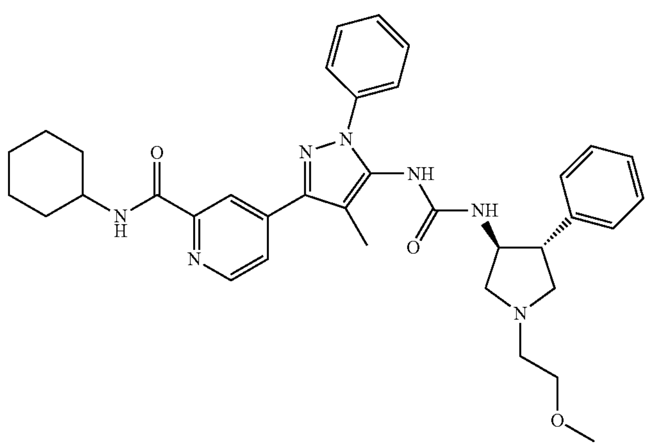 [SMILES: COCCN1C[C@@H](NC(=O)Nc2c(C)c(-c3ccnc(C(=O)NC4CCCCC4)c3)nn2-c2ccccc2)[C@H](c2ccccc2)C1] | 3 | 2.45 | 622.5 | racemate |

TABLE 18-continued

| No. | Structure | LCMS method No | RT | MS | configuration |
|---|---|---|---|---|---|
| I-72 | 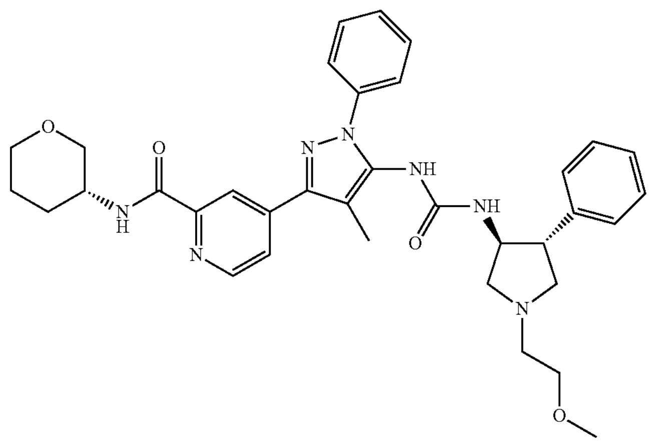 [SMILES: COCCN1C[C@@H](NC(=O)Nc2c(C)c(-c3ccnc(C(=O)N[C@@H]4CCCOC4)c3)nn2-c2ccccc2)[C@H](c2ccccc2)C1] | 3 | 1.97 | 624.4 | Diastereo mixture |

TABLE 19

| No. | Structure | LCMS method No | RT | MS | configuration |
|---|---|---|---|---|---|
| I-73 | 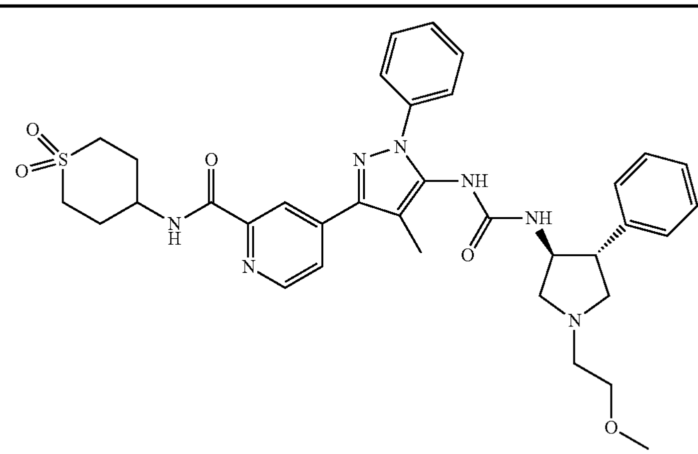 | 3 | 1.76 | 672.4 | racemate |
| I-74 | 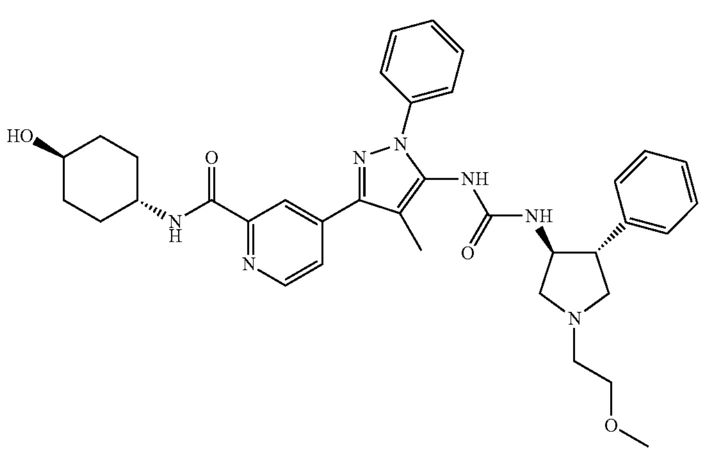 [SMILES: COCCN1C[C@@H](NC(=O)Nc2c(C)c(-c3ccnc(C(=O)N[C@H]4CC[C@H](O)CC4)c3)nn2-c2ccccc2)[C@H](c2ccccc2)C1] | 3 | 1.77 | 638.5 | Diastereo mixture |

TABLE 19-continued

| No. | Structure | LCMS method No | RT | MS | configuration |
|---|---|---|---|---|---|
| I-75 | 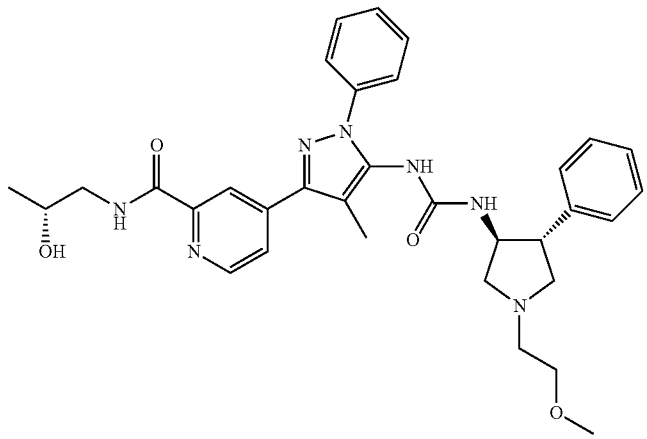 [SMILES: COCCN1C[C@@H](NC(=O)Nc2c(C)c(-c3ccnc(C(=O)NC[C@@H](C)O)c3)nn2-c2ccccc2)[C@H](c2ccccc2)C1] | 3 | 1.7 | 598.5 | Diastereo mixture |
| I-76 | 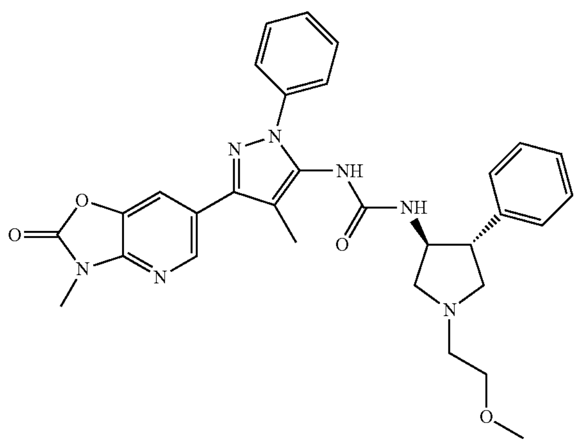 [SMILES: COCCN1C[C@@H](NC(=O)Nc2c(C)c(-c3cnc4c(c3)oc(=O)n4C)nn2-c2ccccc2)[C@H](c2ccccc2)C1] | 1 | 1.18 | 568 | racemate |

TABLE 20

| No. | Structure | LCMS method No | RT | MS | configuration |
|---|---|---|---|---|---|
| I-77 | 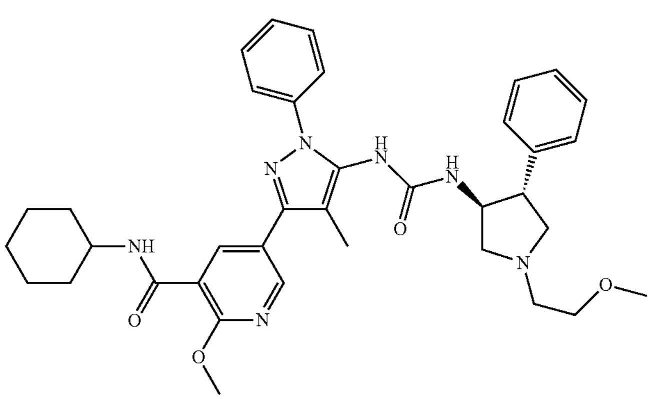 [SMILES: COCCN1C[C@@H](NC(=O)Nc2c(C)c(-c3cnc(OC)c(C(=O)NC4CCCCC4)c3)nn2-c2ccccc2)[C@H](c2ccccc2)C1] | 2 | 1.94 | 652 | racemate |

TABLE 20-continued

| No. | Structure | LCMS method No | RT | MS | configuration |
|---|---|---|---|---|---|
| I-78 | 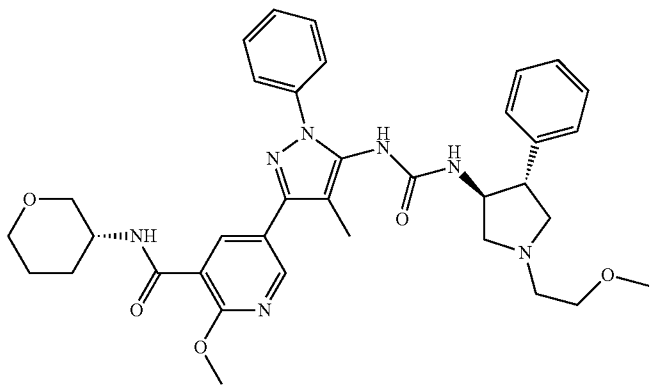 [SMILES: COCCN1C[C@@H](NC(=O)Nc2c(C)c(-c3cnc(OC)c(C(=O)N[C@@H]4CCCOC4)c3)nn2-c2ccccc2)[C@H](c2ccccc2)C1] | 2 | 1.54 | 654 | Diastereo mixture |
| I-79 | 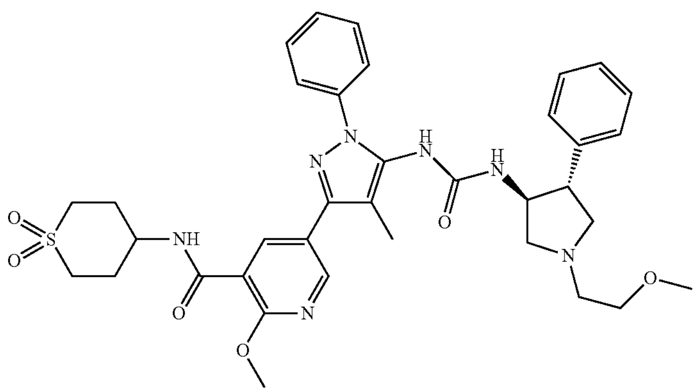 [SMILES: COCCN1C[C@@H](NC(=O)Nc2c(C)c(-c3cnc(OC)c(C(=O)NC4CCS(=O)(=O)CC4)c3)nn2-c2ccccc2)[C@H](c2ccccc2)C1] | 2 | 1.39 | 702 | racemate |
| I-80 | 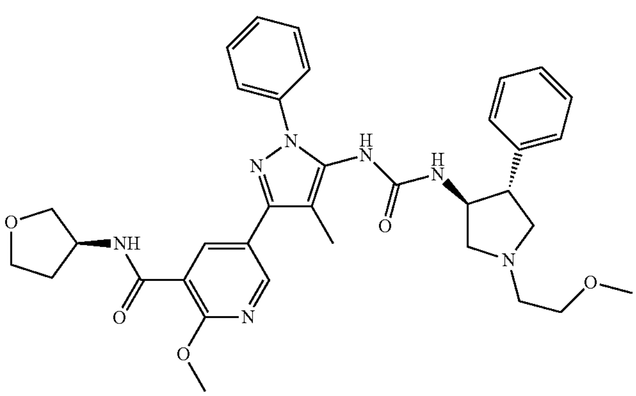 [SMILES: COCCN1C[C@@H](NC(=O)Nc2c(C)c(-c3cnc(OC)c(C(=O)N[C@H]4CCOC4)c3)nn2-c2ccccc2)[C@H](c2ccccc2)C1] | 2 | 1.42 | 640 | Diastereo mixture |

TABLE 21

| No. | Structure | LCMS method No | RT | MS | configuration |
|---|---|---|---|---|---|
| I-81 | 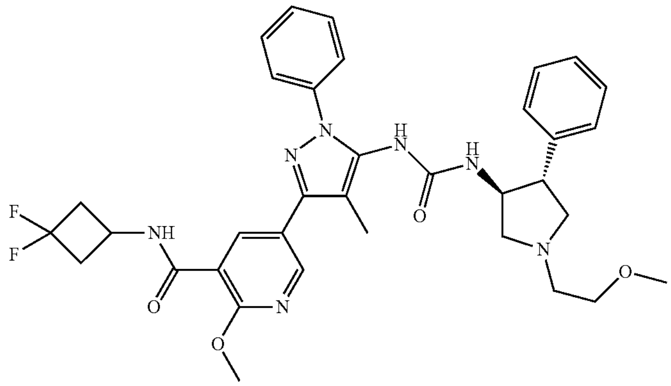 [SMILES: COCCN1C[C@@H](NC(=O)Nc2c(C)c(-c3cnc(OC)c(C(=O)NC4CC(F)(F)C4)c3)nn2-c2ccccc2)[C@H](c2ccccc2)C1] | 2 | 1.71 | 660 | racemate |
| I-82 | 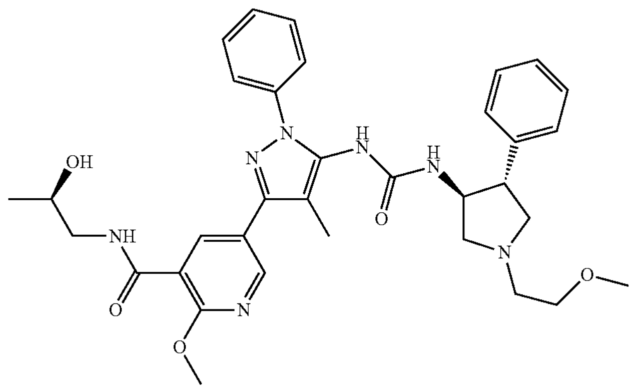 [SMILES: COCCN1C[C@@H](NC(=O)Nc2c(C)c(-c3cnc(OC)c(C(=O)NC[C@@H](C)O)c3)nn2-c2ccccc2)[C@H](c2ccccc2)C1] | 2 | 1.46 | 628 | Diastereo mixture |
| I-83 | 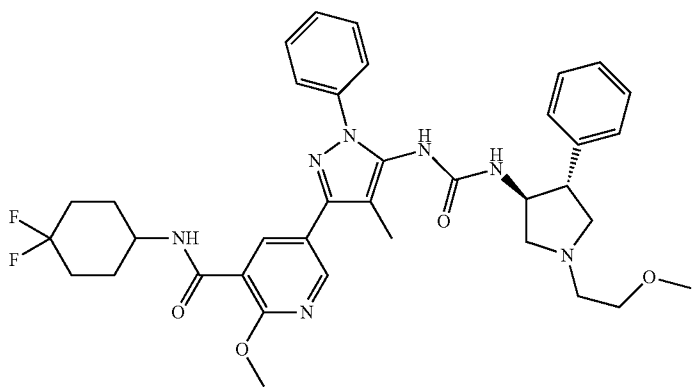 [SMILES: COCCN1C[C@@H](NC(=O)Nc2c(C)c(-c3cnc(OC)c(C(=O)NC4CCC(F)(F)CC4)c3)nn2-c2ccccc2)[C@H](c2ccccc2)C1] | 2 | 1.83 | 688 | racemate |
| I-84 | 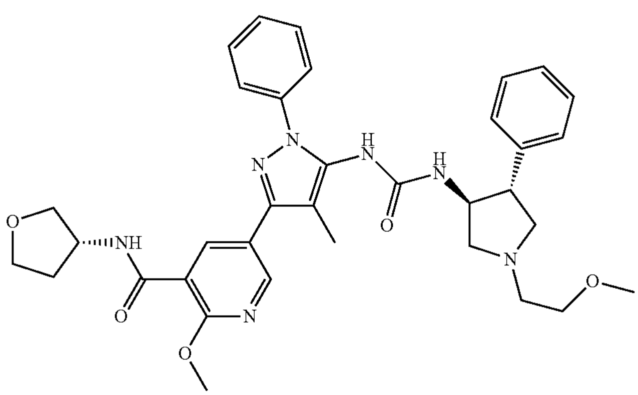 [SMILES: COCCN1C[C@@H](NC(=O)Nc2c(C)c(-c3cnc(OC)c(C(=O)N[C@@H]4CCOC4)c3)nn2-c2ccccc2)[C@H](c2ccccc2)C1] | 2 | 1.43 | 640 | Diastereo mixture |

TABLE 22

| No. | Structure | LCMS method No | RT | MS | configuration |
|---|---|---|---|---|---|
| I-85 | 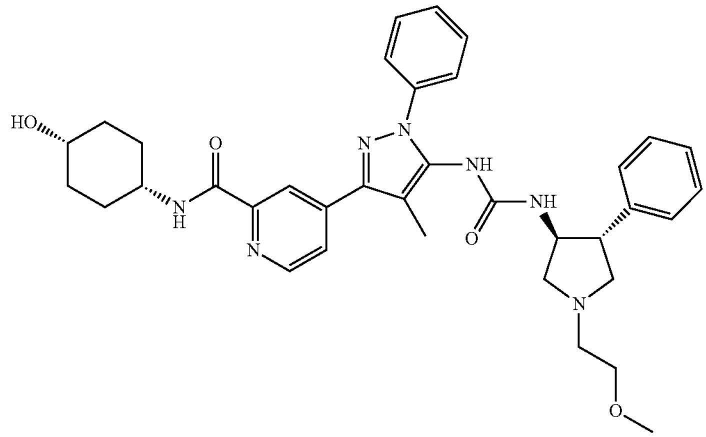 [SMILES: COCCN1C[C@@H](NC(=O)Nc2c(C)c(-c3ccnc(C(=O)N[C@H]4CC[C@@H](O)CC4)c3)nn2-c2ccccc2)[C@H](c2ccccc2)C1] | 1 | 1.18 | 638 | Diastereo mixture |
| I-86 | 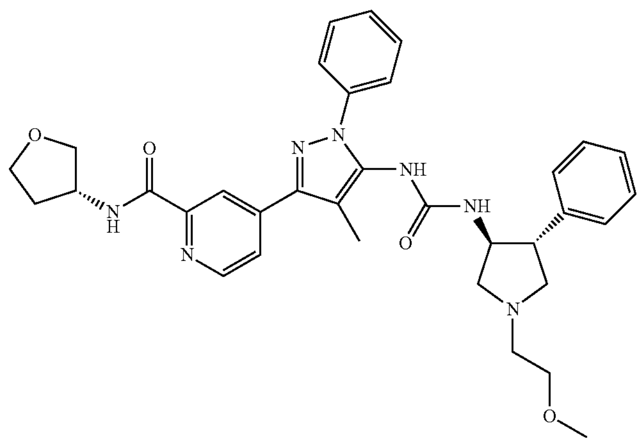 [SMILES: COCCN1C[C@@H](NC(=O)Nc2c(C)c(-c3ccnc(C(=O)N[C@@H]4CCOC4)c3)nn2-c2ccccc2)[C@H](c2ccccc2)C1] | 1 | 1.21 | 610.25 | Diastereo mixture |
| I-87 | 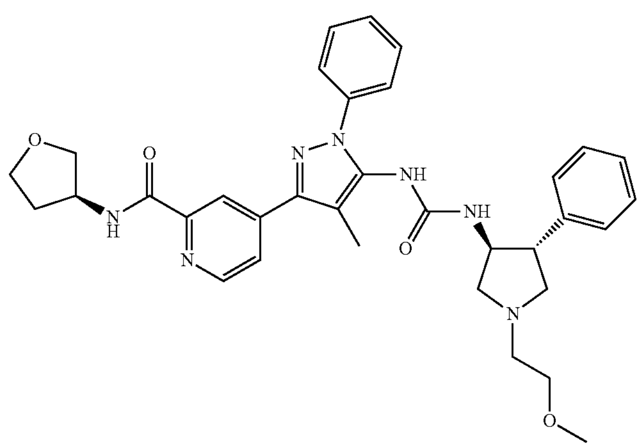 [SMILES: COCCN1C[C@@H](NC(=O)Nc2c(C)c(-c3ccnc(C(=O)N[C@H]4CCOC4)c3)nn2-c2ccccc2)[C@H](c2ccccc2)C1] | 1 | 1.22 | 610.3 | Diastereo mixture |

TABLE 22-continued

| No. | Structure | LCMS method No | RT | MS | configuration |
|---|---|---|---|---|---|
| I-88 | 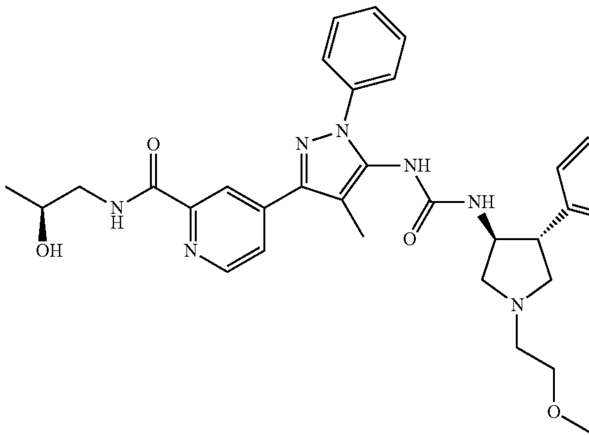 | 1 | 1.12 | 598.3 | Diastereo mixture |

TABLE 23

| No. | Structure | LCMS method No | RT | MS | configuration |
|---|---|---|---|---|---|
| I-89 | 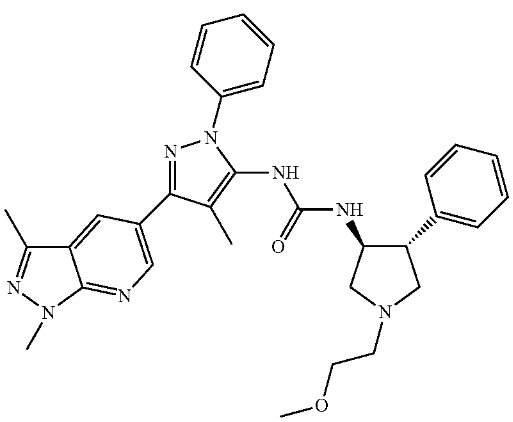 [SMILES: COCCN1C[C@@H](NC(=O)Nc2c(C)c(-c3cnc4c(c3)c(C)nn4C)nn2-c2ccccc2)[C@H](c2ccccc2)C1] | 1 | 1.25 | 565.3 | racemate |
| I-90 | 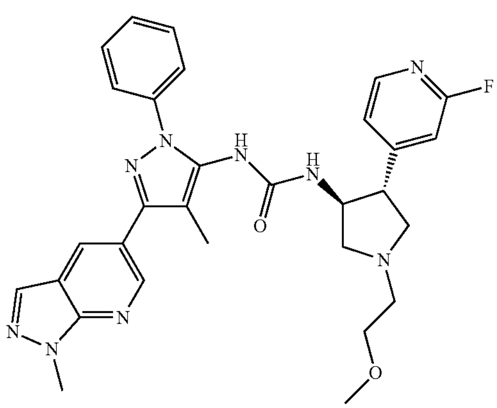 [SMILES: COCCN1C[C@@H](NC(=O)Nc2c(C)c(-c3cnc4c(cnn4C)c3)nn2-c2ccccc2)[C@H](c2ccnc(F)c2)C1] | 1 | 1.07 | 570.25 | racemate |

TABLE 23-continued

| No. | Structure | LCMS method No | RT | MS | configuration |
|---|---|---|---|---|---|
| I-91 | 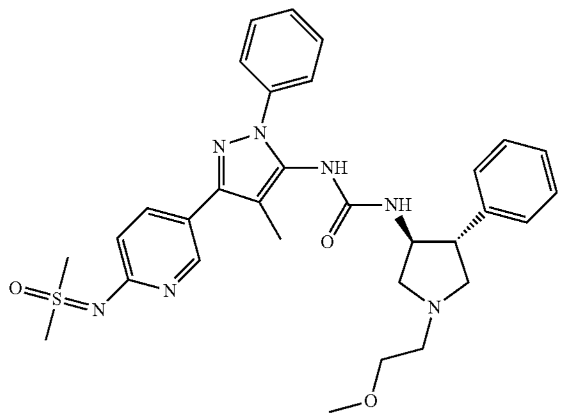 [SMILES: COCCN1C[C@@H](NC(=O)Nc2c(C)c(-c3ccc(N=S(C)(C)=O)nc3)nn2-c2ccccc2)[C@H](c2ccccc2)C1] | 1 | 0.90 | 588.25 | racemate |
| I-92 | 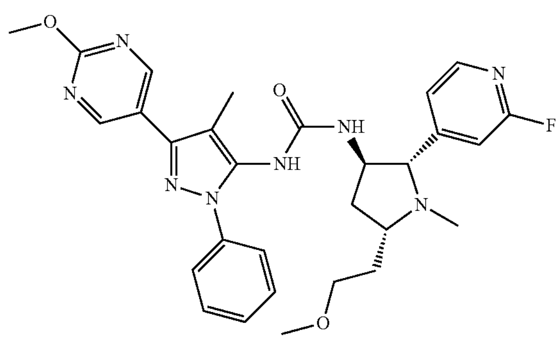 [SMILES: COCC[C@@H]1C[C@@H](NC(=O)Nc2c(C)c(-c3cnc(OC)nc3)nn2-c2ccccc2)[C@H](c2ccnc(F)c2)N1C] | 1 | 1.1 | 561.25 | |

TABLE 24

| No. | Structure | LCMS method No | RT | MS | configuration |
|---|---|---|---|---|---|
| I-93 | 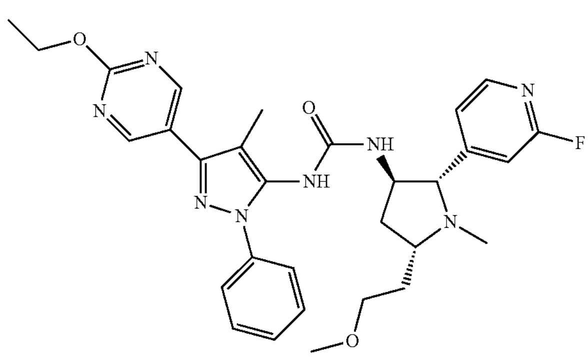 [SMILES: CCOc1ncc(-c2nn(-c3ccccc3)c(NC(=O)N[C@@H]3C[C@@H](CCOC)N(C)[C@H]3c3ccnc(F)c3)c2C)cn1] | 1 | 1.23 | 575.25 | |

TABLE 24-continued

| No. | Structure | LCMS method No | RT | MS | configuration |
|---|---|---|---|---|---|
| I-94 | 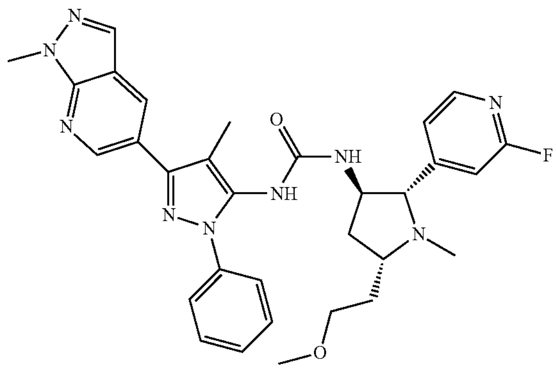 [SMILES: COCC[C@@H]1C[C@@H](NC(=O)Nc2c(C)c(-c3cnc4c(cnn4C)c3)nn2-c2ccccc2)[C@H](c2ccnc(F)c2)N1C] | 1 | 1.16 | 584.25 | |
| I-95 | 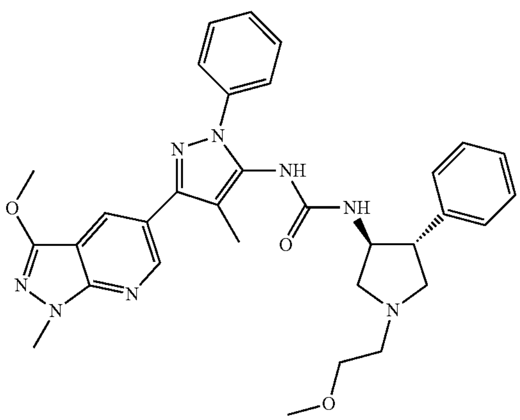 [SMILES: COCCN1C[C@@H](NC(=O)Nc2c(C)c(-c3cnc4c(c3)c(OC)nn4C)nn2-c2ccccc2)[C@H](c2ccccc2)C1] | 1 | 1.31 | 581.25 | racemate |
| I-96 | 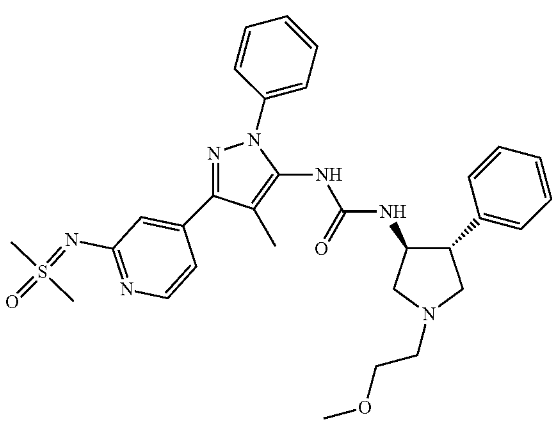 [SMILES: COCCN1C[C@@H](NC(=O)Nc2c(C)c(-c3ccnc(N=S(C)(C)=O)c3)nn2-c2ccccc2)[C@H](c2ccccc2)C1] | 1 | 0.87 | 588.25 | racemate |

TABLE 25

| No. | Structure | LCMS method No | RT | MS | configuration |
|---|---|---|---|---|---|
| I-97 | 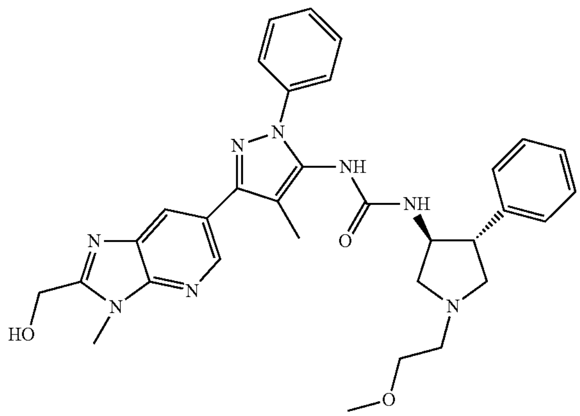 [SMILES: COCCN1C[C@@H](NC(=O)Nc2c(C)c(-c3cnc4c(c3)nc(CO)n4C)nn2-c2ccccc2)[C@H](c2ccccc2)C1] | 1 | 0.98 | 581.3 | racemate |
| I-98 | 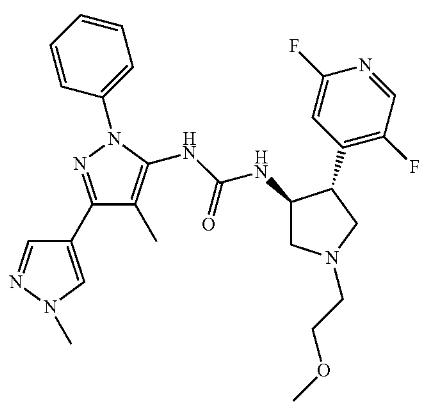 [SMILES: COCCN1C[C@@H](NC(=O)Nc2c(C)c(-c3cnn(C)c3)nn2-c2ccccc2)[C@H](c2cc(F)ncc2F)C1] | 1 | 0.91 | 537.25 | racemate |
| I-99 | 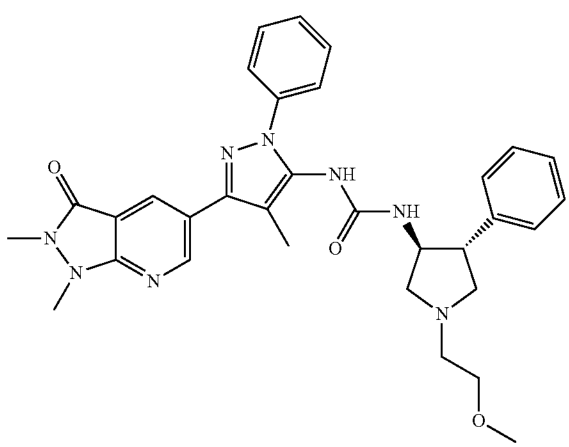 [SMILES: COCCN1C[C@@H](NC(=O)Nc2c(C)c(-c3cnc4c(c3)c(=O)n(C)n4C)nn2-c2ccccc2)[C@H](c2ccccc2)C1] | 1 | 1.08 | 581 | racemate |

TABLE 25-continued

| No. | Structure | LCMS method No | RT | MS | configuration |
|---|---|---|---|---|---|
| I-100 | 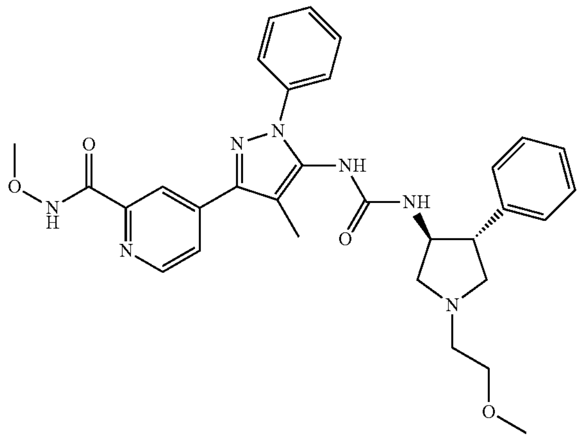 [SMILES: COCCN1C[C@@H](NC(=O)Nc2c(C)c(-c3ccnc(C(=O)NOC)c3)nn2-c2ccccc2)[C@H](c2ccccc2)C1] | 1 | 1.12 | 570 | racemate |

TABLE 26

| No. | Structure | LCMS method No | RT | MS | configuration |
|---|---|---|---|---|---|
| I-101 | 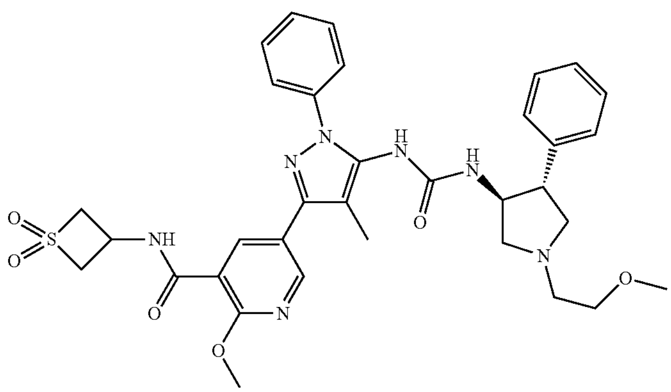 [SMILES: COCCN1C[C@@H](NC(=O)Nc2c(C)c(-c3cnc(OC)c(C(=O)NC4CS(=O)(=O)C4)c3)nn2-c2ccccc2)[C@H](c2ccccc2)C1] | 2 | 1.6 | 674 | racemate |
| I-102 | 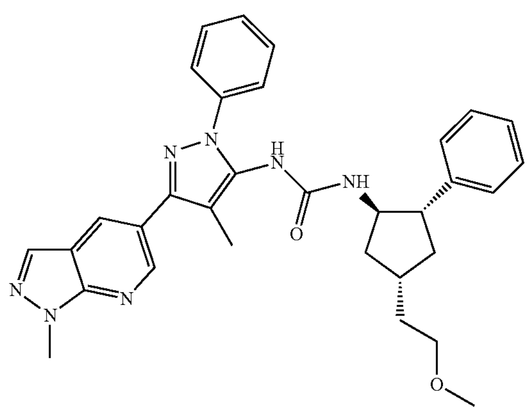 [SMILES: COCC[C@@H]1C[C@@H](NC(=O)Nc2c(C)c(-c3cnc4c(cnn4C)c3)nn2-c2ccccc2)[C@H](c2ccccc2)C1] | 1 | 2.06 | 550 | |

TABLE 26-continued

| No. | Structure | LCMS method No | RT | MS | configuration |
|---|---|---|---|---|---|
| I-103 | 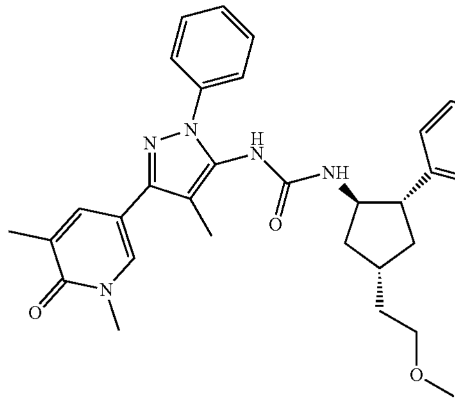 | 2 | 1.97 | 540 | |
| I-104 | 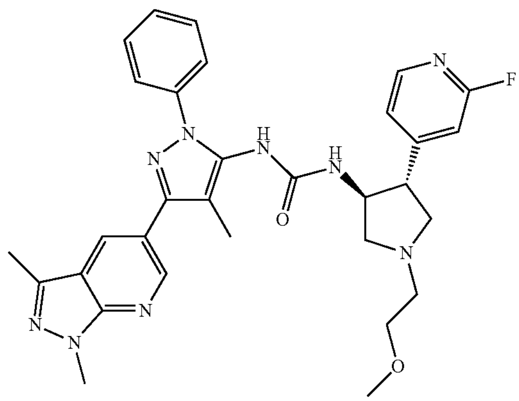 [SMILES: COCCN1C[C@@H](NC(=O)Nc2c(C)c(-c3cnc4c(c3)c(C)nn4C)nn2-c2ccccc2)[C@H](c2ccnc(F)c2)C1] | 1 | 1.12 | 584.2 | racemate |

TABLE 27

| No. | Structure | LCMS method No | RT | MS | configuration |
|---|---|---|---|---|---|
| I-105 | 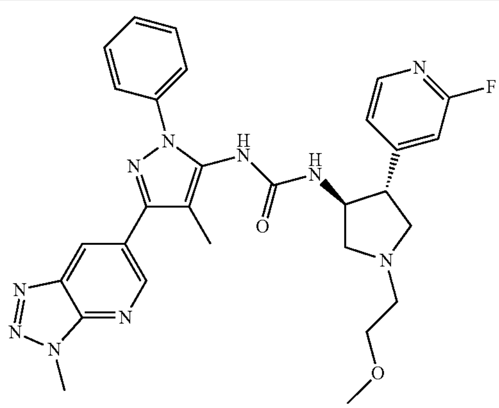 | 1 | 1.03 | 571.2 | racemate |

TABLE 27-continued

| No. | Structure | LCMS method No | RT | MS | configuration |
|---|---|---|---|---|---|
| I-106 | 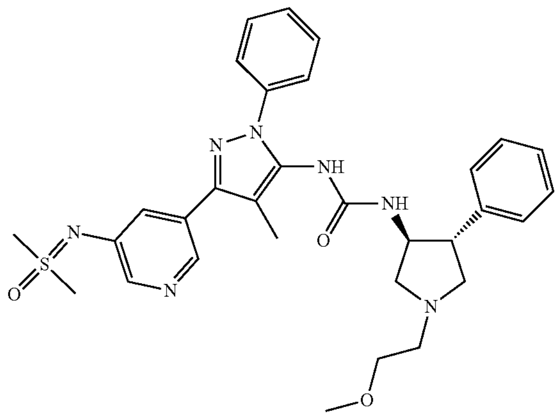 [SMILES: COCCN1C[C@@H](NC(=O)Nc2c(C)c(-c3cncc(N=S(C)(C)=O)c3)nn2-c2ccccc2)[C@H](c2ccccc2)C1] | 1 | 0.87 | 588.25 | racemate |
| I-107 | 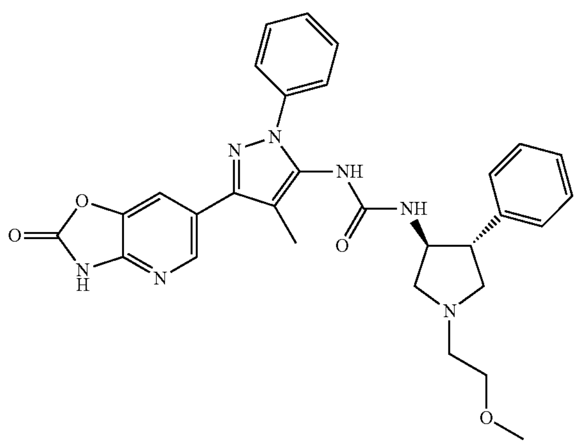 [SMILES: COCCN1C[C@@H](NC(=O)Nc2c(C)c(-c3cnc4[nH]c(=O)oc4c3)nn2-c2ccccc2)[C@H](c2ccccc2)C1] | 1 | 1.12 | 554.25 | racemate |
| I-108 | 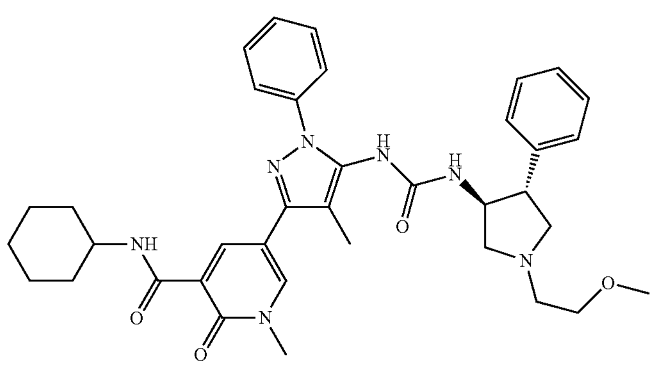 [SMILES: COCCN1C[C@@H](NC(=O)Nc2c(C)c(-c3cc(C(=O)NC4CCCCC4)c(=O)n(C)c3)nn2-c2ccccc2)[C@H](c2ccccc2)C1] | 2 | 2.27 | 652 | racemate |

TABLE 28

| No. | Structure | LCMS method No | RT | MS | configuration |
|---|---|---|---|---|---|
| I-109 | 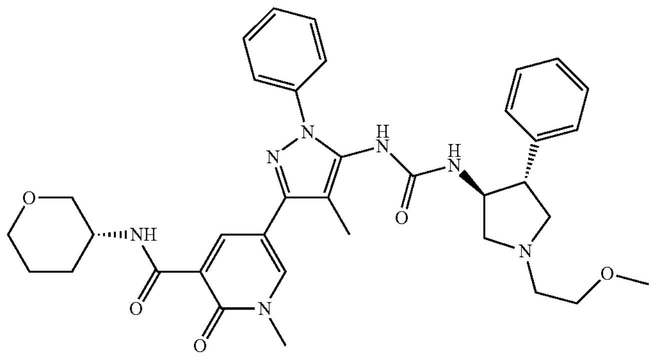 [SMILES: COCCN1C[C@@H](NC(=O)Nc2c(C)c(-c3cc(C(=O)N[C@@H]4CCCOC4)c(=O)n(C)c3)nn2-c2ccccc2)[C@H](c2ccccc2)C1] | 2 | 1.65 | 654 | racemate |
| I-110 | 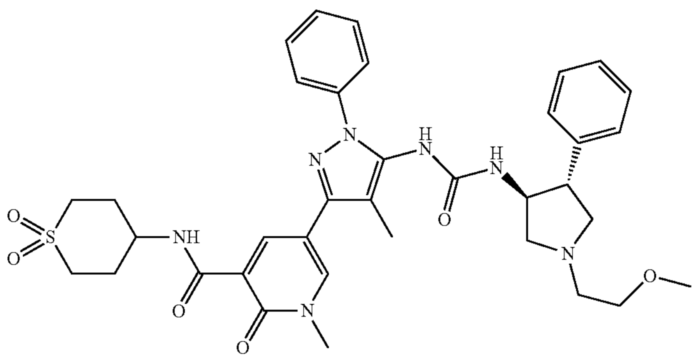 [SMILES: COCCN1C[C@@H](NC(=O)Nc2c(C)c(-c3cc(C(=O)NC4CCS(=O)(=O)CC4)c(=O)n(C)c3)nn2-c2ccccc2)[C@H](c2ccccc2)C1] | 2 | 1.47 | 702 | racemate |
| I-111 | 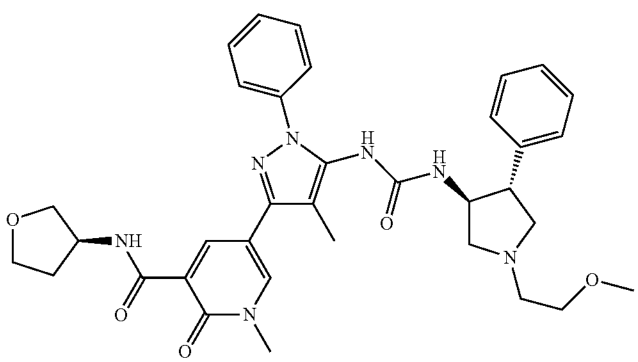 [SMILES: COCCN1C[C@@H](NC(=O)Nc2c(C)c(-c3cc(C(=O)N[C@H]4CCOC4)c(=O)n(C)c3)nn2-c2ccccc2)[C@H](c2ccccc2)C1] | 2 | 1.5 | 640 | racemate |
| I-112 | 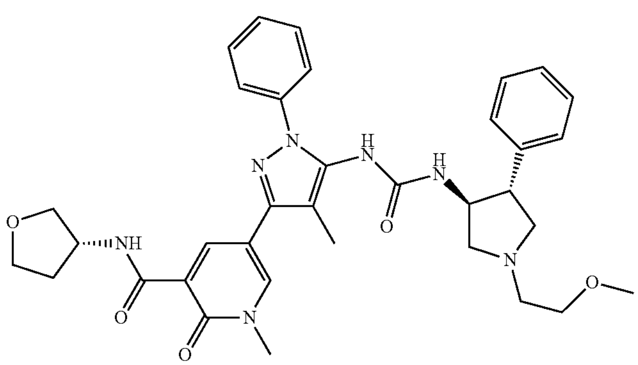 [SMILES: COCCN1C[C@@H](NC(=O)Nc2c(C)c(-c3cc(C(=O)N[C@@H]4CCOC4)c(=O)n(C)c3)nn2-c2ccccc2)[C@H](c2ccccc2)C1] | 2 | 1.5 | 640 | racemate |

TABLE 29

| No. | Structure | LCMS method No | RT | MS | configuration |
|---|---|---|---|---|---|
| I-113 | 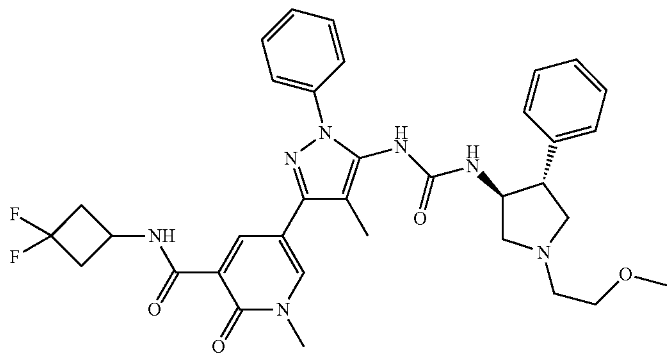 [SMILES: COCCN1C[C@@H](NC(=O)Nc2c(C)c(-c3cc(C(=O)NC4CC(F)(F)C4)c(=O)n(C)c3)nn2-c2ccccc2)[C@H](c2ccccc2)C1] | 2 | 1.93 | 660 | racemate |
| I-114 | 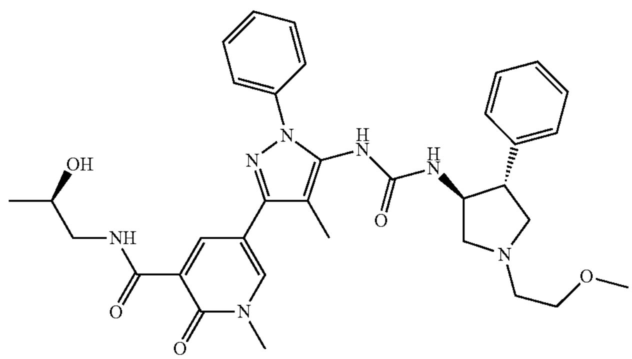 [SMILES: COCCN1C[C@@H](NC(=O)Nc2c(C)c(-c3cc(C(=O)NC[C@@H](C)O)c(=O)n(C)c3)nn2-c2ccccc2)[C@H](c2ccccc2)C1] | 2 | 1.38 | 628 | racemate |
| I-115 | 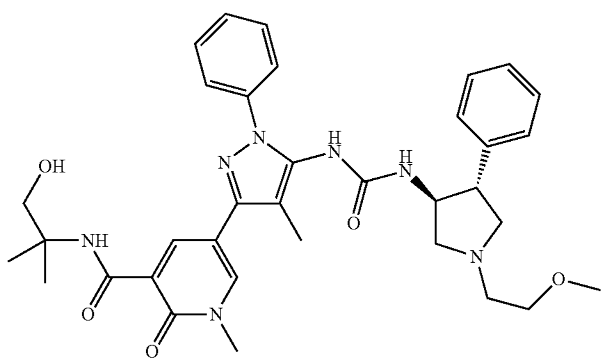 [SMILES: COCCN1C[C@@H](NC(=O)Nc2c(C)c(-c3cc(C(=O)NC(C)(C)CO)c(=O)n(C)c3)nn2-c2ccccc2)[C@H](c2ccccc2)C1] | 2 | 1.55 | 642 | racemate |
| I-116 | 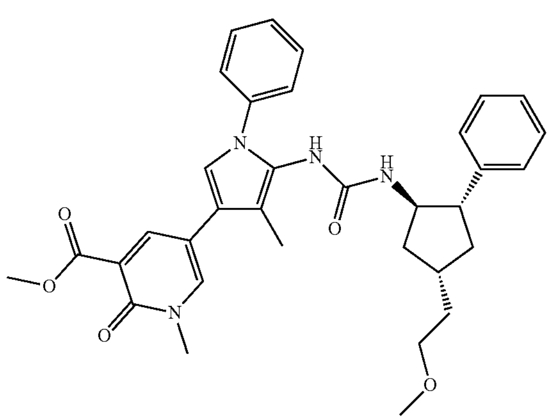 [SMILES: COCC[C@@H]1C[C@@H](NC(=O)Nc2c(C)c(-c3cc(C(=O)OC)c(=O)n(C)c3)cn2-c2ccccc2)[C@H](c2ccccc2)C1] | 1 | 1.86 | 584 | |

TABLE 30

| No. | Structure | LCMS method No | RT | MS | configuration |
|---|---|---|---|---|---|
| I-117 | 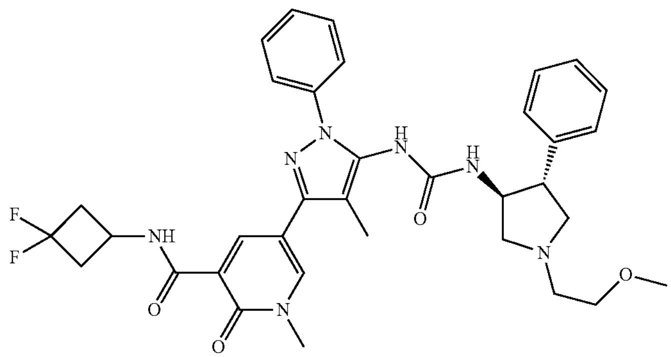 [SMILES: COCCN1C[C@@H](NC(=O)Nc2c(C)c(-c3cc(C(=O)NC4CC(F)(F)C4)c(=O)n(C)c3)nn2-c2ccccc2)[C@H](c2ccccc2)C1] | 2 | 1.92 | 583 | racemate |
| I-118 | 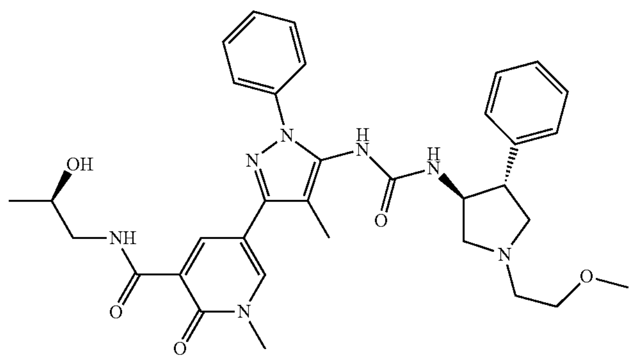 [SMILES: COCCN1C[C@@H](NC(=O)Nc2c(C)c(-c3cc(C(=O)NC[C@@H](C)O)c(=O)n(C)c3)nn2-c2ccccc2)[C@H](c2ccccc2)C1] | 2 | 1.99 | 653 | racemate |
| I-119 | 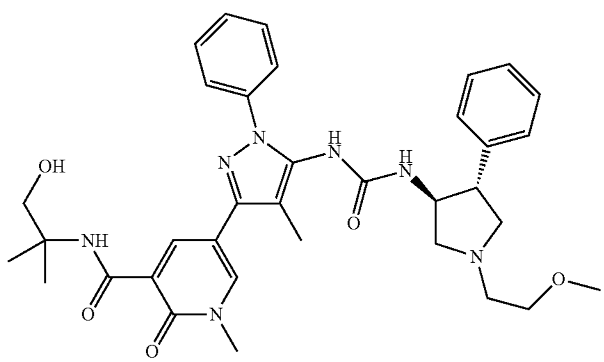 [SMILES: COCCN1C[C@@H](NC(=O)Nc2c(C)c(-c3cc(C(=O)NC(C)(C)CO)c(=O)n(C)c3)nn2-c2ccccc2)[C@H](c2ccccc2)C1] | 2 | 2.3 | 675 | racemate |
| I-120 | 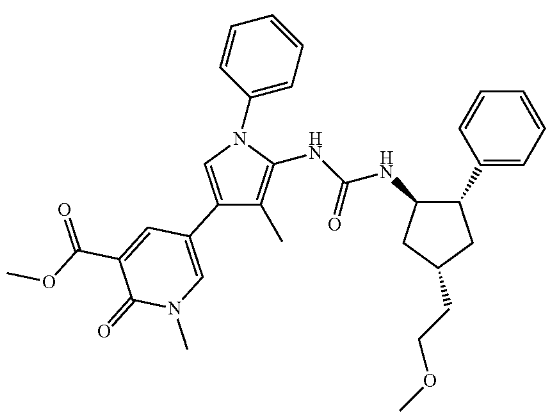 [SMILES: COCC[C@@H]1C[C@@H](NC(=O)Nc2c(C)c(-c3cc(C(=O)OC)c(=O)n(C)c3)cn2-c2ccccc2)[C@H](c2ccccc2)C1] | 2 | 1.78 | 585 | |

TABLE 31

| No. | Structure | LCMS method No | RT | MS | configuration |
|---|---|---|---|---|---|
| I-121 | 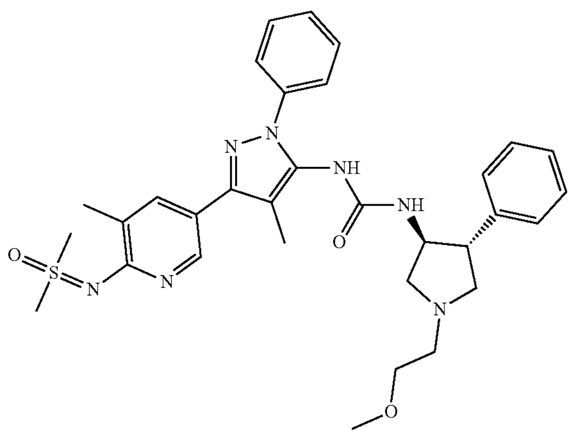 [SMILES: COCCN1C[C@@H](NC(=O)Nc2c(C)c(-c3cnc(N=S(C)(C)=O)c(C)c3)nn2-c2ccccc2)[C@H](c2ccccc2)C1] | 1 | 1.09 | 602.25 | racemate |
| I-122 | 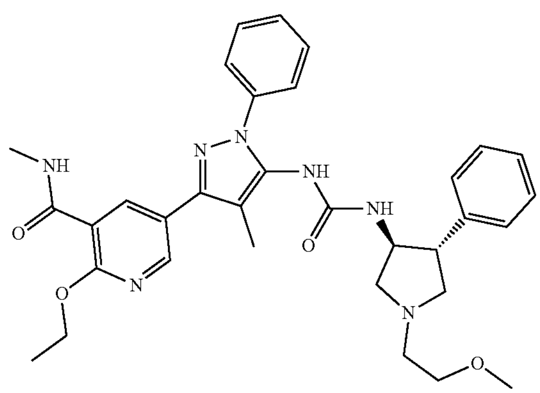 [SMILES: CCOc1ncc(-c2nn(-c3ccccc3)c(NC(=O)N[C@@H]3CN(CCOC)C[C@H]3c3ccccc3)c2C)cc1C(=O)NC] | 2 | 1.85 | 598 | racemate |
| I-123 | 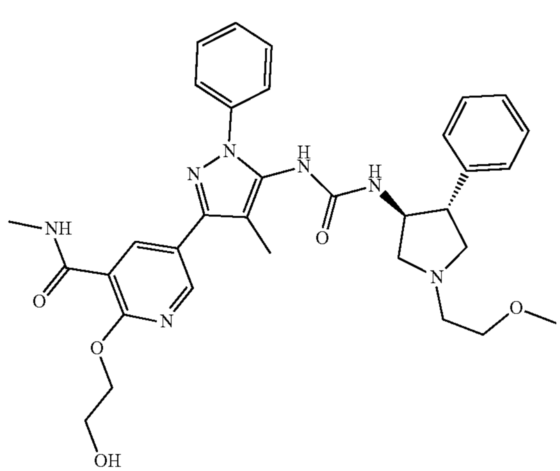 | 2 | 1.67 | 614 | racemate |

TABLE 31-continued

| No. | Structure | LCMS method No | RT | MS | configuration |
|---|---|---|---|---|---|
| I-124 | 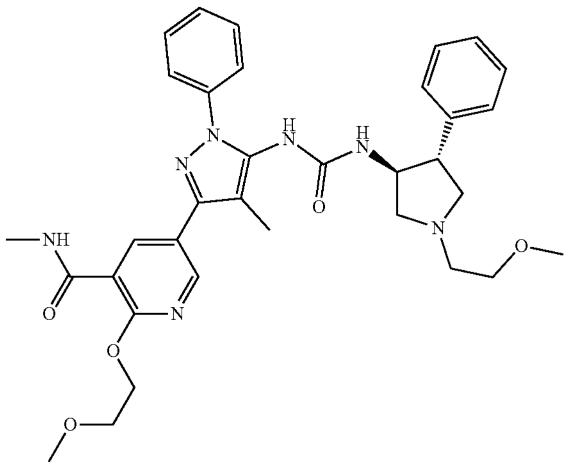 | 2 | 1.88 | 628 | racemate |

TABLE 32

| No. | Structure | LCMS method No | RT | MS | configuration |
|---|---|---|---|---|---|
| I-125 | 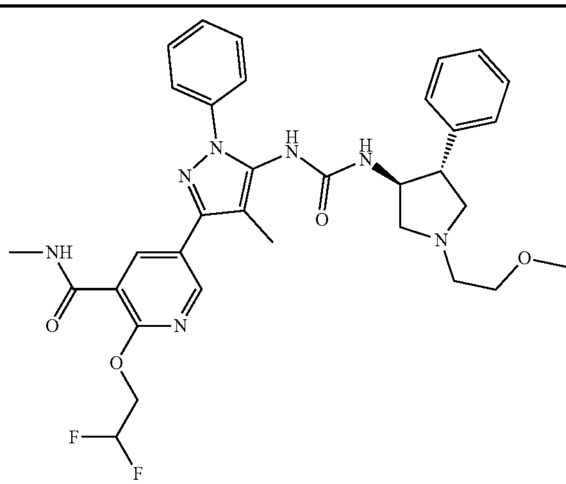 | 2 | 1.92 | 634 | racemate |
| I-126 | 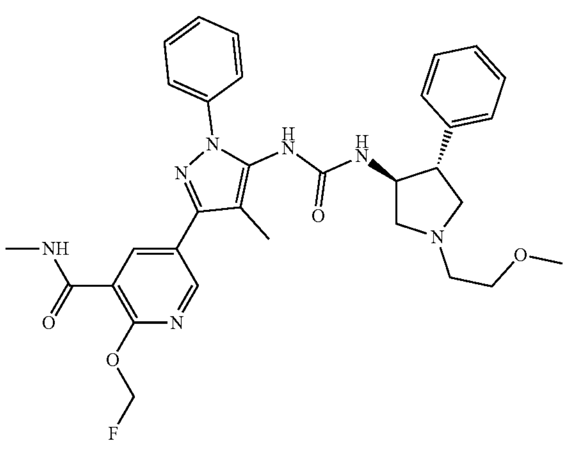 | 3 | 1.84 | 602 | racemate |

TABLE 32-continued

| No. | Structure | LCMS method No | RT | MS | configuration |
|---|---|---|---|---|---|
| I-127 | 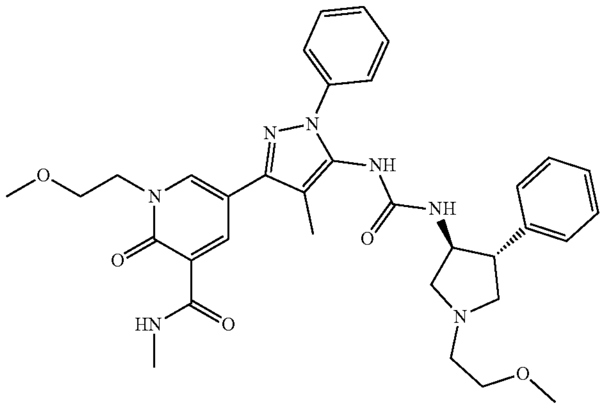 [SMILES: CNC(=O)c1cc(-c2nn(-c3ccccc3)c(NC(=O)N[C@@H]3CN(CCOC)C[C@H]3c3ccccc3)c2C)cn(CCOC)c1=O] | 2 | 1.56 | 628 | racemate |
| I-128 | 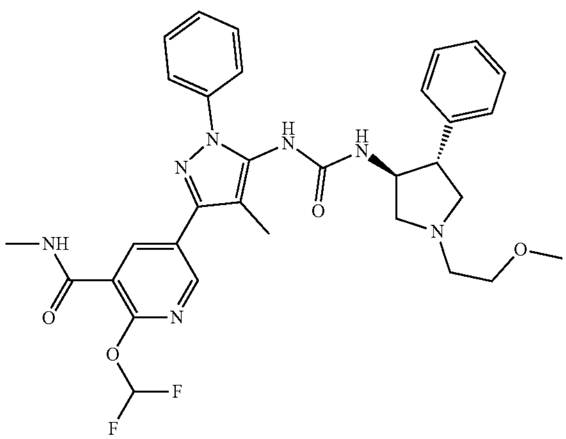 | 2 | 1.96 | 620 | racemate |

TABLE 33

| No. | Structure | LCMS method No | RT | MS | configuration |
|---|---|---|---|---|---|
| I-129 | 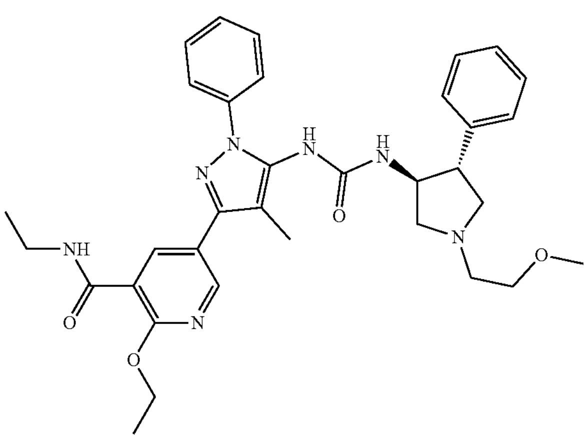 [SMILES: CCNC(=O)c1cc(-c2nn(-c3ccccc3)c(NC(=O)N[C@@H]3CN(CCOC)C[C@H]3c3ccccc3)c2C)cnc1OCC] | 2 | 2.1 | 612 | racemate |

TABLE 33-continued

| No. | Structure | LCMS method No | RT | MS | configuration |
|---|---|---|---|---|---|
| I-130 | 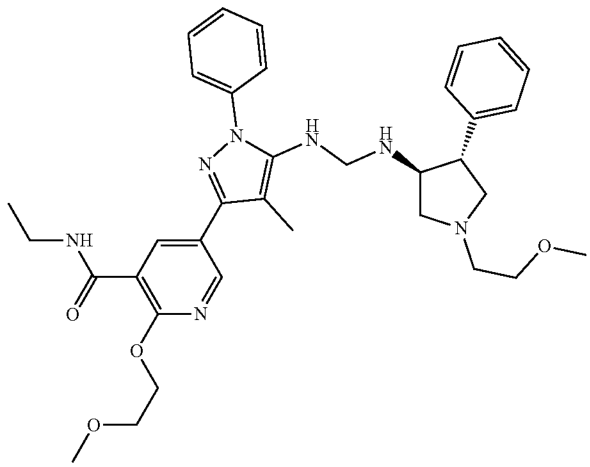 [SMILES: CCNC(=O)c1cc(-c2nn(-c3ccccc3)c(NCN[C@@H]3CN(CCOC)C[C@H]3c3ccccc3)c2C)cnc1OCCOC] | 2 | 1.91 | 642 | racemate |
| I-131 | 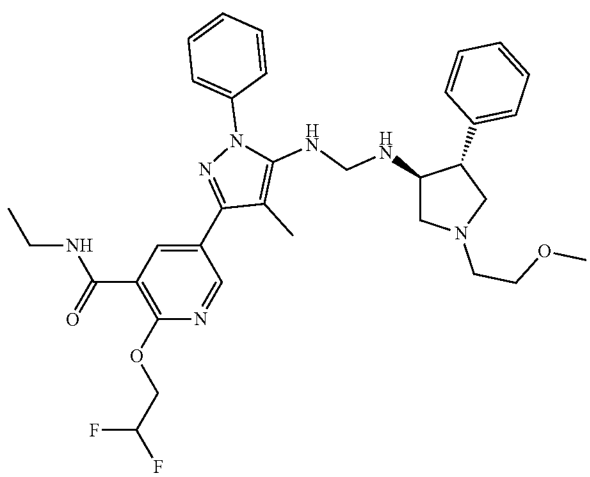 [SMILES: CCNC(=O)c1cc(-c2nn(-c3ccccc3)c(NCN[C@@H]3CN(CCOC)C[C@H]3c3ccccc3)c2C)cnc1OCC(F)F] | 2 | 2.09 | 648 | racemate |
| I-132 | 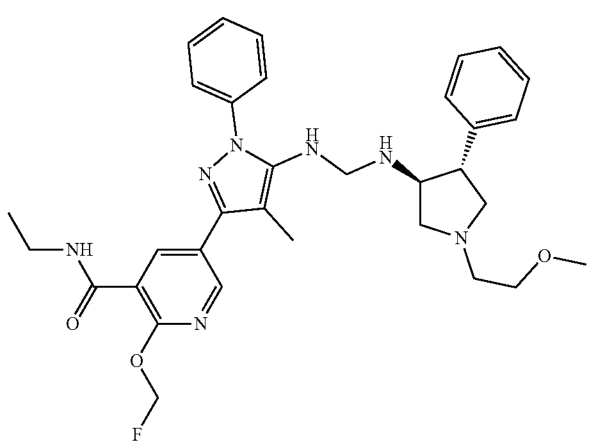 [SMILES: CCNC(=O)c1cc(-c2nn(-c3ccccc3)c(NCN[C@@H]3CN(CCOC)C[C@H]3c3ccccc3)c2C)cnc1OCF] | 2 | 1.85 | 616 | racemate |

TABLE 34

| No. | Structure | LCMS method No | RT | MS | configuration |
|---|---|---|---|---|---|
| I-133 | 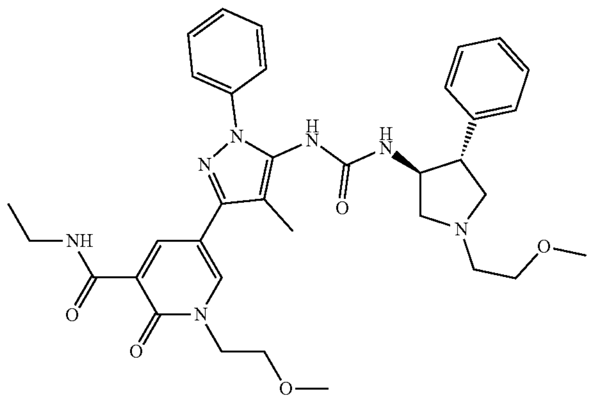 [SMILES: CCNC(=O)c1cc(-c2nn(-c3ccccc3)c(NC(=O)N[C@@H]3CN(CCOC)C[C@H]3c3ccccc3)c2C)cn(CCOC)c1=O] | 2 | 1.72 | 642 | racemate |
| I-134 | 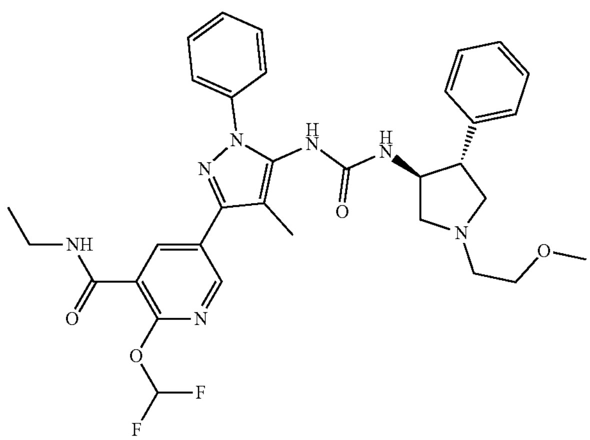 [SMILES: CCNC(=O)c1cc(-c2nn(-c3ccccc3)c(NC(=O)N[C@@H]3CN(CCOC)C[C@H]3c3ccccc3)c2C)cnc1OC(F)F] | 3 | 2.08 | 634 | racemate |
| I-135 | 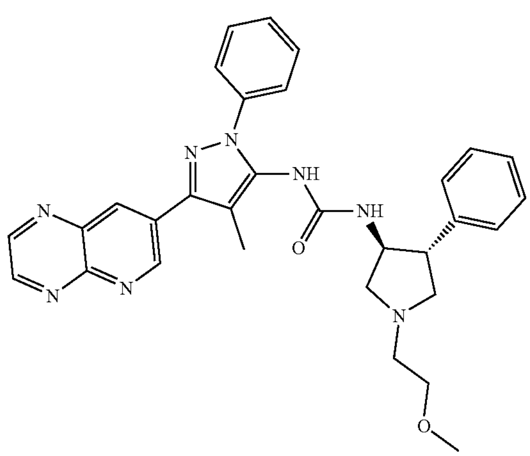 [SMILES: COCCN1C[C@@H](NC(=O)Nc2c(C)c(-c3cnc4nccnc4c3)nn2-c2ccccc2)[C@H](c2ccccc2)C1] | 1 | 1.08 | 549 | racemate |

TABLE 34-continued
| No. | Structure | LCMS method No | RT | MS | configuration |
|---|---|---|---|---|---|
| I-136 | 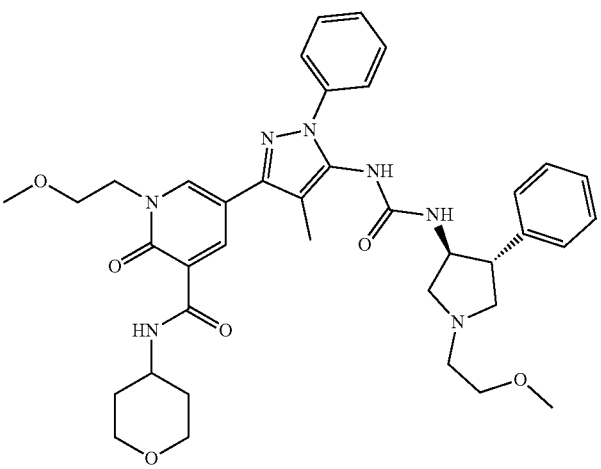 [SMILES: COCCN1C[C@@H](NC(=O)Nc2c(C)c(-c3cc(C(=O)NC4CCOCC4)c(=O)n(CCOC)c3)nn2-c2ccccc2)[C@H](c2ccccc2)C1] | 2 | 1.65 | 698 | racemate |
TABLE 35
| No. | Structure | LCMS method No | RT | MS | configuration |
|---|---|---|---|---|---|
| I-137 | 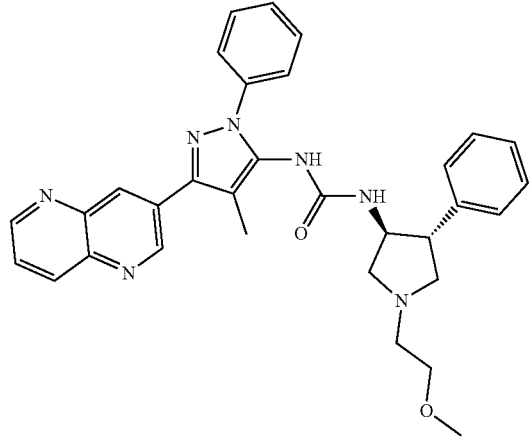 | 1 | 1.15 | 548 | racemate |
| I-138 | 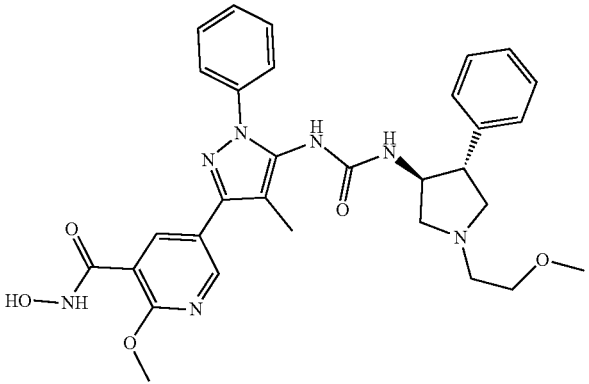 [SMILES: COCCN1C[C@@H](NC(=O)Nc2c(C)c(-c3cnc(OC)c(C(=O)NO)c3)nn2-c2ccccc2)[C@H](c2ccccc2)C1] | 2 | 1.21 | 586 | racemate |

TABLE 35-continued

| No. | Structure | LCMS method No | RT | MS | configuration |
|---|---|---|---|---|---|
| I-139 | 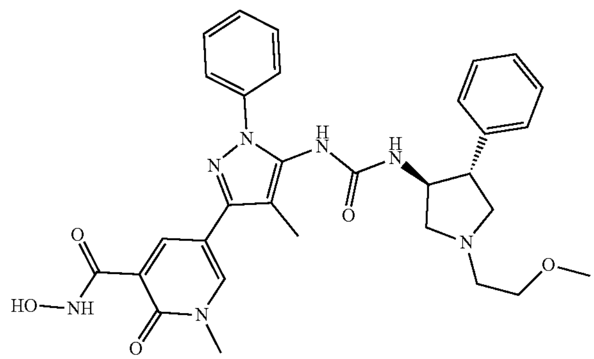 [SMILES: COCCN1C[C@@H](NC(=O)Nc2c(C)c(-c3cc(C(=O)NO)c(=O)n(C)c3)nn2-c2ccccc2)[C@H](c2ccccc2)C1] | 2 | 1.35 | 586 | racemate |
| I-140 | 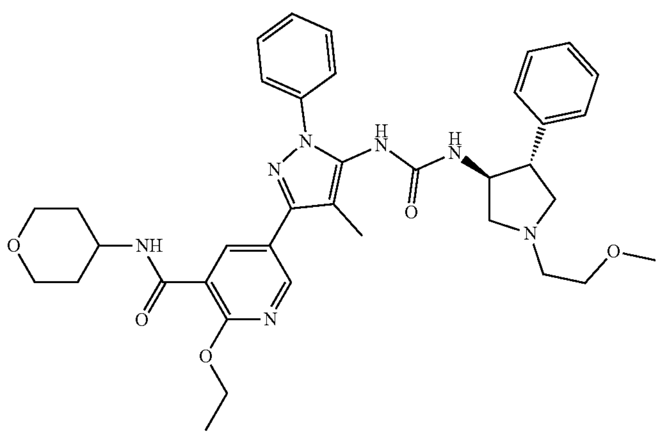 [SMILES: CCOc1ncc(-c2nn(-c3ccccc3)c(NC(=O)N[C@@H]3CN(CCOC)C[C@H]3c3ccccc3)c2C)cc1C(=O)NC1CCOCC1] | 2 | 1.97 | 668 | racemate |

TABLE 36

| No. | Structure | LCMS method No | RT | MS | configuration |
|---|---|---|---|---|---|
| I-141 | 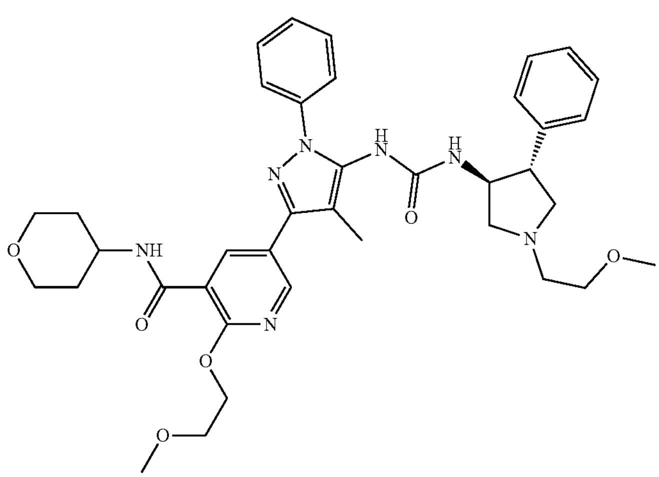 [SMILES: COCCOc1ncc(-c2nn(-c3ccccc3)c(NC(=O)N[C@@H]3CN(CCOC)C[C@H]3c3ccccc3)c2C)cc1C(=O)NC1CCOCC1] | 2 | 1.93 | 698 | racemate |

TABLE 36-continued

| No. | Structure | LCMS method No | RT | MS | configuration |
|---|---|---|---|---|---|
| I-142 | 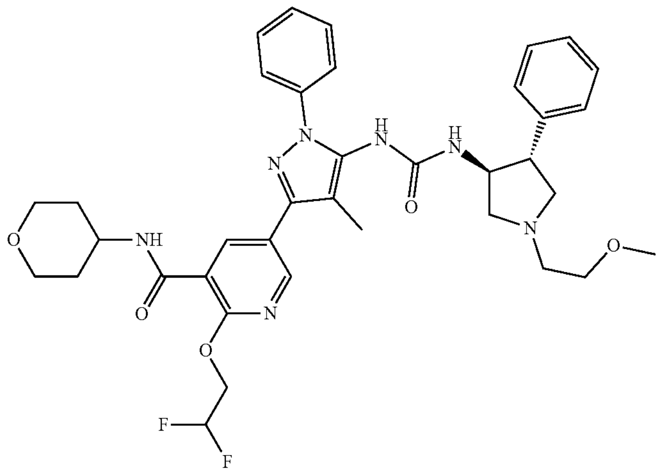 [SMILES: COCCN1C[C@@H](NC(=O)Nc2c(C)c(-c3cnc(OCC(F)F)c(C(=O)NC4CCOCC4)c3)nn2-c2ccccc2)[C@H](c2ccccc2)C1] | 2 | 1.97 | 704 | racemate |
| I-143 | 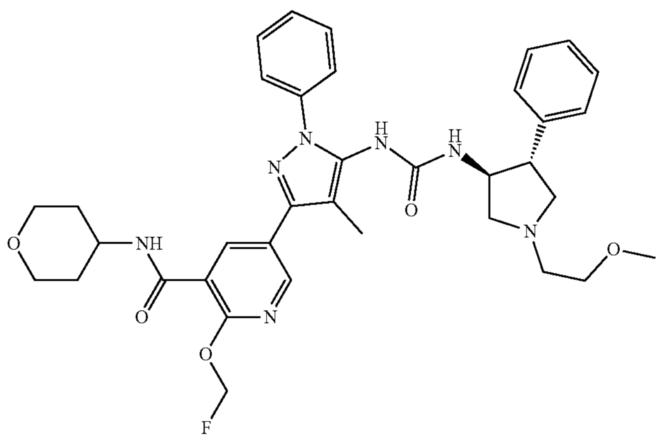 [SMILES: COCCN1C[C@@H](NC(=O)Nc2c(C)c(-c3cnc(OCF)c(C(=O)NC4CCOCC4)c3)nn2-c2ccccc2)[C@H](c2ccccc2)C1] | 2 | 1.76 | 672 | racemate |
| I-144 | 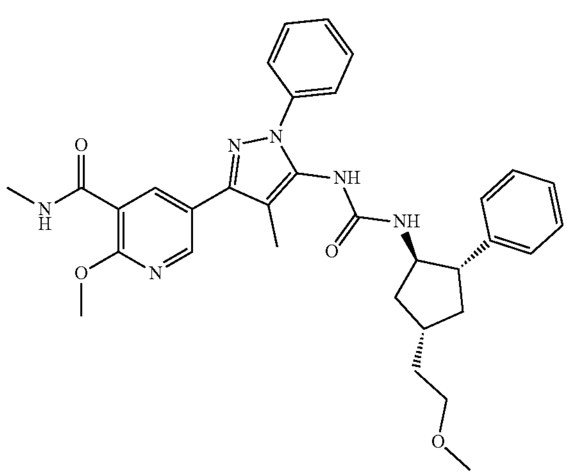 [SMILES: CNC(=O)c1cc(-c2nn(-c3ccccc3)c(NC(=O)N[C@@H]3C[C@@H](CCOC)C[C@H]3c3ccccc3)c2C)cnc1OC] | 2 | 2.24 | 583 | |

TABLE 37

| No. | Structure | LCMS method No | RT | MS | configuration |
|---|---|---|---|---|---|
| I-145 | 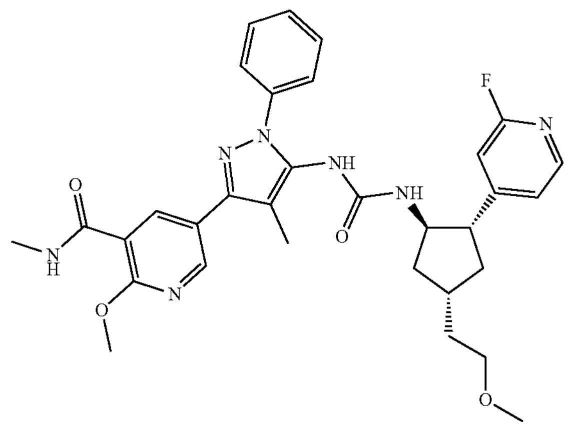 [SMILES: CNC(=O)c1cc(-c2nn(-c3ccccc3)c(NC(=O)N[C@@H]3C[C@@H](CCOC)C[C@H]3c3ccnc(F)c3)c2C)cnc1OC] | 2 | 2.02 | 602 | |
| I-146 | 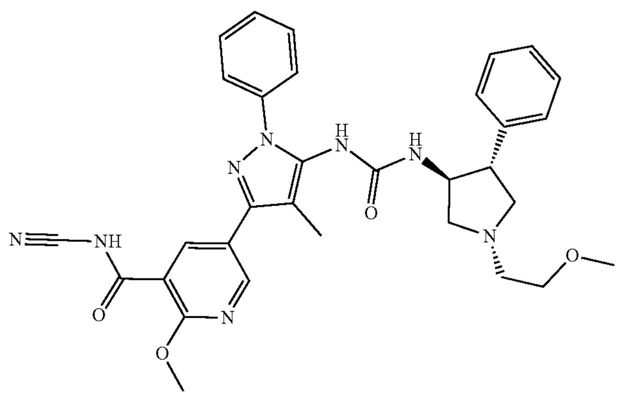 | 3 | 1.38 | 595 | racemate |
| I-147 | 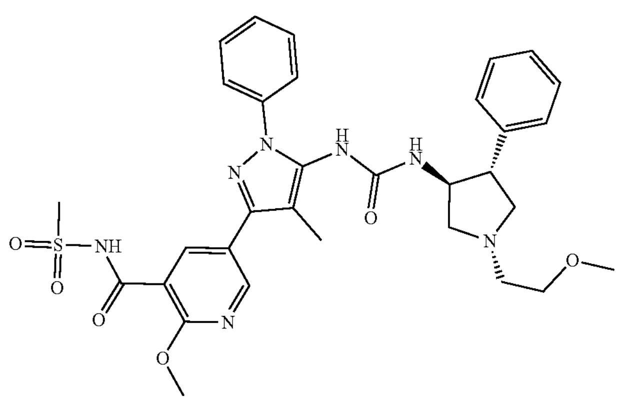 | 3 | 1.32 | 648 | racemate |

TABLE 37-continued

| No. | Structure | LCMS method No | RT | MS | configuration |
|---|---|---|---|---|---|
| I-148 | 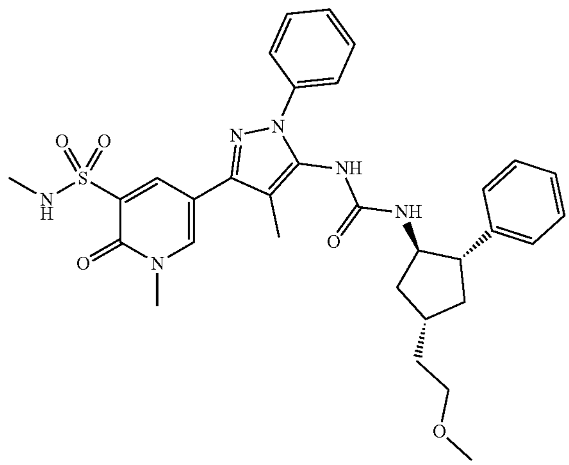 [SMILES: CNS(=O)(=O)c1cc(-c2nn(-c3ccccc3)c(NC(=O)N[C@@H]3C[C@@H](CCOC)C[C@H]3c3ccccc3)c2C)cn(C)c1=O] | 2 | 2.28 | 619 | |

TABLE 38

| No. | Structure | LCMS method No | RT | MS | configuration |
|---|---|---|---|---|---|
| I-149 | 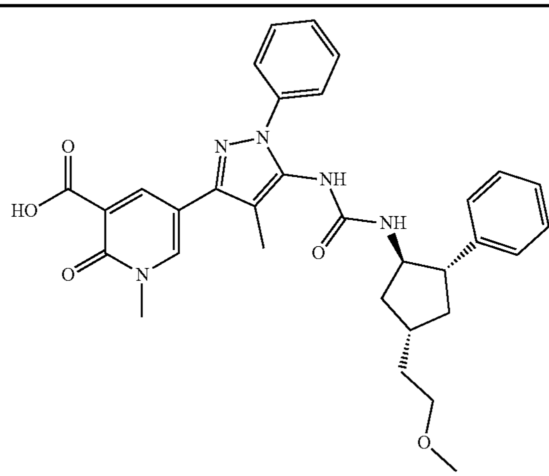 | 2 | 2.06 | 570 | |
| I-150 | 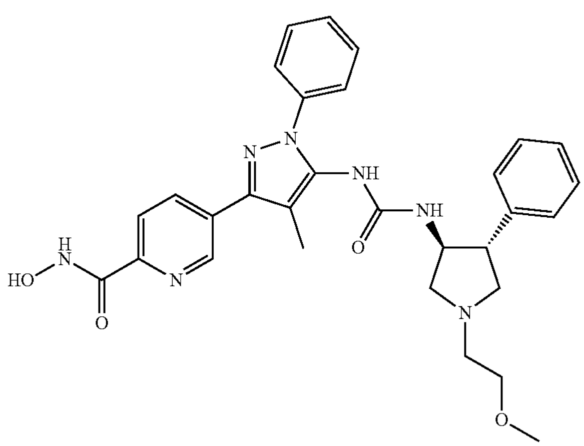 [SMILES: COCCN1C[C@@H](NC(=O)Nc2c(C)c(-c3ccc(C(=O)NO)nc3)nn2-c2ccccc2)[C@H](c2ccccc2)C1] | 1 | 1.03 | 556.25 | racemate |

TABLE 38-continued

| No. | Structure | LCMS method No | RT | MS | configuration |
|---|---|---|---|---|---|
| I-151 | 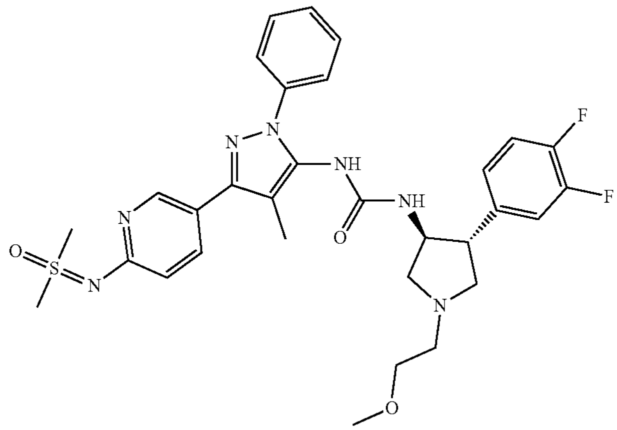 [SMILES: COCCN1C[C@@H](NC(=O)Nc2c(C)c(-c3ccc(N=S(C)(C)=O)nc3)nn2-c2ccccc2)[C@H](c2ccc(F)c(F)c2)C1] | 1 | 1.14 | 624.25 | |
| I-152 | 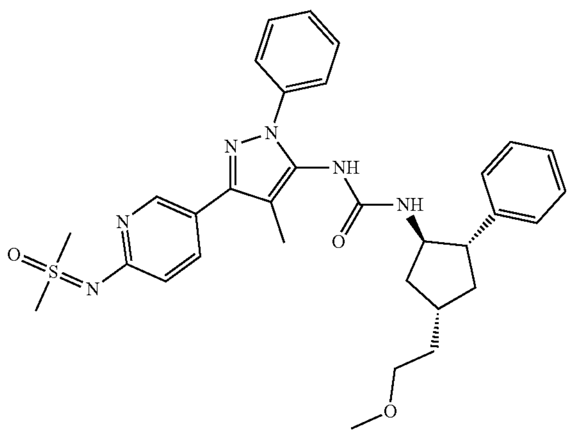 [SMILES: COCC[C@@H]1C[C@@H](NC(=O)Nc2c(C)c(-c3ccc(N=S(C)(C)=O)nc3)nn2-c2ccccc2)[C@H](c2ccccc2)C1] | 1 | 1.52 | 587.25 | |

TABLE 39

| No. | Structure | LCMS method No | RT | MS | configuration |
|---|---|---|---|---|---|
| I-153 | 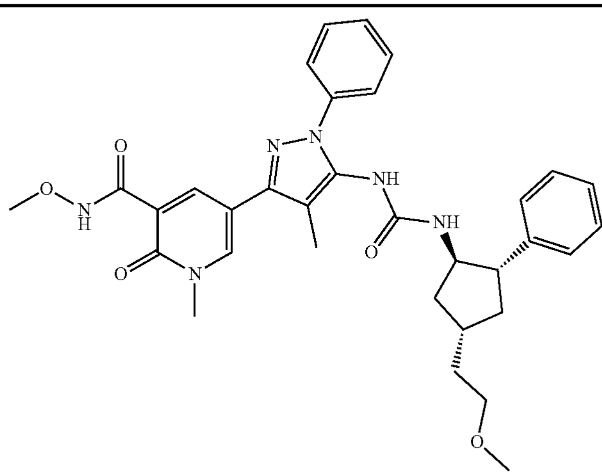 | 1 | 1.84 | 599 | |

TABLE 39-continued

| No. | Structure | LCMS method No | RT | MS | configuration |
|---|---|---|---|---|---|
| I-154 | 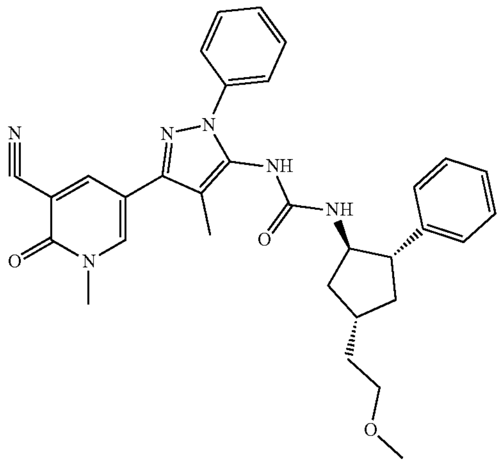 [SMILES: COCC[C@@H]1C[C@@H](NC(=O)Nc2c(C)c(-c3cc(C#N)c(=O)n(C)c3)nn2-c2ccccc2)[C@H](c2ccccc2)C1] | 2 | 2.02 | 551 | |
| I-155 | 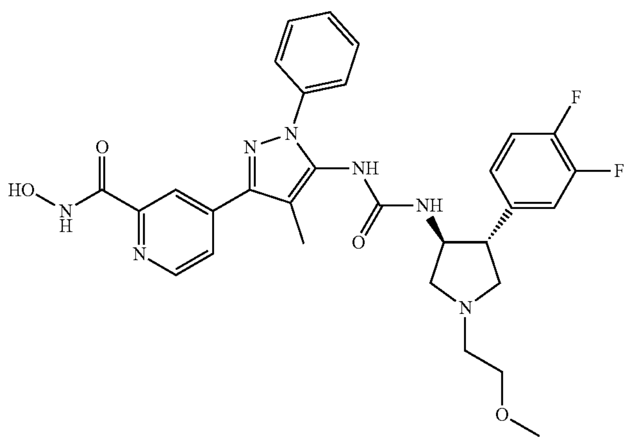 [SMILES: COCCN1C[C@@H](NC(=O)Nc2c(C)c(-c3ccnc(C(=O)NO)c3)nn2-c2ccccc2)[C@H](c2ccc(F)c(F)c2)C1] | 1 | 1.13 | 592.25 | |
| I-156 | 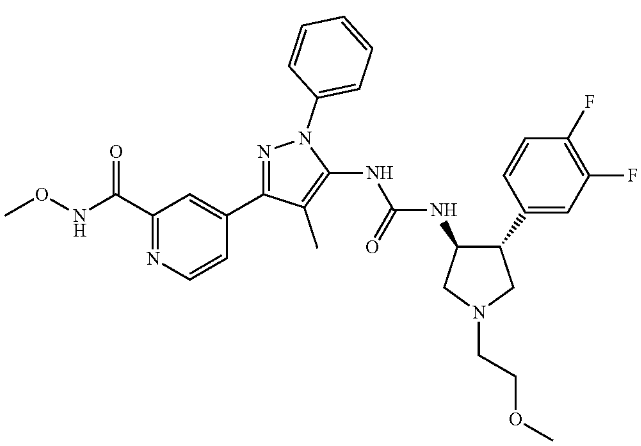 [SMILES: COCCN1C[C@@H](NC(=O)Nc2c(C)c(-c3ccnc(C(=O)NOC)c3)nn2-c2ccccc2)[C@H](c2ccc(F)c(F)c2)C1] | 1 | 1.28 | 606.25 | |

TABLE 40

| No. | Structure | LCMS method No | RT | MS | configuration |
|---|---|---|---|---|---|
| I-157 | 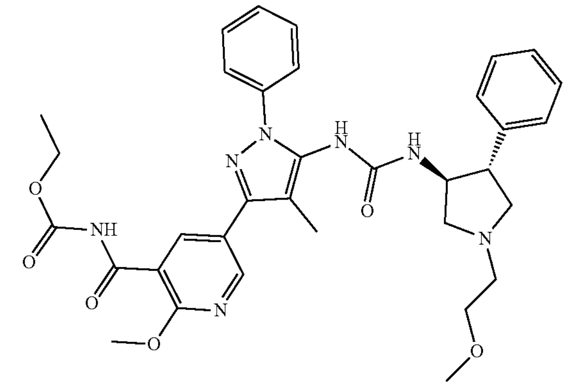 [SMILES: CCOC(=O)NC(=O)c1cc(-c2nn(-c3ccccc3)c(NC(=O)N[C@@H]3CN(CCOC)C[C@H]3c3ccccc3)c2C)cnc1OC] | 2 | 2.13 | 642 | racemate |
| I-158 | 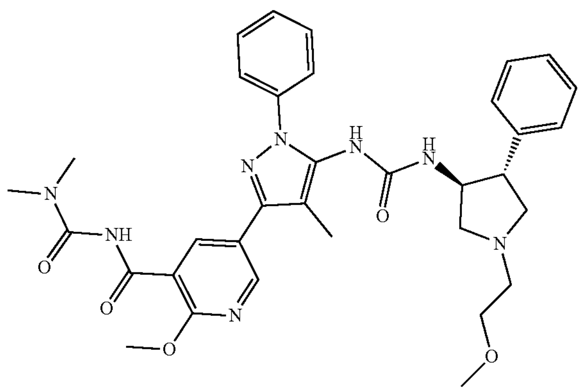 [SMILES: COCCN1C[C@@H](NC(=O)Nc2c(C)c(-c3cnc(OC)c(C(=O)NC(=O)N(C)C)c3)nn2-c2ccccc2)[C@H](c2ccccc2)C1] | 2 | 1.72 | 641 | racemate |
| I-159 | 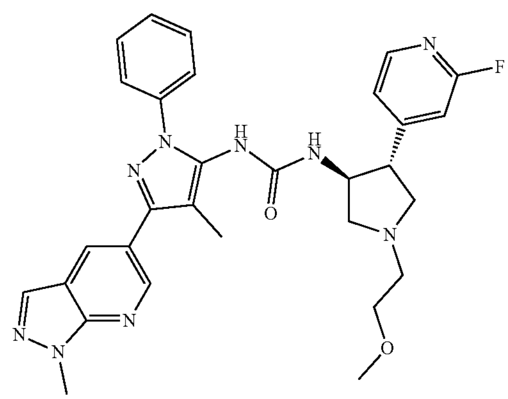 [SMILES: COCCN1C[C@@H](NC(=O)Nc2c(C)c(-c3cnc4c(cnn4C)c3)nn2-c2ccccc2)[C@H](c2ccnc(F)c2)C1] | 1 | 1.15 | 570.25 | |
| I-160 | 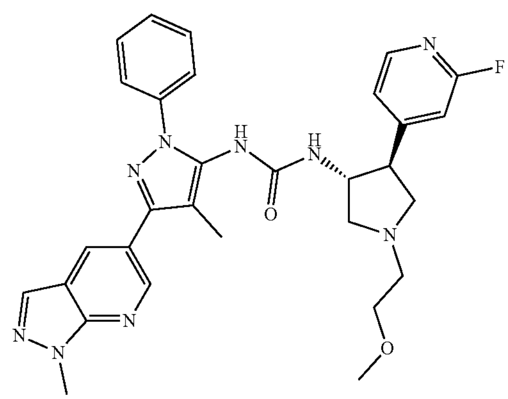 [SMILES: COCCN1C[C@H](NC(=O)Nc2c(C)c(-c3cnc4c(cnn4C)c3)nn2-c2ccccc2)[C@@H](c2ccnc(F)c2)C1] | 1 | 1.14 | 570.25 | |

TABLE 41
| No. | Structure | LCMS method No | RT | MS | configuration |
|---|---|---|---|---|---|
| I-161 | 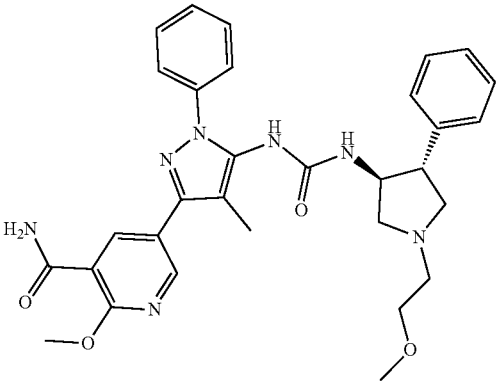 [SMILES: COCCN1C[C@@H](NC(=O)Nc2c(C)c(-c3cnc(OC)c(C(N)=O)c3)nn2-c2ccccc2)[C@H](c2ccccc2)C1] | 2 | 1.36 | 570 | racemate |
| I-162 | 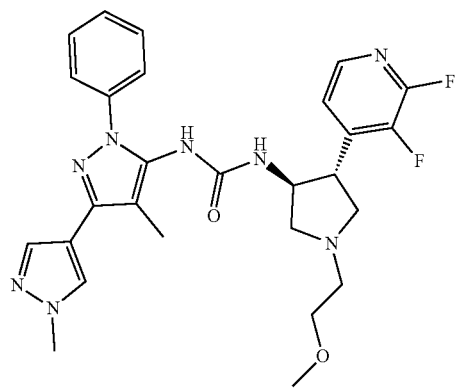 [SMILES: COCCN1C[C@@H](NC(=O)Nc2c(C)c(-c3cnn(C)c3)nn2-c2ccccc2)[C@H](c2ccnc(F)c2F)C1] | 1 | 1 | 537.3 | racemate |
| I-163 | 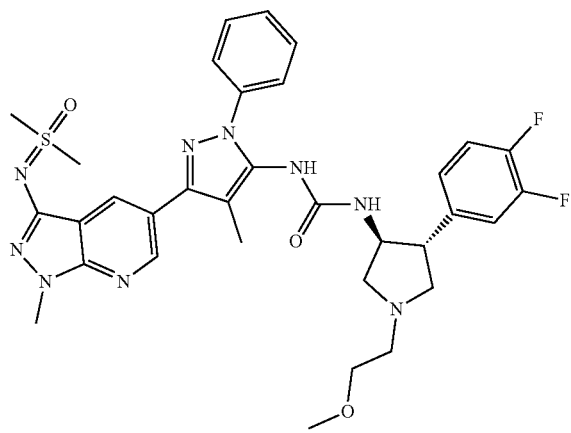 [SMILES: COCCN1C[C@@H](NC(=O)Nc2c(C)c(-c3cnc4c(c3)c(N=S(C)(C)=O)nn4C)nn2-c2ccccc2)[C@H](c2ccc(F)c(F)c2)C1] | 1 | 1.25 | 678.3 | |

TABLE 42

| No. | Structure | LCMS method No | RT | MS | configuration |
|---|---|---|---|---|---|
| I-164 | 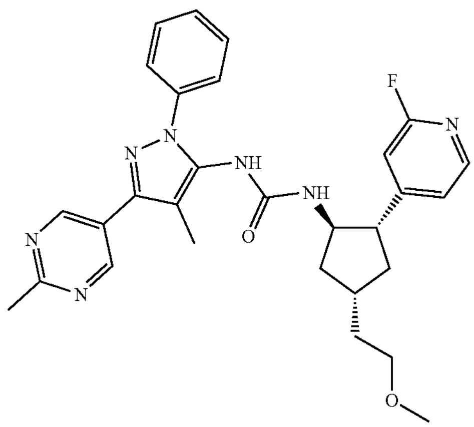 [SMILES: COCC[C@@H]1C[C@@H](NC(=O)Nc2c(C)c(-c3cnc(C)nc3)nn2-c2ccccc2)[C@H](c2ccnc(F)c2)C1] | 2 | 1.68 | 530 | |
| I-165 | 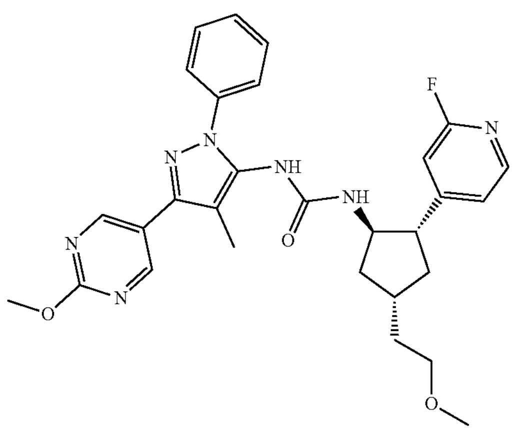 [SMILES: COCC[C@@H]1C[C@@H](NC(=O)Nc2c(C)c(-c3cnc(OC)nc3)nn2-c2ccccc2)[C@H](c2ccnc(F)c2)C1] | 2 | 1.8 | 546 | |
| I-166 | 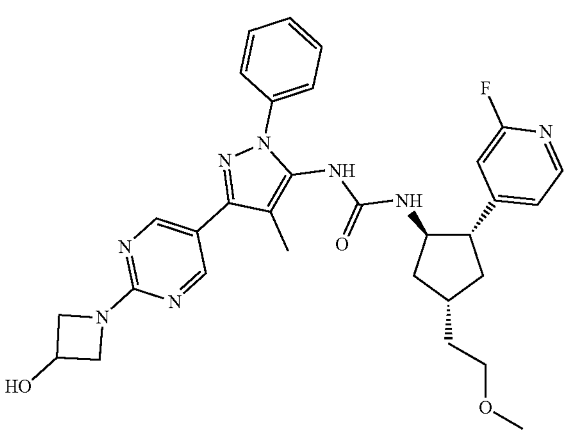 [SMILES: COCC[C@@H]1C[C@@H](NC(=O)Nc2c(C)c(-c3cnc(N4CC(O)C4)nc3)nn2-c2ccccc2)[C@H](c2ccnc(F)c2)C1] | 1 | 1.47 | 587 | |

TABLE 42-continued

| No. | Structure | LCMS method No | RT | MS | configuration |
|---|---|---|---|---|---|
| I-167 | 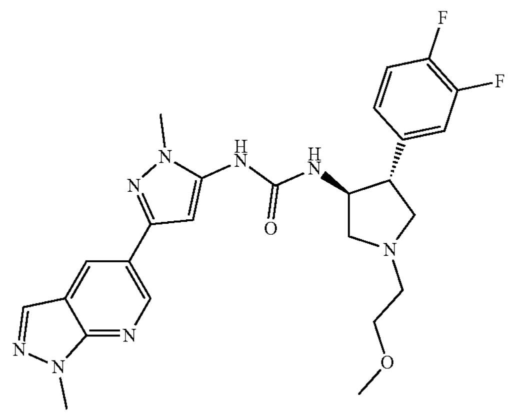 [SMILES: COCCN1C[C@@H](NC(=O)Nc2cc(-c3cnc4c(cnn4C)c3)nn2C)[C@H](c2ccc(F)c(F)c2)C1] | 1 | 1.26 | 511 | |

TABLE 43

| No. | Structure | LCMS method No | RT | MS | configuration |
|---|---|---|---|---|---|
| I-169 | 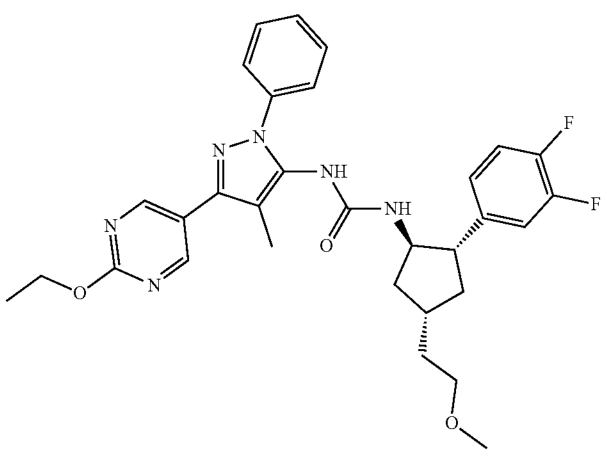 [SMILES: CCOc1ncc(-c2nn(-c3ccccc3)c(NC(=O)N[C@@H]3C[C@@H](CCOC)C[C@H]3c3ccc(F)c(F)c3)c2C)cn1] | 2 | 2.35 | 577 | |
| I-170 | 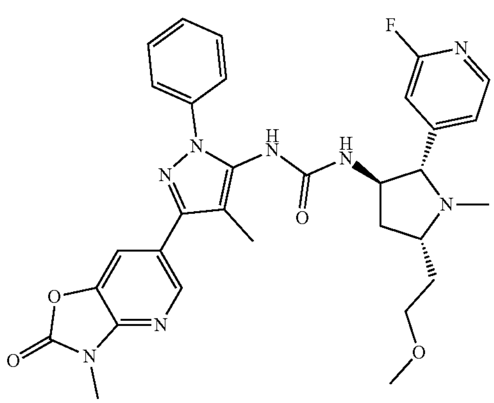 [SMILES: COCC[C@@H]1C[C@@H](NC(=O)Nc2c(C)c(-c3cnc4c(c3)oc(=O)n4C)nn2-c2ccccc2)[C@H](c2ccnc(F)c2)N1C] | 2 | 1.35 | 601 | |

TABLE 43-continued

| No. | Structure | LCMS method No | RT | MS | configuration |
|---|---|---|---|---|---|
| I-171 | 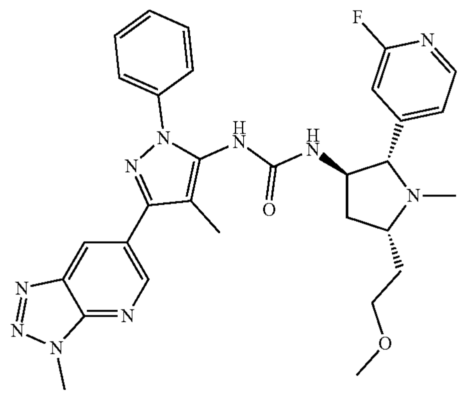 [SMILES: COCC[C@@H]1C[C@@H](NC(=O)Nc2c(C)c(-c3cnc4c(c3)nnn4C)nn2-c2ccccc2)[C@H](c2ccnc(F)c2)N1C] | 2 | 1.3 | 585 | |
| I-172 | 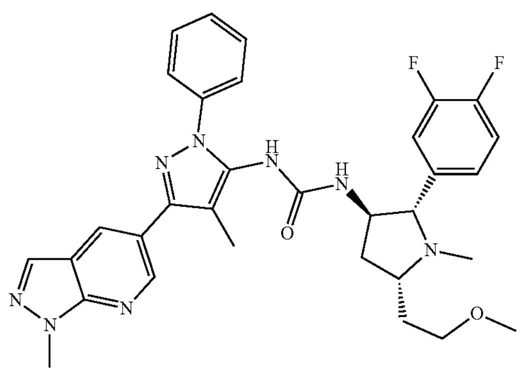 [SMILES: COCC[C@@H]1C[C@@H](NC(=O)Nc2c(C)c(-c3cnc4c(cnn4C)c3)nn2-c2ccccc2)[C@H](c2ccc(F)c(F)c2)N1C] | 2 | 1.47 | 601 | |

TABLE 44

| No. | Structure | LCMS method No | RT | MS | configuration |
|---|---|---|---|---|---|
| I-173 | 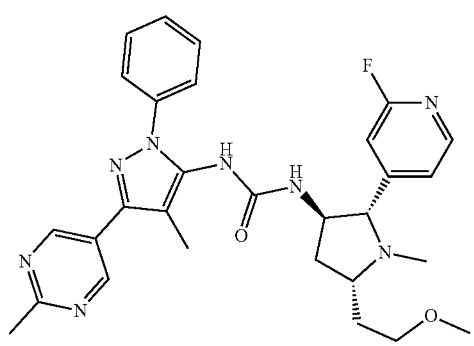 | 2 | 1.15 | 545 | |

… TABLE 44-continued
| No. | Structure | LCMS method No | RT | MS | configuration |
|---|---|---|---|---|---|
| I-174 | 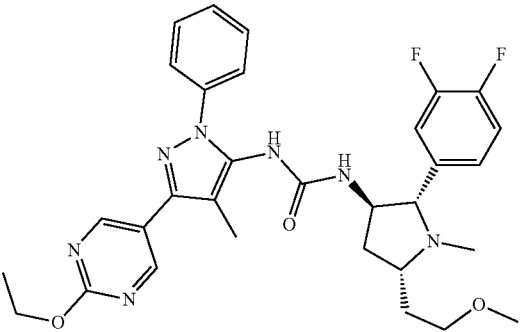 [SMILES: CCOc1ncc(-c2nn(-c3ccccc3)c(NC(=O)N[C@@H]3C[C@@H](CCOC)N(C)[C@H]3c3ccc(F)c(F)c3)c2C)cn1] | 2 | 1.56 | 592 | |
| I-175 | 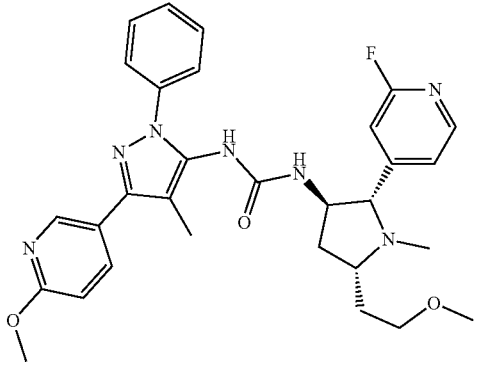 [SMILES: COCC[C@@H]1C[C@@H](NC(=O)Nc2c(C)c(-c3ccc(OC)nc3)nn2-c2ccccc2)[C@H](c2ccnc(F)c2)N1C] | 3 | 1.59 | 560 | |
| I-176 | 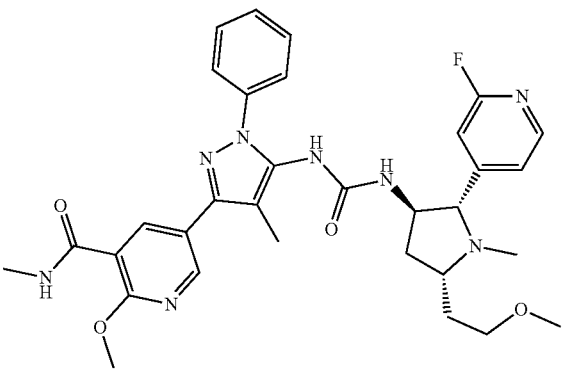 | 3 | 1.71 | 617 | |

TABLE 45

| No. | Structure | LCMS method No | RT | MS | configuration |
|---|---|---|---|---|---|
| I-177 | 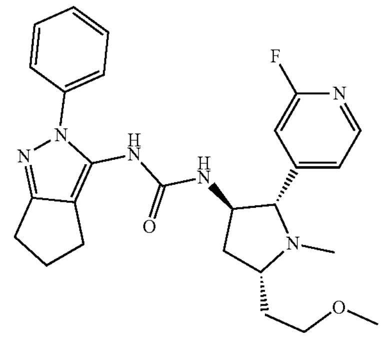 [SMILES: COCC[C@@H]1C[C@@H](NC(=O)Nc2c3c(nn2-c2ccccc2)CCC3)[C@H](c2ccnc(F)c2)N1C] | 3 | 1.69 | 479 | |
| I-178 | 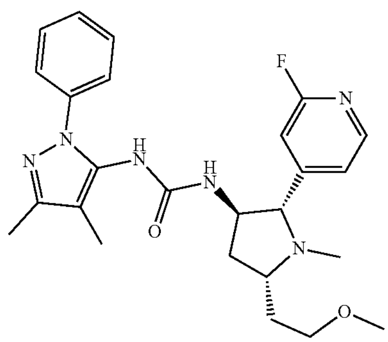 | 3 | 1.59 | 467 | |
| I-179 | 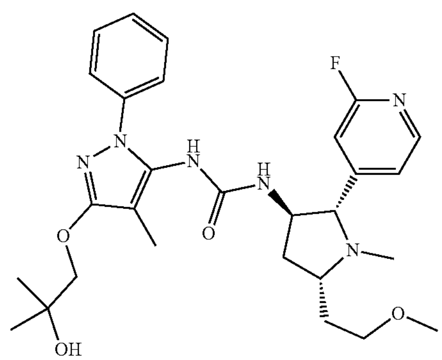 [SMILES: COCC[C@@H]1C[C@@H](NC(=O)Nc2c(C)c(OCC(C)(C)O)nn2-c2ccccc2)[C@H](c2ccnc(F)c2)N1C] | 3 | 1.69 | 541 | |
| I-180 | 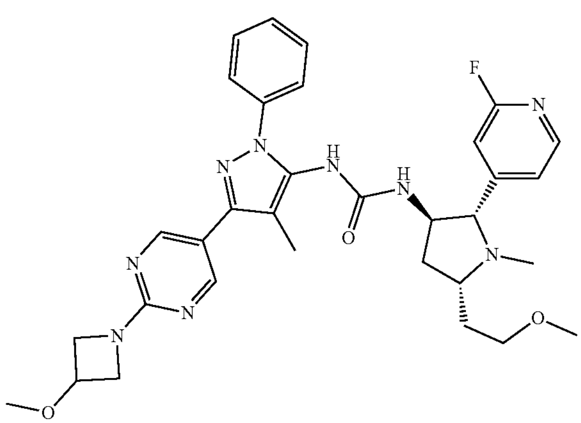 | 3 | 1.65 | 616 | |

Test Example 1

The Growth Inhibition Assay Using TF-1 Cells

To produce the stable cells expressing four types of NT receptors (TrkA, TrkB, TrkC and p75) highly and simultaneously, each human NT receptor gene was transfected by a retrovirus vector into human erythroleukemic cell line TF-1 cells (ATCC Number:CRL-2003). The inhibition assay against NGF, BDNF and NT-3 were done in TF-1 cells expressing TrkA+p75, TrkB+p75 and TrkC+p75, respectively. Two hundred nL per well of each compound (final concentration: 20 μmol/L-1 nmol/L) dissolved in DMSO was applied in a white 384 well flat-bottom plate. The cells were suspended in RPMI-1640 medium containing 10% fetal bovine serum and seeded in each well at 400 cells for the TF1 cells expressing TrkA and p75 or TrkC and p'75, and 800 cells for the TF cells expressing TrkB and p75. Forty μL of human NGF (final concentration: 4 ng/mL), human BDNF (final concentration: 8 ng/mL) or human NT-3 (final concentration: 8 ng/mL) was added in each well and the plate was incubated for 3 days. Then, twenty μL of CellTiter-Glo reagent for CellTiter-Glo Luminescent Cell Viability Assay (manufactured by Promega) was added in each well and chemiluminescence was measured by a microplate reader to evaluate the growth of TF-1 cells. Luminescence value in the well incubated with or without each growth factor is 0% or 100% inhibition, respectively. The inhibitory activity of each compound was calculated by the following formula.

Inhibition (%)=(1-(luminescence value with compound−luminescence value of 100% inhibitory activity)/(luminescence value of 0% inhibitory activity−luminescence value of 100% inhibitory activity))×100

The 50% inhibitory concentration (IC50) was determined by the logistic regression using the inhibition data in 10 points of 3-fold dilution series at a compound concentration range of 1 μmol/L to 0.05 nmol/L.

Test Example 2

Human TrkA Inhibition Assay

Seven point five μL per well of human TrkA (PV3144, Lifetechnologies, final concentration: 1 nmol/L) suspended in the assay buffer (100 mmol/L 4-(2-hydroxyethyl)-1-piperazineethanesulfonic acid (HEPES), 10 mmol/L magnesium chloride, 0.003 vol % Brij-35, 0.004 vol % Tween20 and 1 mmol/L dithiothreitol (DTT)) was applied in a 384 well plate and the plate was pre-incubated for 15 min at room temperature with 0.4 μL of each compound (final concentration: 200 μmol/L-0.1 nM) dissolved in DMSO. Then, fluorescent substrate (FL-peptide 27, 760424, PerkinElmer, final concentration: 1.5 μmol/L) and ATP (final concentration 500 μmol/L) dissolved in the assay buffer was added in each well. After the incubation of 120 min at 37° C., fifteen μL of termination buffer (100 mmol/L HEPES, 40 mmol/L ethylenediaminetetraacetic acid (EDTA), 10 mmol/L magnesium chloride, 0.003 vol % Brij-35, 0.004 vol % Tween20, 1 mmol/L DTT and 0.16 vol % Coating Reagent 3) was added in each well to stop the enzyme reaction. Fluorescent intensities (FI) of phosphorylated and non-phosphorylated fluorescent substrates were measured by LabChip EZReader II (Caliper LifeSciences, Inc.), and conversion ratio (CR) was calculated by the following formula-1. The CR in the well applied with DMSO alone was used as a negative control and the CR in the well without applying TrkA was used as a positive control. The inhibitory effect of each compound on TrkA phosphorylation was calculated by the following formula-2.

CR (%)=(FI of phosphorylated substrate/(FI of phosphorylated substrate+FI of non-phosphorylated substrate))×100    (Formula-1)

Phosphorylation inhibition (%)=(1-(CR with compound treatment−CR of positive control)/(CR of negative control−CR of positive control))×100    (Formula-2)

IC50 values (nmol/L) were determined by the logistic regression using the inhibition data in 10 points of 3-fold dilution series at a compound concentration range of 2 μmol/L to 0.1 nmol/L, or 15 points of 3-fold dilution series at the range of 200 μmol/L to 0.04 nmol/L.

(Result)

The evaluation results of the compounds in the present invention are indicated as follows. IC50 values of 0 to 100 nM, 100 to 1000 nM and over 1000 nM were shown as "A", "B" and "C", respectively.

In the compounds of the present invention, Compound I-24 has an IC50 value of 0.81 nM, Compound I-56 has an IC50 value of 0.98 nM, Compound I-57 has an IC50 value of 1 nM, Compound I-76 has an IC50 value of 3.1 nM, Compound I-90 has an IC50 value of 2.2 nM, Compound I-92 has an IC50 value of 0.74 nM, Compound I-100 has an IC50 value of 6.8 nM, Compound I-102 has an IC50 value of 0.66 nM, Compound I-151 has an IC50 value of 1.5 nM, Compound I-159 has an IC50 value of 1 nM, Compound I-164 has an IC50 value of 1.8 nM, Compound I-167 has an IC50 value of 28 nM, Compound I-172 has an IC50 value of 0.94 nM, and Compound I-173 has an IC50 value of 0.92 nM.

TABLE 46

| No. | IC50_nM |
|---|---|
| I-1 | A |
| I-2 | A |
| I-3 | A |
| I-4 | B |
| I-5 | A |
| I-6 | A |
| I-7 | A |
| I-8 | A |
| I-9 | A |
| I-10 | A |
| I-11 | A |
| I-12 | A |
| I-13 | A |
| I-14 | A |
| I-15 | A |
| I-16 | A |
| I-17 | A |
| I-18 | C |
| I-19 | A |
| I-20 | A |
| I-21 | A |
| I-22 | A |
| I-23 | A |
| I-25 | A |
| I-26 | A |
| I-27 | A |
| I-28 | A |
| I-29 | A |
| I-30 | A |
| I-31 | A |
| I-32 | A |
| I-33 | A |
| I-34 | A |
| I-35 | A |

TABLE 46-continued

| No. | IC50_nM |
|---|---|
| I-36 | A |
| I-37 | A |
| I-38 | A |
| I-39 | A |
| I-40 | A |
| I-41 | A |
| I-42 | A |
| I-43 | A |
| I-44 | A |
| I-45 | A |
| I-46 | A |
| I-47 | A |
| I-48 | A |
| I-49 | A |
| I-50 | A |
| I-51 | A |
| I-52 | A |
| I-53 | A |
| I-54 | A |
| I-55 | A |
| I-58 | A |
| I-59 | A |
| I-60 | A |
| I-61 | A |
| I-62 | A |
| I-63 | A |
| I-64 | A |
| I-65 | A |
| I-66 | A |
| I-67 | A |
| I-68 | A |
| I-69 | A |
| I-70 | A |
| I-71 | A |
| I-72 | A |
| I-73 | A |
| I-74 | A |
| I-75 | A |
| I-77 | A |
| I-78 | A |
| I-79 | A |
| I-80 | A |
| I-81 | A |
| I-82 | A |
| I-83 | A |
| I-84 | A |
| I-85 | A |
| I-86 | A |
| I-87 | A |
| I-88 | A |
| I-89 | A |
| I-91 | A |
| I-93 | A |
| I-94 | A |
| I-95 | A |
| I-96 | A |
| I-97 | A |
| I-98 | A |
| I-99 | A |
| I-101 | A |
| I-103 | A |
| I-104 | A |
| I-105 | A |
| I-106 | A |
| I-107 | A |
| I-108 | A |
| I-109 | A |
| I-110 | A |
| I-111 | A |
| I-112 | A |
| I-113 | A |
| I-114 | A |
| I-115 | A |
| I-116 | A |
| I-117 | A |
| I-118 | A |
| I-119 | A |
| I-120 | A |
| I-121 | A |
| I-122 | A |
| I-123 | A |
| I-124 | A |
| I-125 | A |
| I-126 | A |
| I-127 | A |
| I-128 | A |
| I-129 | A |
| I-130 | A |
| I-131 | A |
| I-132 | A |
| I-133 | A |
| I-134 | A |
| I-135 | A |
| I-136 | A |
| I-137 | A |
| I-138 | A |
| I-139 | A |
| I-140 | A |
| I-141 | A |
| I-142 | A |
| I-143 | A |
| I-144 | A |
| I-145 | A |
| I-146 | A |
| I-147 | A |
| I-148 | A |
| I-149 | A |
| I-150 | A |
| I-152 | A |
| I-153 | A |
| I-154 | A |
| I-155 | A |
| I-156 | A |
| I-157 | A |
| I-158 | A |
| I-160 | C |
| I-161 | A |
| I-162 | A |
| I-163 | A |

TABLE 47

| No. | IC50_nM |
|---|---|
| I-165 | A |
| I-166 | A |
| I-169 | A |
| I-170 | A |
| I-171 | A |
| I-174 | A |
| I-175 | A |
| I-176 | A |
| I-177 | A |
| I-178 | A |
| I-179 | A |
| I-180 | A |

Test Example 3 hERG Test

For the purpose of assessing risk of an electrocardiogram QT interval prolongation of the compound of the present invention, effects of the compound of the present invention on delayed rectifier K+ current (IKr), which plays an important role in the ventricular repolarization process, was studied using CHO cells expressing human ether-a-go-go related gene (hERG) channel.

After a cell was retained at a membrane potential of −80 mV by whole cell patch clamp method using an automated patch clamp system (QPatch; Sophion Bioscience A/S) and gave a leak potential of −50 mV, IKr induced by depolarization pulse stimulation at +20 mV for 2 seconds, and further, repolarization pulse stimulation at −50 mV for 2 seconds, was recorded. A vehicle, which is the 0.1-0.3% dimethyle sulfoxide solution in extracellular solution (NaCl: 145 mmol/L, KCl: 4 mmol/L, $CaCl_2$: 2 mmol/L, $MgCl_2$: 1 mmol/L, glucose:10 mmol/L, HEPES (4-(2-hydroxyethyl)-1-piperazineethanesulfonic acid): 10 mmol/L, pH7.4), or the compound of the present invention had been dissolved at an objective concentration in the extracellular solution is applied to the cell at room temperature for 7 minutes or more. From the recording IKr, an absolute value of the tail peak current was measured based on the current value at the resting membrane potential using analysis software (QPatch assay software; Sophion Bioscience A/S). Further, the % inhibition of tail peak current for the compound of the present invention relative to the tail peak current after application of the vehicle is calculated to assess influence of the compound of the present invention on IKr.

(Result) % inhibition was shown at 5, 10 or 30 μmol/L of test compound.

Compound I-5: 35.3% (30 μmol/L)
Compound I-10: 34.6% (5 μmol/L)
Compound I-66: 22.6% (5 μmol/L)
Compound I-67: 16.3% (5 μmol/L)
Compound I-68: 12.8% (30 μmol/L)
Compound I-92: 19.3% (30 μmol/L)
Compound I-93: 11.6% (5 μmol/L)
Compound I-169: 21.0% (10 μmol/L)
Compound I-174: 33.6% (10 μmol/L)

Test Example 4

CYP Inhibition Test

Using commercially available pooled human liver microsomes, an inhibitory degree of each metabolite production amount by the compound of the present invention is assessed as marker reactions of human main five CYP isoforms (CYP1A2, 2C9, 2C19, 2D6, and 3A4), 7-ethoxyresorufin O-deethylation (CYP1A2), tolbutamide methylhydroxylation (CYP2C9), mephenytoin 4'-hydroxylation (CYP2C19), dextromethorphan O-demethylation (CYP2D6), and terfenedine hydroxylation.

The reaction conditions are as follows: substrate, 0.5 μmol/L ethoxyresorufin (CYP1A2), 100 μmol/L tolbutamide (CYP2C9), 50 μ/mol/L S-mephenitoin (CYP2C19), 5 μl/L dextromethorphan (CYP2D6), 1 μmol/L terfenedine (CYP3A4); reaction time, 15 minutes; reaction temperature, 37° C.; enzyme, pooled human liver microsomes 0.2 mg protein/mL; concentrations of the compound of the present invention, 1.0, 5.0, 10, 20 μmol/L (four points).

Each five kinds of substrates, human liver microsomes, or compound of the present invention in 50 mmol/L Hepes buffer are added to a 96-well plate at the composition as described above, and NADPH, as a cofactor is added to initiate metabolism reactions. After the incubation at 37° C. for 15 minutes, a methanol/acetonitrile=1/1 (v/v) solution is added to stop the reaction. After the centrifugation at 3000 rpm for 15 minutes, resorufin (CYP1A2 metabolite) in the supernatant is quantified by a fluorescent multilabel counter or LC/MS/MS and hydroxytolbutamide (CYP2C9 metabolite), 4' hydroxymephenytoin (CYP2C19 metabolite), dextromethorphan (CYP2D6 metabolite), and terfenadine alcohol metabolite (CYP3A4 metabolite) are quantified by LC/MS/MS.

The sample adding only DMSO as a solvent to a reaction system instead of a solution dissolving a compound of the present invention is adopted as a control (100%). Remaining activity (%) is calculated and IC50 is calculated by reverse presumption by a logistic model using a concentration and an inhibition rate.

Test Example 5

CYP3A4 (MDZ) MBI Test

CYP3A4 (MDZ) MBI test is a test of investigating mechanism based inhibition potential on CYP3A4 by the enhancement of inhibitory degree of a metabolic reaction caused by the compound of the present invention. CYP3A4 inhibition was evaluated using pooled human liver microsomes by 1-hydroxylation reaction of midazolam (MDZ) as a marker reaction.

The reaction conditions are as follows: substrate, 10 μmol/L MDZ; pre-reaction time, 0 or 30 minutes; substrate reaction time, 2 minutes; reaction temperature, 37° C.; protein content of pooled human liver microsomes, at pre-reaction time 0.5 mg/mL, at reaction time 0.05 pmg/mL (at 10-fold dilution); concentrations of the compound of the present invention, 1, 5, 10, 20 μmol/L (four points).

Pooled human liver microsomes and a solution of the compound of the present invention in K-Pi buffer (pH 7.4) as a pre-reaction solution were added to a 96-well plate at the composition of the pre-reaction. A part of pre-reaction solution was transferred to another 96-well plate, and 1/10 diluted by K-Pi buffer containing a substrate. NADPH as a co-factor was added to initiate a reaction as a marker reaction (preincubation 0 min). After a predetermined time of a reaction, methanol/acetonitrile=1/1 (v/v) solution was added to stop the reaction. In addition, NADPH was added to a remaining pre-reaction solution to initiate a pre-reaction (preincubation 30 min). After a predetermined time of a pre-reaction, a part was transferred to another 96-well plate, and 1/10 diluted by K-Pi buffer containing a substrate to initiate a reaction as a marker reaction. After a predetermined time of a reaction, methanol/acetonitrile=1/1 (v/v) solution was added to stop the reaction. After centrifuged at 3000 rpm for 15 minutes, 1-hydroxymidazolam in the supernatant was quantified by LC/MS/MS.

The sample adding DMSO as a solvent to a reaction system instead of a solution dissolving the compound of the present invention was adopted as a control (100%). Remaining activity (%) was calculated at each concentration of the compound of the present invention compared to a control, and IC value was calculated by reverse-presumption by a logistic model using a concentration and an inhibition rate. Shifted IC value was calculated as "IC of preincubation at 0 min/ IC of preincubation at 30 min". When a shifted IC is 1.5 or more, this is defined as positive. When a shifted IC is 1.0 or less, this is defined as negative.

(Results)
Compound 1-5: Negative
Compound 1-68: Negative
Compound 1-164: Negative
Compound 1-173: Negative Test Example 6

BA Test

Materials and methods for experiments to evaluate oral absorption
(1) Experimental animals: Mice or SD rats are used.
(2) Rearing condition: Mice or SD rats are allowed free access to solid feed and sterilized tap water.
(3) Setting of dosage and grouping: Oral administration and intravenous administration are performed with a predetermined dosage. Grouping is set as follows. (dosage changed per compound)

Oral administration: 0.5 to 30 mg/kg (n=2 to 3)

Intravenous administration: 0.1 to 10 mg/kg (n=2 to 3)

(4) Preparation of administration solution: Oral administration is performed in the form of a suspension or a solution. Intravenous administration is performed after solubilization.

(5) Routes of administration: Oral administration is performed mandatory into the stomach by oral sonde. Intravenous administration is performed from caudal vein by syringes with needle.

(6) Evaluation items: Blood is collected serially and concentration of a compound of the present invention in plasma is measured by LC/MS/MS.

(7) Statistical analysis: About transition of concentration of a compound of the present invention in plasma, the area under the plasma concentration versus time curve (AUC) is calculated by non-linear least-squares method program, WinNonlin (a registered trademark), and bioavailability (BA) of a compound of the present invention is calculated from AUCs of the oral administration group and the intravenous administration group.

Test Example 7

Clearance Test

Materials and Methods for Experiments
(1) Experimental animals: Mice or SD rats are used.
(2) Rearing condition: Mice or SD rats are allowed free access to solid feed and sterilized tap water.
(3) Setting of dosage and grouping: Intravenous administration is performed with the predetermined dosage. Grouping is set as below. (Dosage is changed per compound) Intravenous administration 0.1 to 10 mg/kg (n=2 to 3)
(4) Preparation of administration solutions: Administration is performed after solubilization.
(5) Routes of administration: Intravenous administration is performed from caudal vein by syringes with needle.
(6) Evaluation items: Blood is collected serially and concentration of a compound of the present invention in plasma is measured by LC/MS/MS.
(7) Statistical analysis: About transition of concentration of a compound of the present invention in plasma, Total Clearance (CLtot) of a compound of the present invention is calculated by non-linear least-squares method program, WinNonlin (a registered trademark).

Test Example 8

Fluctuation Ames Test

Mutagenicity of compounds of the present invention is evaluated.

A 20 µL of freezing-stored Salmonella typhimurium (TA98 strain, TA100 strain) is inoculated on 10 mL of a liquid nutrient medium (2.5% Oxoid nutrient broth No. 2), and this is incubated at 37° C. for 10 hours under shaking. The 8 mL of TA98 culture medium is centrifuged (2000×g, 10 minutes) and TA98 is suspended in 8 mL Micro F buffer ($K_2HPO_4$: 3.5 g/L, $KH_2PO_4$: 1 g/L, $(NH4)2SO4$: 1 g/L, trisodium citrate dehydrate: 0.25 g/L, $MgSO_4 \cdot 7H_2O$: 0.1 g/L) after removing the culture medium. The TA98 suspension is mixed with 120 mL Exposure medium (Micro F buffer containing Biotin: 8 µg/mL, histidine: 0.2 µg/mL, glucose: 8 mg/mL). The 3.1 mL of TA100 culture medium strain is mixed with 130 mL Exposure medium. Each 12 µL of DMSO solution of the compound of the present invention (several stage dilution from maximum dose 50 mg/mL at 2 to 3 fold ratio), DMSO as a negative control, and 50 µg/mL of 4-nitroquinoline 1-oxide DMSO solution for the TA98 strain and 0.25 µg/mL of 2-(2-furyl)-3-(5-nitro-2-furyl)acrylamide DMSO solution for the TA100 strain in the assay without metabolic activation, 40 µg/mL of 2-aminoanthracene DMSO solution for the TA98 strain and 20 µg/mL of 2-aminoanthracene DMSO solution for the TA100 strain in the assay with metabolic activation as a positive control, and 588 µL of the test bacterial suspension (498 µL and 90 µL of S9 mixture in the case of metabolic activation assay) are mixed, and this is incubated at 37° C. for 90 minutes under shaking. A 230 µL of the mixture is mixed with 1150 µL of Indicator medium (Micro F buffer containing 8 µg/mL biotin, 0.2 µg/mL histidine, 8 mg/mL glucose, 37.5 µg/mL bromocresol purple), each 50 µL is dispensed to microplate 48 wells/dose, and this is incubated at 37° C. for 3 days. Since the wells containing the bacteria which gained growth ability by point mutation in amino acid (histidine) synthesizing enzyme gene turns from purple to yellow due to a pH change, the number of yellow wells in 48 wells is counted per dose, and is compared with the negative control group. (−) and (+) means negative and positive in mutagenicity respectively.

Test Example 9

Metabolism Stability Test

Using commercially available pooled human hepatic microsomes, a compound of the present invention is reacted for a constant time, and a remaining rate is calculated by comparing a reacted sample and an unreacted sample, thereby, a degree of metabolism in liver is assessed.

A reaction is performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction solution is added to 100 µL of a methanol/acetonitrile=1/1 (v/v), mixed and centrifuged at 3000 rpm for 15 minutes. The compound of the present invention in the supernatant is quantified by LC/MS/MS or Solid Phase Extraction (SPE)/MS, and a remaining amount of the compound of the present invention after the reaction is calculated, letting a compound amount at 0 minute reaction time to be 100%.

Test Example 10

Powder Solubility Test

Appropriate quantity of the compound of the present invention is put in a suitable container and 200 µL of pH 4 citrate buffer (100 mmol/L citric acid monohydrate aqueous solution and 100 mmol/L trisodium citrate dihydrate aqueous solution are mixed in appropriate quantity to adjust pH to 4) or JP-2 fluid (1 volume of water is added to 1 volume of the solution in which 3.40 g of potassium dihydrogen phosphate and 3.55 g of anhydrous disodium hydrogen phosphate are dissolved in water to reach 1000 mL) is independently added to each container. When total amount is dissolved after adding the test reagent, the compound of the present invention is added appropriately. After sealing and shaking at 25° C. or 37° C. for 1 hour, solution is filtrated and 100 µL of methanol is added to 100 µL of each filtrate to dilute two-fold. The dilution rate is changed as necessary. After checking that there is no bubble and precipitate, the container is sealed and shaken. The compound of the present invention is measured using HPLC by absolute calibration curve method.

Test Example 11

Solubility Test

The solubility of the compound of the present invention is determined under 1% DMSO addition conditions. A 10 mmol/L solution of the compound is prepared with DMSO, and 2 µL of the solution of the compound of the present invention is added, respectively, to 198 µL of JP-2 fluid (see below). The mixture is shaken for 1 hour at a room temperature, and the mixture is filtered. The filtrate is ten or hundred-fold diluted with methanol/water=1/1(v/v) or acetonitrile/methanol/water=1/1/2(V/V/V) and the compound concentration in the filtrate is measured with LC/MS or Solid Phase Extraction (SPE)/MS by the absolute calibration method.

A: 3.40 g of potassium dihydrogen phosphate and 3.55 g of anhydrous disodium hydrogen phosphate is dissolved in water to reach 1000 mL.

B: 1 volume of water is added 1 volume of the solution that 3.40 g of potassium dihydrogen phosphate and 3.55 g of sodium dihydrogen phosphate anhydrous are dissolved in water to be 1000 mL.

Formulation Example

The following Formulation Examples are only exemplified and not intended to limit the scope of the invention.

Formulation Example 1

Tablets

The compounds of the present invention, lactose and calcium stearate are mixed. The mixture is crushed, granulated and dried to give a suitable size of granules. Next, calcium stearate is added to the granules, and the mixture is compressed and molded to give tablets.

Formulation Example 2

Capsules

The compounds of the present invention, lactose and calcium stearate are mixed uniformly to obtain powder medicines in the form of powders or fine granules. The powder medicines are filled into capsule containers to give capsules.

Formulation Example 3

Granules

The compounds of the present invention, lactose and calcium stearate are mixed uniformly and the mixture is compressed and molded. Then, it is crushed, granulated and sieved to give suitable sizes of granules.

Formulation Example 4

Orally Disintegrating Tablets

The compounds of the present invention and crystalline cellulose are mixed, granulated and tablets are made to give orally disintegrating tablets.

Formulation Example 5

Dry Syrups

The compounds of the present invention and lactose are mixed, crushed, granulated and sieved to give suitable sizes of dry syrups.

Formulation Example 6

Injections

The compounds of the present invention and phosphate buffer are mixed to give injection.

Formulation Example 7

Infusions

The compounds of the present invention and phosphate buffer are mixed to give injection.

Formulation Example 8

Inhalations

The compound of the present invention and lactose are mixed and crushed finely to give inhalations.

Formulation Example 9

Ointments

The compounds of the present invention and petrolatum are mixed to give ointments.

Formulation Example 10

Patches

The compounds of the present invention and base such as adhesive plaster are mixed to give patches.

INDUSTRIAL APPLICABILITY

The compound of the present invention has TrkA inhibitory activity and it can be useful for a TrkA mediated disorder such as pain associated with osteoarthritis, rheumatoid arthritis, fracture, interstitial cystitis, chronic pancreatitis and prostate inflammation; and nociceptive pain as typified by chronic low back pain, diabetic peripheral neuropathy pain, postoperative pain, pelvic pain and cancer pain; neuropathic pain, acute pain, chronic pain, cancer, inflammatory disease, allergic disease, dermatological disease and the like.

What is claimed is:
1. A compound represented by Formula (I):

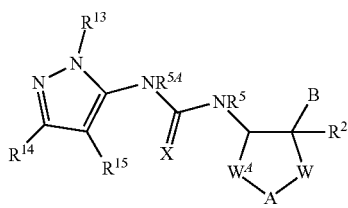

wherein =X is =O, =S, =NR$^{10}$ or =CR$^{11}$R$^{12}$;
—W$^A$— is —C(R$^3$R$^4$)—;
—W— is —C(R$^8$R$^9$)—;
—A— is —CR$^{1D}$R$^{1E}$—;
B is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkyl, or substituted or unsubstituted alkyloxy;
R$^{1D}$ and R$^{1E}$ are each independently a hydrogen atom, hydroxy, halogen, carboxy, substituted or unsubstituted alkyl, substituted or unsubstituted alkenyl, substituted or unsubstituted acyl, substituted or unsubstituted alkyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted amino, substituted or unsubstituted alkyl sulfonyl, substituted or unsubstituted alkenyl sulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsufonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl; or R$^{1D}$ and R$^{1E}$ may be taken together to form =CR$^{1F}$R$^{1G}$, oxo, =N—O—R$^{1H}$, a substituted or unsubstituted non-aromatic carbocycle, or a substituted or unsubstituted non-aromatic heterocycle;
R$^{1F}$ and R$^{1G}$ are each independently a hydrogen atom, substituted or unsubstituted alkyl, substituted or unsubstituted alkyloxy, or substituted or unsubstituted alkyloxycarbonyl;
R$^{1H}$ is a hydrogen atom, substituted or unsubstituted alkyl, substituted or unsubstituted alkenyl, or substituted or unsubstituted alkynyl;
R$^2$ is a hydrogen atom, substituted or unsubstituted alkyl, substituted or unsubstituted alkyloxy, cyano, carboxy, substituted or unsubstituted alkyloxycarbonyl, substituted or unsubstituted carbamoyl, halogen, or hydroxy;
R$^3$ is each independently a hydrogen atom, substituted or unsubstituted alkyl, substituted or unsubstituted alkenyl, substituted or unsubstituted alkynyl, substituted or unsubstituted alkyloxycarbonyl, or substituted or unsubstituted carbamoyl;
R$^4$ is each independently a hydrogen atom, substituted or unsubstituted alkyl, substituted or unsubstituted alkenyl, or substituted or unsubstituted alkynyl, or R$^3$ and R$^4$ may be taken together to form oxo;
R$^5$ and R$^{5A}$ are each independently a hydrogen atom, or substituted or unsubstituted alkyl;
R$^8$ is each independently a hydrogen atom, halogen, hydroxy, substituted or unsubstituted alkyl, substituted or unsubstituted alkenyl, substituted or unsubstituted alkynyl, or substituted or unsubstituted alkyloxy;
R$^9$ is each independently a hydrogen atom, halogen, hydroxy, substituted or unsubstituted alkyl, substituted or unsubstituted alkenyl, substituted or unsubstituted alkynyl, or substituted or unsubstituted alkyloxy, or R$^8$ and R$^9$ may be taken together to form oxo;
R$^{10}$ is substituted or unsubstituted alkyl, substituted or unsubstituted acyl, substituted or unsubstituted alkyloxycarbonyl, substituted or unsubstituted alkylsulfonyl, nitro, substituted or unsubstituted alkyloxy, or hydroxy;
R$^{11}$ is a hydrogen atom, cyano, substituted or unsubstituted acyl, substituted or unsubstituted alkyloxycarbonyl, substituted or unsubstituted carbamoyl, substituted or unsubstituted alkylsulfonyl, or nitro;
R$^{12}$ is a hydrogen atom or cyano;
R$^{13}$ is a hydrogen atom, substituted or unsubstituted alkyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;
R$^{14}$ is a hydrogen atom, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted carbamoyl, substituted or unsubstituted alkyl sulfonyl, substituted or unsubstituted alkenyl sulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;
R$^{15}$ is a hydrogen atom, halogen, cyano, substituted or unsubstituted alkyl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

or $R^{14}$ and $R^{15}$ may be taken together to form a substituted or unsubstituted non-aromatic carbocycle or a substituted or unsubstituted non-aromatic heterocycle;

provided that (α)

when —$W^A$— is —$CH_2$—, and —A— is —$CR^{1D}R^{1E}$—, (1) B is a group represented by the following formula:

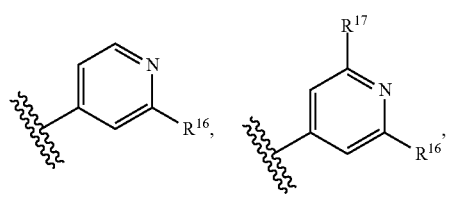

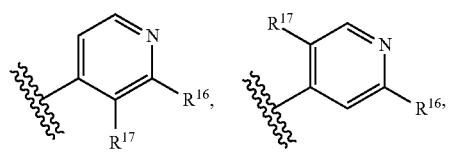

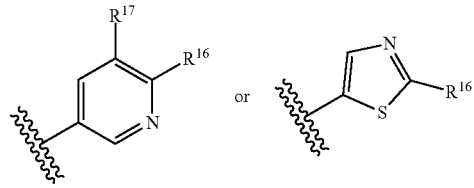

wherein $R^{16}$ and $R^{17}$ are each independently halogen; or (2) $R^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

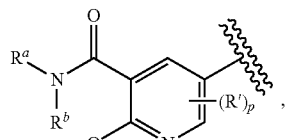

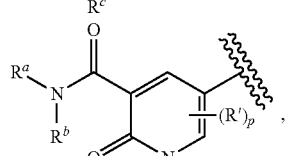

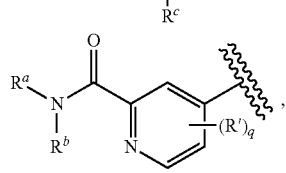

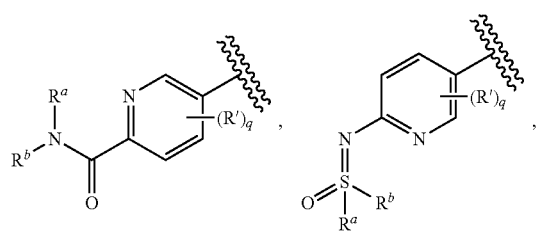

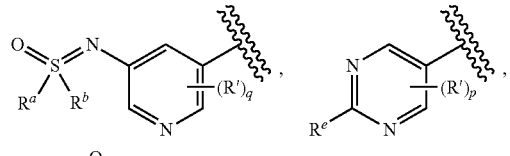

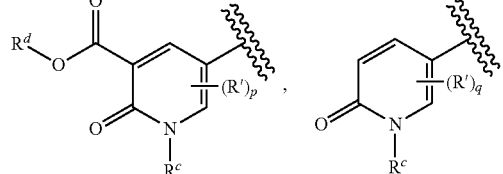

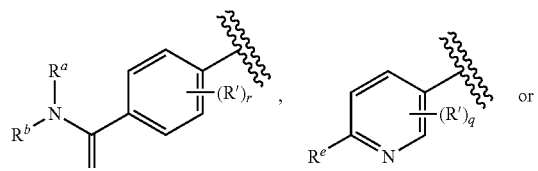

wherein $R^a$ and $R^b$ are each independently a hydrogen atom, cyano, hydroxy, substituted or unsubstituted alkyl, substituted or unsubstituted alkyloxy, substituted or unsubstituted alkyloxycarbonyl, substituted or unsubstituted alkylsulfonyl, substituted or unsubstituted carbamoyl, substituted or unsubstituted non-aromatic carbocyclyl, or substituted or unsubstituted non-aromatic heterocyclyl; $R^a$ is a hydrogen atom, substituted or unsubstituted alkyl (excluding unsubstituted methyl), substituted or unsubstituted non-aromatic carbocyclyl, or substituted or unsubstituted non-aromatic heterocyclyl; $R^c$ is a hydrogen atom, or substituted or unsubstituted alkyl; $R^d$ is a hydrogen atom, or substituted or unsubstituted alkyl; $R^e$ is a hydrogen atom, hydroxy, cyano, halogen, carboxy, substituted or unsubstituted alkyl, substituted or unsubstituted alkyloxy, substituted or unsubstituted amino, substituted or unsubstituted non-aromatic carbocyclyl, or substituted or unsubstituted non-aromatic heterocyclyl; R' is each independently halogen, cyano, hydroxy, carboxy, substituted or unsubstituted alkyl, substituted or unsubstituted alkyloxy, substituted or unsubstituted carbamoyl, or substituted or unsubstituted sulfamoyl;

p is 0, 1 or 2;

q is 0, 1, 2 or 3;

r is 0, 1, 2, 3 or 4;

provided that the following compounds are excluded:
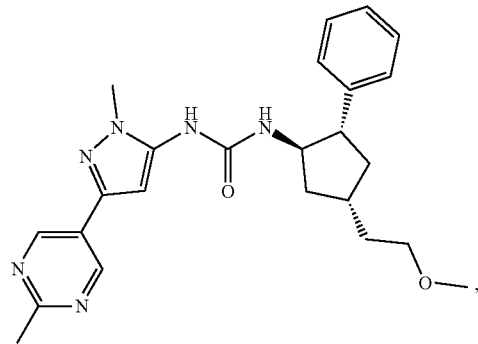
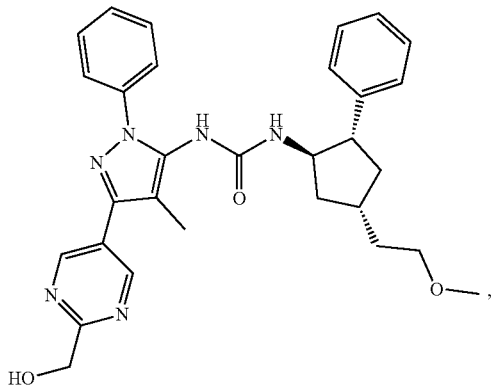
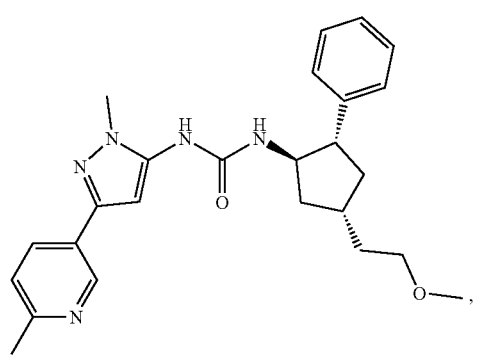
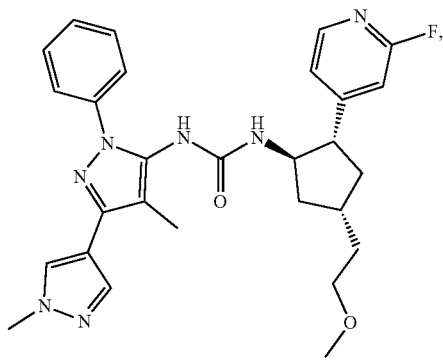
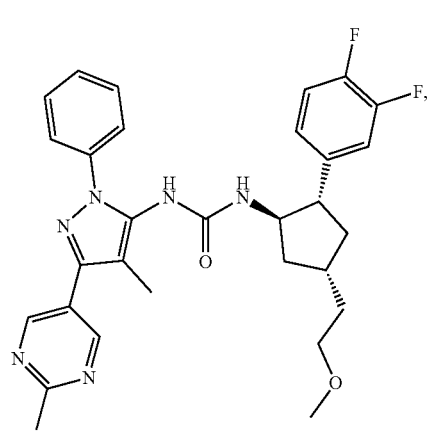
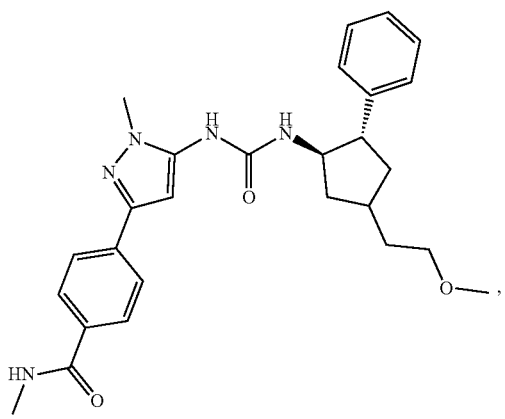
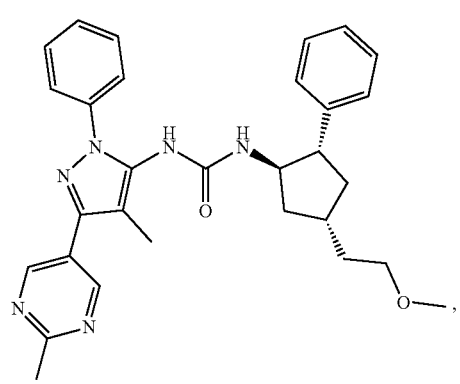
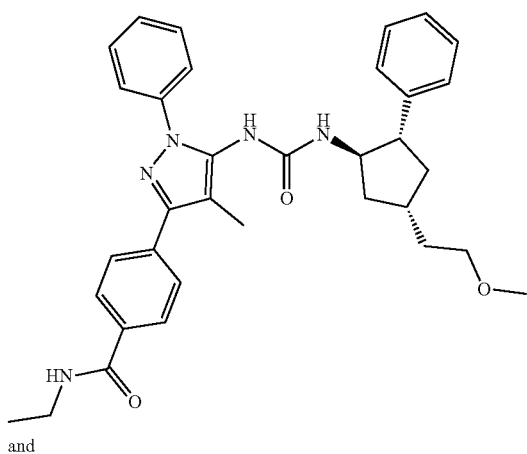
and

253

-continued

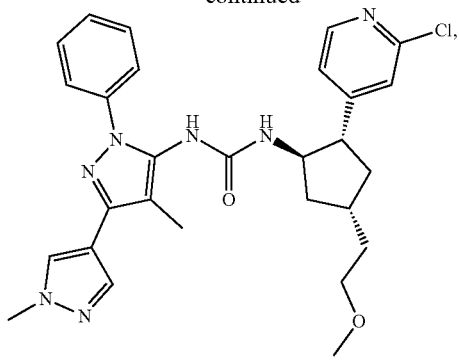

or a pharmaceutically acceptable salt thereof.

2. The compound according to claim 1,
wherein B is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl,
or a pharmaceutically acceptable salt thereof.

3. The compound according to claim 2,
wherein $R^3$ is substituted or unsubstituted alkyl, and $R^4$ is a hydrogen atom, or a pharmaceutically acceptable salt thereof.

4. The compound according to claim 1,
wherein —$W^A$— is —$CH_2$—, —W— is —$CH_2$—, $R^{1D}$ is substituted or unsubstituted alkyl, and $R^{1E}$ is a hydrogen atom,
or a pharmaceutically acceptable salt thereof.

5. The compound according to claim 2,
wherein $R^5$ and $R^{5A}$ are hydrogen atoms, and =X is =O,
or a pharmaceutically acceptable salt thereof.

6. The compound according to claim 2,
wherein $R^2$ is a hydrogen atom,
or a pharmaceutically acceptable salt thereof.

7. The compound according to claim 2,
wherein $R^{13}$ is substituted or unsubstituted aromatic carbocyclyl, substituted or unsubstituted alkyl, or substituted or unsubstituted non-aromatic carbocyclyl,
or a pharmaceutically acceptable salt thereof.

8. The compound according to claim 2,
wherein $R^{14}$ is substituted or unsubstituted 9- to 10-membered bicyclic aromatic heterocyclyl, substituted or unsubstituted 9- to 10-membered bicyclic non-aromatic heterocyclyl, or a group represented by the following formula:

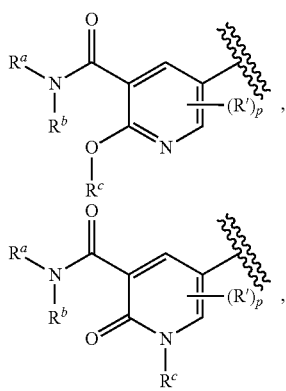

254

-continued

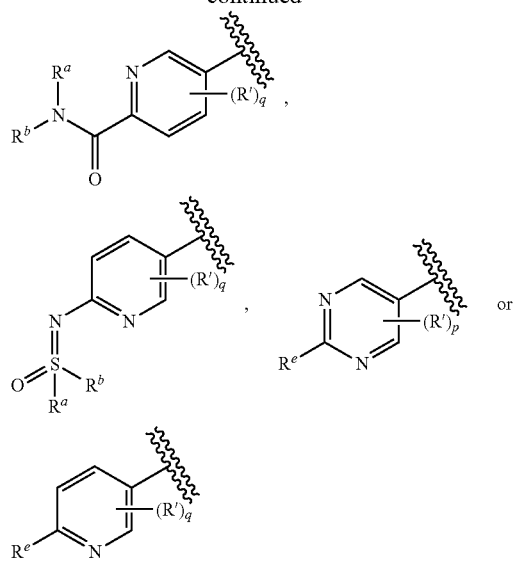

wherein $R^a$, $R^b$, $R^c$, R', p and q are the same as defined in claim 1,
or a pharmaceutically acceptable salt thereof.

9. The compound according to claim 2,
wherein $R^{15}$ is a hydrogen atom, or substituted or unsubstituted alkyl,
or a pharmaceutically acceptable salt thereof.

10. The compound according to claim 2, represented by Formula (I″):

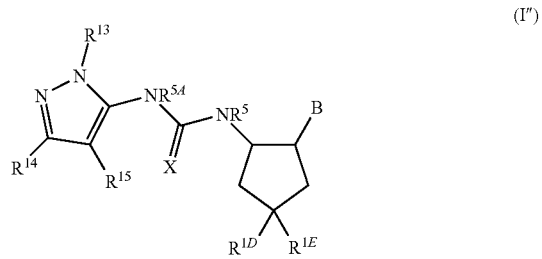

wherein =X, $R^{1D}$, $R^{1E}$, $R^5$, $R^{5A}$, $R^{13}$ and $R^{15}$ are the same as defined in claim 1;

B is a group represented by the following formula:

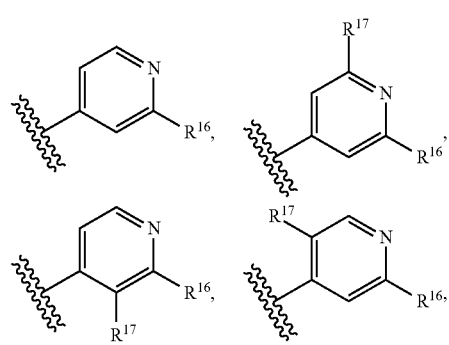

-continued

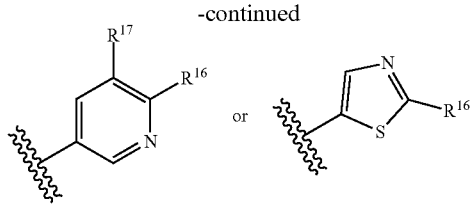

wherein R¹⁶ and R¹⁷ are the same as defined in claim 1;
R¹⁴ is substituted or unsubstituted 9- to 10-membered bicyclic aromatic heterocyclyl, substituted or unsubstituted 9- to 10-membered bicyclic non-aromatic heterocyclyl, or a group represented by the following formula:

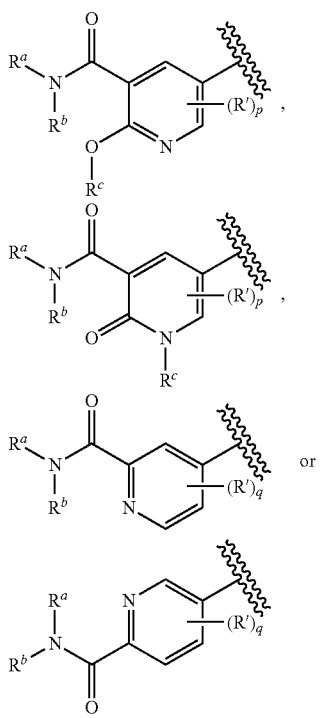

wherein $R^a$, $R^b$, $R^c$, R', p and q are the same as defined in claim 1,
or a pharmaceutically acceptable salt thereof.

11. The compound according to claim 2, represented by Formula (I''):

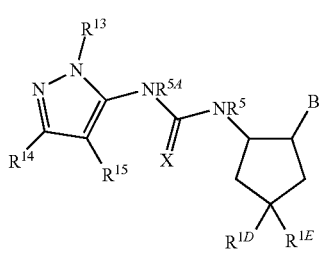

wherein =x, $R^{1D}$, $R^{1E}$, $R^5$, $R^{5A}$, $R^{13}$ and $R^{15}$ are the same as defined in claim 1;

B is a group represented by the following formula:

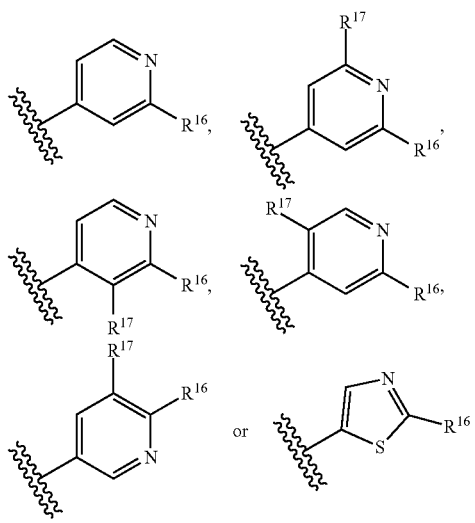

wherein R¹⁶ and R¹⁷ are the same as defined in claim 1;
R¹⁴ is a hydrogen atom, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted carbamoyl, substituted or unsubstituted alkyl sulfonyl, substituted or unsubstituted alkenyl sulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl,
or a pharmaceutically acceptable salt thereof.

12. The compound according to claim 1, selected from the group consisting of

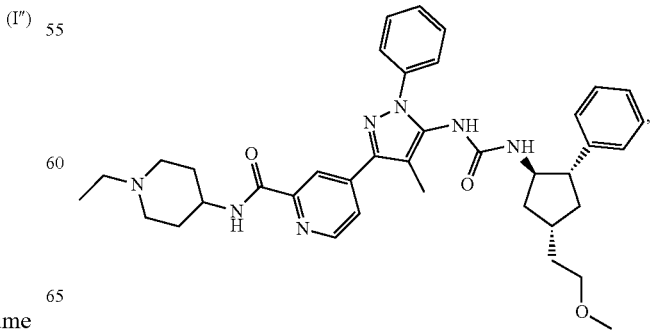

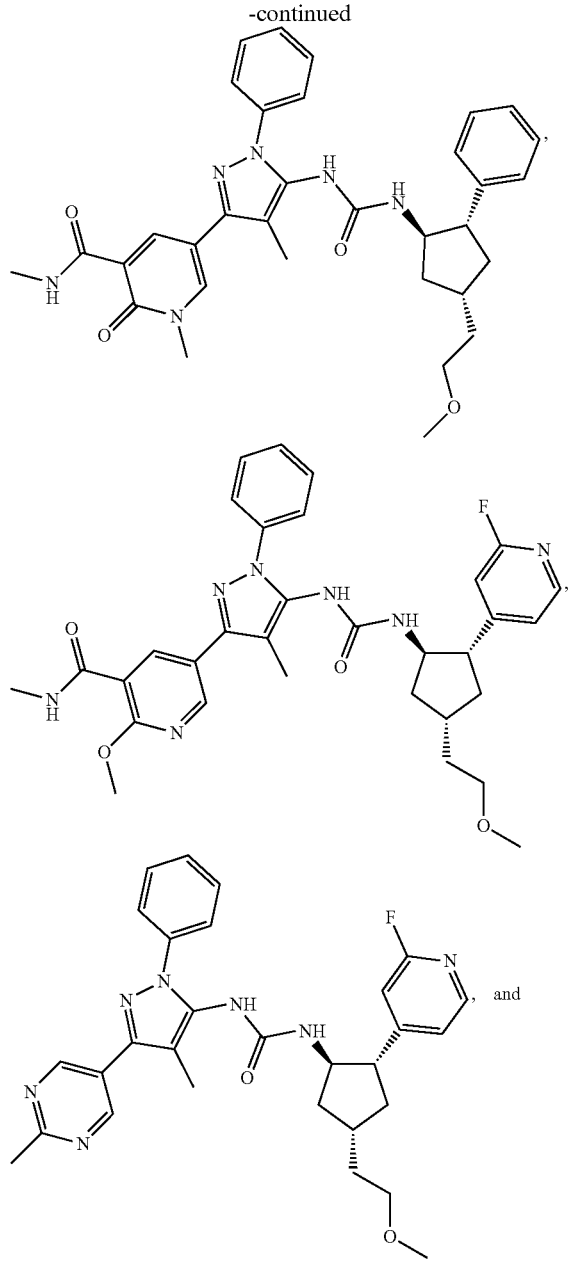

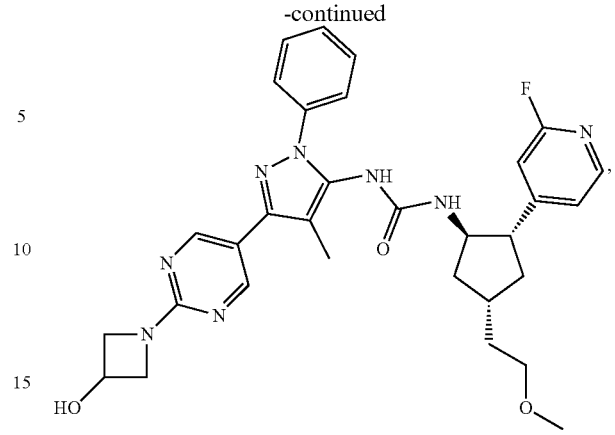

or a pharmaceutically acceptable salt thereof.

13. A pharmaceutical composition comprising the compound according to claim 1, or a pharmaceutically acceptable salt thereof.

14. A method for treating pain comprising administering a therapeutically effective amount of the compound according to claim 1, or a pharmaceutically acceptable salt thereof to a patient in need of said treating.

15. The method of claim 14, wherein the pain is pain associated with osteoarthritis, rheumatoid arthritis, fracture, interstitial cystitis, chronic pancreatitis or prostate inflammation.

16. The method of claim 14, wherein the pain is nociceptive pain as typified by chronic low back pain, diabetic peripheral neuropathy pain, postoperative pain, pelvic pain or cancer pain.

17. The method of claim 14, wherein the pain is neuropathic pain, acute pain, or chronic pain.

* * * * *